US012653119B2

(12) United States Patent
Xu et al.

(10) Patent No.: US 12,653,119 B2
(45) Date of Patent: Jun. 16, 2026

(54) GENETIC LOCI ASSOCIATED WITH EAR ROT RESISTANCE IN MAIZE

(71) Applicants: CHINA AGRICULTURAL UNIVERSITY, Beijing (CN); SYNGENTA CROP PROTECTION AG, Basel (CH)

(72) Inventors: Mingliang Xu, Beijing (CN); Lishan Yao, Beijing (CN); Yanmei Li, Beijing (CN); Chuanyu Ma, Beijing (CN); Lixiu Tong, Beijing (CN); Feili Du, Beijing (CN); Qingli Liu, Durham, NC (US); Becky Welsh Breitinger, Durham, NC (US)

(73) Assignees: China Agricultural University, Beijing (CN); Syngenta Crop Protection AG, Basel (CH)

( * ) Notice: Subject to any disclaimer, the term of this patent is extended or adjusted under 35 U.S.C. 154(b) by 657 days.

(21) Appl. No.: 17/635,225

(22) PCT Filed: Aug. 12, 2020

(86) PCT No.: PCT/US2020/045854
§ 371 (c)(1),
(2) Date: Feb. 14, 2022

(87) PCT Pub. No.: WO2021/030391
PCT Pub. Date: Feb. 18, 2021

(65) Prior Publication Data
US 2022/0287258 A1       Sep. 15, 2022

(30) Foreign Application Priority Data

Aug. 15, 2019    (WO) ................ PCT/CN2019/100801

(51) Int. Cl.
| *A01H 6/46* | (2018.01) |
| *A01H 1/00* | (2006.01) |
| *A01H 1/04* | (2006.01) |
| *A01H 5/10* | (2018.01) |
| *C12Q 1/6895* | (2018.01) |

(52) U.S. Cl.
CPC ........... *A01H 1/1255* (2021.01); *A01H 1/045* (2021.01); *A01H 5/10* (2013.01); *A01H*

*6/4684* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

| 9,694,052 B2 | 7/2017 | Arce | |
| 2009/0293158 A1 | 11/2009 | Abad et al. | |
| 2014/0237679 A1* | 8/2014 | Luck ........................ | A01H 5/10 |
| | | | 800/275 |
| 2015/0245571 A1 | 9/2015 | Tomas et al. | |

OTHER PUBLICATIONS

Written Opinion of the International Searching Authority and International Search Report for PCT/US2020/045854 mailed Jan. 13, 2021.
Han et al., Genomic Prediction and GWAS of Gibberella Ear Rot Resistance Traits in Dent and Flint Lines of a Public Maize Breeding Program, Euphytica 2018, vol. 214, No. 6, pp. 1-20.
Hansey et al., "Maize (*Zea mays* L.) Genome Diversity as Revealed by RNA-Sequencing," PLoS One, Mar. 2012, vol. 7, No. 3, Article e33071, pp. 1-10.
Maschietto, et al., "QTL Mapping and Candidate Genes for Resistance to Fusarium Ear Rot and Fumonisin Contamination in Maize," BMC Plain Biology, Jan. 21, 2017, vol. 17, Article 20, pp. 1-21.
Ali, M., et al., "Molecular mapping of QTLs for resistance to *Gibberella* ear rot, in corn, caused by *Fusarium graminearum*," Genome, 2005, vol. 48, 521-533.

* cited by examiner

*Primary Examiner* — Brent T Page
(74) *Attorney, Agent, or Firm* — Womble Bond Dickinson (US) LLP

(57) ABSTRACT
Compositions and methods for identifying, selecting and producing maize plants with enhanced ear rot resistance are provided. Ear rot resistance maize plants and germplasms are also provided. In some embodiments, methods of identifying an ear rot resistance maize plant or germplasm are provided. Such methods may comprise detecting, in the plant or germplasm, a marker associated with enhanced ear rot resistance.

14 Claims, 41 Drawing Sheets

Specification includes a Sequence Listing.

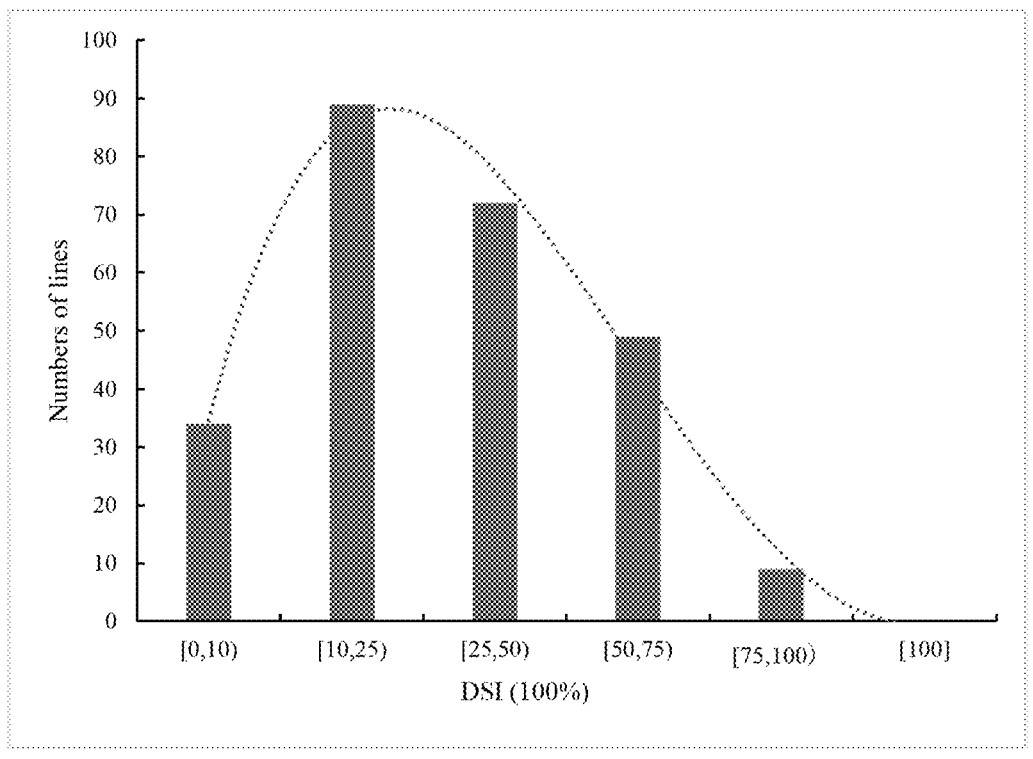
FIG. 1. Distribution of disease severity index (DSI) estimated with BLUP among the GWAS population.

A
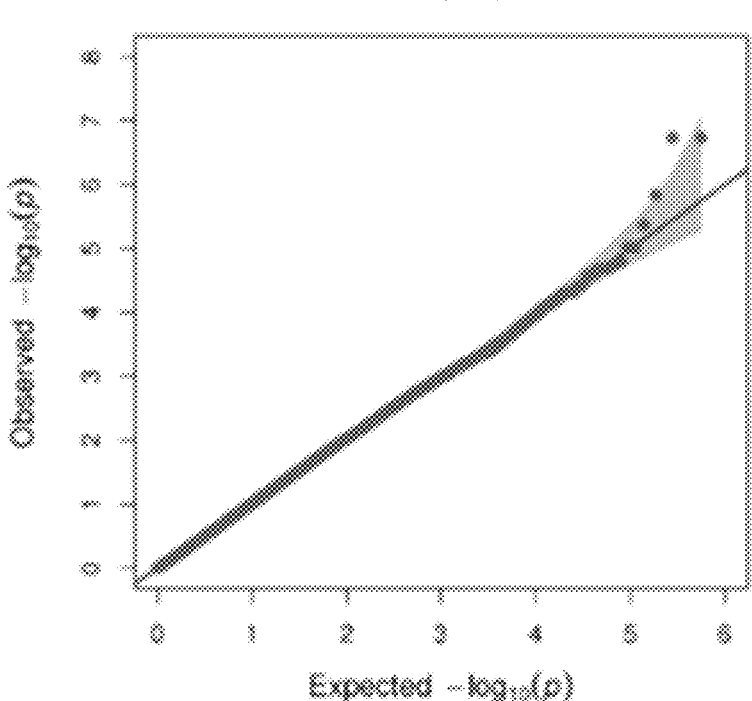
B
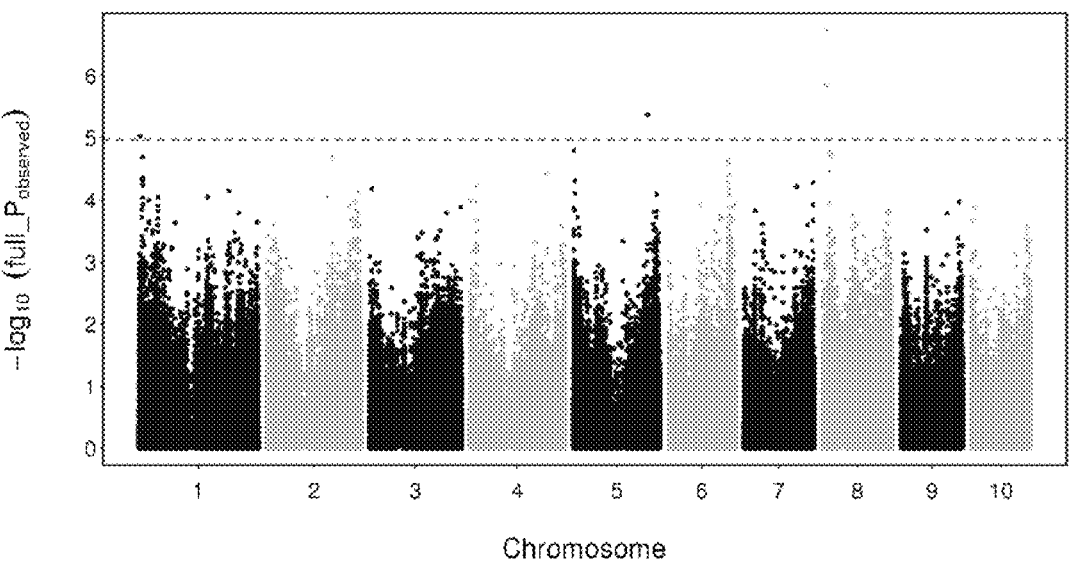
FIG. 2A. Quantile-quantile and manhattan plots for maize ear rot in Beijing in 2017 summer (A, B).

C
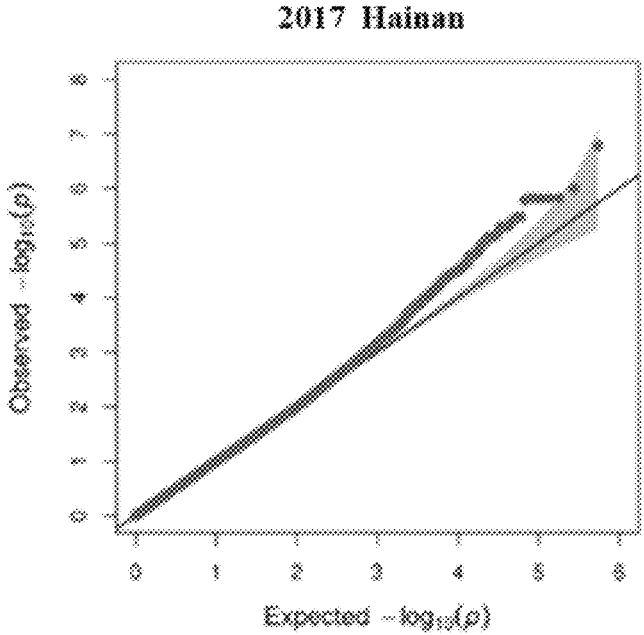
D
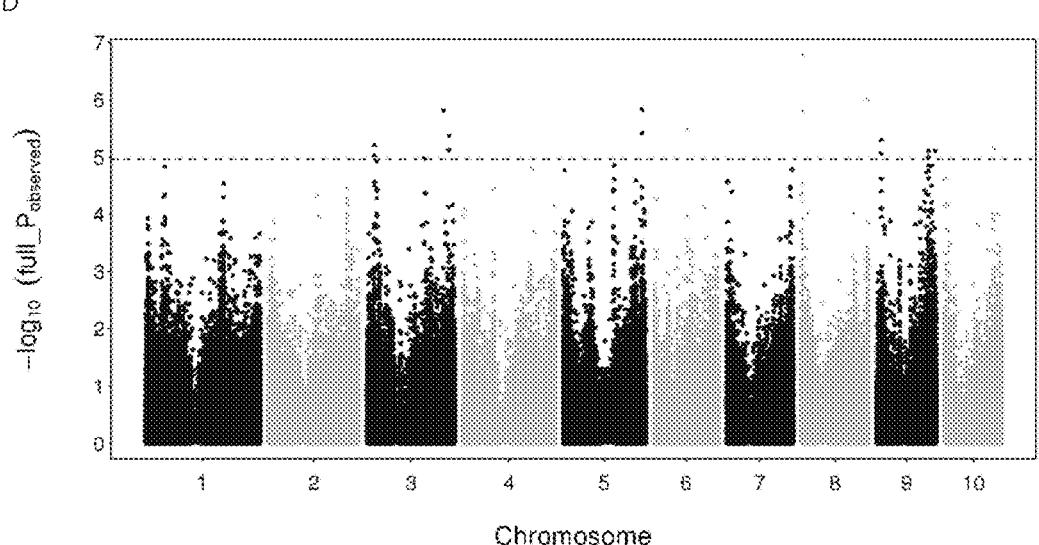
FIG. 2B. Quantile-quantile and manhattan plots for maize ear rot in Beijing in Hainan in 2017 winter (C, D).

E
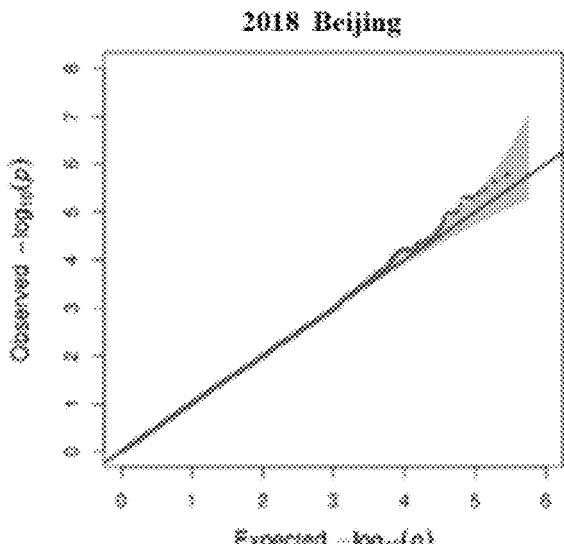
F
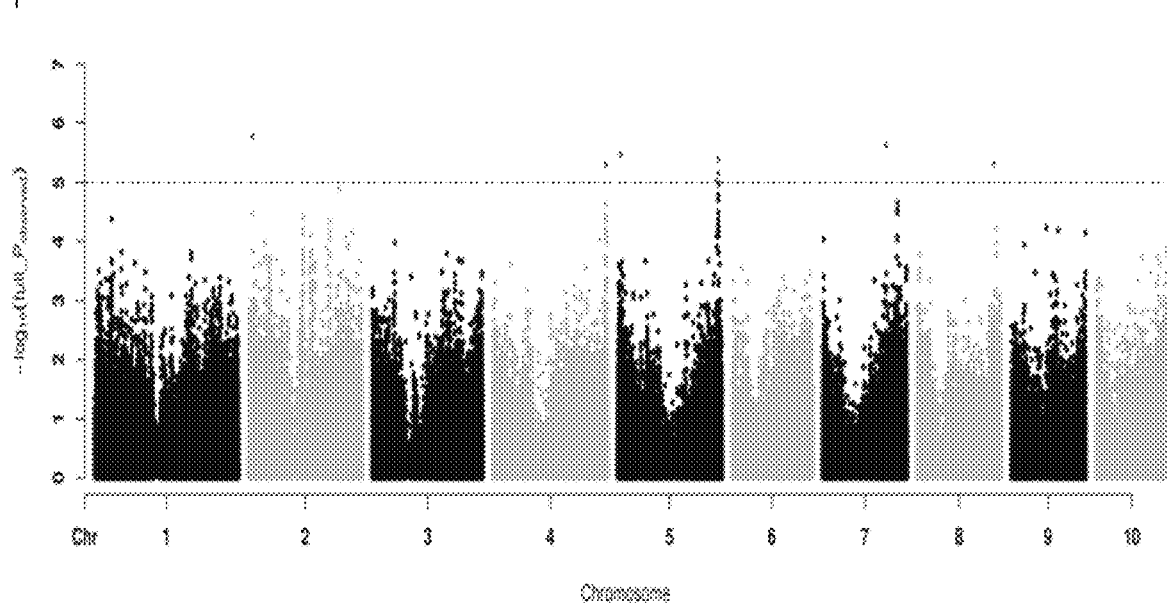
FIG. 2C. Quantile-quantile and manhattan plots for maize ear rot in Beijing in 2018 summer (E, F).

G
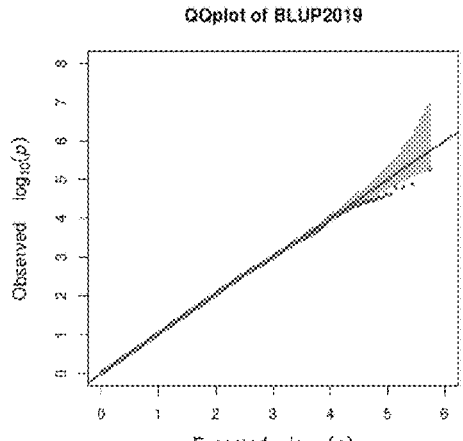
H
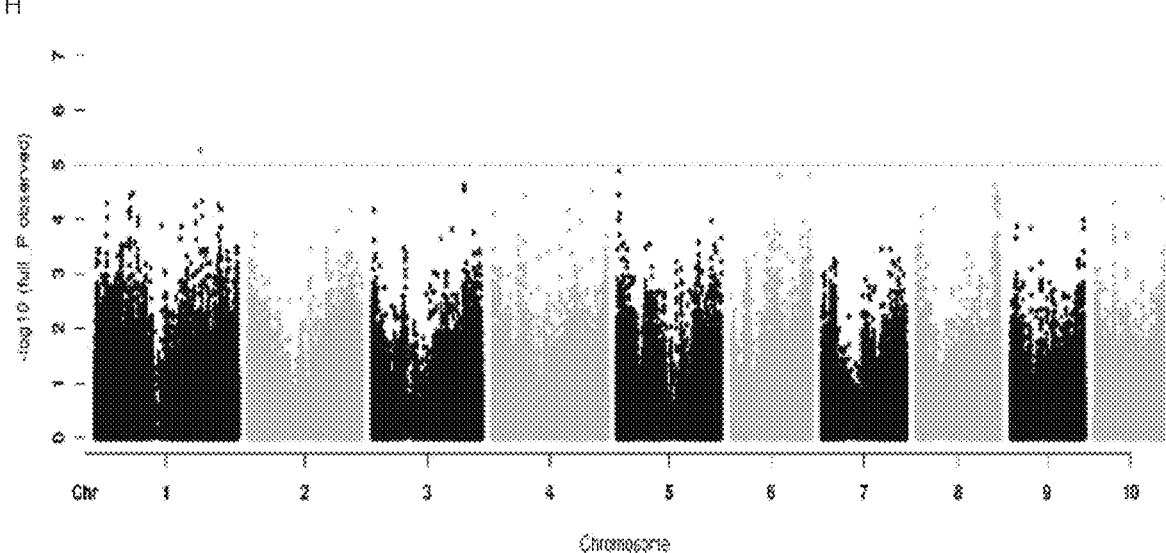
FIG. 2D. Quantile-quantile and manhattan plots for maize ear rot in BLUP (G, H).

A
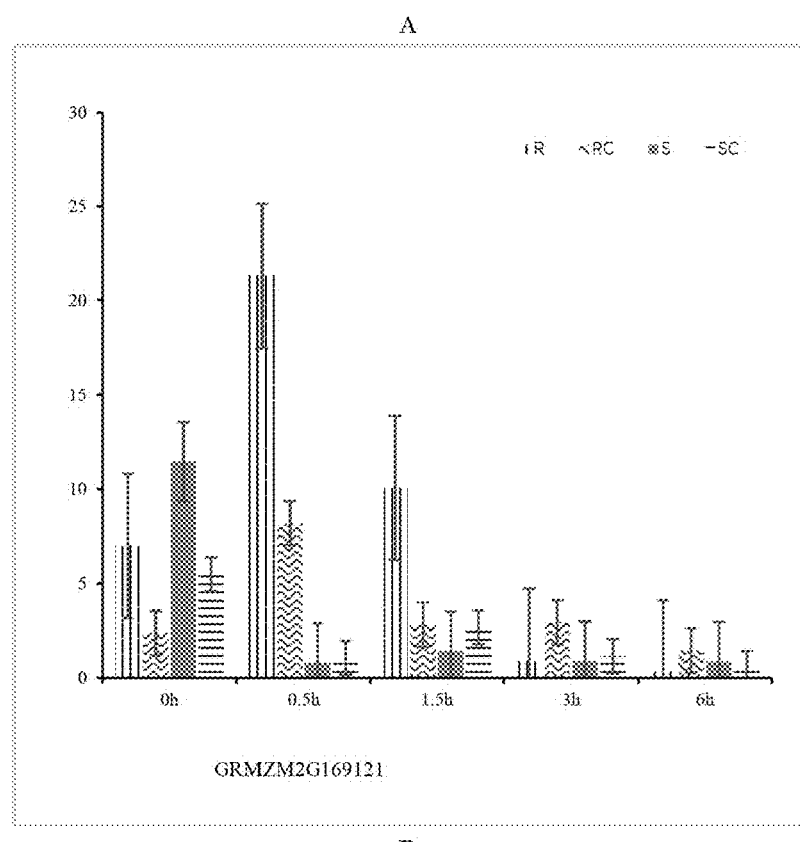
GRMZM2G169121
B
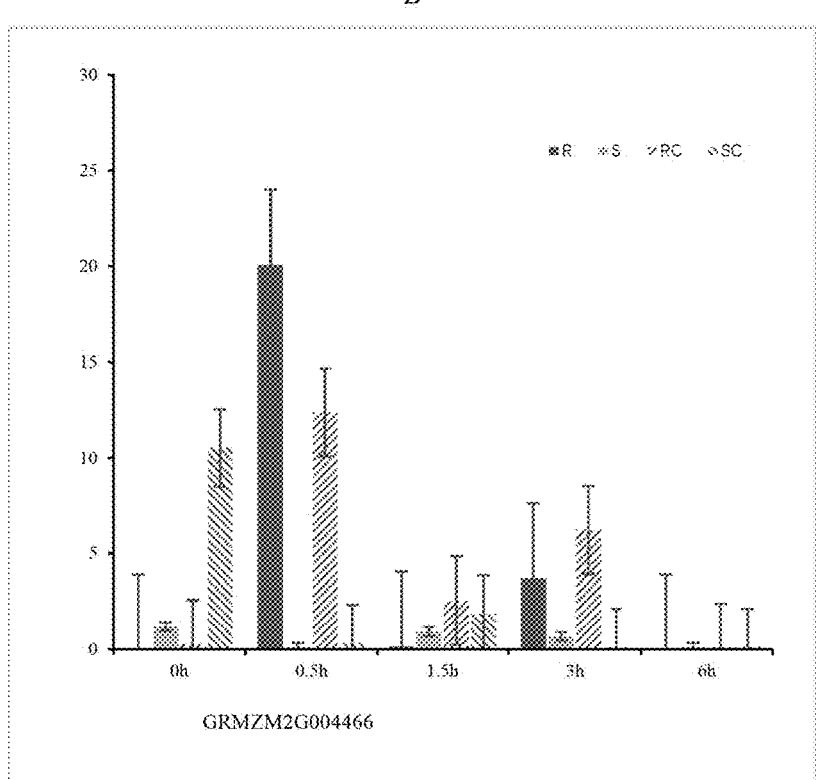
GRMZM2G004466
FIG. 3 (A & B). Dynamic expression patterns of genes in the early time post inoculation.

C
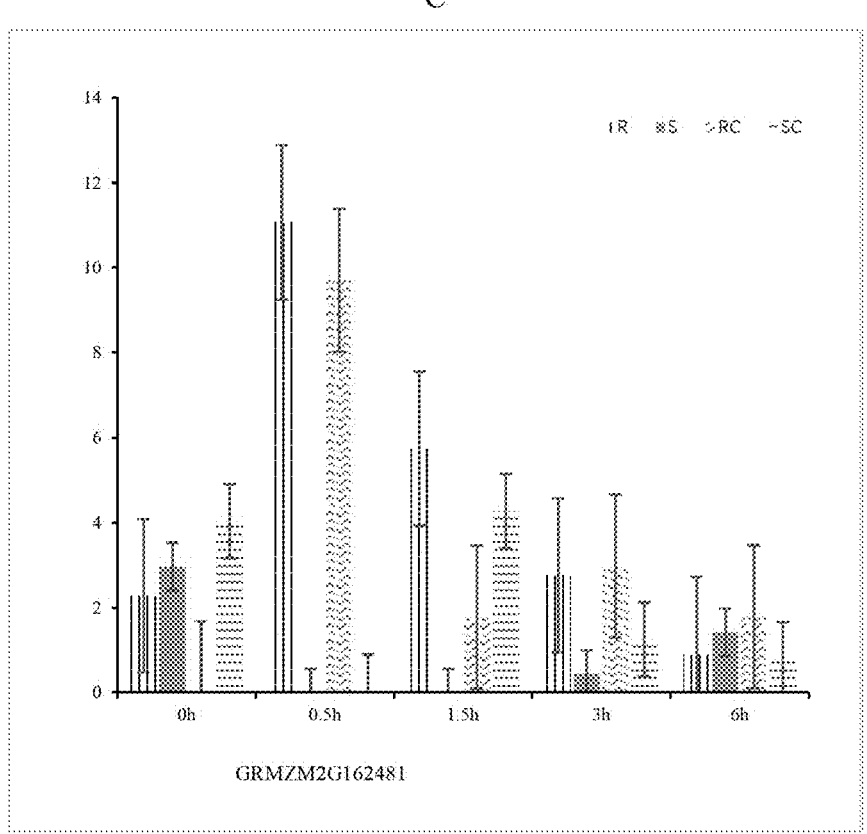
GRMZM2G162481
D.
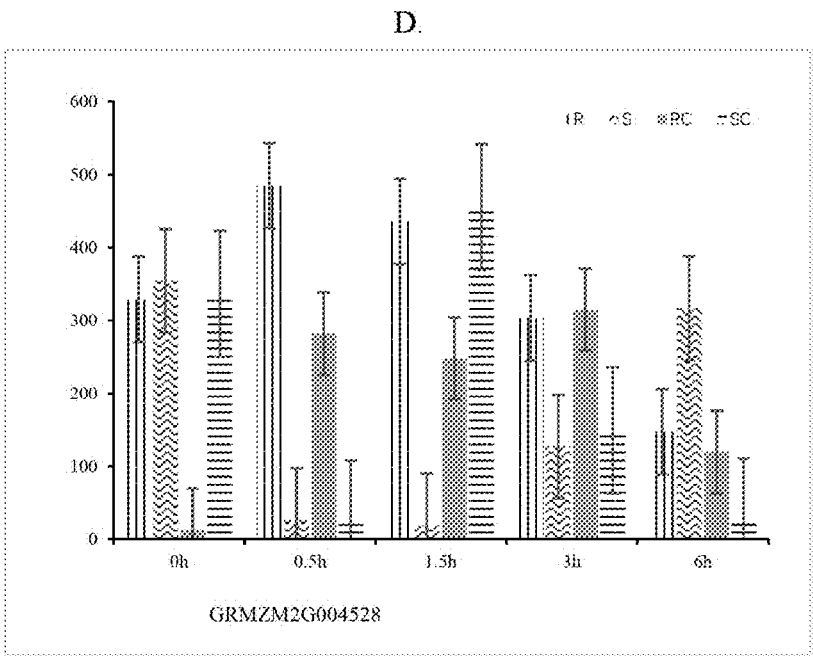
GRMZM2G004528
FIG. 3 (C & D). Dynamic expression patterns of genes in the early time post inoculation.

E
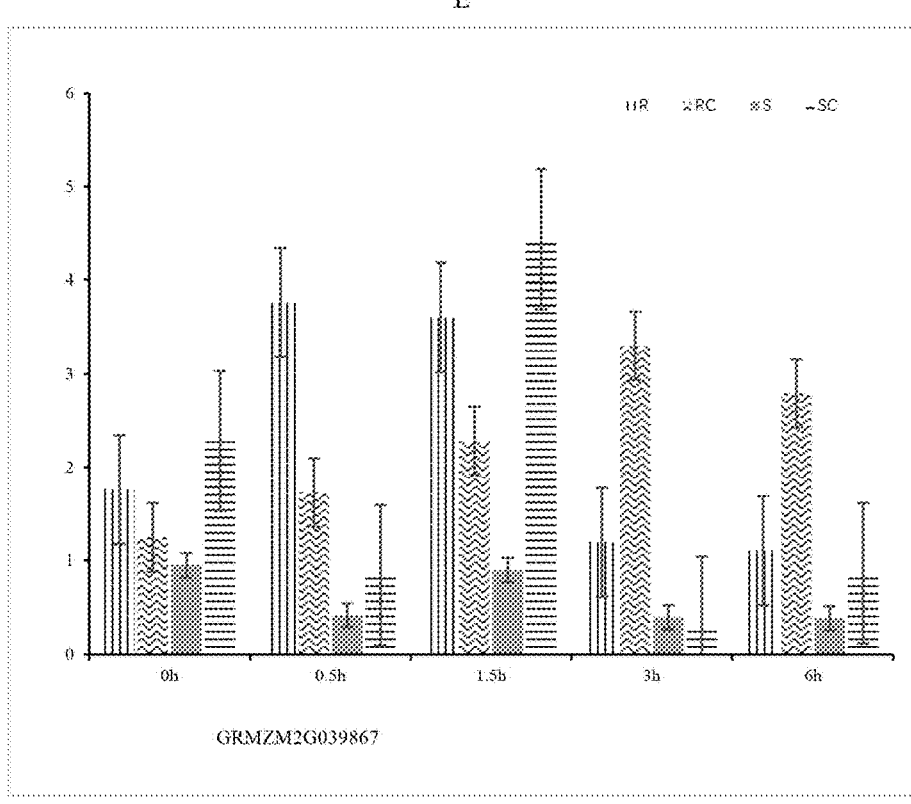
GRMZM2G039867
F
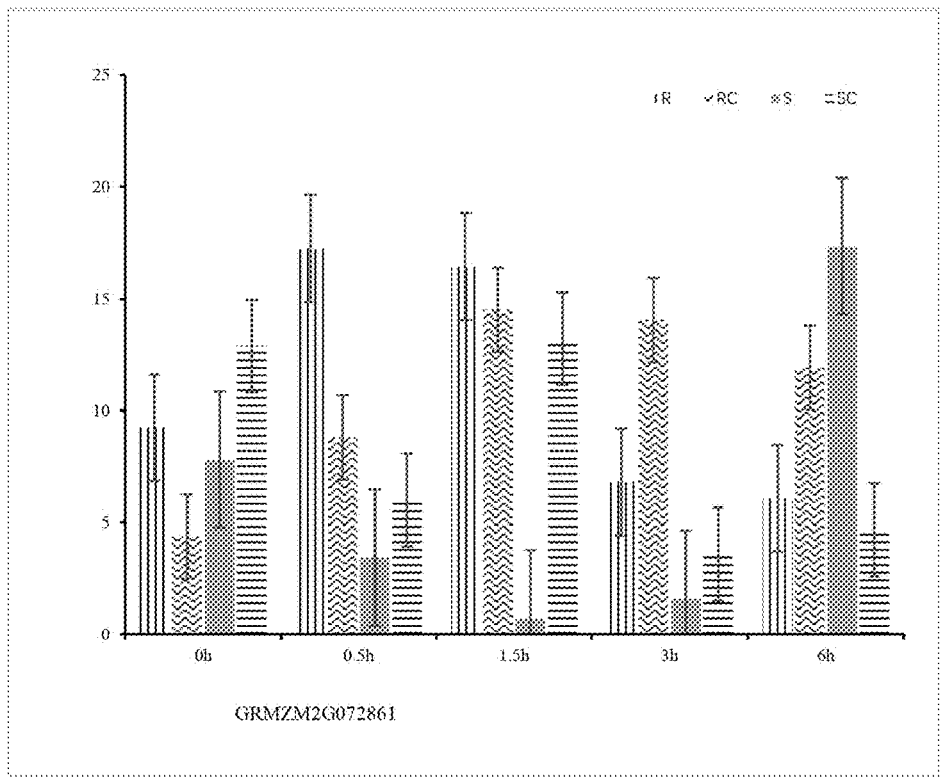
GRMZM2G072861
FIG. 3 (E & F). Dynamic expression patterns of genes in the early time post inoculation.

G.
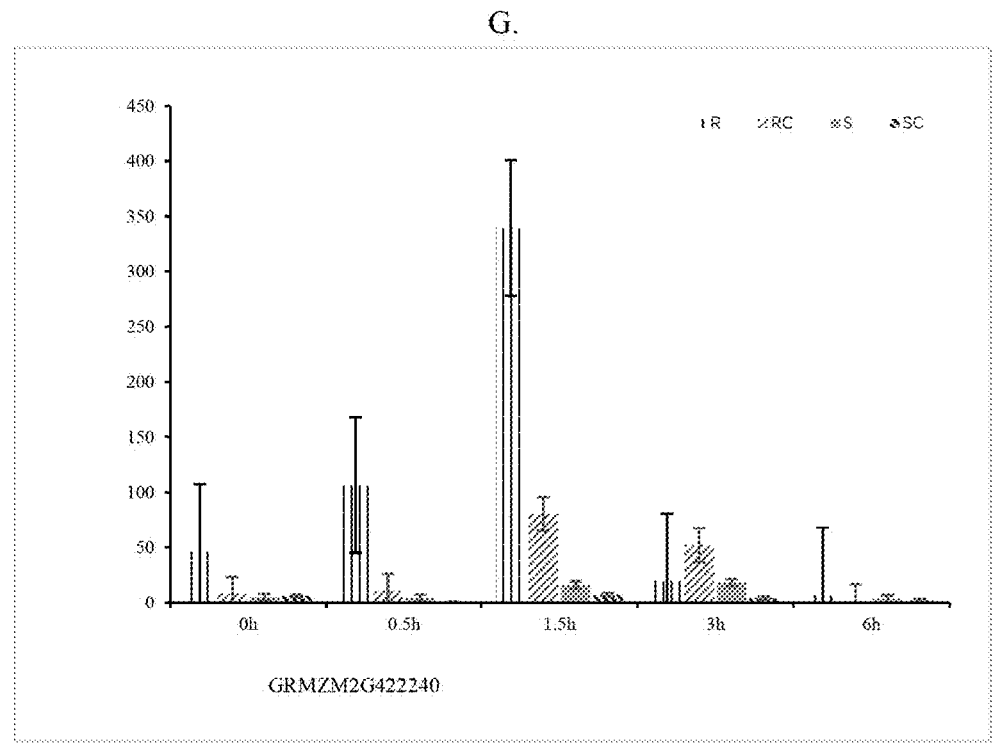
GRMZM2G422240
H
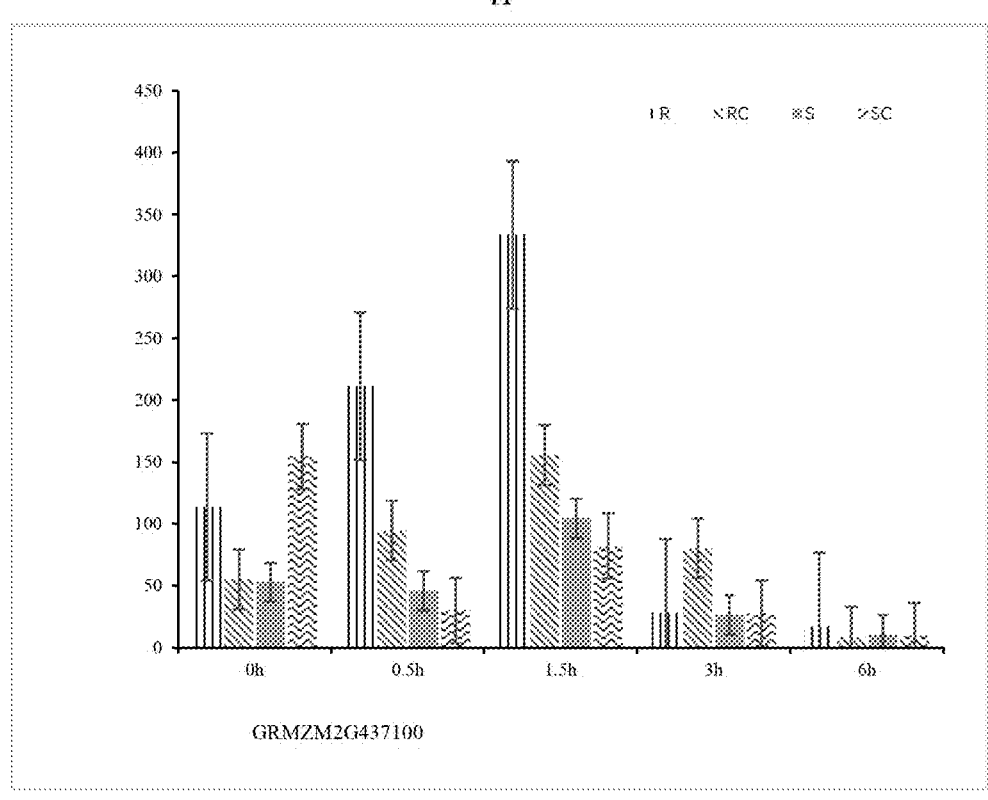
GRMZM2G437100
FIG. 3 (G & H). Dynamic expression patterns of genes in the early time post inoculation.

I
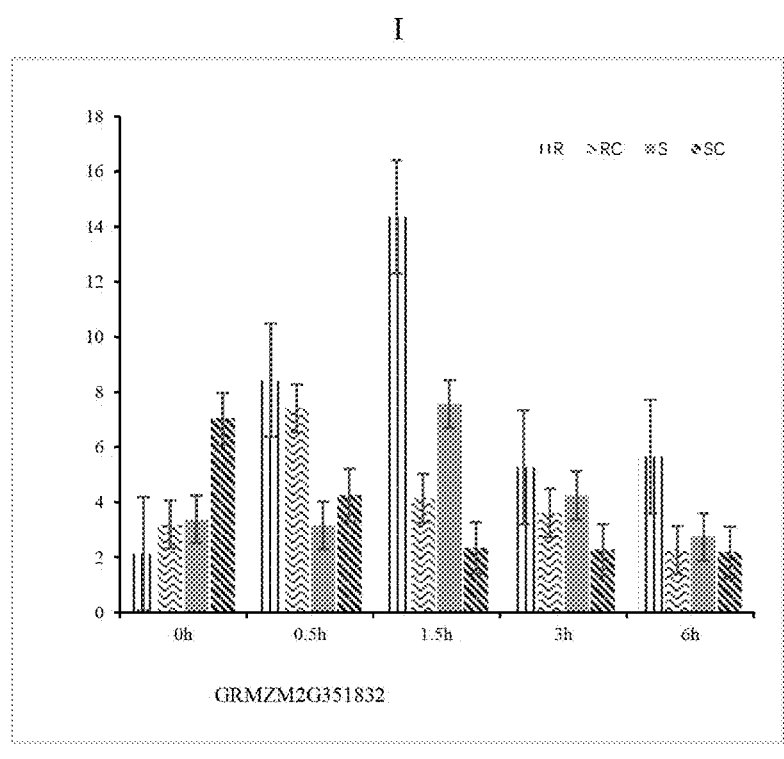
GRMZM2G351832
J.
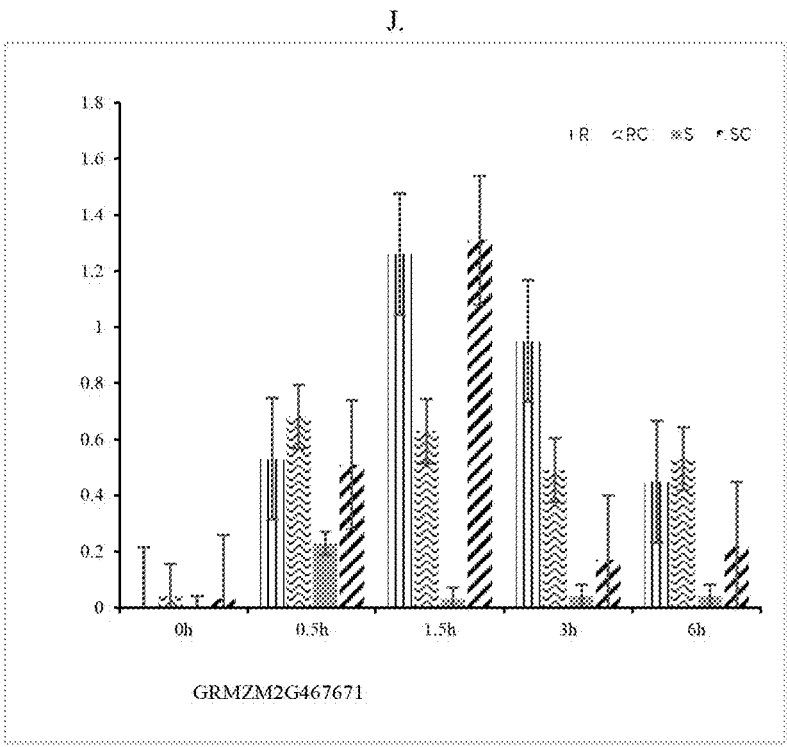
GRMZM2G467671
FIG. 3 (I & J). Dynamic expression patterns of genes in the early time post inoculation.

K
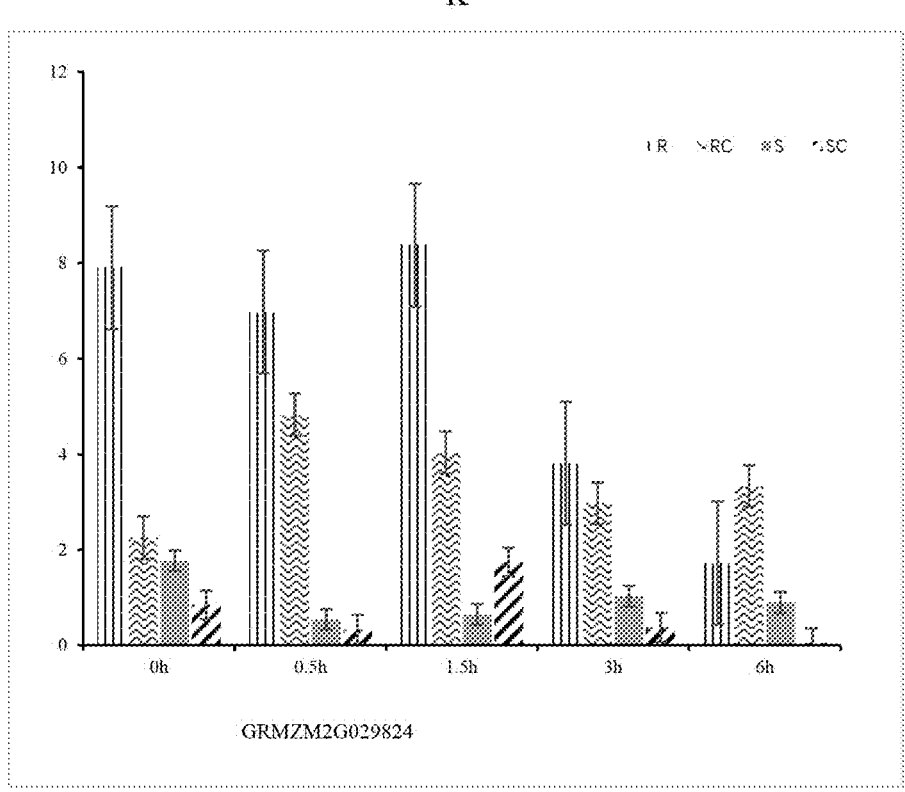
GRMZM2G029824
L
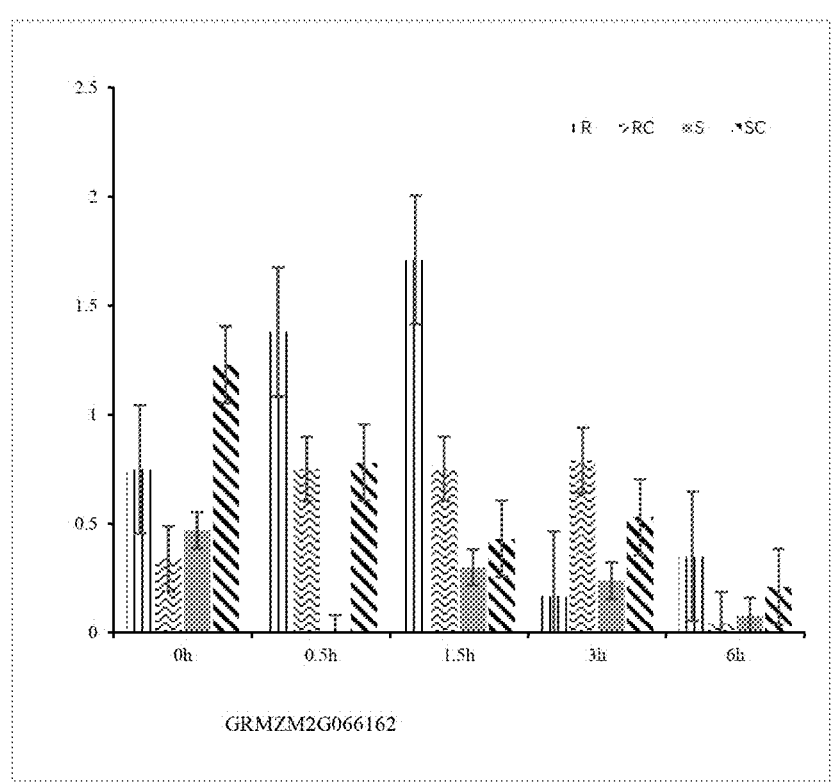
GRMZM2G066162
FIG. 3 (K & L). Dynamic expression patterns of genes in the early time post inoculation.

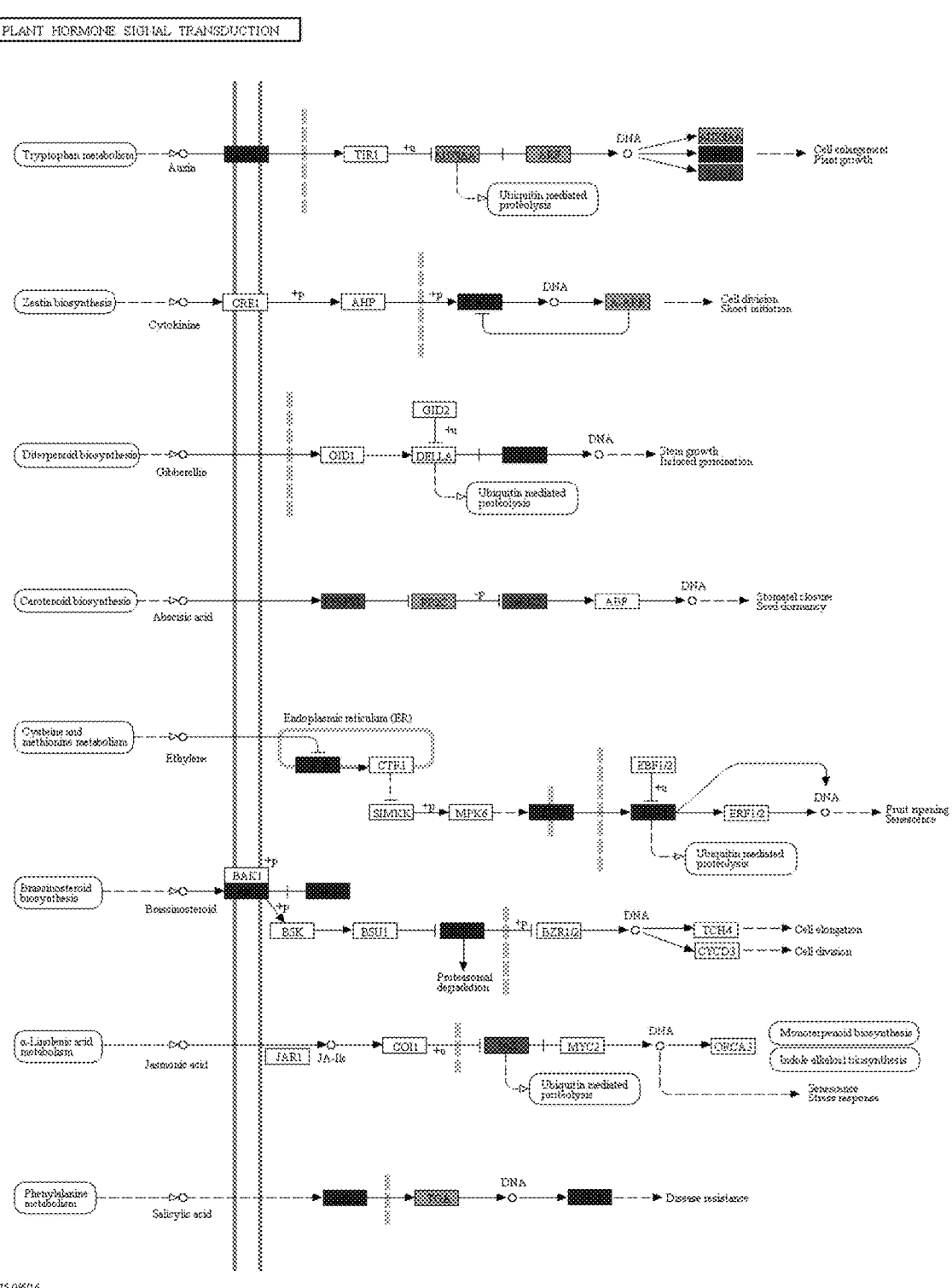
FIG. 4. The differentially expressed genes (DEGs) involved in plant hormone signal transduction pathways. Red and blue colors separately mark the up- and down-regulated DEGs in CIMBL47 compared with SY1035; while green colors indicate mixed (both up and down) regulated DEGs.

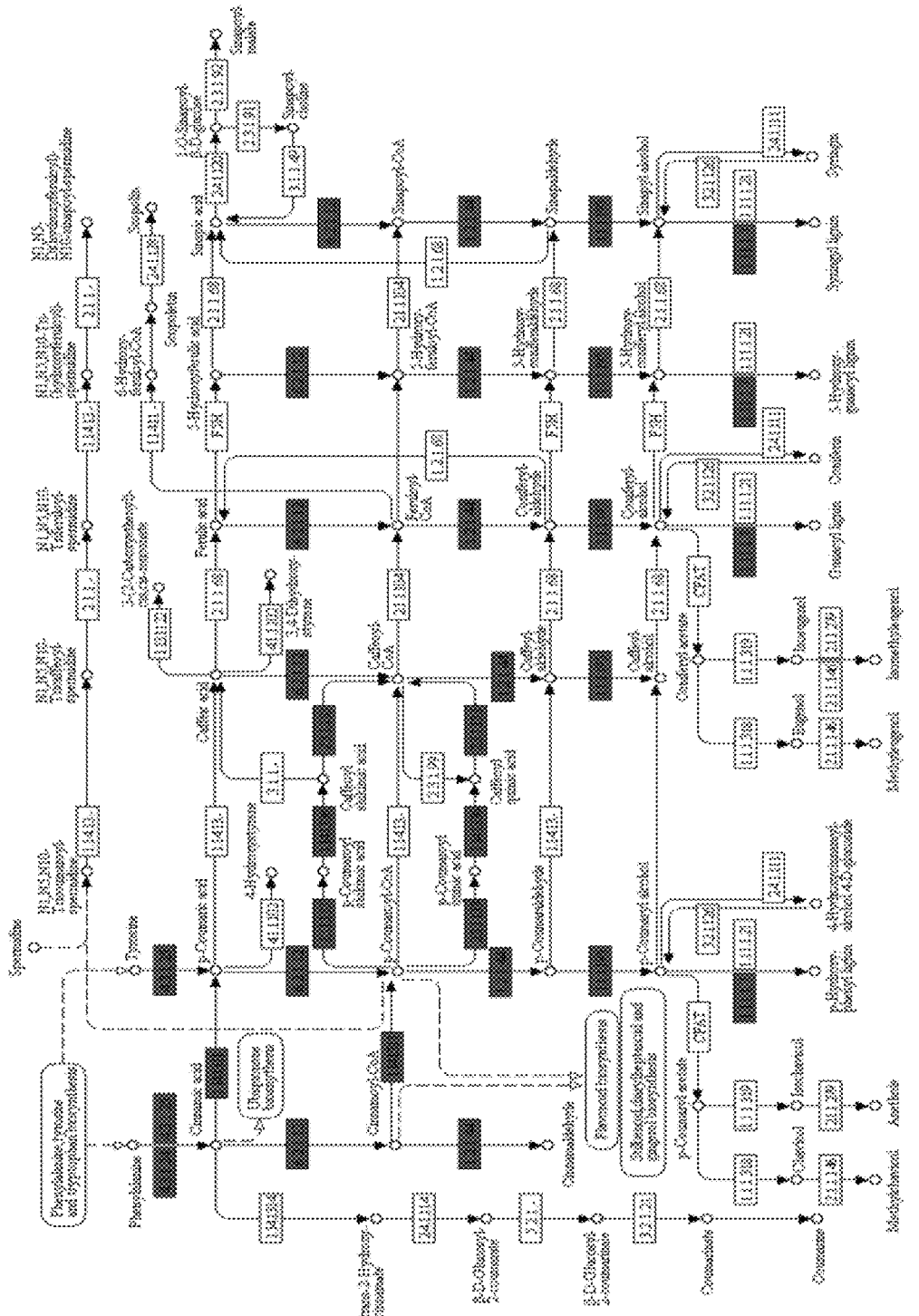
FIG. 5. The differentially expressed genes (DEGs) involved in Phenylpropanoid biosynthesis. Only up-regulated DEGs (marked as red colors) were detected at 1.5hpi in CIMBL47 compared with SY1035.

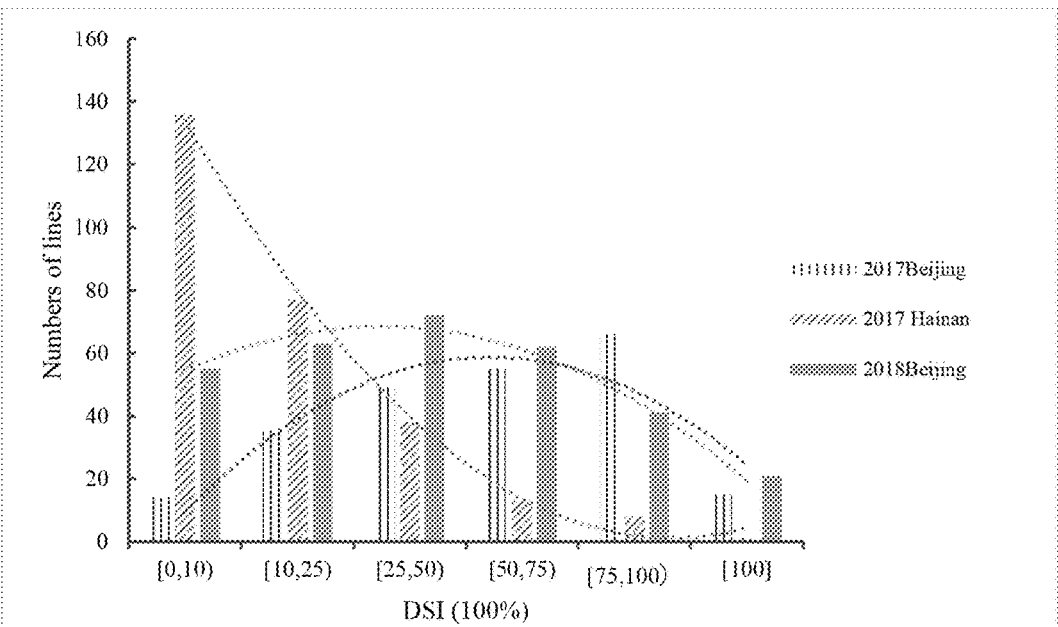
FIG. 6. Distribution of disease severity index (DSI) of the GWAS population under three environmental conditions.

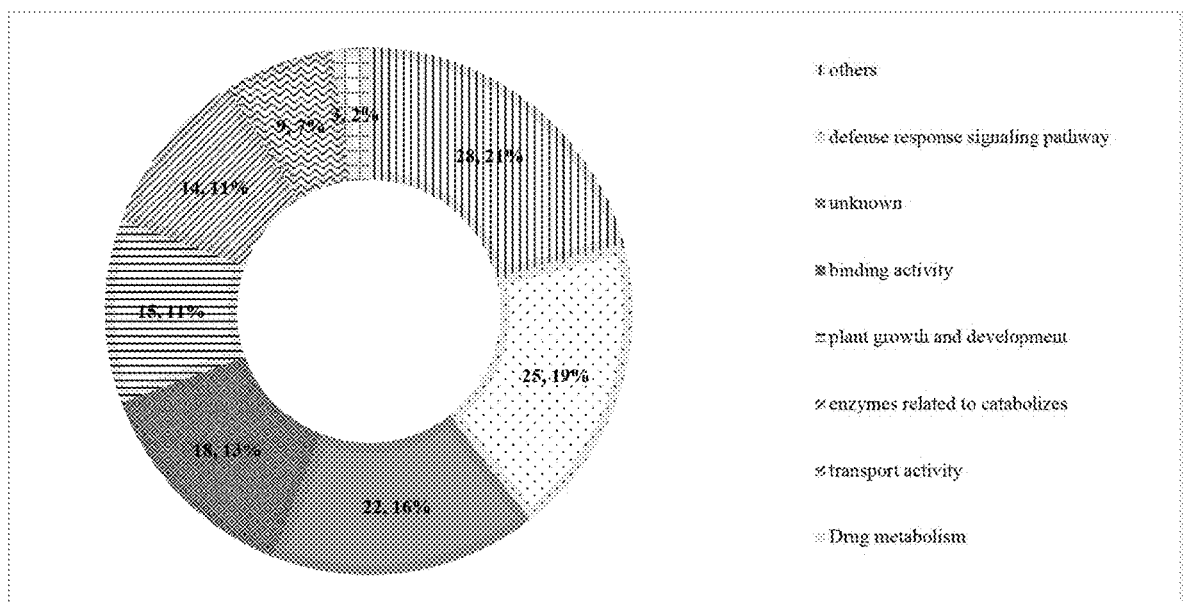
FIG. 7. Functional categories of the potential resistance genes revealed by GWAS.

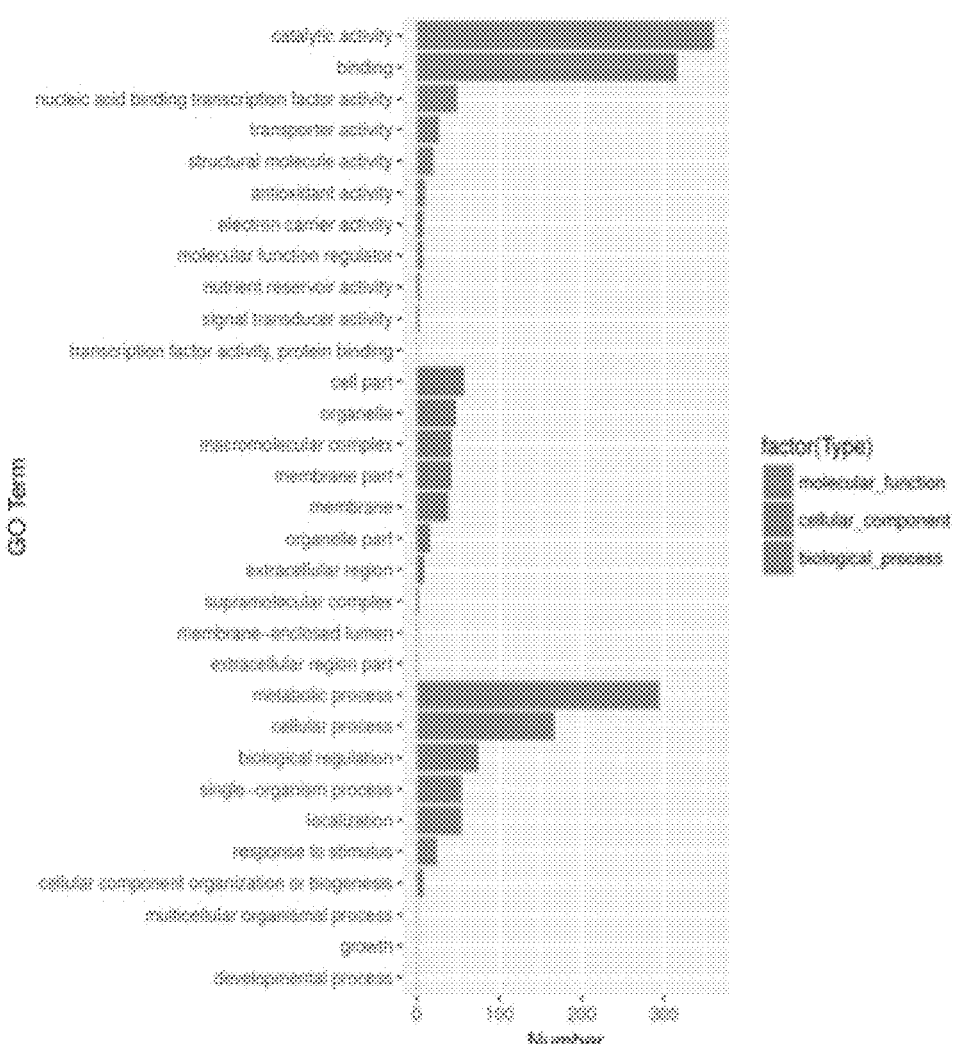

8A. Enriched GO term R-0hpi VS S-0hpi

FIG. 8A. GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

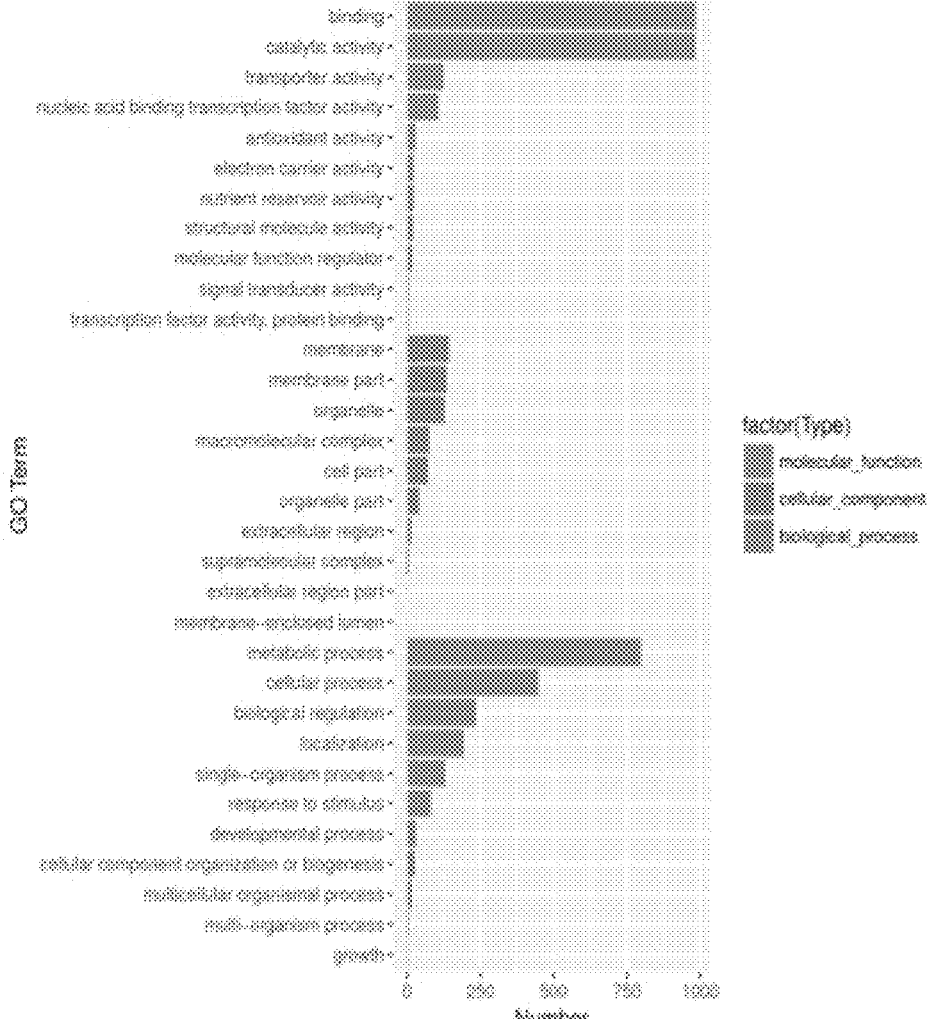

8B          Enriched GO term R-0.5hpi VS S-0.5hpi

FIG. 8B. GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

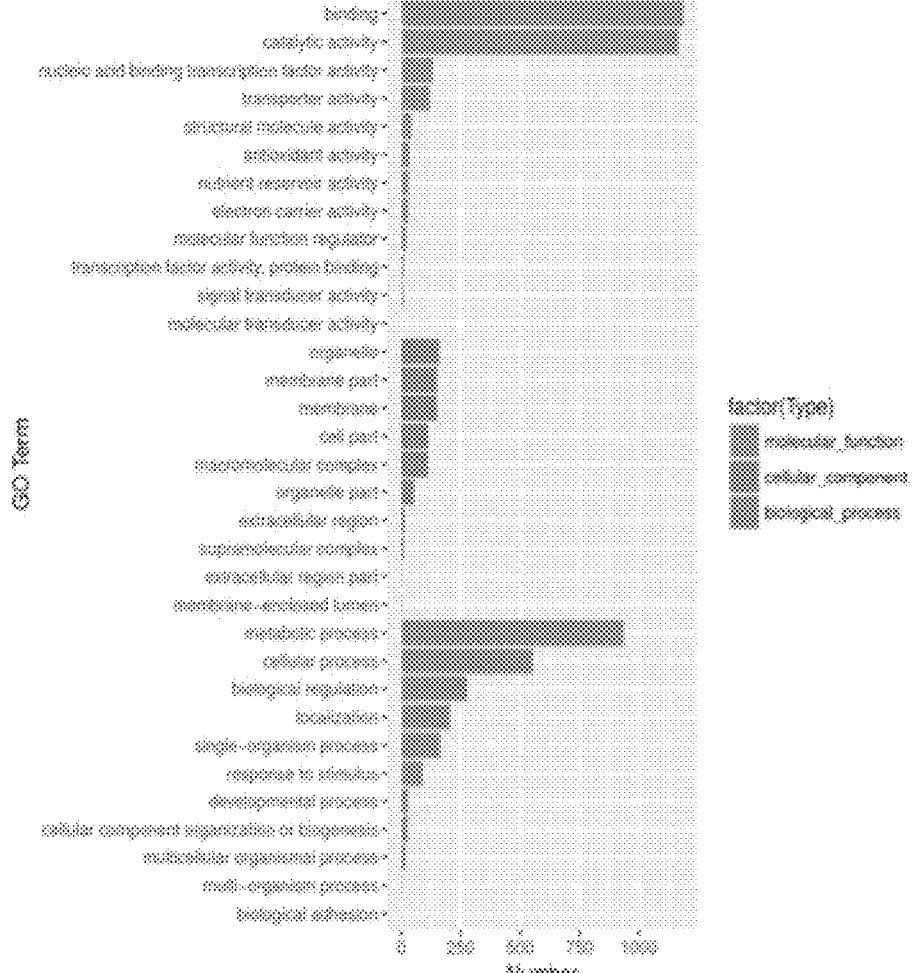

8C. Enriched GO term R-1.5hpi VS S-1.5hpi

FIG. 8C.   GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

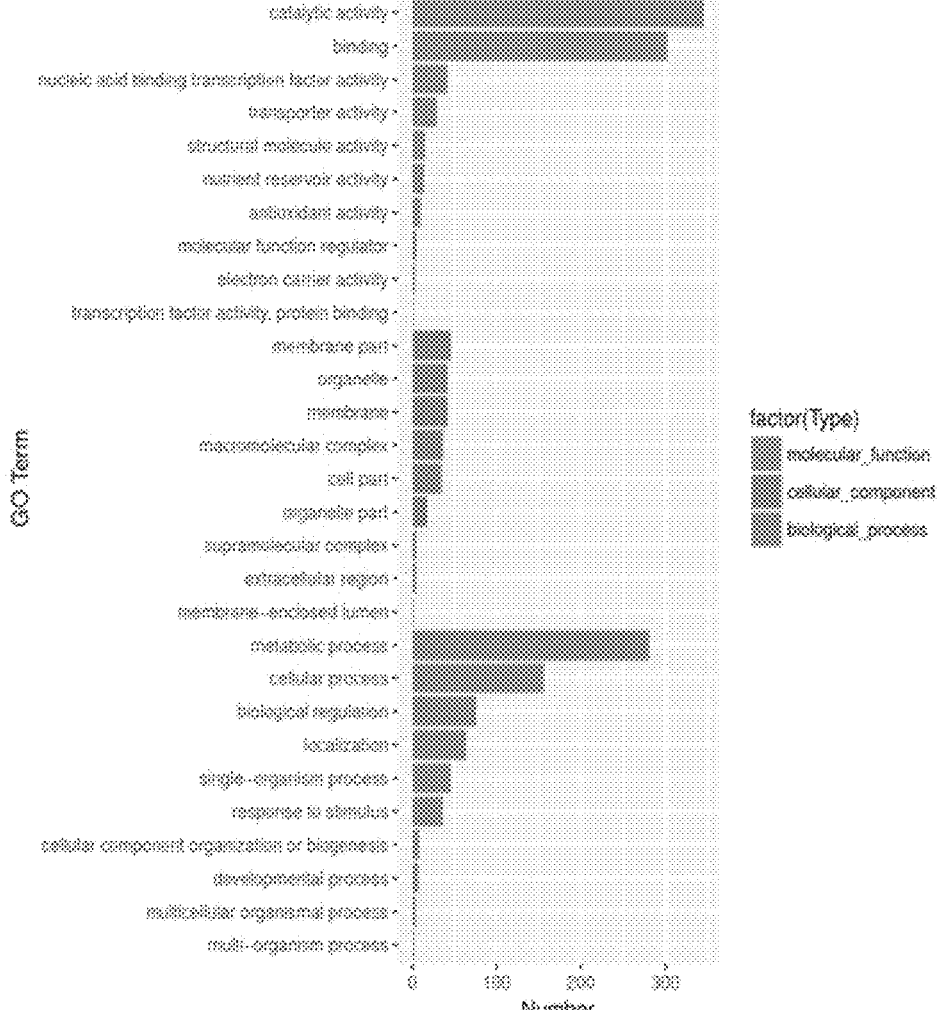

8D          Enriched GO term R-3hpi VS S-3hpi

FIG. 8D. GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

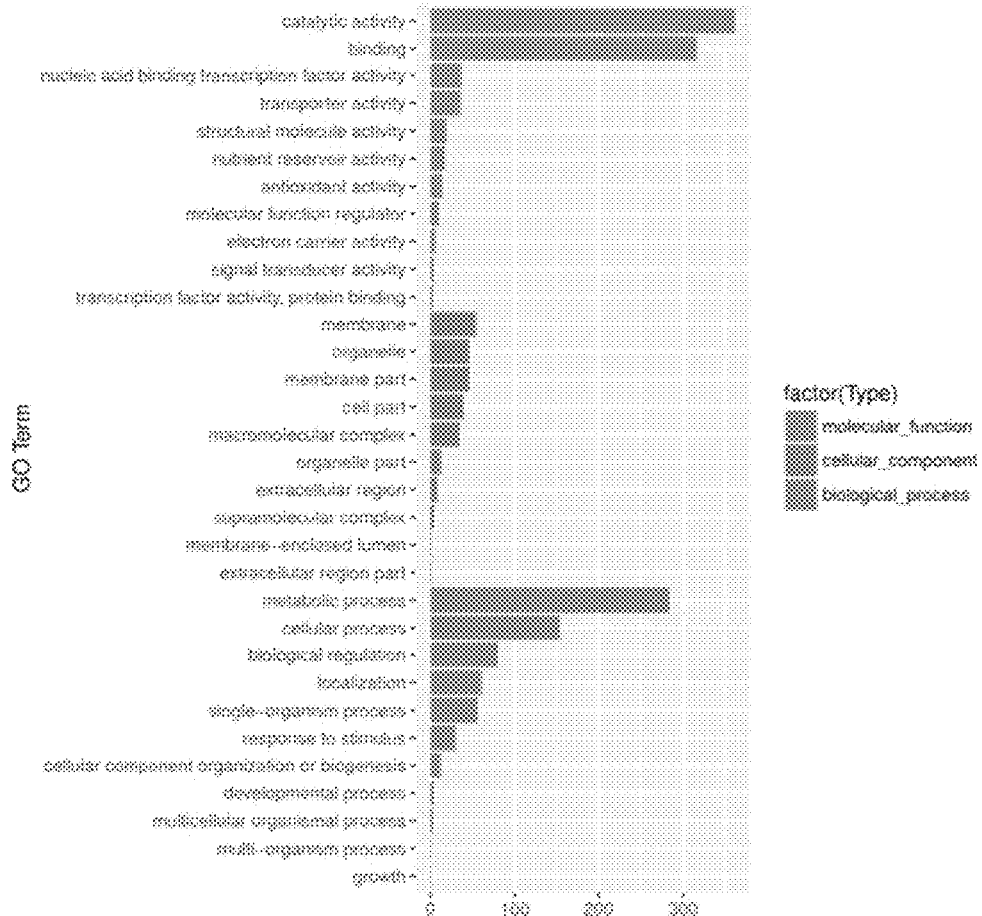

8E. Enriched GO term R-6hpi VS S-6hpi

FIG. 8E. GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

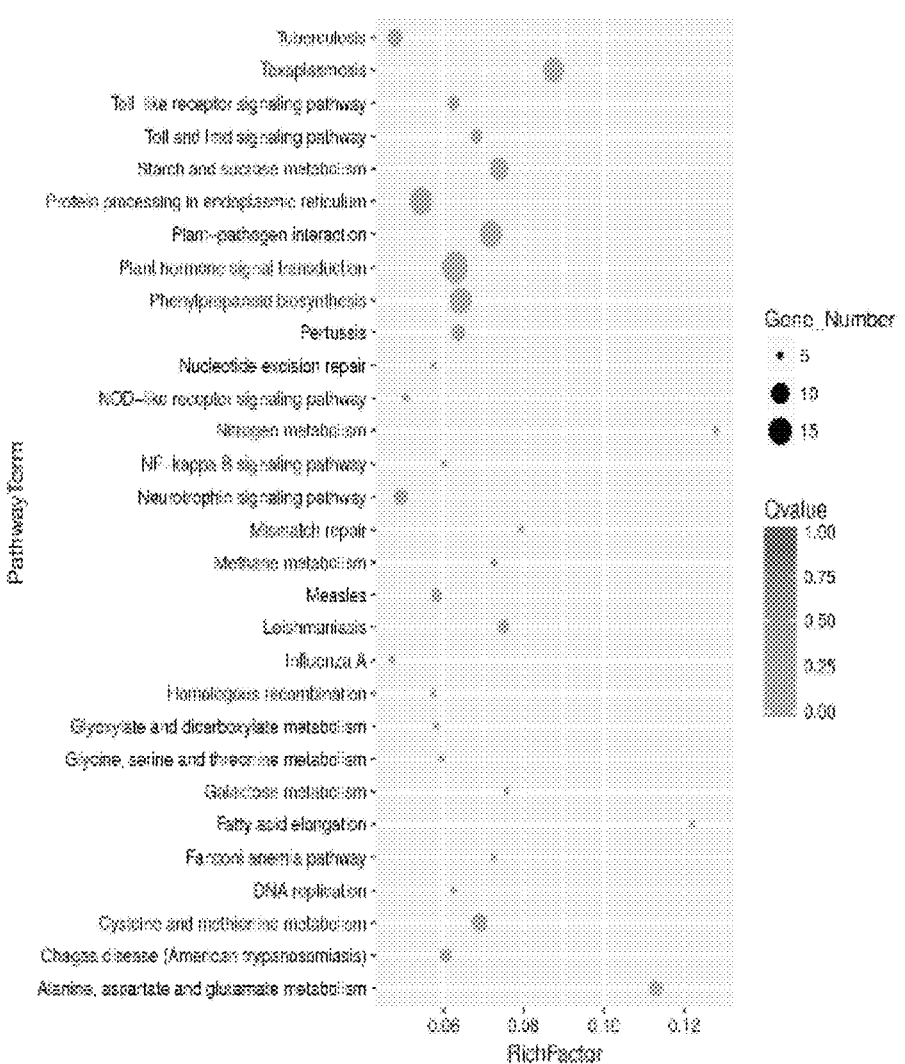
FIG. 9A.    KEGG enrichment of differentially expressed genes (DEGs) between the resistant CIMBL47 (R) and susceptible SY1035 (S) lines at R-0hpi VS S-0hpi

FIG. 9B. KEGG enrichment of differentially expressed genes (DEGs) between the resistant CIMBL47 (R) and susceptible SY1035 (S) lines at R-0.5hpi VS S-0.5hpi

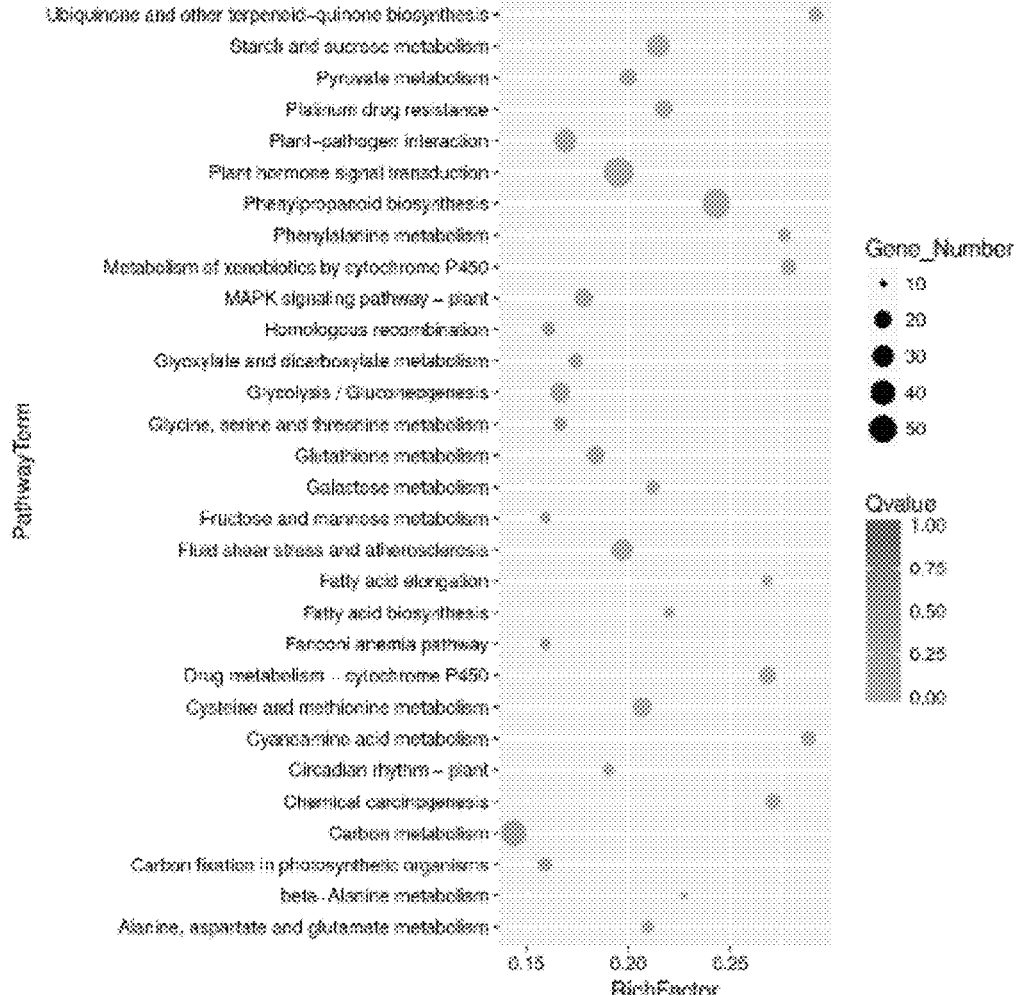
FIG. 9C.  KEGG enrichment of differentially expressed genes (DEGs) between the resistant CIMBL47 (R) and susceptible SY1035 (S) lines at R-1.5hpi VS S-1.5hpi

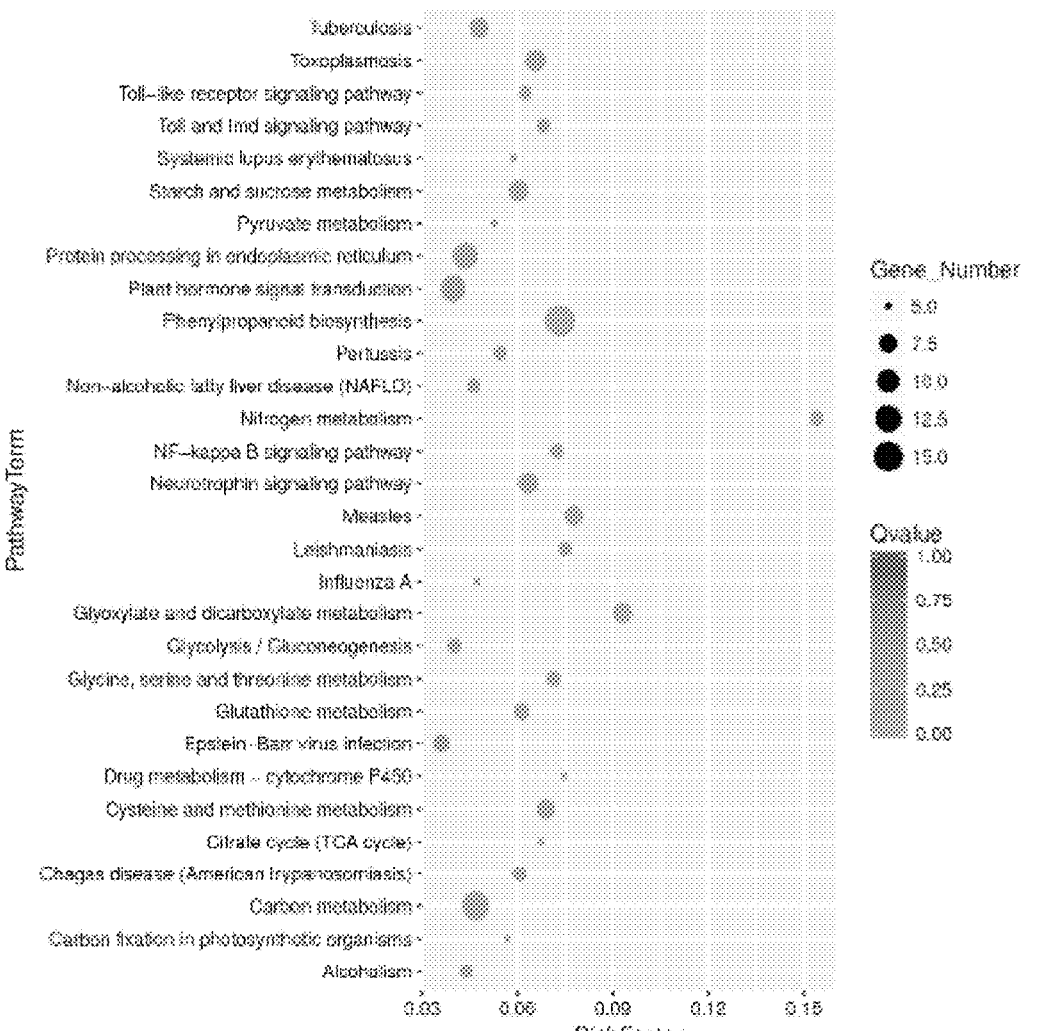
FIG. 9D. KEGG enrichment of differentially expressed genes (DEGs) between the resistant CIMBL47 (R) and susceptible SY1035 (S) lines at R-3hpi VS S-3hpi

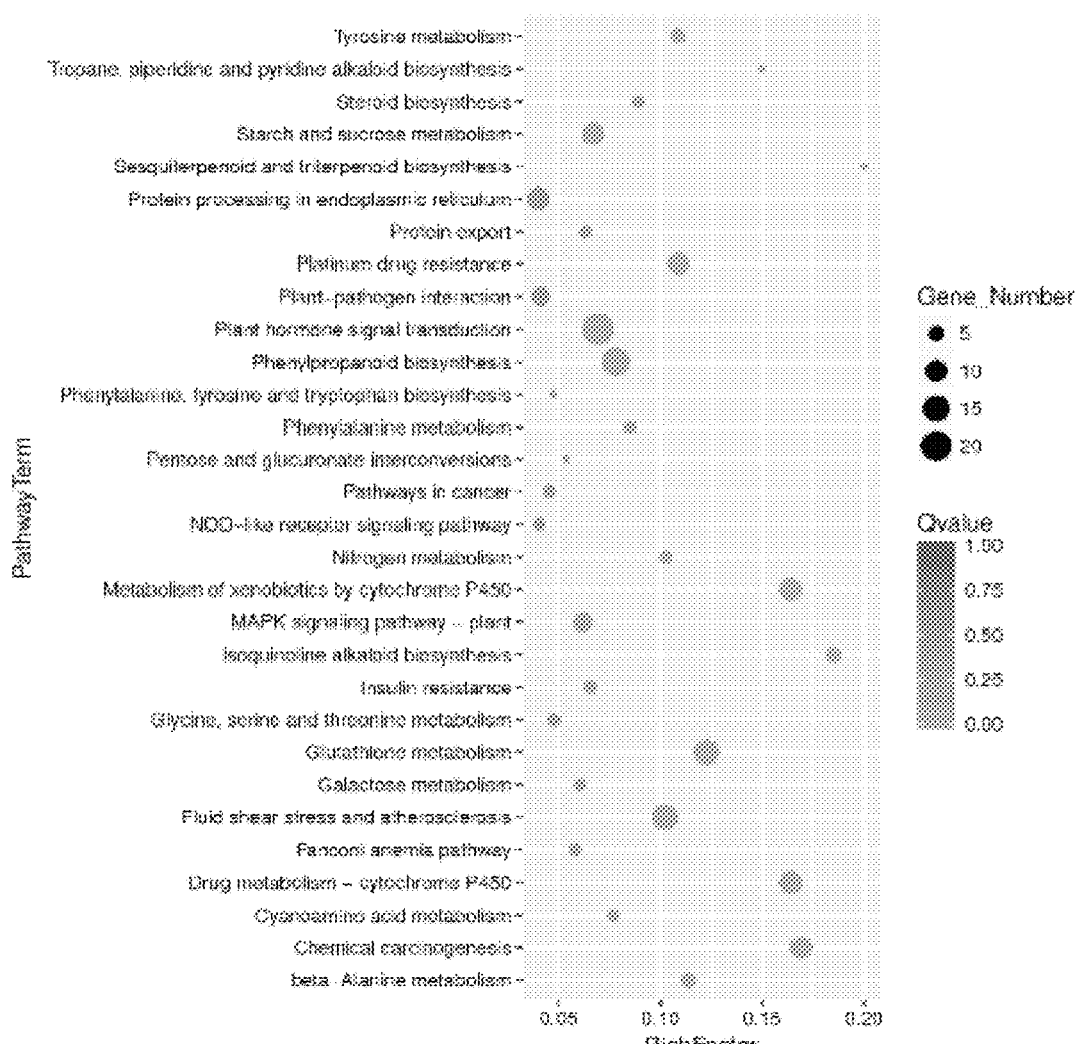
FIG. 9E.   KEGG enrichment of differentially expressed genes (DEGs) between the resistant CIMBL47 (R) and susceptible SY1035 (S) lines at R-6hpi VS S-6hpi A.  0hpi.
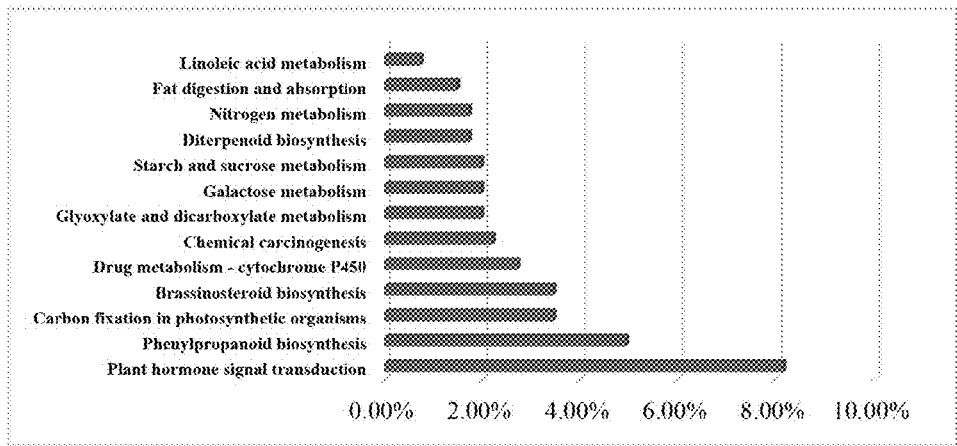
B.  0.5hpi.
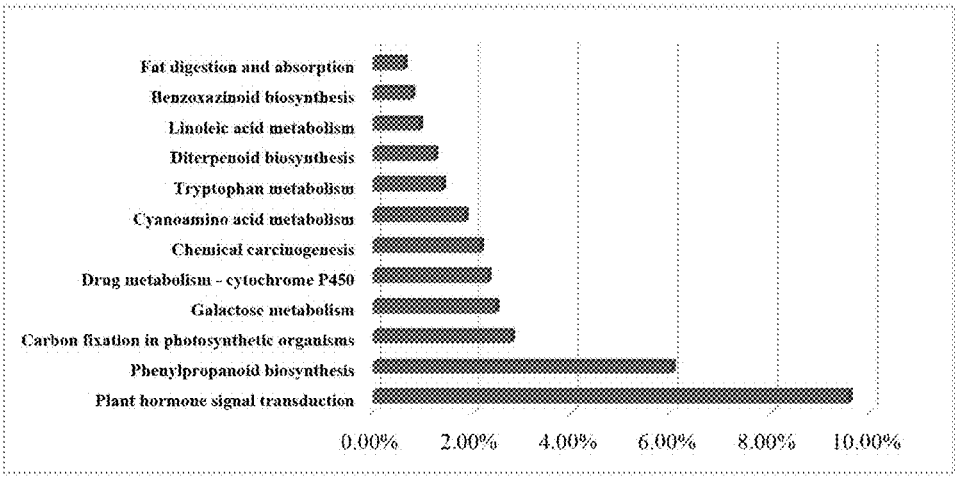
C.  1.5hpi.
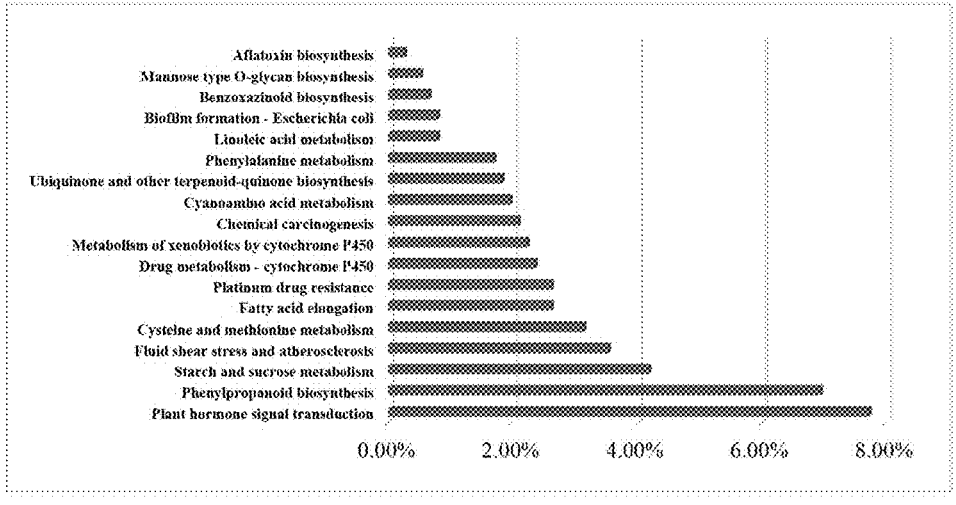
FIG. 10 (A, B, C). Distribution of DEGs for differential pathways between the resistant CIMBL47 (R) and susceptible
SY1035 (S) lines. Percentages of DEGs were estimated for differential pathways of R vs S post inoculation.

D.  3hpi.
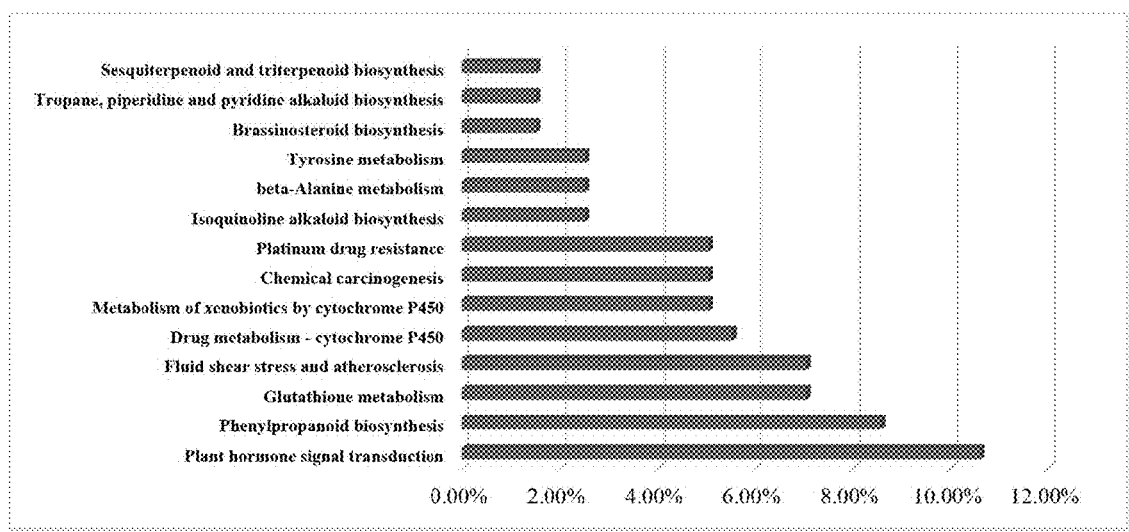
E.  6hpi.
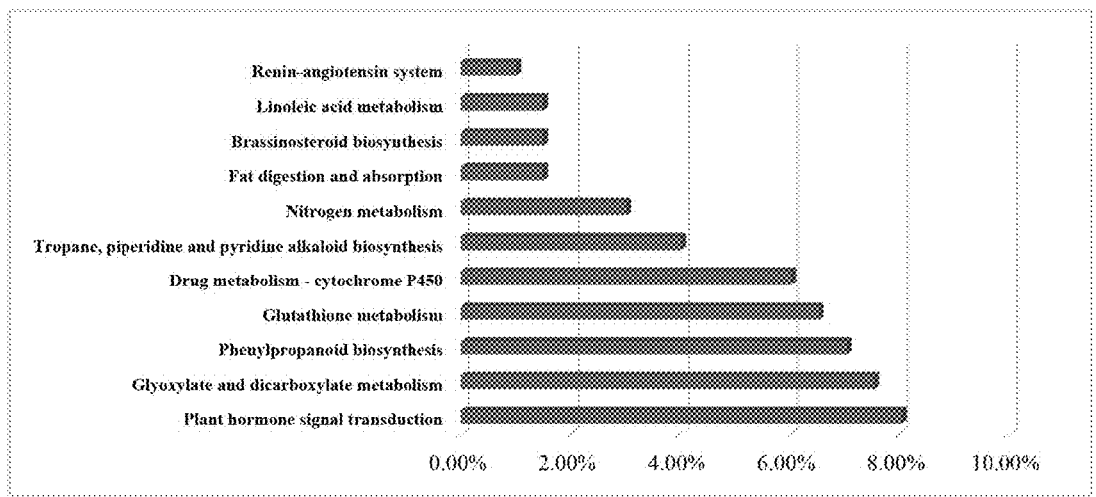
FIG. 10 (D, E). Distribution of DEGs for differential pathways between the resistant CIMBL47 (R) and susceptible SY1035 (S) lines. Percentages of DEGs were estimated for differential pathways of R vs S at 0 (A), 0.5 (B), 1.5 (C), 3 (D), and 6 (E) hours post inoculation.

A
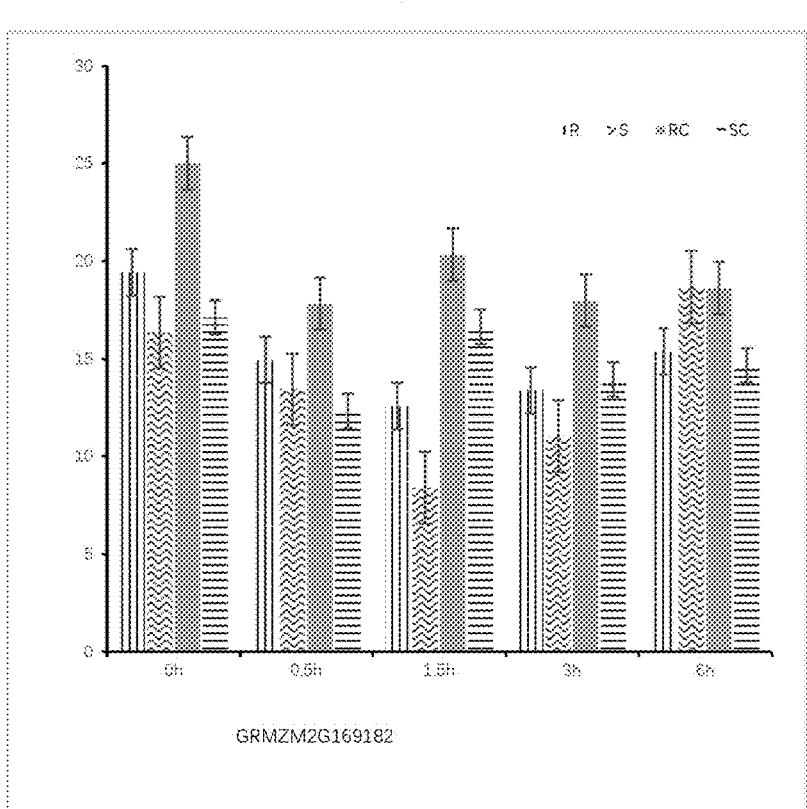
GRMZM2G169182
B
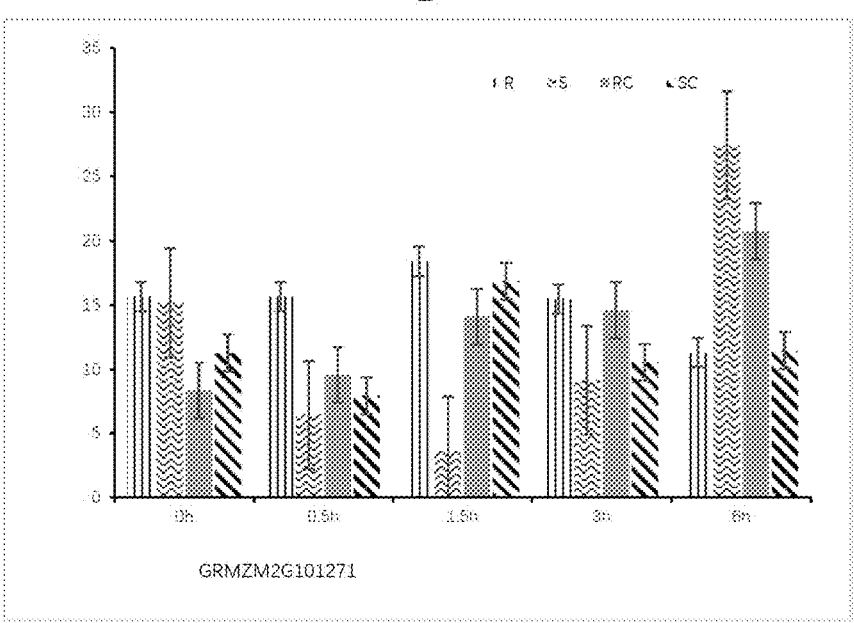
GRMZM2G101271
FIG. 11 (A, B) Dynamic expression patterns of genes in the early time post inoculation. The genes in the susceptible line SY1035 were downregulated to their lowest points at 1.5hpi.

C
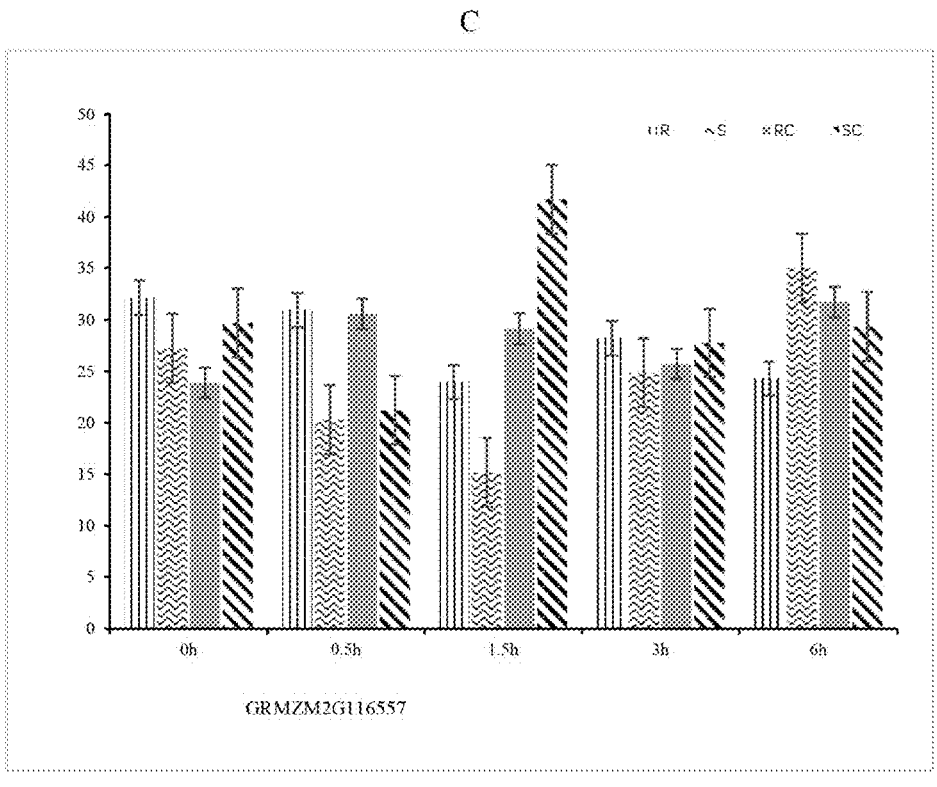
D.
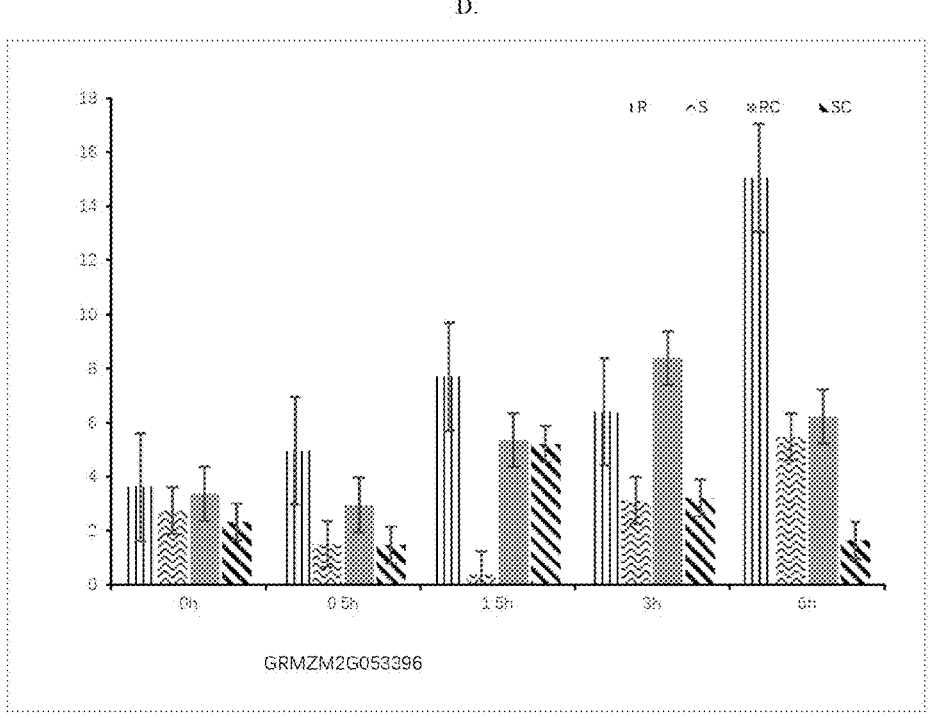
FIG. 11 (C, D) Dynamic expression patterns of genes in the early time post inoculation. The genes in the susceptible line SY1035 were downregulated to their lowest points at 1.5hpi.

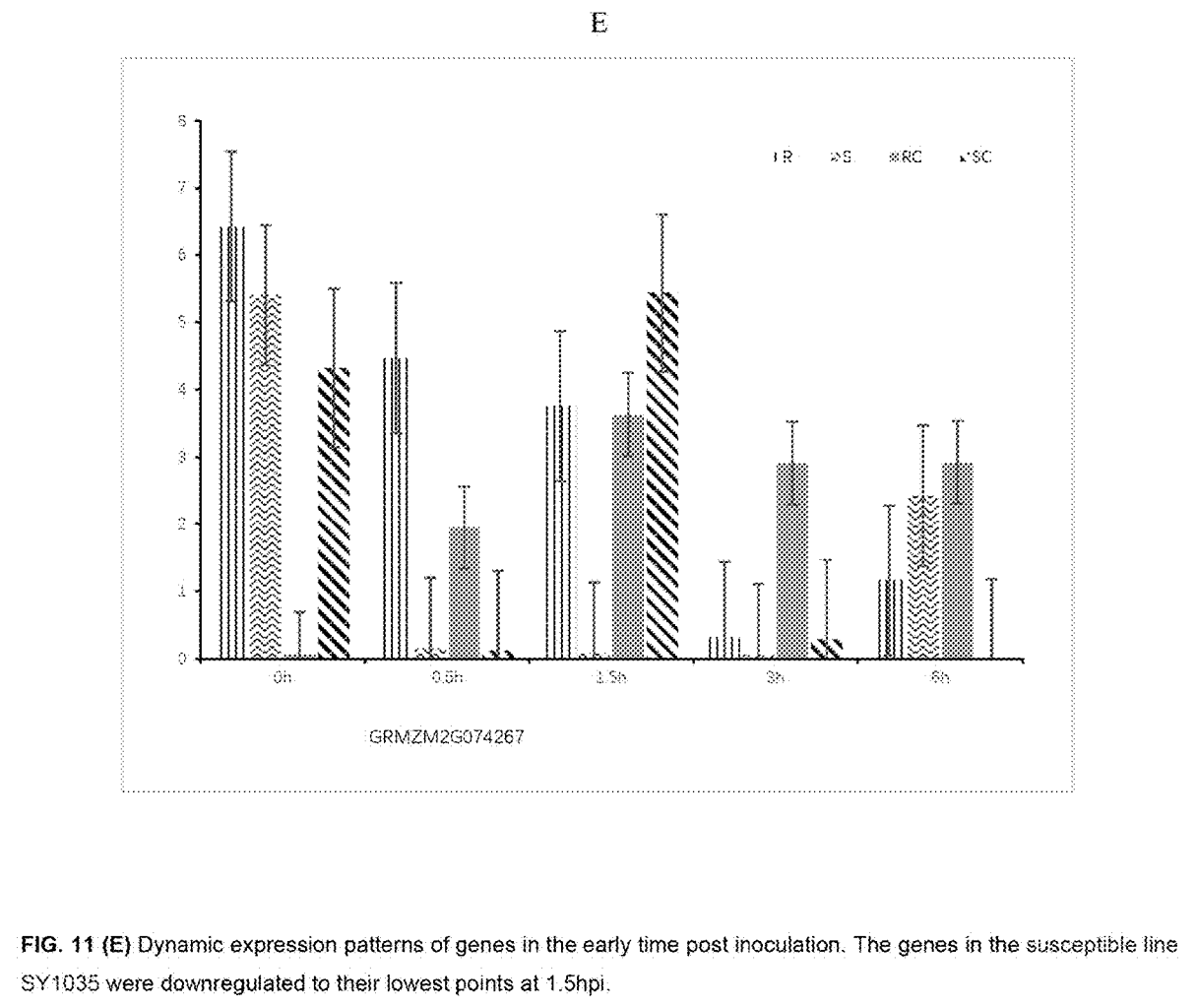

E

GRMZM2G074267

FIG. 11 (E) Dynamic expression patterns of genes in the early time post inoculation. The genes in the susceptible line SY1035 were downregulated to their lowest points at 1.5hpi.

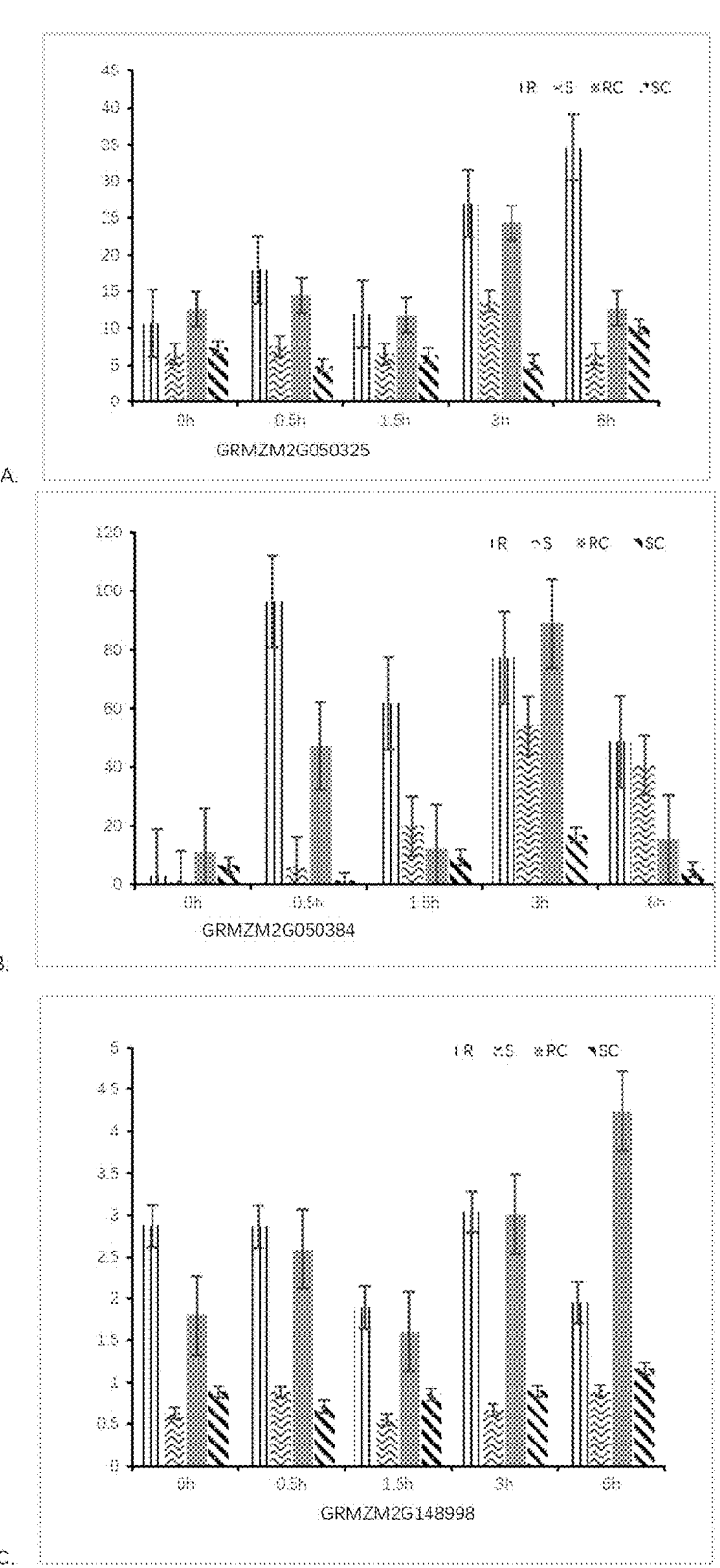
A.
B.
C.
FIG. 12. Dynamic expression patterns of genes in the early time post inoculation. Genes were highly expressed in the resistant line CIMBL47 compared to susceptible line SY1035.

A.
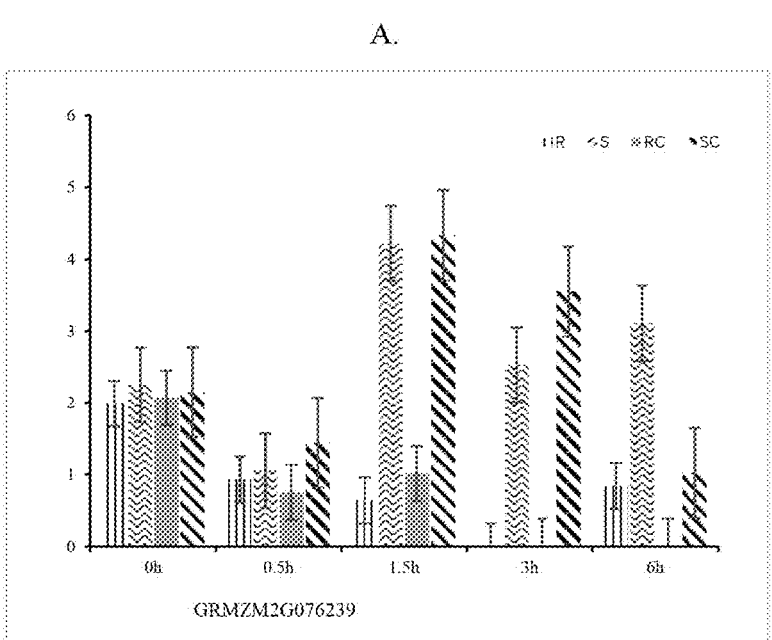
B.
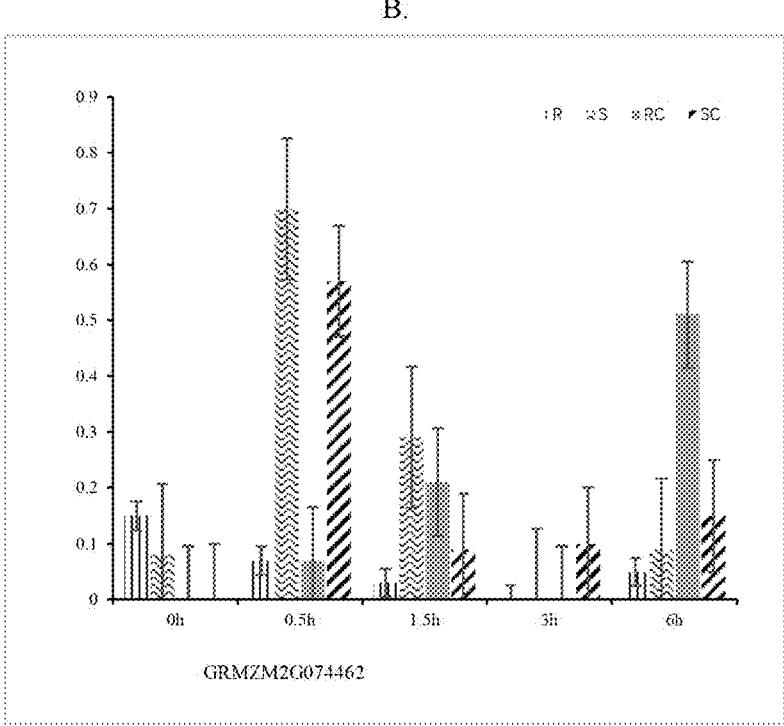
FIG. 13. Dynamic expression patterns of genes in the early time post inoculation. Genes were highly expressed in the susceptible line SY1035 compared to resistant line CIMBL47.

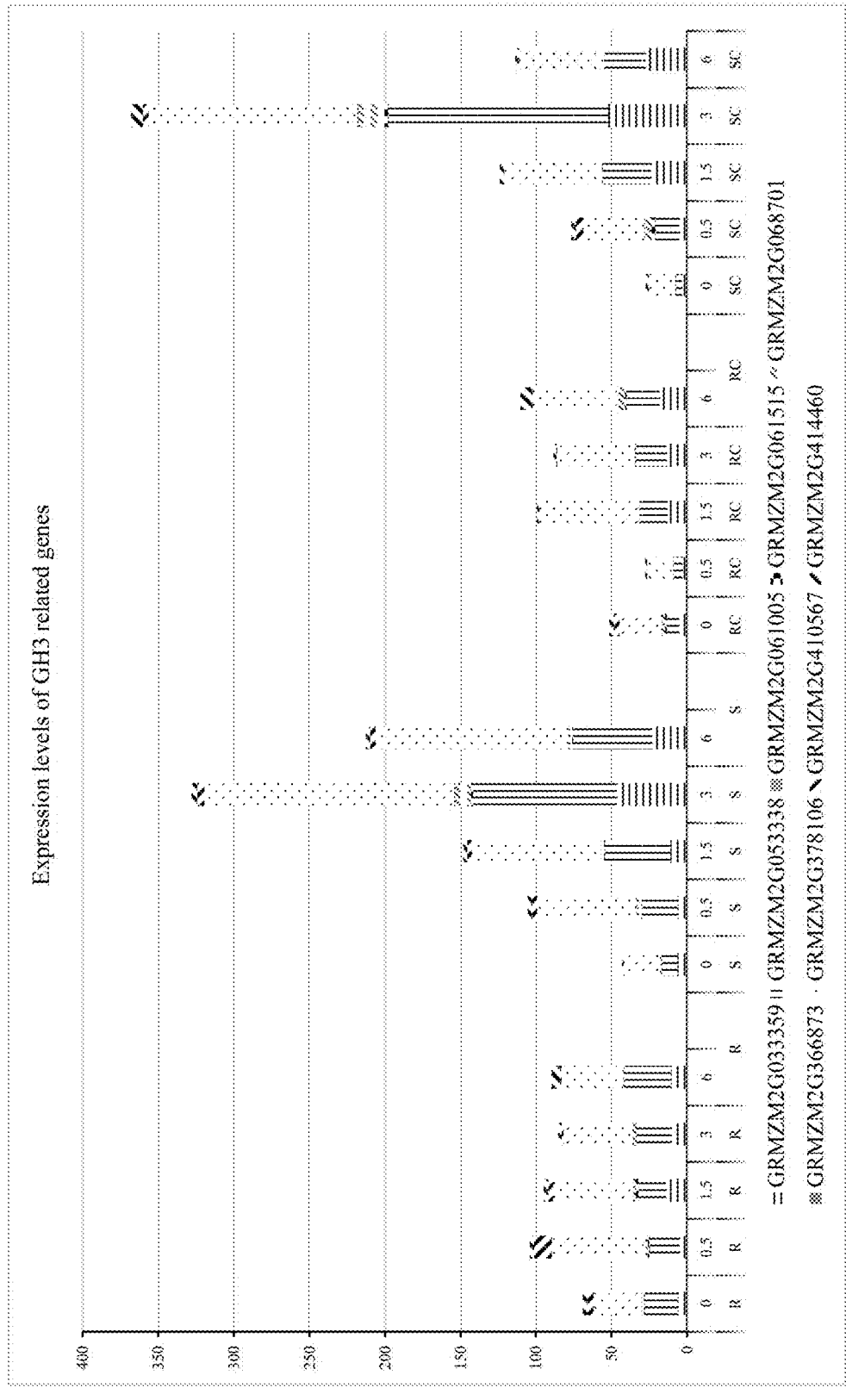
FIG. 14(a). Changes in expression levels of genes encoding hormone synthesis related to plant hormone signaling pathway.

FIG. 14(b) Changes in expression levels of genes encoding hormone synthesis related to plant hormone signaling pathway.
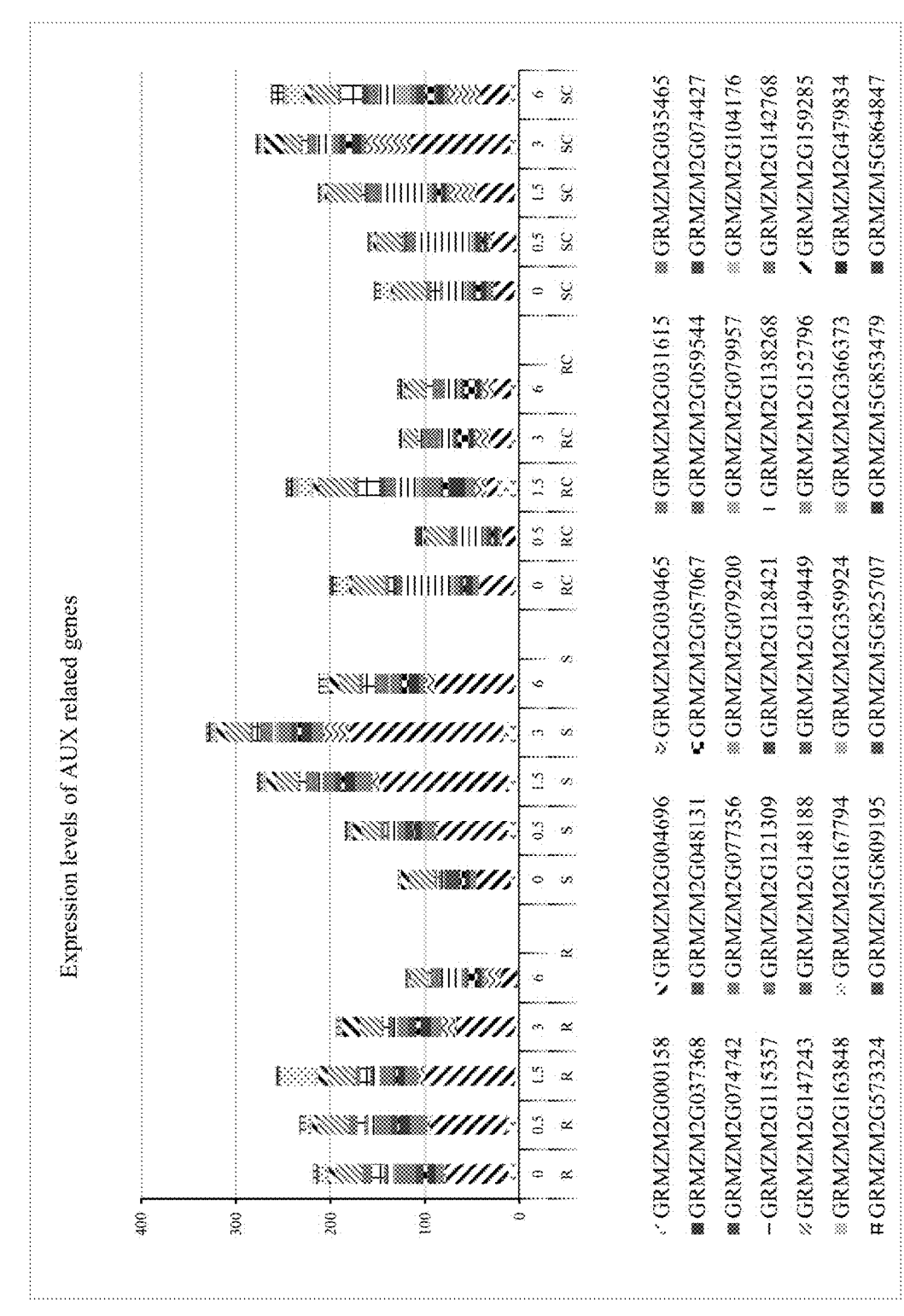
Expression levels of AUX related genes FIG. 14(c) Changes in expression levels of genes encoding hormone synthesis related to plant hormone signaling pathway.

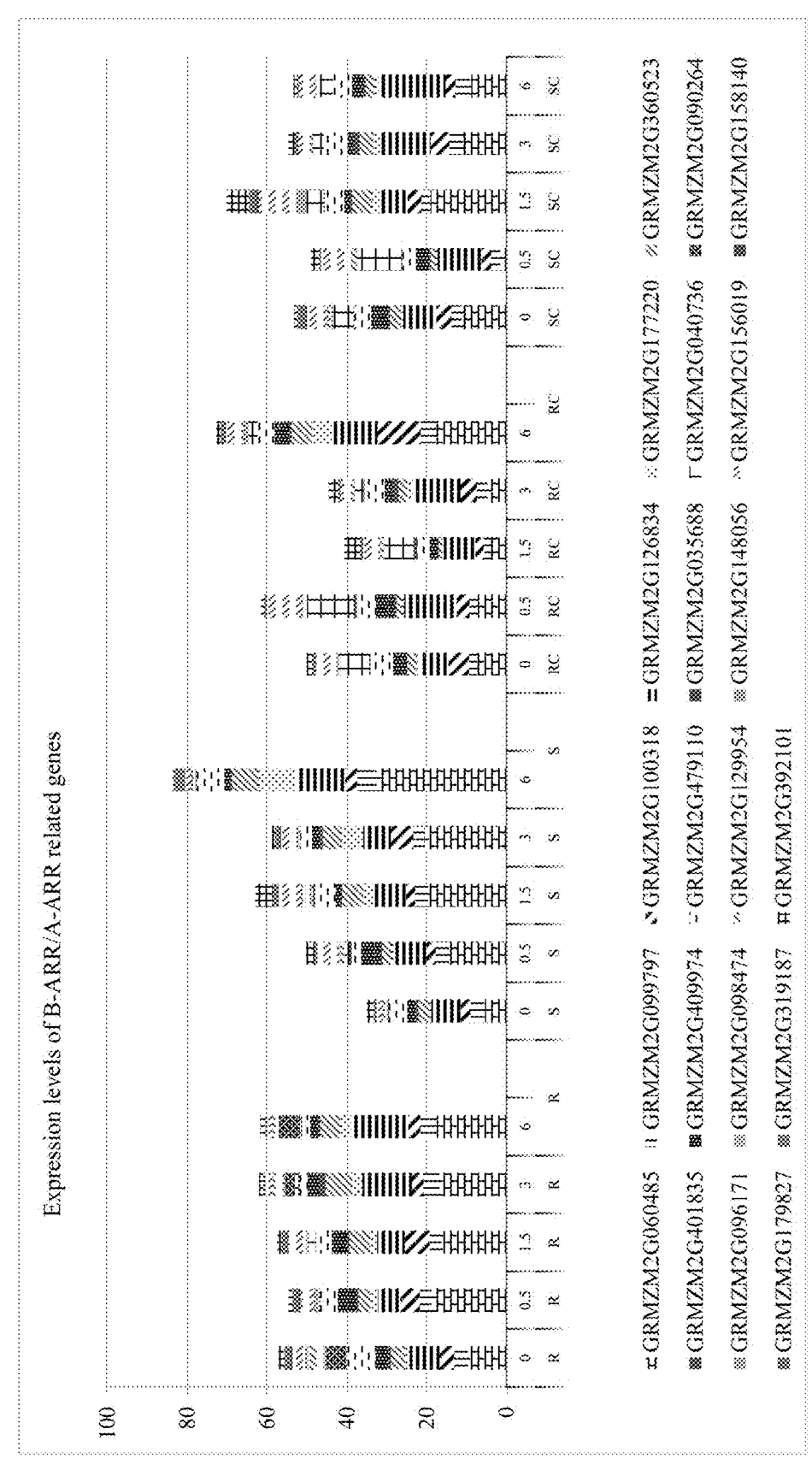
FIG. 14(d) Changes in expression levels of genes encoding hormone synthesis related to plant hormone signaling pathway.

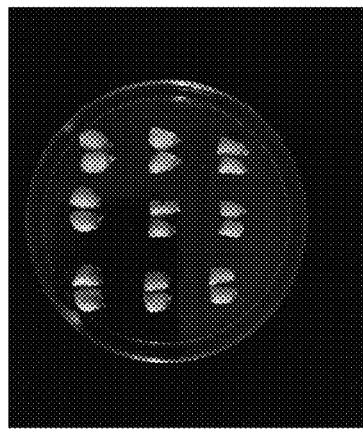
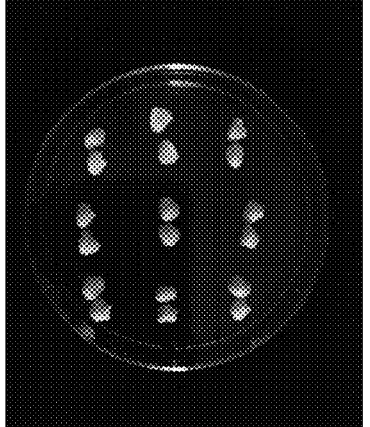
FIG. 16. Half-kernels used in the RNA-seq analysis.
A.
B.
A: resistant line CIMBL47; B: susceptible line SY1035

SEQUENCE LISTING

<160> NUMBER OF SEQ ID NOS: 1392

<210> SEQ ID NO 1
<211> LENGTH: 21
<212> TYPE: DNA
<213> ORGANISM: Zea mays;

<400> SEQUENCE: 1
agaccaattc gttcttttc t                                    21

<210> SEQ ID NO 2
<211> LENGTH: 19
<212> TYPE: DNA
<213> ORGANISM: Zea mays;

<400> SEQUENCE: 2
accaattcgt tcctttct                                       19

-continued

```
<210> SEQ ID NO 3
<211> LENGTH: 25
<212> TYPE: DNA
<213> ORGANISM: Zea mays;

<400> SEQUENCE: 3
tttgtacatg tttcgcggag atttc                                          25

<210> SEQ ID NO 4
<211> LENGTH: 19
<212> TYPE: DNA
<213> ORGANISM: Zea mays;

<400> SEQUENCE: 4
tggctggtac acgcagaag                                                 19

<210> SEQ ID NO 5
<211> LENGTH: 16
<212> TYPE: DNA
<213> ORGANISM: Zea mays;

<400> SEQUENCE: 5
caggtccagt tctgca                                                    16

<210> SEQ ID NO 6
<211> LENGTH: 16
<212> TYPE: DNA
<213> ORGANISM: Zea mays;

<400> SEQUENCE: 6
caggtccagt cctgca                                                    16

<210> SEQ ID NO 7
<211> LENGTH: 24
<212> TYPE: DNA
<213> ORGANISM: Zea mays;

<400> SEQUENCE: 7
gcatgatgct gatgggaaag atta                                           24

<210> SEQ ID NO 8
<211> LENGTH: 20
<212> TYPE: DNA
<213> ORGANISM: Zea mays;

<400> SEQUENCE: 8
gcccctttca gtcatcgaac                                                20

<210> SEQ ID NO 9
<211> LENGTH: 14
<212> TYPE: DNA
<213> ORGANISM: Zea mays;

<400> SEQUENCE: 9
tcccgcaacc aaat                                                      14

<210> SEQ ID NO 10
<211> LENGTH: 14
<212> TYPE: DNA
<213> ORGANISM: Zea mays;

<400> SEQUENCE: 10
tcccgcaacc aaac                                                      14
```

-continued

<210> SEQ ID NO 11
<211> LENGTH: 24
<212> TYPE: DNA
<213> ORGANISM: Zea mays;

<400> SEQUENCE: 11
tccccagtta tccctcaaaa ttgg                                                    24

<210> SEQ ID NO 12
<211> LENGTH: 21
<212> TYPE: DNA
<213> ORGANISM: Zea mays;

<400> SEQUENCE: 12
tgaagccacg caaccactta g                                                       21

<210> SEQ ID NO 13
<211> LENGTH: 18
<212> TYPE: DNA
<213> ORGANISM: Zea mays;

<400> SEQUENCE: 13
tcaacttgaa tggattgg                                                           18

<210> SEQ ID NO 14
<211> LENGTH: 17
<212> TYPE: DNA
<213> ORGANISM: Zea mays;

<400> SEQUENCE: 14
caacttgaat ggactgg                                                            17

<210> SEQ ID NO 15
<211> LENGTH: 22
<212> TYPE: DNA
<213> ORGANISM: Zea mays;

<400> SEQUENCE: 15
tttatctgaa tttggaagtc ct                                                      22

<210> SEQ ID NO 16
<211> LENGTH: 19
<212> TYPE: DNA
<213> ORGANISM: Zea mays;

<400> SEQUENCE: 16
catgggtcct agtattcgt                                                          19

<210> SEQ ID NO 17
<211> LENGTH: 17
<212> TYPE: DNA
<213> ORGANISM: Zea mays;

<400> SEQUENCE: 17
agcgggaaat gccacat                                                            17

<210> SEQ ID NO 18
<211> LENGTH: 18
<212> TYPE: DNA
<213> ORGANISM: Zea mays;

<400> SEQUENCE: 18

-continued

```
tagcgggaaa agccacat                                              18

<210> SEQ ID NO 19
<211> LENGTH: 25
<212> TYPE: DNA
<213> ORGANISM: Zea mays;

<400> SEQUENCE: 19
gaatcaggta gtccaatagt agagc                                      25

<210> SEQ ID NO 20
<211> LENGTH: 17
<212> TYPE: DNA
<213> ORGANISM: Zea mays;

<400> SEQUENCE: 20
tctgcagtcg ccttccg                                               17

<210> SEQ ID NO 21
<211> LENGTH: 18
<212> TYPE: DNA
<213> ORGANISM: Zea mays;

<400> SEQUENCE: 21
catcatgtgc ctagaaag                                              18

<210> SEQ ID NO 22
<211> LENGTH: 18
<212> TYPE: DNA
<213> ORGANISM: Zea mays;

<400> SEQUENCE: 22
catcatgtgc ctagaaaa                                              18

<210> SEQ ID NO 23
<211> LENGTH: 27
<212> TYPE: DNA
<213> ORGANISM: Zea mays;

<400> SEQUENCE: 23
gcatgataga gatatgccta ggagaag                                    27

<210> SEQ ID NO 24
<211> LENGTH: 21
<212> TYPE: DNA
<213> ORGANISM: Zea mays;

<400> SEQUENCE: 24
tgcccctaat ttcctagcaa c                                          21

<210> SEQ ID NO 25
<211> LENGTH: 17
<212> TYPE: DNA
<213> ORGANISM: Zea mays;

<400> SEQUENCE: 25
tcattgtata tctcggc                                               17

<210> SEQ ID NO 26
<211> LENGTH: 21
<212> TYPE: DNA
<213> ORGANISM: Zea mays;

<400> SEQUENCE: 26
```

-continued

```
catattcatt gtagatctcg g                                        21

<210> SEQ ID NO 27
<211> LENGTH: 24
<212> TYPE: DNA
<213> ORGANISM: Zea mays;

<400> SEQUENCE: 27
acctagaatg ctcaaaaggg aaca                                     24

<210> SEQ ID NO 28
<211> LENGTH: 23
<212> TYPE: DNA
<213> ORGANISM: Zea mays;

<400> SEQUENCE: 28
catgctgcgt catcaatcat ctg                                      23

<210> SEQ ID NO 29
<211> LENGTH: 15
<212> TYPE: DNA
<213> ORGANISM: Zea mays;

<400> SEQUENCE: 29
cggcgctagc tgcag                                               15

<210> SEQ ID NO 30
<211> LENGTH: 13
<212> TYPE: DNA
<213> ORGANISM: Zea mays;

<400> SEQUENCE: 30
ccggcgccag ctg                                                 13

<210> SEQ ID NO 31
<211> LENGTH: 18
<212> TYPE: DNA
<213> ORGANISM: Zea mays;

<400> SEQUENCE: 31
aggtcgcagg acgcgaag                                            18

<210> SEQ ID NO 32
<211> LENGTH: 20
<212> TYPE: DNA
<213> ORGANISM: Zea mays;

<400> SEQUENCE: 32
ggcgactcca tctgtaagca                                          20

<210> SEQ ID NO 33
<211> LENGTH: 14
<212> TYPE: DNA
<213> ORGANISM: Zea mays;

<400> SEQUENCE: 33
ctgatgttca ggcc                                                14

<210> SEQ ID NO 34
<211> LENGTH: 15
<212> TYPE: DNA
<213> ORGANISM: Zea mays;
```

<400> SEQUENCE: 34
ctgatgttca agcct                                                        15

<210> SEQ ID NO 35
<211> LENGTH: 21
<212> TYPE: DNA
<213> ORGANISM: Zea mays;

<400> SEQUENCE: 35
ccacgaggaa cattcgacca t                                                 21

<210> SEQ ID NO 36
<211> LENGTH: 23
<212> TYPE: DNA
<213> ORGANISM: Zea mays;

<400> SEQUENCE: 36
tctcgtcaag tccgctctta ttg                                               23

<210> SEQ ID NO 37
<211> LENGTH: 13
<212> TYPE: DNA
<213> ORGANISM: Zea mays;

<400> SEQUENCE: 37
actcctcgcc tgc                                                          13

<210> SEQ ID NO 38
<211> LENGTH: 15
<212> TYPE: DNA
<213> ORGANISM: Zea mays;

<400> SEQUENCE: 38
aagtactccc cgcct                                                        15

<210> SEQ ID NO 39
<211> LENGTH: 18
<212> TYPE: DNA
<213> ORGANISM: Zea mays;

<400> SEQUENCE: 39
tcctgactcc ggatccac                                                     18

<210> SEQ ID NO 40
<211> LENGTH: 18
<212> TYPE: DNA
<213> ORGANISM: Zea mays;

<400> SEQUENCE: 40
aggcacaggc tggcagtg                                                     18

<210> SEQ ID NO 41
<211> LENGTH: 13
<212> TYPE: DNA
<213> ORGANISM: Zea mays;

<400> SEQUENCE: 41
ccgaacacgc cct                                                          13

<210> SEQ ID NO 42
<211> LENGTH: 12
<212> TYPE: DNA
<213> ORGANISM: Zea mays;

-continued

```
<400> SEQUENCE: 42
cgaacacgcc cc                                                    12

<210> SEQ ID NO 43
<211> LENGTH: 22
<212> TYPE: DNA
<213> ORGANISM: Zea mays;

<400> SEQUENCE: 43
ctgcaacagt gtcggcttgt ag                                         22

<210> SEQ ID NO 44
<211> LENGTH: 20
<212> TYPE: DNA
<213> ORGANISM: Zea mays;

<400> SEQUENCE: 44
gctccaagag cgagggatac                                            20

<210> SEQ ID NO 45
<211> LENGTH: 21
<212> TYPE: DNA
<213> ORGANISM: Zea mays;

<400> SEQUENCE: 45
aagtttcaaa ttataatggt a                                          21

<210> SEQ ID NO 46
<211> LENGTH: 22
<212> TYPE: DNA
<213> ORGANISM: Zea mays;

<400> SEQUENCE: 46
tttcaaatta taatgataga gt                                         22

<210> SEQ ID NO 47
<211> LENGTH: 23
<212> TYPE: DNA
<213> ORGANISM: Zea mays;

<400> SEQUENCE: 47
tgactgatgg aggttcgaag ttg                                        23

<210> SEQ ID NO 48
<211> LENGTH: 28
<212> TYPE: DNA
<213> ORGANISM: Zea mays;

<400> SEQUENCE: 48
cgactaataa aaagaaacgg agggagta                                   28

<210> SEQ ID NO 49
<211> LENGTH: 19
<212> TYPE: DNA
<213> ORGANISM: Zea mays;

<400> SEQUENCE: 49
tgggtaattt ctaggaaac                                             19

<210> SEQ ID NO 50
<211> LENGTH: 19
<212> TYPE: DNA
```

-continued

```
<213> ORGANISM: Zea mays;

<400> SEQUENCE: 50
tggtgggtaa tttctaaga                                          19

<210> SEQ ID NO 51
<211> LENGTH: 23
<212> TYPE: DNA
<213> ORGANISM: Zea mays;

<400> SEQUENCE: 51
cgattcggtg gattataatg gca                                     23

<210> SEQ ID NO 52
<211> LENGTH: 21
<212> TYPE: DNA
<213> ORGANISM: Zea mays;

<400> SEQUENCE: 52
gctttcgtta gggcctgttt g                                       21

<210> SEQ ID NO 53
<211> LENGTH: 19
<212> TYPE: DNA
<213> ORGANISM: Zea mays;

<400> SEQUENCE: 53
atagaactcc tagcaggca                                          19

<210> SEQ ID NO 54
<211> LENGTH: 16
<212> TYPE: DNA
<213> ORGANISM: Zea mays;

<400> SEQUENCE: 54
aactccttgc aggcaa                                             16

<210> SEQ ID NO 55
<211> LENGTH: 21
<212> TYPE: DNA
<213> ORGANISM: Zea mays;

<400> SEQUENCE: 55
gggatgttgc aagcaagaga a                                       21

<210> SEQ ID NO 56
<211> LENGTH: 18
<212> TYPE: DNA
<213> ORGANISM: Zea mays;

<400> SEQUENCE: 56
gtcacgagcc gtgtgaaa                                           18

<210> SEQ ID NO 57
<211> LENGTH: 20
<212> TYPE: DNA
<213> ORGANISM: Zea mays;

<400> SEQUENCE: 57
catcttgagt gatgtaaatg                                         20

<210> SEQ ID NO 58
<211> LENGTH: 19
```

```
<212> TYPE: DNA
<213> ORGANISM: Zea mays;

<400> SEQUENCE: 58
catcttgagt gatgtacat                                              19

<210> SEQ ID NO 59
<211> LENGTH: 21
<212> TYPE: DNA
<213> ORGANISM: Zea mays;

<400> SEQUENCE: 59
ggcagggcta aatcaacttg c                                           21

<210> SEQ ID NO 60
<211> LENGTH: 26
<212> TYPE: DNA
<213> ORGANISM: Zea mays;

<400> SEQUENCE: 60
caacagattg gtgagatcaa gagctg                                      26

<210> SEQ ID NO 61
<211> LENGTH: 14
<212> TYPE: DNA
<213> ORGANISM: Zea mays;

<400> SEQUENCE: 61
acggacccac cttg                                                   14

<210> SEQ ID NO 62
<211> LENGTH: 15
<212> TYPE: DNA
<213> ORGANISM: Zea mays;

<400> SEQUENCE: 62
acggacccac cttaa                                                  15

<210> SEQ ID NO 63
<211> LENGTH: 23
<212> TYPE: DNA
<213> ORGANISM: Zea mays;

<400> SEQUENCE: 63
acggtcctgt atatgacaag cag                                         23

<210> SEQ ID NO 64
<211> LENGTH: 18
<212> TYPE: DNA
<213> ORGANISM: Zea mays;

<400> SEQUENCE: 64
tgggctgagt ggtgaagc                                               18

<210> SEQ ID NO 65
<211> LENGTH: 16
<212> TYPE: DNA
<213> ORGANISM: Zea mays;

<400> SEQUENCE: 65
tgcagttgca ggtacg                                                 16

<210> SEQ ID NO 66
```

-continued

```
<211> LENGTH: 18
<212> TYPE: DNA
<213> ORGANISM: Zea mays;

<400> SEQUENCE: 66
attgcagttg caggtacc                                                      18

<210> SEQ ID NO 67
<211> LENGTH: 20
<212> TYPE: DNA
<213> ORGANISM: Zea mays;

<400> SEQUENCE: 67
acagccactg gtggttggtc                                                    20

<210> SEQ ID NO 68
<211> LENGTH: 24
<212> TYPE: DNA
<213> ORGANISM: Zea mays;

<400> SEQUENCE: 68
ggcgtacgtg ccacttatat agtc                                               24

<210> SEQ ID NO 69
<211> LENGTH: 15
<212> TYPE: DNA
<213> ORGANISM: Zea mays;

<400> SEQUENCE: 69
tggagcgtct acacc                                                         15

<210> SEQ ID NO 70
<211> LENGTH: 17
<212> TYPE: DNA
<213> ORGANISM: Zea mays;

<400> SEQUENCE: 70
catggagcat ctacacc                                                       17

<210> SEQ ID NO 71
<211> LENGTH: 22
<212> TYPE: DNA
<213> ORGANISM: Zea mays;

<400> SEQUENCE: 71
cttgttctaa gcgcctcctg at                                                 22

<210> SEQ ID NO 72
<211> LENGTH: 22
<212> TYPE: DNA
<213> ORGANISM: Zea mays;

<400> SEQUENCE: 72
tggtgactct tgatggagtt ca                                                 22

<210> SEQ ID NO 73
<211> LENGTH: 19
<212> TYPE: DNA
<213> ORGANISM: Zea mays;

<400> SEQUENCE: 73
ttctgtaatt ttatcaatt                                                     19
```

-continued

```
<210> SEQ ID NO 74
<211> LENGTH: 16
<212> TYPE: DNA
<213> ORGANISM: Zea mays;

<400> SEQUENCE: 74
ttctgtaatt ttacca                                              16

<210> SEQ ID NO 75
<211> LENGTH: 17
<212> TYPE: DNA
<213> ORGANISM: Zea mays;

<400> SEQUENCE: 75
ctgcctacat gcagttt                                             17

<210> SEQ ID NO 76
<211> LENGTH: 17
<212> TYPE: DNA
<213> ORGANISM: Zea mays;

<400> SEQUENCE: 76
tgccacgata agaaagg                                             17

<210> SEQ ID NO 77
<211> LENGTH: 16
<212> TYPE: DNA
<213> ORGANISM: Zea mays;

<400> SEQUENCE: 77
tctccaggag ttcgag                                              16

<210> SEQ ID NO 78
<211> LENGTH: 16
<212> TYPE: DNA
<213> ORGANISM: Zea mays;

<400> SEQUENCE: 78
ctccaggagt tcaagg                                              16

<210> SEQ ID NO 79
<211> LENGTH: 25
<212> TYPE: DNA
<213> ORGANISM: Zea mays;

<400> SEQUENCE: 79
cctttggtgc aatctatgat caggt                                    25

<210> SEQ ID NO 80
<211> LENGTH: 24
<212> TYPE: DNA
<213> ORGANISM: Zea mays;

<400> SEQUENCE: 80
cgaaacgtag ccaacgtaaa caac                                     24

<210> SEQ ID NO 81
<211> LENGTH: 17
<212> TYPE: DNA
<213> ORGANISM: Zea mays;

<400> SEQUENCE: 81
cgcggaaatc cgagtag                                             17
```

```
<210> SEQ ID NO 82
<211> LENGTH: 15
<212> TYPE: DNA
<213> ORGANISM: Zea mays;

<400> SEQUENCE: 82
cggaaatccg agcag                                                    15

<210> SEQ ID NO 83
<211> LENGTH: 20
<212> TYPE: DNA
<213> ORGANISM: Zea mays;

<400> SEQUENCE: 83
gggtggactc actccgaatg                                               20

<210> SEQ ID NO 84
<211> LENGTH: 19
<212> TYPE: DNA
<213> ORGANISM: Zea mays;

<400> SEQUENCE: 84
gagcccctct ctcctcgtt                                                19

<210> SEQ ID NO 85
<211> LENGTH: 11
<212> TYPE: DNA
<213> ORGANISM: Zea mays;

<400> SEQUENCE: 85
ctgcgccgcg t                                                        11

<210> SEQ ID NO 86
<211> LENGTH: 12
<212> TYPE: DNA
<213> ORGANISM: Zea mays;

<400> SEQUENCE: 86
ctgcgccgca tg                                                       12

<210> SEQ ID NO 87
<211> LENGTH: 17
<212> TYPE: DNA
<213> ORGANISM: Zea mays;

<400> SEQUENCE: 87
cgtcgccctg agcctac                                                  17

<210> SEQ ID NO 88
<211> LENGTH: 20
<212> TYPE: DNA
<213> ORGANISM: Zea mays;

<400> SEQUENCE: 88
tgcgacggtg atagacgatg                                               20

<210> SEQ ID NO 89
<211> LENGTH: 16
<212> TYPE: DNA
<213> ORGANISM: Zea mays;

<400> SEQUENCE: 89
ccctataccc cactac                                                   16
```

-continued

<210> SEQ ID NO 90
<211> LENGTH: 15
<212> TYPE: DNA
<213> ORGANISM: Zea mays;

<400> SEQUENCE: 90 cctataccccc acaac                                                    15

<210> SEQ ID NO 91
<211> LENGTH: 21
<212> TYPE: DNA
<213> ORGANISM: Zea mays;

<400> SEQUENCE: 91
tccaccctgt acaatggttc c                                              21

<210> SEQ ID NO 92
<211> LENGTH: 24
<212> TYPE: DNA
<213> ORGANISM: Zea mays;

<400> SEQUENCE: 92
gcgtacacca gtatttgtca gttc                                           24

<210> SEQ ID NO 93
<211> LENGTH: 17
<212> TYPE: DNA
<213> ORGANISM: Zea mays;

<400> SEQUENCE: 93
tccttgtcag gatcatc                                                   17

<210> SEQ ID NO 94
<211> LENGTH: 17
<212> TYPE: DNA
<213> ORGANISM: Zea mays;

<400> SEQUENCE: 94
tccttgtcag catcatc                                                   17

<210> SEQ ID NO 95
<211> LENGTH: 25
<212> TYPE: DNA
<213> ORGANISM: Zea mays;

<400> SEQUENCE: 95
cgccattaat tcatgcttgt ctctg                                          25

<210> SEQ ID NO 96
<211> LENGTH: 21
<212> TYPE: DNA
<213> ORGANISM: Zea mays;

<400> SEQUENCE: 96
acacgctgcg ttggagaatc c                                              21

<210> SEQ ID NO 97
<211> LENGTH: 17
<212> TYPE: DNA
<213> ORGANISM: Zea mays;

<400> SEQUENCE: 97

-continued

```
cagccaaaat cgaacca                                                    17

<210> SEQ ID NO 98
<211> LENGTH: 16
<212> TYPE: DNA
<213> ORGANISM: Zea mays;

<400> SEQUENCE: 98
cagccaaaac cgaacc                                                     16

<210> SEQ ID NO 99
<211> LENGTH: 15
<212> TYPE: DNA
<213> ORGANISM: Zea mays;

<400> SEQUENCE: 99
gagcgagccg cctga                                                      15

<210> SEQ ID NO 100
<211> LENGTH: 18
<212> TYPE: DNA
<213> ORGANISM: Zea mays;

<400> SEQUENCE: 100
ccgtggcaac tggtcctg                                                   18

<210> SEQ ID NO 101
<211> LENGTH: 13
<212> TYPE: DNA
<213> ORGANISM: Zea mays;

<400> SEQUENCE: 101
ccctgcgaac gcc                                                        13

<210> SEQ ID NO 102
<211> LENGTH: 13
<212> TYPE: DNA
<213> ORGANISM: Zea mays;

<400> SEQUENCE: 102
ccctgccaac gcc                                                        13

<210> SEQ ID NO 103
<211> LENGTH: 18
<212> TYPE: DNA
<213> ORGANISM: Zea mays;

<400> SEQUENCE: 103
tggaggccaa gtcgaacg                                                   18

<210> SEQ ID NO 104
<211> LENGTH: 15
<212> TYPE: DNA
<213> ORGANISM: Zea mays;

<400> SEQUENCE: 104
ggctcgggtc cagca                                                      15

<210> SEQ ID NO 105
<211> LENGTH: 20
<212> TYPE: DNA
<213> ORGANISM: Zea mays;

<400> SEQUENCE: 105
```

-continued

```
ctgcttgtga tagaaataaa                                        20

<210> SEQ ID NO 106
<211> LENGTH: 21
<212> TYPE: DNA
<213> ORGANISM: Zea mays;

<400> SEQUENCE: 106
cttgtgatag aaacaaagat g                                      21

<210> SEQ ID NO 107
<211> LENGTH: 18
<212> TYPE: DNA
<213> ORGANISM: Zea mays;

<400> SEQUENCE: 107
atgaagggaa gaccgcat                                          18

<210> SEQ ID NO 108
<211> LENGTH: 19
<212> TYPE: DNA
<213> ORGANISM: Zea mays;

<400> SEQUENCE: 108
tgggacatat tagaccatc                                         19

<210> SEQ ID NO 109
<211> LENGTH: 18
<212> TYPE: DNA
<213> ORGANISM: Zea mays;

<400> SEQUENCE: 109
ctttctctag ccgtacta                                          18

<210> SEQ ID NO 110
<211> LENGTH: 18
<212> TYPE: DNA
<213> ORGANISM: Zea mays;

<400> SEQUENCE: 110
ctttctctag ccctacta                                          18

<210> SEQ ID NO 111
<211> LENGTH: 21
<212> TYPE: DNA
<213> ORGANISM: Zea mays;

<400> SEQUENCE: 111
agctttgctt cctgggtgct t                                      21

<210> SEQ ID NO 112
<211> LENGTH: 20
<212> TYPE: DNA
<213> ORGANISM: Zea mays;

<400> SEQUENCE: 112
tcggcatcac ctgtatcaga                                        20

<210> SEQ ID NO 113
<211> LENGTH: 19
<212> TYPE: DNA
<213> ORGANISM: Zea mays;
```

-continued

```
<400> SEQUENCE: 113
catgaaagtt aatcctcaa                                              19

<210> SEQ ID NO 114
<211> LENGTH: 20
<212> TYPE: DNA
<213> ORGANISM: Zea mays;

<400> SEQUENCE: 114
ttcatgaaag ttaatcatca                                            20

<210> SEQ ID NO 115
<211> LENGTH: 28
<212> TYPE: DNA
<213> ORGANISM: Zea mays;

<400> SEQUENCE: 115
cagctttttg gtcgtttttc tttgattg                                   28

<210> SEQ ID NO 116
<211> LENGTH: 23
<212> TYPE: DNA
<213> ORGANISM: Zea mays;

<400> SEQUENCE: 116
ggtgagcttg tgttatgttc tca                                        23

<210> SEQ ID NO 117
<211> LENGTH: 17
<212> TYPE: DNA
<213> ORGANISM: Zea mays;

<400> SEQUENCE: 117
cgctagaccg tgatggt                                               17

<210> SEQ ID NO 118
<211> LENGTH: 17
<212> TYPE: DNA
<213> ORGANISM: Zea mays;

<400> SEQUENCE: 118
cgctagaccc tgatggt                                               17

<210> SEQ ID NO 119
<211> LENGTH: 21
<212> TYPE: DNA
<213> ORGANISM: Zea mays;

<400> SEQUENCE: 119
tgcaaccagt gaatgtcctt g                                          21

<210> SEQ ID NO 120
<211> LENGTH: 23
<212> TYPE: DNA
<213> ORGANISM: Zea mays;

<400> SEQUENCE: 120
gtcgtttgga gctagtagtt gac                                        23

<210> SEQ ID NO 121
<211> LENGTH: 18
<212> TYPE: DNA
<213> ORGANISM: Zea mays;
```

-continued

<400> SEQUENCE: 121
atggctgctg cttcatac                                                         18

<210> SEQ ID NO 122
<211> LENGTH: 17
<212> TYPE: DNA
<213> ORGANISM: Zea mays;

<400> SEQUENCE: 122
atggctgctg cgtcata                                                          17

<210> SEQ ID NO 123
<211> LENGTH: 24
<212> TYPE: DNA
<213> ORGANISM: Zea mays;

<400> SEQUENCE: 123
gttggacctt ctctctgtaa gtca                                                  24

<210> SEQ ID NO 124
<211> LENGTH: 18
<212> TYPE: DNA
<213> ORGANISM: Zea mays;

<400> SEQUENCE: 124
tgcttgcctc gctgtgat                                                         18

<210> SEQ ID NO 125
<211> LENGTH: 21
<212> TYPE: DNA
<213> ORGANISM: Zea mays;

<400> SEQUENCE: 125
attttattat tcgtccgtct a                                                     21

<210> SEQ ID NO 126
<211> LENGTH: 17
<212> TYPE: DNA
<213> ORGANISM: Zea mays;

<400> SEQUENCE: 126
tattattcgc ccgtcta                                                          17

<210> SEQ ID NO 127
<211> LENGTH: 22
<212> TYPE: DNA
<213> ORGANISM: Zea mays;

<400> SEQUENCE: 127
tccaaggtta cctgaaccct aa                                                    22

<210> SEQ ID NO 128
<211> LENGTH: 24
<212> TYPE: DNA
<213> ORGANISM: Zea mays;

<400> SEQUENCE: 128
gagcatggac attacatggc ataa                                                  24

<210> SEQ ID NO 129
<211> LENGTH: 16
<212> TYPE: DNA

-continued

```
<213> ORGANISM: Zea mays;

<400> SEQUENCE: 129
aattgatcac gcacta                                              16

<210> SEQ ID NO 130
<211> LENGTH: 18
<212> TYPE: DNA
<213> ORGANISM: Zea mays;

<400> SEQUENCE: 130
aattgatcac acactatc                                            18

<210> SEQ ID NO 131
<211> LENGTH: 20
<212> TYPE: DNA
<213> ORGANISM: Zea mays;

<400> SEQUENCE: 131
aggcaagctc gatggttcac                                          20

<210> SEQ ID NO 132
<211> LENGTH: 21
<212> TYPE: DNA
<213> ORGANISM: Zea mays;

<400> SEQUENCE: 132
ccatgtggtc gtgggttcaa g                                        21

<210> SEQ ID NO 133
<211> LENGTH: 15
<212> TYPE: DNA
<213> ORGANISM: Zea mays;

<400> SEQUENCE: 133
cgcaaagggc gtgtg                                               15

<210> SEQ ID NO 134
<211> LENGTH: 17
<212> TYPE: DNA
<213> ORGANISM: Zea mays;

<400> SEQUENCE: 134
acgcaaagag cgtgtgg                                             17

<210> SEQ ID NO 135
<211> LENGTH: 18
<212> TYPE: DNA
<213> ORGANISM: Zea mays;

<400> SEQUENCE: 135
acccgcggca accgtaaa                                            18

<210> SEQ ID NO 136
<211> LENGTH: 17
<212> TYPE: DNA
<213> ORGANISM: Zea mays;

<400> SEQUENCE: 136
cgtcgtcgtc ggagaca                                             17

<210> SEQ ID NO 137
<211> LENGTH: 19
```

-continued

```
<212> TYPE: DNA
<213> ORGANISM: Zea mays;

<400> SEQUENCE: 137
tctttcaaga ttaatgaag                                                        19

<210> SEQ ID NO 138
<211> LENGTH: 19
<212> TYPE: DNA
<213> ORGANISM: Zea mays;

<400> SEQUENCE: 138
ctttcaagat taaagaagg                                                        19

<210> SEQ ID NO 139
<211> LENGTH: 23
<212> TYPE: DNA
<213> ORGANISM: Zea mays;

<400> SEQUENCE: 139
gcagtgggtt gacatcaaca atg                                                   23

<210> SEQ ID NO 140
<211> LENGTH: 22
<212> TYPE: DNA
<213> ORGANISM: Zea mays;

<400> SEQUENCE: 140
gtttagcaag ctgaaagggt ga                                                    22

<210> SEQ ID NO 141
<211> LENGTH: 18
<212> TYPE: DNA
<213> ORGANISM: Zea mays;

<400> SEQUENCE: 141
caggtattcg tgtgcatc                                                         18

<210> SEQ ID NO 142
<211> LENGTH: 17
<212> TYPE: DNA
<213> ORGANISM: Zea mays;

<400> SEQUENCE: 142
caggtattcg cgtgcat                                                          17

<210> SEQ ID NO 143
<211> LENGTH: 20
<212> TYPE: DNA
<213> ORGANISM: Zea mays;

<400> SEQUENCE: 143
agggcactca ggcacatgat                                                       20

<210> SEQ ID NO 144
<211> LENGTH: 20
<212> TYPE: DNA
<213> ORGANISM: Zea mays;

<400> SEQUENCE: 144
ccaccactcg cactaggaaa                                                       20

<210> SEQ ID NO 145
```

-continued

```
<211> LENGTH: 21
<212> TYPE: DNA
<213> ORGANISM: Zea mays;

<400> SEQUENCE: 145
aggttagtcg ttcgaattgg a                                               21

<210> SEQ ID NO 146
<211> LENGTH: 21
<212> TYPE: DNA
<213> ORGANISM: Zea mays;

<400> SEQUENCE: 146
aaggttagtc gttcaaattg g                                               21

<210> SEQ ID NO 147
<211> LENGTH: 23
<212> TYPE: DNA
<213> ORGANISM: Zea mays;

<400> SEQUENCE: 147
gtttggtttg tggctaaatg tgc                                             23

<210> SEQ ID NO 148
<211> LENGTH: 21
<212> TYPE: DNA
<213> ORGANISM: Zea mays;

<400> SEQUENCE: 148
aggtgagtgt gacgtgcata g                                               21

<210> SEQ ID NO 149
<211> LENGTH: 14
<212> TYPE: DNA
<213> ORGANISM: Zea mays;

<400> SEQUENCE: 149
catgctgcgg tcgc                                                       14

<210> SEQ ID NO 150
<211> LENGTH: 13
<212> TYPE: DNA
<213> ORGANISM: Zea mays;

<400> SEQUENCE: 150
atgcggcggt cgc                                                        13

<210> SEQ ID NO 151
<211> LENGTH: 22
<212> TYPE: DNA
<213> ORGANISM: Zea mays;

<400> SEQUENCE: 151
acatgtagat gatgcggtcg tg                                              22

<210> SEQ ID NO 152
<211> LENGTH: 18
<212> TYPE: DNA
<213> ORGANISM: Zea mays;

<400> SEQUENCE: 152
accagctccc gtttctgc                                                   18
```

-continued

```
<210> SEQ ID NO 153
<211> LENGTH: 13
<212> TYPE: DNA
<213> ORGANISM: Zea mays;

<400> SEQUENCE: 153
ccccgccttc gaa                                               13

<210> SEQ ID NO 154
<211> LENGTH: 13
<212> TYPE: DNA
<213> ORGANISM: Zea mays;

<400> SEQUENCE: 154
tgccccacct tcg                                               13

<210> SEQ ID NO 155
<211> LENGTH: 18
<212> TYPE: DNA
<213> ORGANISM: Zea mays;

<400> SEQUENCE: 155
gggccatcag cgttcgtc                                          18

<210> SEQ ID NO 156
<211> LENGTH: 20
<212> TYPE: DNA
<213> ORGANISM: Zea mays;

<400> SEQUENCE: 156
agatggcgtg ctcggtgttc                                        20

<210> SEQ ID NO 157
<211> LENGTH: 19
<212> TYPE: DNA
<213> ORGANISM: Zea mays;

<400> SEQUENCE: 157
ccatccaatg tatcaattg                                         19

<210> SEQ ID NO 158
<211> LENGTH: 19
<212> TYPE: DNA
<213> ORGANISM: Zea mays;

<400> SEQUENCE: 158
catccaatgt atcaactga                                         19

<210> SEQ ID NO 159
<211> LENGTH: 23
<212> TYPE: DNA
<213> ORGANISM: Zea mays;

<400> SEQUENCE: 159
gaacttgata tgtagctaaa gac                                    23

<210> SEQ ID NO 160
<211> LENGTH: 21
<212> TYPE: DNA
<213> ORGANISM: Zea mays;

<400> SEQUENCE: 160
tcatgttgaa gttgaattgg t                                      21
```

-continued

```
<210> SEQ ID NO 161
<211> LENGTH: 19
<212> TYPE: DNA
<213> ORGANISM: Zea mays;

<400> SEQUENCE: 161
cgagaggatg acactataa                                             19

<210> SEQ ID NO 162
<211> LENGTH: 19
<212> TYPE: DNA
<213> ORGANISM: Zea mays;

<400> SEQUENCE: 162
agaggatgac actacaagt                                             19

<210> SEQ ID NO 163
<211> LENGTH: 22
<212> TYPE: DNA
<213> ORGANISM: Zea mays;

<400> SEQUENCE: 163
gctatcgccc accaataaag tg                                         22

<210> SEQ ID NO 164
<211> LENGTH: 23
<212> TYPE: DNA
<213> ORGANISM: Zea mays;

<400> SEQUENCE: 164
atgtgtcctc aacccttaga tga                                        23

<210> SEQ ID NO 165
<211> LENGTH: 17
<212> TYPE: DNA
<213> ORGANISM: Zea mays;

<400> SEQUENCE: 165
tcaactggac taaataa                                               17

<210> SEQ ID NO 166
<211> LENGTH: 16
<212> TYPE: DNA
<213> ORGANISM: Zea mays;

<400> SEQUENCE: 166
aagtcaactg gacaaa                                                16

<210> SEQ ID NO 167
<211> LENGTH: 21
<212> TYPE: DNA
<213> ORGANISM: Zea mays;

<400> SEQUENCE: 167
tccaagcagc tatcagatcc a                                          21

<210> SEQ ID NO 168
<211> LENGTH: 22
<212> TYPE: DNA
<213> ORGANISM: Zea mays;

<400> SEQUENCE: 168
gctcttgcct tctgttcttc ac                                         22
```

-continued

<210> SEQ ID NO 169
<211> LENGTH: 21
<212> TYPE: DNA
<213> ORGANISM: Zea mays;

<400> SEQUENCE: 169
aacaggacta ctcagattat a                                           21

<210> SEQ ID NO 170
<211> LENGTH: 17
<212> TYPE: DNA
<213> ORGANISM: Zea mays;

<400> SEQUENCE: 170
caggactact cagacta                                                17

<210> SEQ ID NO 171
<211> LENGTH: 25
<212> TYPE: DNA
<213> ORGANISM: Zea mays;

<400> SEQUENCE: 171
gagggcattc ttgtcttcct catac                                       25

<210> SEQ ID NO 172
<211> LENGTH: 21
<212> TYPE: DNA
<213> ORGANISM: Zea mays;

<400> SEQUENCE: 172
gcttcgggcc tgtttgttta c                                           21

<210> SEQ ID NO 173
<211> LENGTH: 14
<212> TYPE: DNA
<213> ORGANISM: Zea mays;

<400> SEQUENCE: 173
cccgatgcga cgtc                                                   14

<210> SEQ ID NO 174
<211> LENGTH: 14
<212> TYPE: DNA
<213> ORGANISM: Zea mays;

<400> SEQUENCE: 174
cccgaggcga cgtc                                                   14

<210> SEQ ID NO 175
<211> LENGTH: 15
<212> TYPE: DNA
<213> ORGANISM: Zea mays;

<400> SEQUENCE: 175
cgccttggcg gcctt                                                  15

<210> SEQ ID NO 176
<211> LENGTH: 20
<212> TYPE: DNA
<213> ORGANISM: Zea mays;

<400> SEQUENCE: 176

-continued

```
ccgcgtcaag tgtttcatca                                          20

<210> SEQ ID NO 177
<211> LENGTH: 20
<212> TYPE: DNA
<213> ORGANISM: Zea mays;

<400> SEQUENCE: 177
agcatggaaa tcttgtcttc                                          20

<210> SEQ ID NO 178
<211> LENGTH: 20
<212> TYPE: DNA
<213> ORGANISM: Zea mays;

<400> SEQUENCE: 178
tagcatggaa atcctgtctt                                          20

<210> SEQ ID NO 179
<211> LENGTH: 23
<212> TYPE: DNA
<213> ORGANISM: Zea mays;

<400> SEQUENCE: 179
tccacccaaa agatatcatc cga                                      23

<210> SEQ ID NO 180
<211> LENGTH: 21
<212> TYPE: DNA
<213> ORGANISM: Zea mays;

<400> SEQUENCE: 180
ccacctggga atgcaaggaa t                                        21

<210> SEQ ID NO 181
<211> LENGTH: 19
<212> TYPE: DNA
<213> ORGANISM: Zea mays;

<400> SEQUENCE: 181
caaagcatgt accattaat                                           19

<210> SEQ ID NO 182
<211> LENGTH: 18
<212> TYPE: DNA
<213> ORGANISM: Zea mays;

<400> SEQUENCE: 182
aaagcatgta ccatcaat                                            18

<210> SEQ ID NO 183
<211> LENGTH: 19
<212> TYPE: DNA
<213> ORGANISM: Zea mays;

<400> SEQUENCE: 183
acgtatcccg gccgtctac                                           19

<210> SEQ ID NO 184
<211> LENGTH: 22
<212> TYPE: DNA
<213> ORGANISM: Zea mays;

<400> SEQUENCE: 184
```

-continued gcggtgaagg aagatcatgg tt                                                    22

<210> SEQ ID NO 185
<211> LENGTH: 17
<212> TYPE: DNA
<213> ORGANISM: Zea mays;

<400> SEQUENCE: 185
tccaggaagg gccaaag                                                          17

<210> SEQ ID NO 186
<211> LENGTH: 18
<212> TYPE: DNA
<213> ORGANISM: Zea mays;

<400> SEQUENCE: 186
ccaggaaggc ccaaagat                                                         18

<210> SEQ ID NO 187
<211> LENGTH: 20
<212> TYPE: DNA
<213> ORGANISM: Zea mays;

<400> SEQUENCE: 187
gcagacgtga tcctgaagca                                                       20

<210> SEQ ID NO 188
<211> LENGTH: 17
<212> TYPE: DNA
<213> ORGANISM: Zea mays;

<400> SEQUENCE: 188
tcaggcacgg gctgaac                                                          17

<210> SEQ ID NO 189
<211> LENGTH: 15
<212> TYPE: DNA
<213> ORGANISM: Zea mays;

<400> SEQUENCE: 189
ccccggttgt cacat                                                            15

<210> SEQ ID NO 190
<211> LENGTH: 16
<212> TYPE: DNA
<213> ORGANISM: Zea mays;

<400> SEQUENCE: 190
cccggttatc acatgc                                                           16

<210> SEQ ID NO 191
<211> LENGTH: 23
<212> TYPE: DNA
<213> ORGANISM: Zea mays;

<400> SEQUENCE: 191
ggcaaagagg gattgctaca ctt                                                   23

<210> SEQ ID NO 192
<211> LENGTH: 25
<212> TYPE: DNA
<213> ORGANISM: Zea mays;

-continued

```
<400> SEQUENCE: 192
catccacaac acaaacactg acatc                                    25

<210> SEQ ID NO 193
<211> LENGTH: 20
<212> TYPE: DNA
<213> ORGANISM: Zea mays;

<400> SEQUENCE: 193
tcttcgtaga gaaagtatgt                                          20

<210> SEQ ID NO 194
<211> LENGTH: 20
<212> TYPE: DNA
<213> ORGANISM: Zea mays;

<400> SEQUENCE: 194
cgtagagaaa gataccgtat                                          20

<210> SEQ ID NO 195
<211> LENGTH: 17
<212> TYPE: DNA
<213> ORGANISM: Zea mays;

<400> SEQUENCE: 195
tgttcaggta acacgag                                             17

<210> SEQ ID NO 196
<211> LENGTH: 20
<212> TYPE: DNA
<213> ORGANISM: Zea mays;

<400> SEQUENCE: 196
cactcaatac tccaaacagt                                          20

<210> SEQ ID NO 197
<211> LENGTH: 19
<212> TYPE: DNA
<213> ORGANISM: Zea mays;

<400> SEQUENCE: 197
tccaatttct ggttcacat                                           19

<210> SEQ ID NO 198
<211> LENGTH: 17
<212> TYPE: DNA
<213> ORGANISM: Zea mays;

<400> SEQUENCE: 198
ccaatttctg gctcaca                                             17

<210> SEQ ID NO 199
<211> LENGTH: 21
<212> TYPE: DNA
<213> ORGANISM: Zea mays;

<400> SEQUENCE: 199
cctccaggcc aaagatgcaa t                                        21

<210> SEQ ID NO 200
<211> LENGTH: 23
<212> TYPE: DNA
<213> ORGANISM: Zea mays;
```

-continued

<400> SEQUENCE: 200
cccgctctat ccgttacact tct                                              23

<210> SEQ ID NO 201
<211> LENGTH: 16
<212> TYPE: DNA
<213> ORGANISM: Zea mays;

<400> SEQUENCE: 201
taactaatag caatgc                                                      16

<210> SEQ ID NO 202
<211> LENGTH: 19
<212> TYPE: DNA
<213> ORGANISM: Zea mays;

<400> SEQUENCE: 202
taataactaa tagcaatac                                                   19

<210> SEQ ID NO 203
<211> LENGTH: 21
<212> TYPE: DNA
<213> ORGANISM: Zea mays;

<400> SEQUENCE: 203
atgaaccata tatcctagga a                                                21

<210> SEQ ID NO 204
<211> LENGTH: 17
<212> TYPE: DNA
<213> ORGANISM: Zea mays;

<400> SEQUENCE: 204
gaggtgctcc aatcttc                                                     17

<210> SEQ ID NO 205
<211> LENGTH: 16
<212> TYPE: DNA
<213> ORGANISM: Zea mays;

<400> SEQUENCE: 205
cagtaggttg ggcaac                                                      16

<210> SEQ ID NO 206
<211> LENGTH: 14
<212> TYPE: DNA
<213> ORGANISM: Zea mays;

<400> SEQUENCE: 206
ccagtaggtt gcgc                                                        14

<210> SEQ ID NO 207
<211> LENGTH: 23
<212> TYPE: DNA
<213> ORGANISM: Zea mays;

<400> SEQUENCE: 207
tgttagtcca ggccttctga atc                                              23

<210> SEQ ID NO 208
<211> LENGTH: 25
<212> TYPE: DNA

-continued

<213> ORGANISM: Zea mays;

<400> SEQUENCE: 208
acagcagagg ttaaagtagc atagc                                                   25

<210> SEQ ID NO 209
<211> LENGTH: 16
<212> TYPE: DNA
<213> ORGANISM: Zea mays;

<400> SEQUENCE: 209
tggctttgga tcgggt                                                             16

<210> SEQ ID NO 210
<211> LENGTH: 18
<212> TYPE: DNA
<213> ORGANISM: Zea mays;

<400> SEQUENCE: 210
ttggctttgg atcgagtt                                                           18

<210> SEQ ID NO 211
<211> LENGTH: 20
<212> TYPE: DNA
<213> ORGANISM: Zea mays;

<400> SEQUENCE: 211
ttgacgtatc gggtcggatt                                                         20

<210> SEQ ID NO 212
<211> LENGTH: 22
<212> TYPE: DNA
<213> ORGANISM: Zea mays;

<400> SEQUENCE: 212
cgggctaagt acaagccatg at                                                      22

<210> SEQ ID NO 213
<211> LENGTH: 15
<212> TYPE: DNA
<213> ORGANISM: Zea mays;

<400> SEQUENCE: 213
tccgacggct agaga                                                              15

<210> SEQ ID NO 214
<211> LENGTH: 18
<212> TYPE: DNA
<213> ORGANISM: Zea mays;

<400> SEQUENCE: 214
caatatccga cagctaga                                                           18

<210> SEQ ID NO 215
<211> LENGTH: 25
<212> TYPE: DNA
<213> ORGANISM: Zea mays;

<400> SEQUENCE: 215
cagactacca tgaagagagt tgtga                                                   25

<210> SEQ ID NO 216
<211> LENGTH: 25

```
<212> TYPE: DNA
<213> ORGANISM: Zea mays;

<400> SEQUENCE: 216
ggtagttgat ttcttgtccg ctgat                                          25

<210> SEQ ID NO 217
<211> LENGTH: 17
<212> TYPE: DNA
<213> ORGANISM: Zea mays;

<400> SEQUENCE: 217
cgtttaggaa tctctgg                                                   17

<210> SEQ ID NO 218
<211> LENGTH: 18
<212> TYPE: DNA
<213> ORGANISM: Zea mays;

<400> SEQUENCE: 218
cgtttaggaa tatctggg                                                  18

<210> SEQ ID NO 219
<211> LENGTH: 15
<212> TYPE: DNA
<213> ORGANISM: Zea mays;

<400> SEQUENCE: 219
ggcgagaatg actgc                                                     15

<210> SEQ ID NO 220
<211> LENGTH: 21
<212> TYPE: DNA
<213> ORGANISM: Zea mays;

<400> SEQUENCE: 220
aatgacatgt gatctttgtt t                                              21

<210> SEQ ID NO 221
<211> LENGTH: 19
<212> TYPE: DNA
<213> ORGANISM: Zea mays;

<400> SEQUENCE: 221
cgagagtgta ttatggtag                                                 19

<210> SEQ ID NO 222
<211> LENGTH: 19
<212> TYPE: DNA
<213> ORGANISM: Zea mays;

<400> SEQUENCE: 222
cgagagtgta ttatgggag                                                 19

<210> SEQ ID NO 223
<211> LENGTH: 17
<212> TYPE: DNA
<213> ORGANISM: Zea mays;

<400> SEQUENCE: 223
tcctggcaac cgagacc                                                   17

<210> SEQ ID NO 224
```

-continued

<211> LENGTH: 20
<212> TYPE: DNA
<213> ORGANISM: Zea mays;

<400> SEQUENCE: 224
acaggccagc aggcagatag                                                                 20

<210> SEQ ID NO 225
<211> LENGTH: 16
<212> TYPE: DNA
<213> ORGANISM: Zea mays;

<400> SEQUENCE: 225
tgttggtctg cgaggt                                                                     16

<210> SEQ ID NO 226
<211> LENGTH: 18
<212> TYPE: DNA
<213> ORGANISM: Zea mays;

<400> SEQUENCE: 226
tgtgttggtc tacgaggt                                                                   18

<210> SEQ ID NO 227
<211> LENGTH: 18
<212> TYPE: DNA
<213> ORGANISM: Zea mays;

<400> SEQUENCE: 227
cgtcaggtgc ttcaccga                                                                   18

<210> SEQ ID NO 228
<211> LENGTH: 21
<212> TYPE: DNA
<213> ORGANISM: Zea mays;

<400> SEQUENCE: 228
gagggtggag acgcaagata c                                                               21

<210> SEQ ID NO 229
<211> LENGTH: 18
<212> TYPE: DNA
<213> ORGANISM: Zea mays;

<400> SEQUENCE: 229
tcacattcca ttggttgg                                                                   18

<210> SEQ ID NO 230
<211> LENGTH: 17
<212> TYPE: DNA
<213> ORGANISM: Zea mays;

<400> SEQUENCE: 230
cacattccat cggttgg                                                                    17

<210> SEQ ID NO 231
<211> LENGTH: 18
<212> TYPE: DNA
<213> ORGANISM: Zea mays;

<400> SEQUENCE: 231
ggtggaggcg cataggtt                                                                   18

-continued

```
<210> SEQ ID NO 232
<211> LENGTH: 19
<212> TYPE: DNA
<213> ORGANISM: Zea mays;

<400> SEQUENCE: 232
acggcaggag aggaaggaa                                              19

<210> SEQ ID NO 233
<211> LENGTH: 18
<212> TYPE: DNA
<213> ORGANISM: Zea mays;

<400> SEQUENCE: 233
atactatcct ctccggga                                              18

<210> SEQ ID NO 234
<211> LENGTH: 14
<212> TYPE: DNA
<213> ORGANISM: Zea mays;

<400> SEQUENCE: 234
tatcccctcc ggga                                                  14

<210> SEQ ID NO 235
<211> LENGTH: 23
<212> TYPE: DNA
<213> ORGANISM: Zea mays;

<400> SEQUENCE: 235
tgatttggat ttgggaattg gga                                        23

<210> SEQ ID NO 236
<211> LENGTH: 21
<212> TYPE: DNA
<213> ORGANISM: Zea mays;

<400> SEQUENCE: 236
aaacgagcag gtgtttagcc a                                          21

<210> SEQ ID NO 237
<211> LENGTH: 16
<212> TYPE: DNA
<213> ORGANISM: Zea mays;

<400> SEQUENCE: 237
aatgacaccc ccttcc                                                16

<210> SEQ ID NO 238
<211> LENGTH: 15
<212> TYPE: DNA
<213> ORGANISM: Zea mays;

<400> SEQUENCE: 238
atgacacccc ctccc                                                 15

<210> SEQ ID NO 239
<211> LENGTH: 20
<212> TYPE: DNA
<213> ORGANISM: Zea mays;

<400> SEQUENCE: 239
ccaaccattt cttgctgcca                                            20
```

-continued

```
<210> SEQ ID NO 240
<211> LENGTH: 21
<212> TYPE: DNA
<213> ORGANISM: Zea mays;

<400> SEQUENCE: 240
ttgagagctc cgcgaaatga g                                           21

<210> SEQ ID NO 241
<211> LENGTH: 17
<212> TYPE: DNA
<213> ORGANISM: Zea mays;

<400> SEQUENCE: 241
tcaccaagta ctcccta                                                17

<210> SEQ ID NO 242
<211> LENGTH: 16
<212> TYPE: DNA
<213> ORGANISM: Zea mays;

<400> SEQUENCE: 242
caccaagtac tcccca                                                 16

<210> SEQ ID NO 243
<211> LENGTH: 21
<212> TYPE: DNA
<213> ORGANISM: Zea mays;

<400> SEQUENCE: 243
agcaaaggtg cggatgccat t                                           21

<210> SEQ ID NO 244
<211> LENGTH: 24
<212> TYPE: DNA
<213> ORGANISM: Zea mays;

<400> SEQUENCE: 244
gcttccaaat cgctaccttg tttc                                        24

<210> SEQ ID NO 245
<211> LENGTH: 18
<212> TYPE: DNA
<213> ORGANISM: Zea mays;

<400> SEQUENCE: 245
ctcgtatgcc gttttgtt                                               18

<210> SEQ ID NO 246
<211> LENGTH: 18
<212> TYPE: DNA
<213> ORGANISM: Zea mays;

<400> SEQUENCE: 246
tcgtatgcca ttttgttc                                               18

<210> SEQ ID NO 247
<211> LENGTH: 25
<212> TYPE: DNA
<213> ORGANISM: Zea mays;

<400> SEQUENCE: 247
tccatcatca aaccctaaac accag                                       25
```

-continued

```
<210> SEQ ID NO 248
<211> LENGTH: 24
<212> TYPE: DNA
<213> ORGANISM: Zea mays;

<400> SEQUENCE: 248
gaatgccaac catcagaagt caac                                          24

<210> SEQ ID NO 249
<211> LENGTH: 24
<212> TYPE: DNA
<213> ORGANISM: Zea mays;

<400> SEQUENCE: 249
ccatgtatgt tgataatttc taaa                                          24

<210> SEQ ID NO 250
<211> LENGTH: 23
<212> TYPE: DNA
<213> ORGANISM: Zea mays;

<400> SEQUENCE: 250
accatgtatg ttgataactt cta                                           23

<210> SEQ ID NO 251
<211> LENGTH: 23
<212> TYPE: DNA
<213> ORGANISM: Zea mays;

<400> SEQUENCE: 251
gcagtatggc ctatgtttgt tgc                                           23

<210> SEQ ID NO 252
<211> LENGTH: 19
<212> TYPE: DNA
<213> ORGANISM: Zea mays;

<400> SEQUENCE: 252
ccggtaccct ggtgtcgtt                                                19

<210> SEQ ID NO 253
<211> LENGTH: 19
<212> TYPE: DNA
<213> ORGANISM: Zea mays;

<400> SEQUENCE: 253
ttgaaggaga gaggacaga                                                19

<210> SEQ ID NO 254
<211> LENGTH: 20
<212> TYPE: DNA
<213> ORGANISM: Zea mays;

<400> SEQUENCE: 254
tttgaaggag agaggacaaa                                               20

<210> SEQ ID NO 255
<211> LENGTH: 24
<212> TYPE: DNA
<213> ORGANISM: Zea mays;

<400> SEQUENCE: 255
```

-continued

```
aggagcacct catttggtta gaaa                                24

<210> SEQ ID NO 256
<211> LENGTH: 19
<212> TYPE: DNA
<213> ORGANISM: Zea mays;

<400> SEQUENCE: 256
ccgagcgaag tcgagaacc                                      19

<210> SEQ ID NO 257
<211> LENGTH: 18
<212> TYPE: DNA
<213> ORGANISM: Zea mays;

<400> SEQUENCE: 257
ctgaggaacg atcgattc                                       18

<210> SEQ ID NO 258
<211> LENGTH: 18
<212> TYPE: DNA
<213> ORGANISM: Zea mays;

<400> SEQUENCE: 258
tgaggaacga ccgattct                                       18

<210> SEQ ID NO 259
<211> LENGTH: 23
<212> TYPE: DNA
<213> ORGANISM: Zea mays;

<400> SEQUENCE: 259
gctagtcaac acacacccac aag                                 23

<210> SEQ ID NO 260
<211> LENGTH: 21
<212> TYPE: DNA
<213> ORGANISM: Zea mays;

<400> SEQUENCE: 260
ggagccaggc tcatcacata c                                   21

<210> SEQ ID NO 261
<211> LENGTH: 13
<212> TYPE: DNA
<213> ORGANISM: Zea mays;

<400> SEQUENCE: 261
cagtcggagc ggg                                            13

<210> SEQ ID NO 262
<211> LENGTH: 14
<212> TYPE: DNA
<213> ORGANISM: Zea mays;

<400> SEQUENCE: 262
agtcggagca gggc                                           14

<210> SEQ ID NO 263
<211> LENGTH: 24
<212> TYPE: DNA
<213> ORGANISM: Zea mays;

<400> SEQUENCE: 263
```

-continued

```
aactcggttg ttgtcagtct tacc                                    24

<210> SEQ ID NO 264
<211> LENGTH: 20
<212> TYPE: DNA
<213> ORGANISM: Zea mays;

<400> SEQUENCE: 264
ctgaccgacc tgacaggaaa                                         20

<210> SEQ ID NO 265
<211> LENGTH: 20
<212> TYPE: DNA
<213> ORGANISM: Zea mays;

<400> SEQUENCE: 265
cggattctct ctgaatgatg                                         20

<210> SEQ ID NO 266
<211> LENGTH: 19
<212> TYPE: DNA
<213> ORGANISM: Zea mays;

<400> SEQUENCE: 266
acggattctc tccgaatga                                          19

<210> SEQ ID NO 267
<211> LENGTH: 23
<212> TYPE: DNA
<213> ORGANISM: Zea mays;

<400> SEQUENCE: 267
gatttgtgtt cgacagtggg atg                                     23

<210> SEQ ID NO 268
<211> LENGTH: 25
<212> TYPE: DNA
<213> ORGANISM: Zea mays;

<400> SEQUENCE: 268
gcaagcccga accaatataa taacc                                   25

<210> SEQ ID NO 269
<211> LENGTH: 16
<212> TYPE: DNA
<213> ORGANISM: Zea mays;

<400> SEQUENCE: 269
cagtgctttg acctcg                                             16

<210> SEQ ID NO 270
<211> LENGTH: 16
<212> TYPE: DNA
<213> ORGANISM: Zea mays;

<400> SEQUENCE: 270
cagtgctttc acctcg                                             16

<210> SEQ ID NO 271
<211> LENGTH: 24
<212> TYPE: DNA
<213> ORGANISM: Zea mays;
```

-continued

```
<400> SEQUENCE: 271
gccaagatga caagatccaa caac                                          24

<210> SEQ ID NO 272
<211> LENGTH: 19
<212> TYPE: DNA
<213> ORGANISM: Zea mays;

<400> SEQUENCE: 272
tgtccgccat ctccagcat                                                19

<210> SEQ ID NO 273
<211> LENGTH: 18
<212> TYPE: DNA
<213> ORGANISM: Zea mays;

<400> SEQUENCE: 273
cacattgacg ttgatgac                                                 18

<210> SEQ ID NO 274
<211> LENGTH: 17
<212> TYPE: DNA
<213> ORGANISM: Zea mays;

<400> SEQUENCE: 274
cattgacgtt gaggaca                                                  17

<210> SEQ ID NO 275
<211> LENGTH: 18
<212> TYPE: DNA
<213> ORGANISM: Zea mays;

<400> SEQUENCE: 275
gttgacaatg gaaggaga                                                 18

<210> SEQ ID NO 276
<211> LENGTH: 21
<212> TYPE: DNA
<213> ORGANISM: Zea mays;

<400> SEQUENCE: 276
ccggatatgt atatgatgct g                                             21

<210> SEQ ID NO 277
<211> LENGTH: 22
<212> TYPE: DNA
<213> ORGANISM: Zea mays;

<400> SEQUENCE: 277
agtattatag ctaaaaatag ac                                            22

<210> SEQ ID NO 278
<211> LENGTH: 22
<212> TYPE: DNA
<213> ORGANISM: Zea mays;

<400> SEQUENCE: 278
cataagtatt atagctaaaa aa                                            22

<210> SEQ ID NO 279
<211> LENGTH: 25
<212> TYPE: DNA
<213> ORGANISM: Zea mays;
```

```
<400> SEQUENCE: 279
acacatatca caagtcagaa tgctc                                   25

<210> SEQ ID NO 280
<211> LENGTH: 24
<212> TYPE: DNA
<213> ORGANISM: Zea mays;

<400> SEQUENCE: 280
acggttaatt ggtaggcacg gtaa                                    24

<210> SEQ ID NO 281
<211> LENGTH: 15
<212> TYPE: DNA
<213> ORGANISM: Zea mays;

<400> SEQUENCE: 281
cgacattgtg cgctt                                              15

<210> SEQ ID NO 282
<211> LENGTH: 17
<212> TYPE: DNA
<213> ORGANISM: Zea mays;

<400> SEQUENCE: 282
ttcgacattg tacgctt                                            17

<210> SEQ ID NO 283
<211> LENGTH: 23
<212> TYPE: DNA
<213> ORGANISM: Zea mays;

<400> SEQUENCE: 283
tttatgtcag aaagcttgag gca                                     23

<210> SEQ ID NO 284
<211> LENGTH: 22
<212> TYPE: DNA
<213> ORGANISM: Zea mays;

<400> SEQUENCE: 284
tgtcggctaa tcatctcaag ga                                      22

<210> SEQ ID NO 285
<211> LENGTH: 18
<212> TYPE: DNA
<213> ORGANISM: Zea mays;

<400> SEQUENCE: 285
ttcactaacg atgtaatt                                           18

<210> SEQ ID NO 286
<211> LENGTH: 16
<212> TYPE: DNA
<213> ORGANISM: Zea mays;

<400> SEQUENCE: 286
tcactaacga tggaat                                             16

<210> SEQ ID NO 287
<211> LENGTH: 19
<212> TYPE: DNA
```

-continued

```
<213> ORGANISM: Zea mays;

<400> SEQUENCE: 287
agtccctatg ggtttccaa                                              19

<210> SEQ ID NO 288
<211> LENGTH: 18
<212> TYPE: DNA
<213> ORGANISM: Zea mays;

<400> SEQUENCE: 288
cctcttccca tgagaact                                               18

<210> SEQ ID NO 289
<211> LENGTH: 19
<212> TYPE: DNA
<213> ORGANISM: Zea mays;

<400> SEQUENCE: 289
tttatgctag tcaaacttt                                              19

<210> SEQ ID NO 290
<211> LENGTH: 19
<212> TYPE: DNA
<213> ORGANISM: Zea mays;

<400> SEQUENCE: 290
tttatgctag tcaaacatt                                              19

<210> SEQ ID NO 291
<211> LENGTH: 23
<212> TYPE: DNA
<213> ORGANISM: Zea mays;

<400> SEQUENCE: 291
tcagttaagt atcgtctaga ttt                                         23

<210> SEQ ID NO 292
<211> LENGTH: 18
<212> TYPE: DNA
<213> ORGANISM: Zea mays;

<400> SEQUENCE: 292
accgcgatac atcattgg                                               18

<210> SEQ ID NO 293
<211> LENGTH: 17
<212> TYPE: DNA
<213> ORGANISM: Zea mays;

<400> SEQUENCE: 293
ttgagaacct tcagtac                                                17

<210> SEQ ID NO 294
<211> LENGTH: 17
<212> TYPE: DNA
<213> ORGANISM: Zea mays;

<400> SEQUENCE: 294
ttgagaacca tcagtac                                                17

<210> SEQ ID NO 295
<211> LENGTH: 20
```

-continued

```
<212> TYPE: DNA
<213> ORGANISM: Zea mays;

<400> SEQUENCE: 295
cgttgtcagc attggtggac                                          20

<210> SEQ ID NO 296
<211> LENGTH: 20
<212> TYPE: DNA
<213> ORGANISM: Zea mays;

<400> SEQUENCE: 296
gatcgtcgca cggatgtcta                                          20

<210> SEQ ID NO 297
<211> LENGTH: 20
<212> TYPE: DNA
<213> ORGANISM: Zea mays;

<400> SEQUENCE: 297
caaaccatcg aatctgtaac                                          20

<210> SEQ ID NO 298
<211> LENGTH: 19
<212> TYPE: DNA
<213> ORGANISM: Zea mays;

<400> SEQUENCE: 298
accatcgaat ccgtaacaa                                           19

<210> SEQ ID NO 299
<211> LENGTH: 23
<212> TYPE: DNA
<213> ORGANISM: Zea mays;

<400> SEQUENCE: 299
ttgccagagt tgattccacc taa                                      23

<210> SEQ ID NO 300
<211> LENGTH: 21
<212> TYPE: DNA
<213> ORGANISM: Zea mays;

<400> SEQUENCE: 300
ctgcgacatt gcctctaacc a                                        21

<210> SEQ ID NO 301
<211> LENGTH: 15
<212> TYPE: DNA
<213> ORGANISM: Zea mays;

<400> SEQUENCE: 301
atcggactct cggct                                               15

<210> SEQ ID NO 302
<211> LENGTH: 15
<212> TYPE: DNA
<213> ORGANISM: Zea mays;

<400> SEQUENCE: 302
aatcggactc tcagc                                               15

<210> SEQ ID NO 303
```

-continued

```
<211> LENGTH: 21
<212> TYPE: DNA
<213> ORGANISM: Zea mays;

<400> SEQUENCE: 303
caatccggtc tcagtggttg g                                              21

<210> SEQ ID NO 304
<211> LENGTH: 20
<212> TYPE: DNA
<213> ORGANISM: Zea mays;

<400> SEQUENCE: 304
cctgagctgg ctactgatga                                                20

<210> SEQ ID NO 305
<211> LENGTH: 22
<212> TYPE: DNA
<213> ORGANISM: Zea mays;

<400> SEQUENCE: 305
atagcattag attctgagca tt                                             22

<210> SEQ ID NO 306
<211> LENGTH: 20
<212> TYPE: DNA
<213> ORGANISM: Zea mays;

<400> SEQUENCE: 306
agcattagat tctgagcata                                                20

<210> SEQ ID NO 307
<211> LENGTH: 22
<212> TYPE: DNA
<213> ORGANISM: Zea mays;

<400> SEQUENCE: 307
ttcggcgtct acttcctgta tc                                             22

<210> SEQ ID NO 308
<211> LENGTH: 25
<212> TYPE: DNA
<213> ORGANISM: Zea mays;

<400> SEQUENCE: 308
tgctttgtgt tcgtatgcat gaata                                          25

<210> SEQ ID NO 309
<211> LENGTH: 15
<212> TYPE: DNA
<213> ORGANISM: Zea mays;

<400> SEQUENCE: 309
ctgctgctgt ttgca                                                     15

<210> SEQ ID NO 310
<211> LENGTH: 16
<212> TYPE: DNA
<213> ORGANISM: Zea mays;

<400> SEQUENCE: 310
tgctgctgct atttgc                                                    16
```

-continued

```
<210> SEQ ID NO 311
<211> LENGTH: 24
<212> TYPE: DNA
<213> ORGANISM: Zea mays;

<400> SEQUENCE: 311
ccaagacaaa ctctccctgt atgc                                        24

<210> SEQ ID NO 312
<211> LENGTH: 22
<212> TYPE: DNA
<213> ORGANISM: Zea mays;

<400> SEQUENCE: 312
ggctcggaag gtctcaaaga ag                                          22

<210> SEQ ID NO 313
<211> LENGTH: 17
<212> TYPE: DNA
<213> ORGANISM: Zea mays;

<400> SEQUENCE: 313
tggttgtagt attgcaa                                                17

<210> SEQ ID NO 314
<211> LENGTH: 19
<212> TYPE: DNA
<213> ORGANISM: Zea mays;

<400> SEQUENCE: 314
ttggttgtag tattgaaaa                                              19

<210> SEQ ID NO 315
<211> LENGTH: 25
<212> TYPE: DNA
<213> ORGANISM: Zea mays;

<400> SEQUENCE: 315
ggtttgctct tgctgatcga tatgt                                       25

<210> SEQ ID NO 316
<211> LENGTH: 21
<212> TYPE: DNA
<213> ORGANISM: Zea mays;

<400> SEQUENCE: 316
gctcagctac tccctctgtt c                                           21

<210> SEQ ID NO 317
<211> LENGTH: 17
<212> TYPE: DNA
<213> ORGANISM: Zea mays;

<400> SEQUENCE: 317
cgaggtggtg acgatgt                                                17

<210> SEQ ID NO 318
<211> LENGTH: 17
<212> TYPE: DNA
<213> ORGANISM: Zea mays;

<400> SEQUENCE: 318
cgaggtggtc acgatgt                                                17
```

-continued

```
<210> SEQ ID NO 319
<211> LENGTH: 20
<212> TYPE: DNA
<213> ORGANISM: Zea mays;

<400> SEQUENCE: 319
cgggtcaagt tctgctgtga                                                   20

<210> SEQ ID NO 320
<211> LENGTH: 22
<212> TYPE: DNA
<213> ORGANISM: Zea mays;

<400> SEQUENCE: 320
atcatacggc ggaagtagtt ca                                                22

<210> SEQ ID NO 321
<211> LENGTH: 21
<212> TYPE: DNA
<213> ORGANISM: Zea mays;

<400> SEQUENCE: 321
aaacatgaat actcgatctg c                                                 21

<210> SEQ ID NO 322
<211> LENGTH: 20
<212> TYPE: DNA
<213> ORGANISM: Zea mays;

<400> SEQUENCE: 322
caaacatgaa tacccgatct                                                   20

<210> SEQ ID NO 323
<211> LENGTH: 21
<212> TYPE: DNA
<213> ORGANISM: Zea mays;

<400> SEQUENCE: 323
tggcttgagc cattacctga t                                                 21

<210> SEQ ID NO 324
<211> LENGTH: 22
<212> TYPE: DNA
<213> ORGANISM: Zea mays;

<400> SEQUENCE: 324
gaaactgcaa gaggcatgaa ac                                                22

<210> SEQ ID NO 325
<211> LENGTH: 19
<212> TYPE: DNA
<213> ORGANISM: Zea mays;

<400> SEQUENCE: 325
tgatgcgatt tcgttgaat                                                    19

<210> SEQ ID NO 326
<211> LENGTH: 20
<212> TYPE: DNA
<213> ORGANISM: Zea mays;

<400> SEQUENCE: 326
cgtgatgcga tttagttgaa                                                   20
```

```
<210> SEQ ID NO 327
<211> LENGTH: 22
<212> TYPE: DNA
<213> ORGANISM: Zea mays;

<400> SEQUENCE: 327
cggattacaa ctctctgttg cc                                       22

<210> SEQ ID NO 328
<211> LENGTH: 24
<212> TYPE: DNA
<213> ORGANISM: Zea mays;

<400> SEQUENCE: 328
cacactcaag gtgacttaga ccaa                                     24

<210> SEQ ID NO 329
<211> LENGTH: 18
<212> TYPE: DNA
<213> ORGANISM: Zea mays;

<400> SEQUENCE: 329
cagttgtttg tatagaca                                            18

<210> SEQ ID NO 330
<211> LENGTH: 20
<212> TYPE: DNA
<213> ORGANISM: Zea mays;

<400> SEQUENCE: 330
atacagttgt ttgtataaac                                          20

<210> SEQ ID NO 331
<211> LENGTH: 17
<212> TYPE: DNA
<213> ORGANISM: Zea mays;

<400> SEQUENCE: 331
ggattggacc agcagat                                             17

<210> SEQ ID NO 332
<211> LENGTH: 19
<212> TYPE: DNA
<213> ORGANISM: Zea mays;

<400> SEQUENCE: 332
gtgagacaag gctacatac                                           19

<210> SEQ ID NO 333
<211> LENGTH: 11
<212> TYPE: DNA
<213> ORGANISM: Zea mays;

<400> SEQUENCE: 333
ccggccgcag t                                                   11

<210> SEQ ID NO 334
<211> LENGTH: 13
<212> TYPE: DNA
<213> ORGANISM: Zea mays;

<400> SEQUENCE: 334
```

-continued ccgcagcggt gat                                                    13

<210> SEQ ID NO 335
<211> LENGTH: 19
<212> TYPE: DNA
<213> ORGANISM: Zea mays;

<400> SEQUENCE: 335
cgtcgcggtc ctctctgat                                             19

<210> SEQ ID NO 336
<211> LENGTH: 21
<212> TYPE: DNA
<213> ORGANISM: Zea mays;

<400> SEQUENCE: 336
ctgcgaatcg tccatcctgt a                                          21

<210> SEQ ID NO 337
<211> LENGTH: 18
<212> TYPE: DNA
<213> ORGANISM: Zea mays;

<400> SEQUENCE: 337
ccttgtgaga aaactcta                                              18

<210> SEQ ID NO 338
<211> LENGTH: 18
<212> TYPE: DNA
<213> ORGANISM: Zea mays;

<400> SEQUENCE: 338
cttgtgagaa aaccctag                                              18

<210> SEQ ID NO 339
<211> LENGTH: 16
<212> TYPE: DNA
<213> ORGANISM: Zea mays;

<400> SEQUENCE: 339
gtgcaatggc tgactc                                                16

<210> SEQ ID NO 340
<211> LENGTH: 20
<212> TYPE: DNA
<213> ORGANISM: Zea mays;

<400> SEQUENCE: 340
gcacgattat gcatgattag                                            20

<210> SEQ ID NO 341
<211> LENGTH: 18
<212> TYPE: DNA
<213> ORGANISM: Zea mays;

<400> SEQUENCE: 341
tcaaagctag gtttatgc                                              18

<210> SEQ ID NO 342
<211> LENGTH: 18
<212> TYPE: DNA
<213> ORGANISM: Zea mays;

<400> SEQUENCE: 342

-continued

```
tcaaagctag gtttaggc                                              18

<210> SEQ ID NO 343
<211> LENGTH: 21
<212> TYPE: DNA
<213> ORGANISM: Zea mays;

<400> SEQUENCE: 343
agggttaggg tttcacttcc a                                          21

<210> SEQ ID NO 344
<211> LENGTH: 19
<212> TYPE: DNA
<213> ORGANISM: Zea mays;

<400> SEQUENCE: 344
agcactggcg aggctacag                                             19

<210> SEQ ID NO 345
<211> LENGTH: 21
<212> TYPE: DNA
<213> ORGANISM: Zea mays;

<400> SEQUENCE: 345
agatctgatt ggtatagggc a                                          21

<210> SEQ ID NO 346
<211> LENGTH: 17
<212> TYPE: DNA
<213> ORGANISM: Zea mays;

<400> SEQUENCE: 346
ctgattggta cagggca                                               17

<210> SEQ ID NO 347
<211> LENGTH: 19
<212> TYPE: DNA
<213> ORGANISM: Zea mays;

<400> SEQUENCE: 347
aaggcagagg tgcttcggt                                             19

<210> SEQ ID NO 348
<211> LENGTH: 24
<212> TYPE: DNA
<213> ORGANISM: Zea mays;

<400> SEQUENCE: 348
gtgctgcatt tctaaggtgt caag                                       24

<210> SEQ ID NO 349
<211> LENGTH: 22
<212> TYPE: DNA
<213> ORGANISM: Zea mays;

<400> SEQUENCE: 349
ctagggaagt tgtcgtttga aa                                         22

<210> SEQ ID NO 350
<211> LENGTH: 19
<212> TYPE: DNA
<213> ORGANISM: Zea mays;
```

-continued

<400> SEQUENCE: 350
agggaagttg tcgcttgaa                                             19

<210> SEQ ID NO 351
<211> LENGTH: 21
<212> TYPE: DNA
<213> ORGANISM: Zea mays;

<400> SEQUENCE: 351
ggtgcaggca agagagcatt t                                          21

<210> SEQ ID NO 352
<211> LENGTH: 25
<212> TYPE: DNA
<213> ORGANISM: Zea mays;

<400> SEQUENCE: 352
tggattatat ggaaggtccg aaggt                                      25

<210> SEQ ID NO 353
<211> LENGTH: 15
<212> TYPE: DNA
<213> ORGANISM: Zea mays;

<400> SEQUENCE: 353
aggcggcgac caact                                                 15

<210> SEQ ID NO 354
<211> LENGTH: 15
<212> TYPE: DNA
<213> ORGANISM: Zea mays;

<400> SEQUENCE: 354
aggcggccac caact                                                 15

<210> SEQ ID NO 355
<211> LENGTH: 18
<212> TYPE: DNA
<213> ORGANISM: Zea mays;

<400> SEQUENCE: 355
acgttcgccg acgaggag                                              18

<210> SEQ ID NO 356
<211> LENGTH: 20
<212> TYPE: DNA
<213> ORGANISM: Zea mays;

<400> SEQUENCE: 356
cgcagcatgt cgacgatctc                                            20

<210> SEQ ID NO 357
<211> LENGTH: 19
<212> TYPE: DNA
<213> ORGANISM: Zea mays;

<400> SEQUENCE: 357
agcggagcaa tgactactt                                             19

<210> SEQ ID NO 358
<211> LENGTH: 17
<212> TYPE: DNA
<213> ORGANISM: Zea mays;

-continued

```
<400> SEQUENCE: 358
cggagcaacg actactt                                          17

<210> SEQ ID NO 359
<211> LENGTH: 17
<212> TYPE: DNA
<213> ORGANISM: Zea mays;

<400> SEQUENCE: 359
ggtgcacacc ggactgt                                          17

<210> SEQ ID NO 360
<211> LENGTH: 19
<212> TYPE: DNA
<213> ORGANISM: Zea mays;

<400> SEQUENCE: 360
caactgcgcg tcctctgtc                                        19

<210> SEQ ID NO 361
<211> LENGTH: 19
<212> TYPE: DNA
<213> ORGANISM: Zea mays;

<400> SEQUENCE: 361
ccagtttctt ctgtgagtg                                        19

<210> SEQ ID NO 362
<211> LENGTH: 18
<212> TYPE: DNA
<213> ORGANISM: Zea mays;

<400> SEQUENCE: 362
cagtttcttc cgtgagtg                                         18

<210> SEQ ID NO 363
<211> LENGTH: 23
<212> TYPE: DNA
<213> ORGANISM: Zea mays;

<400> SEQUENCE: 363
tgcatctgag ttcctgattg ttg                                   23

<210> SEQ ID NO 364
<211> LENGTH: 18
<212> TYPE: DNA
<213> ORGANISM: Zea mays;

<400> SEQUENCE: 364
ccgcagcacg acatcctt                                         18

<210> SEQ ID NO 365
<211> LENGTH: 23
<212> TYPE: DNA
<213> ORGANISM: Zea mays;

<400> SEQUENCE: 365
ccatatatag gttagttgat cga                                   23

<210> SEQ ID NO 366
<211> LENGTH: 24
<212> TYPE: DNA
```

-continued

<213> ORGANISM: Zea mays;

<400> SEQUENCE: 366
ccatatatag gttagttcat cgat                                                    24

<210> SEQ ID NO 367
<211> LENGTH: 23
<212> TYPE: DNA
<213> ORGANISM: Zea mays;

<400> SEQUENCE: 367
gcggtgagta caagttaatc caa                                                     23

<210> SEQ ID NO 368
<211> LENGTH: 23
<212> TYPE: DNA
<213> ORGANISM: Zea mays;

<400> SEQUENCE: 368
gccgtcactt gacttgattc ttc                                                     23

<210> SEQ ID NO 369
<211> LENGTH: 12
<212> TYPE: DNA
<213> ORGANISM: Zea mays;

<400> SEQUENCE: 369
acccagcccc ct                                                                 12

<210> SEQ ID NO 370
<211> LENGTH: 12
<212> TYPE: DNA
<213> ORGANISM: Zea mays;

<400> SEQUENCE: 370
acccagcccc cg                                                                 12

<210> SEQ ID NO 371
<211> LENGTH: 21
<212> TYPE: DNA
<213> ORGANISM: Zea mays;

<400> SEQUENCE: 371
tgatctggct cacgtgggta g                                                       21

<210> SEQ ID NO 372
<211> LENGTH: 20
<212> TYPE: DNA
<213> ORGANISM: Zea mays;

<400> SEQUENCE: 372
cgcatgaacg tccatggaag                                                         20

<210> SEQ ID NO 373
<211> LENGTH: 18
<212> TYPE: DNA
<213> ORGANISM: Zea mays;

<400> SEQUENCE: 373
cacatgcaca gtgctata                                                           18

<210> SEQ ID NO 374
<211> LENGTH: 19

-continued

<212> TYPE: DNA
<213> ORGANISM: Zea mays;

<400> SEQUENCE: 374
ccacatgcac agtactata                                           19

<210> SEQ ID NO 375
<211> LENGTH: 22
<212> TYPE: DNA
<213> ORGANISM: Zea mays;

<400> SEQUENCE: 375
gagacccagc tagagagttg ac                                       22

<210> SEQ ID NO 376
<211> LENGTH: 19
<212> TYPE: DNA
<213> ORGANISM: Zea mays;

<400> SEQUENCE: 376
tgggcacata ggccagtag                                           19

<210> SEQ ID NO 377
<211> LENGTH: 16
<212> TYPE: DNA
<213> ORGANISM: Zea mays;

<400> SEQUENCE: 377
tgcaaacagg agcatg                                              16

<210> SEQ ID NO 378
<211> LENGTH: 19
<212> TYPE: DNA
<213> ORGANISM: Zea mays;

<400> SEQUENCE: 378
aaatgcaaac aggaacatg                                           19

<210> SEQ ID NO 379
<211> LENGTH: 19
<212> TYPE: DNA
<213> ORGANISM: Zea mays;

<400> SEQUENCE: 379
gttgctgaaa tgctaatgg                                           19

<210> SEQ ID NO 380
<211> LENGTH: 16
<212> TYPE: DNA
<213> ORGANISM: Zea mays;

<400> SEQUENCE: 380
gtgtcgtcgt cttctc                                              16

<210> SEQ ID NO 381
<211> LENGTH: 14
<212> TYPE: DNA
<213> ORGANISM: Zea mays;

<400> SEQUENCE: 381
ccaccaccgg aatt                                                14

<210> SEQ ID NO 382

-continued

```
<211> LENGTH: 14
<212> TYPE: DNA
<213> ORGANISM: Zea mays;

<400> SEQUENCE: 382
caccaccgca attg                                                        14

<210> SEQ ID NO 383
<211> LENGTH: 20
<212> TYPE: DNA
<213> ORGANISM: Zea mays;

<400> SEQUENCE: 383
gagttcatca agtagctcgt                                                  20

<210> SEQ ID NO 384
<211> LENGTH: 17
<212> TYPE: DNA
<213> ORGANISM: Zea mays;

<400> SEQUENCE: 384
tgcacatcag cattctc                                                     17

<210> SEQ ID NO 385
<211> LENGTH: 19
<212> TYPE: DNA
<213> ORGANISM: Zea mays;

<400> SEQUENCE: 385
cggttaccat tgttgtgta                                                   19

<210> SEQ ID NO 386
<211> LENGTH: 20
<212> TYPE: DNA
<213> ORGANISM: Zea mays;

<400> SEQUENCE: 386
tcggttacca ttattgtgta                                                  20

<210> SEQ ID NO 387
<211> LENGTH: 25
<212> TYPE: DNA
<213> ORGANISM: Zea mays;

<400> SEQUENCE: 387
ccttgtttga aacctccttg tgttg                                            25

<210> SEQ ID NO 388
<211> LENGTH: 19
<212> TYPE: DNA
<213> ORGANISM: Zea mays;

<400> SEQUENCE: 388
gtccaggtcg ccttactga                                                   19

<210> SEQ ID NO 389
<211> LENGTH: 15
<212> TYPE: DNA
<213> ORGANISM: Zea mays;

<400> SEQUENCE: 389
tacaaagccg ggttg                                                       15
```

-continued

```
<210> SEQ ID NO 390
<211> LENGTH: 16
<212> TYPE: DNA
<213> ORGANISM: Zea mays;

<400> SEQUENCE: 390
tacaaagccg ggatgt                                                        16

<210> SEQ ID NO 391
<211> LENGTH: 20
<212> TYPE: DNA
<213> ORGANISM: Zea mays;

<400> SEQUENCE: 391
gaactgattc atctgggtaa                                                    20

<210> SEQ ID NO 392
<211> LENGTH: 16
<212> TYPE: DNA
<213> ORGANISM: Zea mays;

<400> SEQUENCE: 392
ctcctgctgt ggtcac                                                        16

<210> SEQ ID NO 393
<211> LENGTH: 22
<212> TYPE: DNA
<213> ORGANISM: Zea mays;

<400> SEQUENCE: 393
caagtgaaat ggtatataat ac                                                 22

<210> SEQ ID NO 394
<211> LENGTH: 21
<212> TYPE: DNA
<213> ORGANISM: Zea mays;

<400> SEQUENCE: 394
aagtgaaatg gtatataaca c                                                  21

<210> SEQ ID NO 395
<211> LENGTH: 21
<212> TYPE: DNA
<213> ORGANISM: Zea mays;

<400> SEQUENCE: 395
catgccacaa ttgcagaagc a                                                  21

<210> SEQ ID NO 396
<211> LENGTH: 23
<212> TYPE: DNA
<213> ORGANISM: Zea mays;

<400> SEQUENCE: 396
gcatagctca acatgtgaac tca                                                23

<210> SEQ ID NO 397
<211> LENGTH: 14
<212> TYPE: DNA
<213> ORGANISM: Zea mays;

<400> SEQUENCE: 397
ccggctcaag ccta                                                          14
```

-continued

```
<210> SEQ ID NO 398
<211> LENGTH: 14
<212> TYPE: DNA
<213> ORGANISM: Zea mays;

<400> SEQUENCE: 398
ccggcacaag ccta                                                    14

<210> SEQ ID NO 399
<211> LENGTH: 19
<212> TYPE: DNA
<213> ORGANISM: Zea mays;

<400> SEQUENCE: 399
cgccctagtg ctgggaatc                                               19

<210> SEQ ID NO 400
<211> LENGTH: 22
<212> TYPE: DNA
<213> ORGANISM: Zea mays;

<400> SEQUENCE: 400
ggaccgacac gatccaataa ag                                           22

<210> SEQ ID NO 401
<211> LENGTH: 15
<212> TYPE: DNA
<213> ORGANISM: Zea mays;

<400> SEQUENCE: 401
cgggcggagt acgtg                                                   15

<210> SEQ ID NO 402
<211> LENGTH: 14
<212> TYPE: DNA
<213> ORGANISM: Zea mays;

<400> SEQUENCE: 402
cgggcggact acgt                                                    14

<210> SEQ ID NO 403
<211> LENGTH: 16
<212> TYPE: DNA
<213> ORGANISM: Zea mays;

<400> SEQUENCE: 403
agagggcgcg gtctga                                                  16

<210> SEQ ID NO 404
<211> LENGTH: 19
<212> TYPE: DNA
<213> ORGANISM: Zea mays;

<400> SEQUENCE: 404
tggtcgcact tccttcttc                                               19

<210> SEQ ID NO 405
<211> LENGTH: 14
<212> TYPE: DNA
<213> ORGANISM: Zea mays;

<400> SEQUENCE: 405
cgacagcgga ggag                                                    14
```

-continued

```
<210> SEQ ID NO 406
<211> LENGTH: 15
<212> TYPE: DNA
<213> ORGANISM: Zea mays;

<400> SEQUENCE: 406
cgacagcgga agagg                                                    15

<210> SEQ ID NO 407
<211> LENGTH: 17
<212> TYPE: DNA
<213> ORGANISM: Zea mays;

<400> SEQUENCE: 407
ctcgtgcttg ctttacg                                                  17

<210> SEQ ID NO 408
<211> LENGTH: 17
<212> TYPE: DNA
<213> ORGANISM: Zea mays;

<400> SEQUENCE: 408
cgcaagaggt tgatagg                                                  17

<210> SEQ ID NO 409
<211> LENGTH: 15
<212> TYPE: DNA
<213> ORGANISM: Zea mays;

<400> SEQUENCE: 409
accagctact gcagc                                                    15

<210> SEQ ID NO 410
<211> LENGTH: 14
<212> TYPE: DNA
<213> ORGANISM: Zea mays;

<400> SEQUENCE: 410
ccagcgactg cagc                                                     14

<210> SEQ ID NO 411
<211> LENGTH: 19
<212> TYPE: DNA
<213> ORGANISM: Zea mays;

<400> SEQUENCE: 411
gtccctgccc gttttgtct                                                19

<210> SEQ ID NO 412
<211> LENGTH: 21
<212> TYPE: DNA
<213> ORGANISM: Zea mays;

<400> SEQUENCE: 412
acacctctcc gtcgtatcaa g                                             21

<210> SEQ ID NO 413
<211> LENGTH: 21
<212> TYPE: DNA
<213> ORGANISM: Zea mays;

<400> SEQUENCE: 413
```

-continued

```
tcattgtaat ccatattacg t                                             21

<210> SEQ ID NO 414
<211> LENGTH: 20
<212> TYPE: DNA
<213> ORGANISM: Zea mays;

<400> SEQUENCE: 414
cattgtaatc catactacgt                                               20

<210> SEQ ID NO 415
<211> LENGTH: 21
<212> TYPE: DNA
<213> ORGANISM: Zea mays;

<400> SEQUENCE: 415
gccaacagtt cactcccagt a                                             21

<210> SEQ ID NO 416
<211> LENGTH: 25
<212> TYPE: DNA
<213> ORGANISM: Zea mays;

<400> SEQUENCE: 416
acttgttacc tttccttgct agaca                                         25

<210> SEQ ID NO 417
<211> LENGTH: 21
<212> TYPE: DNA
<213> ORGANISM: Zea mays;

<400> SEQUENCE: 417
ttactggtac ttagatatat g                                             21

<210> SEQ ID NO 418
<211> LENGTH: 20
<212> TYPE: DNA
<213> ORGANISM: Zea mays;

<400> SEQUENCE: 418
tactggtact tagatagatg                                               20

<210> SEQ ID NO 419
<211> LENGTH: 21
<212> TYPE: DNA
<213> ORGANISM: Zea mays;

<400> SEQUENCE: 419
agatacatga agtaacatgc t                                             21

<210> SEQ ID NO 420
<211> LENGTH: 21
<212> TYPE: DNA
<213> ORGANISM: Zea mays;

<400> SEQUENCE: 420
ggtactcaag aacaattaac c                                             21

<210> SEQ ID NO 421
<211> LENGTH: 18
<212> TYPE: DNA
<213> ORGANISM: Zea mays;

<400> SEQUENCE: 421
```
tcaaagaatc tccggtca 18

<210> SEQ ID NO 422
<211> LENGTH: 17
<212> TYPE: DNA
<213> ORGANISM: Zea mays;

<400> SEQUENCE: 422
caaagaatcc ccggtca 17

<210> SEQ ID NO 423
<211> LENGTH: 20
<212> TYPE: DNA
<213> ORGANISM: Zea mays;

<400> SEQUENCE: 423
ggactgtgcg tagtatgagc 20

<210> SEQ ID NO 424
<211> LENGTH: 22
<212> TYPE: DNA
<213> ORGANISM: Zea mays;

<400> SEQUENCE: 424
gtcacgtcta tcctccagtt ca 22

<210> SEQ ID NO 425
<211> LENGTH: 14
<212> TYPE: DNA
<213> ORGANISM: Zea mays;

<400> SEQUENCE: 425
accccgacac tgct 14

<210> SEQ ID NO 426
<211> LENGTH: 14
<212> TYPE: DNA
<213> ORGANISM: Zea mays;

<400> SEQUENCE: 426
caccccaaca ctgc 14

<210> SEQ ID NO 427
<211> LENGTH: 17
<212> TYPE: DNA
<213> ORGANISM: Zea mays;

<400> SEQUENCE: 427
gtcgacgacg gtgaagc 17

<210> SEQ ID NO 428
<211> LENGTH: 18
<212> TYPE: DNA
<213> ORGANISM: Zea mays;

<400> SEQUENCE: 428
cacgctcgag gtgatcca 18

<210> SEQ ID NO 429
<211> LENGTH: 21
<212> TYPE: DNA
<213> ORGANISM: Zea mays;

-continued

```
<400> SEQUENCE: 429
aagttatctt ccattgtagt g                                              21

<210> SEQ ID NO 430
<211> LENGTH: 18
<212> TYPE: DNA
<213> ORGANISM: Zea mays;

<400> SEQUENCE: 430
agttatcttc cattgcag                                                  18

<210> SEQ ID NO 431
<211> LENGTH: 20
<212> TYPE: DNA
<213> ORGANISM: Zea mays;

<400> SEQUENCE: 431
catgtttatt ttgagagcca                                                20

<210> SEQ ID NO 432
<211> LENGTH: 17
<212> TYPE: DNA
<213> ORGANISM: Zea mays;

<400> SEQUENCE: 432
gaaacgtgtt gctgaag                                                   17

<210> SEQ ID NO 433
<211> LENGTH: 14
<212> TYPE: DNA
<213> ORGANISM: Zea mays;

<400> SEQUENCE: 433
cgacagcctt cgat                                                      14

<210> SEQ ID NO 434
<211> LENGTH: 14
<212> TYPE: DNA
<213> ORGANISM: Zea mays;

<400> SEQUENCE: 434
cgacagcctt caat                                                      14

<210> SEQ ID NO 435
<211> LENGTH: 17
<212> TYPE: DNA
<213> ORGANISM: Zea mays;

<400> SEQUENCE: 435
ctagccgaac tgtccta                                                   17

<210> SEQ ID NO 436
<211> LENGTH: 17
<212> TYPE: DNA
<213> ORGANISM: Zea mays;

<400> SEQUENCE: 436
cacaccaacg gatcaag                                                   17

<210> SEQ ID NO 437
<211> LENGTH: 17
<212> TYPE: DNA
<213> ORGANISM: Zea mays;
```

-continued

```
<400> SEQUENCE: 437
cggtgacgaa tactgat                                          17

<210> SEQ ID NO 438
<211> LENGTH: 17
<212> TYPE: DNA
<213> ORGANISM: Zea mays;

<400> SEQUENCE: 438
cggtgacgaa tactgac                                          17

<210> SEQ ID NO 439
<211> LENGTH: 19
<212> TYPE: DNA
<213> ORGANISM: Zea mays;

<400> SEQUENCE: 439
gaaacatccc aacaacatc                                        19

<210> SEQ ID NO 440
<211> LENGTH: 16
<212> TYPE: DNA
<213> ORGANISM: Zea mays;

<400> SEQUENCE: 440
agccttgcta gtgctg                                           16

<210> SEQ ID NO 441
<211> LENGTH: 20
<212> TYPE: DNA
<213> ORGANISM: Zea mays;

<400> SEQUENCE: 441
catcagaggg aatataattt                                       20

<210> SEQ ID NO 442
<211> LENGTH: 19
<212> TYPE: DNA
<213> ORGANISM: Zea mays;

<400> SEQUENCE: 442
catcagaggg aatagaatt                                        19

<210> SEQ ID NO 443
<211> LENGTH: 23
<212> TYPE: DNA
<213> ORGANISM: Zea mays;

<400> SEQUENCE: 443
agctatattt tagagaccgt gtt                                   23

<210> SEQ ID NO 444
<211> LENGTH: 15
<212> TYPE: DNA
<213> ORGANISM: Zea mays;

<400> SEQUENCE: 444
gcacgatgac gatga                                            15

<210> SEQ ID NO 445
<211> LENGTH: 19
<212> TYPE: DNA
```

-continued

```
<213> ORGANISM: Zea mays;

<400> SEQUENCE: 445
cggtaacatg tagaatgca                                             19

<210> SEQ ID NO 446
<211> LENGTH: 18
<212> TYPE: DNA
<213> ORGANISM: Zea mays;

<400> SEQUENCE: 446
cggtaacatg tagaacgc                                              18

<210> SEQ ID NO 447
<211> LENGTH: 22
<212> TYPE: DNA
<213> ORGANISM: Zea mays;

<400> SEQUENCE: 447
tgaatgctct cagatgccac at                                         22

<210> SEQ ID NO 448
<211> LENGTH: 22
<212> TYPE: DNA
<213> ORGANISM: Zea mays;

<400> SEQUENCE: 448
agcagcttca agaaacaaag ga                                         22

<210> SEQ ID NO 449
<211> LENGTH: 14
<212> TYPE: DNA
<213> ORGANISM: Zea mays;

<400> SEQUENCE: 449
actgcgcgtt gcaa                                                  14

<210> SEQ ID NO 450
<211> LENGTH: 16
<212> TYPE: DNA
<213> ORGANISM: Zea mays;

<400> SEQUENCE: 450
ctactgcgca ttgcaa                                                16

<210> SEQ ID NO 451
<211> LENGTH: 15
<212> TYPE: DNA
<213> ORGANISM: Zea mays;

<400> SEQUENCE: 451
ggccgccaag gtgct                                                 15

<210> SEQ ID NO 452
<211> LENGTH: 20
<212> TYPE: DNA
<213> ORGANISM: Zea mays;

<400> SEQUENCE: 452
gcctggtcga tcctgatgac                                            20

<210> SEQ ID NO 453
<211> LENGTH: 15
```

-continued

```
<212> TYPE: DNA
<213> ORGANISM: Zea mays;

<400> SEQUENCE: 453
catgggccgt gacct                                              15

<210> SEQ ID NO 454
<211> LENGTH: 14
<212> TYPE: DNA
<213> ORGANISM: Zea mays;

<400> SEQUENCE: 454
atgggccgcg acct                                               14

<210> SEQ ID NO 455
<211> LENGTH: 24
<212> TYPE: DNA
<213> ORGANISM: Zea mays;

<400> SEQUENCE: 455
cctttaacag gttgtactca tgcc                                    24

<210> SEQ ID NO 456
<211> LENGTH: 18
<212> TYPE: DNA
<213> ORGANISM: Zea mays;

<400> SEQUENCE: 456
tcgagtcagc acggttcg                                           18

<210> SEQ ID NO 457
<211> LENGTH: 15
<212> TYPE: DNA
<213> ORGANISM: Zea mays;

<400> SEQUENCE: 457
caacctcacg aacct                                              15

<210> SEQ ID NO 458
<211> LENGTH: 15
<212> TYPE: DNA
<213> ORGANISM: Zea mays;

<400> SEQUENCE: 458
cggcaacctc acaaa                                              15

<210> SEQ ID NO 459
<211> LENGTH: 21
<212> TYPE: DNA
<213> ORGANISM: Zea mays;

<400> SEQUENCE: 459
caacctgagc ttcaacagcc t                                       21

<210> SEQ ID NO 460
<211> LENGTH: 15
<212> TYPE: DNA
<213> ORGANISM: Zea mays;

<400> SEQUENCE: 460
ggcggttgct ggaca                                              15

<210> SEQ ID NO 461
```

-continued

```
<211> LENGTH: 17
<212> TYPE: DNA
<213> ORGANISM: Zea mays;

<400> SEQUENCE: 461
attctcaaag ccgtaga                                                    17

<210> SEQ ID NO 462
<211> LENGTH: 19
<212> TYPE: DNA
<213> ORGANISM: Zea mays;

<400> SEQUENCE: 462
agattctcaa aaccgtaga                                                  19

<210> SEQ ID NO 463
<211> LENGTH: 20
<212> TYPE: DNA
<213> ORGANISM: Zea mays;

<400> SEQUENCE: 463
ggcagtttcc gatgtccaga                                                 20

<210> SEQ ID NO 464
<211> LENGTH: 20
<212> TYPE: DNA
<213> ORGANISM: Zea mays;

<400> SEQUENCE: 464
gaacctgacc acgcttcttc                                                 20

<210> SEQ ID NO 465
<211> LENGTH: 17
<212> TYPE: DNA
<213> ORGANISM: Zea mays;

<400> SEQUENCE: 465
cacacaccga gagagag                                                    17

<210> SEQ ID NO 466
<211> LENGTH: 16
<212> TYPE: DNA
<213> ORGANISM: Zea mays;

<400> SEQUENCE: 466
ccacacaccg agaaag                                                     16

<210> SEQ ID NO 467
<211> LENGTH: 20
<212> TYPE: DNA
<213> ORGANISM: Zea mays;

<400> SEQUENCE: 467
agcacacgtt ctcttccaaa                                                 20

<210> SEQ ID NO 468
<211> LENGTH: 21
<212> TYPE: DNA
<213> ORGANISM: Zea mays;

<400> SEQUENCE: 468
cgggttcatc ctcttcgtgg t                                               21
```

```
<210> SEQ ID NO 469
<211> LENGTH: 15
<212> TYPE: DNA
<213> ORGANISM: Zea mays;

<400> SEQUENCE: 469
ctgaagctgc ctcaa                                                      15

<210> SEQ ID NO 470
<211> LENGTH: 13
<212> TYPE: DNA
<213> ORGANISM: Zea mays;

<400> SEQUENCE: 470
tgaagctgcc cca                                                        13

<210> SEQ ID NO 471
<211> LENGTH: 23
<212> TYPE: DNA
<213> ORGANISM: Zea mays;

<400> SEQUENCE: 471
agcaaataaa tttagatgga aca                                             23

<210> SEQ ID NO 472
<211> LENGTH: 20
<212> TYPE: DNA
<213> ORGANISM: Zea mays;

<400> SEQUENCE: 472
gtcaaggtga atatgtccta                                                 20

<210> SEQ ID NO 473
<211> LENGTH: 16
<212> TYPE: DNA
<213> ORGANISM: Zea mays;

<400> SEQUENCE: 473
agccagaaaa cgggca                                                     16

<210> SEQ ID NO 474
<211> LENGTH: 19
<212> TYPE: DNA
<213> ORGANISM: Zea mays;

<400> SEQUENCE: 474
acaagccaga aaacggaca                                                  19

<210> SEQ ID NO 475
<211> LENGTH: 18
<212> TYPE: DNA
<213> ORGANISM: Zea mays;

<400> SEQUENCE: 475
gcgcgtacct gattcaca                                                   18

<210> SEQ ID NO 476
<211> LENGTH: 22
<212> TYPE: DNA
<213> ORGANISM: Zea mays;

<400> SEQUENCE: 476
agccagcagc tgaagagaag ac                                              22
```

-continued

```
<210> SEQ ID NO 477
<211> LENGTH: 14
<212> TYPE: DNA
<213> ORGANISM: Zea mays;

<400> SEQUENCE: 477
ccgccaggtc cgat                                                        14

<210> SEQ ID NO 478
<211> LENGTH: 14
<212> TYPE: DNA
<213> ORGANISM: Zea mays;

<400> SEQUENCE: 478
cgccacgtcc gatg                                                        14

<210> SEQ ID NO 479
<211> LENGTH: 16
<212> TYPE: DNA
<213> ORGANISM: Zea mays;

<400> SEQUENCE: 479
tgggcagcct caccgt                                                      16

<210> SEQ ID NO 480
<211> LENGTH: 19
<212> TYPE: DNA
<213> ORGANISM: Zea mays;

<400> SEQUENCE: 480
cggagctgga aaggatgga                                                   19

<210> SEQ ID NO 481
<211> LENGTH: 21
<212> TYPE: DNA
<213> ORGANISM: Zea mays;

<400> SEQUENCE: 481
caatagtgaa tattgtagtt t                                                21

<210> SEQ ID NO 482
<211> LENGTH: 21
<212> TYPE: DNA
<213> ORGANISM: Zea mays;

<400> SEQUENCE: 482
caatagtgaa tattgtaatt t                                                21

<210> SEQ ID NO 483
<211> LENGTH: 24
<212> TYPE: DNA
<213> ORGANISM: Zea mays;

<400> SEQUENCE: 483
agcagaaaaa cattgggact gtac                                             24

<210> SEQ ID NO 484
<211> LENGTH: 21
<212> TYPE: DNA
<213> ORGANISM: Zea mays;

<400> SEQUENCE: 484
agcctgaagc tgtggatctt c                                                21
```

-continued

```
<210> SEQ ID NO 485
<211> LENGTH: 14
<212> TYPE: DNA
<213> ORGANISM: Zea mays;

<400> SEQUENCE: 485
ctcaccgtgg accg                                              14

<210> SEQ ID NO 486
<211> LENGTH: 15
<212> TYPE: DNA
<213> ORGANISM: Zea mays;

<400> SEQUENCE: 486
cctcacagtg gaccg                                             15

<210> SEQ ID NO 487
<211> LENGTH: 19
<212> TYPE: DNA
<213> ORGANISM: Zea mays;

<400> SEQUENCE: 487
catccgcaag gtcctgctc                                         19

<210> SEQ ID NO 488
<211> LENGTH: 21
<212> TYPE: DNA
<213> ORGANISM: Zea mays;

<400> SEQUENCE: 488
gggcgatcga gttgtgcttt g                                      21

<210> SEQ ID NO 489
<211> LENGTH: 21
<212> TYPE: DNA
<213> ORGANISM: Zea mays;

<400> SEQUENCE: 489
cctaaacaga tgtattatat a                                      21

<210> SEQ ID NO 490
<211> LENGTH: 19
<212> TYPE: DNA
<213> ORGANISM: Zea mays;

<400> SEQUENCE: 490
cctaaacaga tgtactata                                         19

<210> SEQ ID NO 491
<211> LENGTH: 21
<212> TYPE: DNA
<213> ORGANISM: Zea mays;

<400> SEQUENCE: 491
agttgtgcca agggctagtt g                                      21

<210> SEQ ID NO 492
<211> LENGTH: 26
<212> TYPE: DNA
<213> ORGANISM: Zea mays;

<400> SEQUENCE: 492
```

```
ggagtcatgc acatttgaga agaaac                                    26

<210> SEQ ID NO 493
<211> LENGTH: 14
<212> TYPE: DNA
<213> ORGANISM: Zea mays;

<400> SEQUENCE: 493
aatggcacca ttag                                                 14

<210> SEQ ID NO 494
<211> LENGTH: 15
<212> TYPE: DNA
<213> ORGANISM: Zea mays;

<400> SEQUENCE: 494
taatggcacc atcag                                                15

<210> SEQ ID NO 495
<211> LENGTH: 20
<212> TYPE: DNA
<213> ORGANISM: Zea mays;

<400> SEQUENCE: 495
tggttgcttc ggaagagttc                                           20

<210> SEQ ID NO 496
<211> LENGTH: 20
<212> TYPE: DNA
<213> ORGANISM: Zea mays;

<400> SEQUENCE: 496
agggttgcgc tcctagttct                                           20

<210> SEQ ID NO 497
<211> LENGTH: 20
<212> TYPE: DNA
<213> ORGANISM: Zea mays;

<400> SEQUENCE: 497
cctaaagaaa ggtgtagcct                                           20

<210> SEQ ID NO 498
<211> LENGTH: 22
<212> TYPE: DNA
<213> ORGANISM: Zea mays;

<400> SEQUENCE: 498
ttcctaaaga aaggtatagc ct                                        22

<210> SEQ ID NO 499
<211> LENGTH: 24
<212> TYPE: DNA
<213> ORGANISM: Zea mays;

<400> SEQUENCE: 499
caagaccagg tctaacagag cata                                      24

<210> SEQ ID NO 500
<211> LENGTH: 25
<212> TYPE: DNA
<213> ORGANISM: Zea mays;

<400> SEQUENCE: 500
```

```
ggacccgtaa attatcattg cttca                                         25

<210> SEQ ID NO 501
<211> LENGTH: 19
<212> TYPE: DNA
<213> ORGANISM: Zea mays;

<400> SEQUENCE: 501
acgtctaaga gattaaaag                                                19

<210> SEQ ID NO 502
<211> LENGTH: 21
<212> TYPE: DNA
<213> ORGANISM: Zea mays;

<400> SEQUENCE: 502
aaatacgtct aagagataaa a                                             21

<210> SEQ ID NO 503
<211> LENGTH: 23
<212> TYPE: DNA
<213> ORGANISM: Zea mays;

<400> SEQUENCE: 503
gtctgcaaat aaattatctt ggt                                           23

<210> SEQ ID NO 504
<211> LENGTH: 18
<212> TYPE: DNA
<213> ORGANISM: Zea mays;

<400> SEQUENCE: 504
gacacaagat ggtctcaa                                                 18

<210> SEQ ID NO 505
<211> LENGTH: 19
<212> TYPE: DNA
<213> ORGANISM: Zea mays;

<400> SEQUENCE: 505
ctgggagtca atttcattg                                                19

<210> SEQ ID NO 506
<211> LENGTH: 19
<212> TYPE: DNA
<213> ORGANISM: Zea mays;

<400> SEQUENCE: 506
ctgggagtca attccattg                                                19

<210> SEQ ID NO 507
<211> LENGTH: 22
<212> TYPE: DNA
<213> ORGANISM: Zea mays;

<400> SEQUENCE: 507
tggccggtaa acaaacaaag tc                                            22

<210> SEQ ID NO 508
<211> LENGTH: 20
<212> TYPE: DNA
<213> ORGANISM: Zea mays;
```

-continued

```
<400> SEQUENCE: 508
tcagtgggtg atccggtaac                                               20

<210> SEQ ID NO 509
<211> LENGTH: 15
<212> TYPE: DNA
<213> ORGANISM: Zea mays;

<400> SEQUENCE: 509
ctgcaggtga agacc                                                    15

<210> SEQ ID NO 510
<211> LENGTH: 15
<212> TYPE: DNA
<213> ORGANISM: Zea mays;

<400> SEQUENCE: 510
ctgcaggtga aaacc                                                    15

<210> SEQ ID NO 511
<211> LENGTH: 16
<212> TYPE: DNA
<213> ORGANISM: Zea mays;

<400> SEQUENCE: 511
gggcgcagcc gtgtag                                                   16

<210> SEQ ID NO 512
<211> LENGTH: 21
<212> TYPE: DNA
<213> ORGANISM: Zea mays;

<400> SEQUENCE: 512
cacgactcca tcaggcactc t                                             21

<210> SEQ ID NO 513
<211> LENGTH: 17
<212> TYPE: DNA
<213> ORGANISM: Zea mays;

<400> SEQUENCE: 513
agcaagagaa gcagctg                                                  17

<210> SEQ ID NO 514
<211> LENGTH: 18
<212> TYPE: DNA
<213> ORGANISM: Zea mays;

<400> SEQUENCE: 514
tgagcaagag aagcaact                                                 18

<210> SEQ ID NO 515
<211> LENGTH: 18
<212> TYPE: DNA
<213> ORGANISM: Zea mays;

<400> SEQUENCE: 515
gtagtagcct cagtagga                                                 18

<210> SEQ ID NO 516
<211> LENGTH: 23
<212> TYPE: DNA
<213> ORGANISM: Zea mays;
```

-continued

```
<400> SEQUENCE: 516
tttgatagtt tcatgataga tac                                          23

<210> SEQ ID NO 517
<211> LENGTH: 16
<212> TYPE: DNA
<213> ORGANISM: Zea mays;

<400> SEQUENCE: 517
cgcgtatctc gattcc                                                  16

<210> SEQ ID NO 518
<211> LENGTH: 17
<212> TYPE: DNA
<213> ORGANISM: Zea mays;

<400> SEQUENCE: 518
cgcgtatctc aattcca                                                 17

<210> SEQ ID NO 519
<211> LENGTH: 22
<212> TYPE: DNA
<213> ORGANISM: Zea mays;

<400> SEQUENCE: 519
cattacaaac gcagccaagg ta                                           22

<210> SEQ ID NO 520
<211> LENGTH: 17
<212> TYPE: DNA
<213> ORGANISM: Zea mays;

<400> SEQUENCE: 520
gcgcccatct ccagcaa                                                 17

<210> SEQ ID NO 521
<211> LENGTH: 22
<212> TYPE: DNA
<213> ORGANISM: Zea mays;

<400> SEQUENCE: 521
tacaacaaag gtcaataagt aa                                           22

<210> SEQ ID NO 522
<211> LENGTH: 20
<212> TYPE: DNA
<213> ORGANISM: Zea mays;

<400> SEQUENCE: 522
caacaaaggt caacaagtaa                                              20

<210> SEQ ID NO 523
<211> LENGTH: 24
<212> TYPE: DNA
<213> ORGANISM: Zea mays;

<400> SEQUENCE: 523
gcaagtggag agaagaacta agga                                         24

<210> SEQ ID NO 524
<211> LENGTH: 21
<212> TYPE: DNA
```

-continued

```
<213> ORGANISM: Zea mays;

<400> SEQUENCE: 524
cctgggcata tcagtggtgt t                                              21

<210> SEQ ID NO 525
<211> LENGTH: 18
<212> TYPE: DNA
<213> ORGANISM: Zea mays;

<400> SEQUENCE: 525
ttcagcagta cttgacgt                                                  18

<210> SEQ ID NO 526
<211> LENGTH: 16
<212> TYPE: DNA
<213> ORGANISM: Zea mays;

<400> SEQUENCE: 526
tcagcagtac ctgacg                                                    16

<210> SEQ ID NO 527
<211> LENGTH: 22
<212> TYPE: DNA
<213> ORGANISM: Zea mays;

<400> SEQUENCE: 527
ccgcaggaaa tcaaacatgg gt                                             22

<210> SEQ ID NO 528
<211> LENGTH: 20
<212> TYPE: DNA
<213> ORGANISM: Zea mays;

<400> SEQUENCE: 528
acgtggtctc cgtcgatgag                                                20

<210> SEQ ID NO 529
<211> LENGTH: 15
<212> TYPE: DNA
<213> ORGANISM: Zea mays;

<400> SEQUENCE: 529
cgaggcgatg gtgcc                                                     15

<210> SEQ ID NO 530
<211> LENGTH: 14
<212> TYPE: DNA
<213> ORGANISM: Zea mays;

<400> SEQUENCE: 530
aggcgacggt gcca                                                      14

<210> SEQ ID NO 531
<211> LENGTH: 17
<212> TYPE: DNA
<213> ORGANISM: Zea mays;

<400> SEQUENCE: 531
gacgtcaggt ccagggt                                                   17

<210> SEQ ID NO 532
<211> LENGTH: 24
```

-continued

```
<212> TYPE: DNA
<213> ORGANISM: Zea mays;

<400> SEQUENCE: 532
agcctcatct cctacactta ctac                                          24

<210> SEQ ID NO 533
<211> LENGTH: 18
<212> TYPE: DNA
<213> ORGANISM: Zea mays;

<400> SEQUENCE: 533
tcagtattag taaggtgc                                                 18

<210> SEQ ID NO 534
<211> LENGTH: 21
<212> TYPE: DNA
<213> ORGANISM: Zea mays;

<400> SEQUENCE: 534
aaatcagtat tagtaagatg c                                             21

<210> SEQ ID NO 535
<211> LENGTH: 24
<212> TYPE: DNA
<213> ORGANISM: Zea mays;

<400> SEQUENCE: 535
gatgtagtta acaagcgagc gtct                                          24

<210> SEQ ID NO 536
<211> LENGTH: 21
<212> TYPE: DNA
<213> ORGANISM: Zea mays;

<400> SEQUENCE: 536
gcctgcactc tttatgcttc a                                             21

<210> SEQ ID NO 537
<211> LENGTH: 16
<212> TYPE: DNA
<213> ORGANISM: Zea mays;

<400> SEQUENCE: 537
agccggttcg ggtact                                                   16

<210> SEQ ID NO 538
<211> LENGTH: 16
<212> TYPE: DNA
<213> ORGANISM: Zea mays;

<400> SEQUENCE: 538
agccggttcc ggtact                                                   16

<210> SEQ ID NO 539
<211> LENGTH: 16
<212> TYPE: DNA
<213> ORGANISM: Zea mays;

<400> SEQUENCE: 539
cgtcgggcct gtgctg                                                   16

<210> SEQ ID NO 540
```

-continued

```
<211> LENGTH: 18
<212> TYPE: DNA
<213> ORGANISM: Zea mays;

<400> SEQUENCE: 540
cacggacgcg ttgttggt                                              18

<210> SEQ ID NO 541
<211> LENGTH: 19
<212> TYPE: DNA
<213> ORGANISM: Zea mays;

<400> SEQUENCE: 541
cagatccgat ctctgttag                                             19

<210> SEQ ID NO 542
<211> LENGTH: 19
<212> TYPE: DNA
<213> ORGANISM: Zea mays;

<400> SEQUENCE: 542
agatccgatc gctgttagt                                             19

<210> SEQ ID NO 543
<211> LENGTH: 22
<212> TYPE: DNA
<213> ORGANISM: Zea mays;

<400> SEQUENCE: 543
gggaggatac atcccttcat ca                                         22

<210> SEQ ID NO 544
<211> LENGTH: 21
<212> TYPE: DNA
<213> ORGANISM: Zea mays;

<400> SEQUENCE: 544
aacaacgact gtgagggttc a                                          21

<210> SEQ ID NO 545
<211> LENGTH: 18
<212> TYPE: DNA
<213> ORGANISM: Zea mays;

<400> SEQUENCE: 545
cagccatagt gtgtggaa                                              18

<210> SEQ ID NO 546
<211> LENGTH: 18
<212> TYPE: DNA
<213> ORGANISM: Zea mays;

<400> SEQUENCE: 546
agccatagtg cgtggaaa                                              18

<210> SEQ ID NO 547
<211> LENGTH: 16
<212> TYPE: DNA
<213> ORGANISM: Zea mays;

<400> SEQUENCE: 547
gggcactgct ggcgtt                                                16
```

-continued

```
<210> SEQ ID NO 548
<211> LENGTH: 21
<212> TYPE: DNA
<213> ORGANISM: Zea mays;

<400> SEQUENCE: 548
ccctcaccta tgcaacagaa c                                           21

<210> SEQ ID NO 549
<211> LENGTH: 19
<212> TYPE: DNA
<213> ORGANISM: Zea mays;

<400> SEQUENCE: 549
tggctacact ttaatcgaa                                              19

<210> SEQ ID NO 550
<211> LENGTH: 17
<212> TYPE: DNA
<213> ORGANISM: Zea mays;

<400> SEQUENCE: 550
tggctacact tcaatcg                                                17

<210> SEQ ID NO 551
<211> LENGTH: 23
<212> TYPE: DNA
<213> ORGANISM: Zea mays;

<400> SEQUENCE: 551
gacagctctc atcactgcat cag                                         23

<210> SEQ ID NO 552
<211> LENGTH: 22
<212> TYPE: DNA
<213> ORGANISM: Zea mays;

<400> SEQUENCE: 552
gcactgcttt cagagttctg gt                                          22

<210> SEQ ID NO 553
<211> LENGTH: 21
<212> TYPE: DNA
<213> ORGANISM: Zea mays;

<400> SEQUENCE: 553
aaaggtttgt tttatttatt g                                           21

<210> SEQ ID NO 554
<211> LENGTH: 21
<212> TYPE: DNA
<213> ORGANISM: Zea mays;

<400> SEQUENCE: 554
taaaggtttg ttttatttat c                                           21

<210> SEQ ID NO 555
<211> LENGTH: 21
<212> TYPE: DNA
<213> ORGANISM: Zea mays;

<400> SEQUENCE: 555
cacgtcagga aaggatgcaa a                                           21
```

-continued

```
<210> SEQ ID NO 556
<211> LENGTH: 22
<212> TYPE: DNA
<213> ORGANISM: Zea mays;

<400> SEQUENCE: 556
gcggatcatc actcccatct tc                                              22

<210> SEQ ID NO 557
<211> LENGTH: 17
<212> TYPE: DNA
<213> ORGANISM: Zea mays;

<400> SEQUENCE: 557
cagccatctt gctgata                                                    17

<210> SEQ ID NO 558
<211> LENGTH: 16
<212> TYPE: DNA
<213> ORGANISM: Zea mays;

<400> SEQUENCE: 558
cagccatcgt gctgat                                                     16

<210> SEQ ID NO 559
<211> LENGTH: 24
<212> TYPE: DNA
<213> ORGANISM: Zea mays;

<400> SEQUENCE: 559
cgtgtcgttg aaatatgcat ggtt                                            24

<210> SEQ ID NO 560
<211> LENGTH: 22
<212> TYPE: DNA
<213> ORGANISM: Zea mays;

<400> SEQUENCE: 560
tcacggtcct ccatcatcta ac                                              22

<210> SEQ ID NO 561
<211> LENGTH: 21
<212> TYPE: DNA
<213> ORGANISM: Zea mays;

<400> SEQUENCE: 561
ctaaaagtga ctaactaaag t                                               21

<210> SEQ ID NO 562
<211> LENGTH: 22
<212> TYPE: DNA
<213> ORGANISM: Zea mays;

<400> SEQUENCE: 562
ctaaaagtga ctaactaaaa tt                                              22

<210> SEQ ID NO 563
<211> LENGTH: 22
<212> TYPE: DNA
<213> ORGANISM: Zea mays;

<400> SEQUENCE: 563
gtcactctct taaactctag tc                                              22
```

-continued

<210> SEQ ID NO 564
<211> LENGTH: 21
<212> TYPE: DNA
<213> ORGANISM: Zea mays;

<400> SEQUENCE: 564
gctatcgcat tgtactagta g                                           21

<210> SEQ ID NO 565
<211> LENGTH: 18
<212> TYPE: DNA
<213> ORGANISM: Zea mays;

<400> SEQUENCE: 565
tcataagctg tctccaaa                                               18

<210> SEQ ID NO 566
<211> LENGTH: 19
<212> TYPE: DNA
<213> ORGANISM: Zea mays;

<400> SEQUENCE: 566
ttcataagct gactccaaa                                              19

<210> SEQ ID NO 567
<211> LENGTH: 24
<212> TYPE: DNA
<213> ORGANISM: Zea mays;

<400> SEQUENCE: 567
tgtgggtgtt tgattcaatg gatg                                        24

<210> SEQ ID NO 568
<211> LENGTH: 19
<212> TYPE: DNA
<213> ORGANISM: Zea mays;

<400> SEQUENCE: 568
tccaaggctc agctcgaaa                                              19

<210> SEQ ID NO 569
<211> LENGTH: 19
<212> TYPE: DNA
<213> ORGANISM: Zea mays;

<400> SEQUENCE: 569
catcgatgta cttcaaaag                                              19

<210> SEQ ID NO 570
<211> LENGTH: 19
<212> TYPE: DNA
<213> ORGANISM: Zea mays;

<400> SEQUENCE: 570
catcgatgta cttcaaaaa                                              19

<210> SEQ ID NO 571
<211> LENGTH: 26
<212> TYPE: DNA
<213> ORGANISM: Zea mays;

<400> SEQUENCE: 571

-continued

```
gcccaagtga tccagaacta atacac                                                  26

<210> SEQ ID NO 572
<211> LENGTH: 26
<212> TYPE: DNA
<213> ORGANISM: Zea mays;

<400> SEQUENCE: 572
tgcagttcat ttttgcacta tttgac                                                  26

<210> SEQ ID NO 573
<211> LENGTH: 16
<212> TYPE: DNA
<213> ORGANISM: Zea mays;

<400> SEQUENCE: 573
tggtggcagt ttaggt                                                             16

<210> SEQ ID NO 574
<211> LENGTH: 15
<212> TYPE: DNA
<213> ORGANISM: Zea mays;

<400> SEQUENCE: 574
tggtggcagt tcagg                                                              15

<210> SEQ ID NO 575
<211> LENGTH: 24
<212> TYPE: DNA
<213> ORGANISM: Zea mays;

<400> SEQUENCE: 575
ccttgaggct tggtttagat tggt                                                    24

<210> SEQ ID NO 576
<211> LENGTH: 24
<212> TYPE: DNA
<213> ORGANISM: Zea mays;

<400> SEQUENCE: 576
ctcacccaca tctttcgcac tatt                                                    24

<210> SEQ ID NO 577
<211> LENGTH: 16
<212> TYPE: DNA
<213> ORGANISM: Zea mays;

<400> SEQUENCE: 577
ttaaacgctt tgttga                                                             16

<210> SEQ ID NO 578
<211> LENGTH: 15
<212> TYPE: DNA
<213> ORGANISM: Zea mays;

<400> SEQUENCE: 578
aaacgctttg ctgat                                                              15

<210> SEQ ID NO 579
<211> LENGTH: 18
<212> TYPE: DNA
<213> ORGANISM: Zea mays;

<400> SEQUENCE: 579
```

-continued

```
tggaactctt cagtcttg                                          18

<210> SEQ ID NO 580
<211> LENGTH: 16
<212> TYPE: DNA
<213> ORGANISM: Zea mays;

<400> SEQUENCE: 580
gaacggtgtt ctaggg                                            16

<210> SEQ ID NO 581
<211> LENGTH: 18
<212> TYPE: DNA
<213> ORGANISM: Zea mays;

<400> SEQUENCE: 581
tgatgtccat attgaagc                                          18

<210> SEQ ID NO 582
<211> LENGTH: 19
<212> TYPE: DNA
<213> ORGANISM: Zea mays;

<400> SEQUENCE: 582
ttgatgtcca tatagaagc                                         19

<210> SEQ ID NO 583
<211> LENGTH: 24
<212> TYPE: DNA
<213> ORGANISM: Zea mays;

<400> SEQUENCE: 583
tgaagtgtta gaagaagttg caca                                   24

<210> SEQ ID NO 584
<211> LENGTH: 18
<212> TYPE: DNA
<213> ORGANISM: Zea mays;

<400> SEQUENCE: 584
aagcaccctt gaggcagt                                          18

<210> SEQ ID NO 585
<211> LENGTH: 14
<212> TYPE: DNA
<213> ORGANISM: Zea mays;

<400> SEQUENCE: 585
cggctgggcg actt                                              14

<210> SEQ ID NO 586
<211> LENGTH: 14
<212> TYPE: DNA
<213> ORGANISM: Zea mays;

<400> SEQUENCE: 586
cggctcggcg actt                                              14

<210> SEQ ID NO 587
<211> LENGTH: 20
<212> TYPE: DNA
<213> ORGANISM: Zea mays;
```

-continued

```
<400> SEQUENCE: 587
tcatgctgga ctcgtcgttc                                         20

<210> SEQ ID NO 588
<211> LENGTH: 21
<212> TYPE: DNA
<213> ORGANISM: Zea mays;

<400> SEQUENCE: 588
gtccgtgtag gaggtcttgt c                                       21

<210> SEQ ID NO 589
<211> LENGTH: 17
<212> TYPE: DNA
<213> ORGANISM: Zea mays;

<400> SEQUENCE: 589
cagtagctgt gatagac                                            17

<210> SEQ ID NO 590
<211> LENGTH: 16
<212> TYPE: DNA
<213> ORGANISM: Zea mays;

<400> SEQUENCE: 590
cagtagctgt gacaga                                             16

<210> SEQ ID NO 591
<211> LENGTH: 19
<212> TYPE: DNA
<213> ORGANISM: Zea mays;

<400> SEQUENCE: 591
ttgcaaggaa aatggaaga                                          19

<210> SEQ ID NO 592
<211> LENGTH: 16
<212> TYPE: DNA
<213> ORGANISM: Zea mays;

<400> SEQUENCE: 592
atcgtgatgg gctgct                                             16

<210> SEQ ID NO 593
<211> LENGTH: 19
<212> TYPE: DNA
<213> ORGANISM: Zea mays;

<400> SEQUENCE: 593
catgttagtt tacccgaaa                                          19

<210> SEQ ID NO 594
<211> LENGTH: 19
<212> TYPE: DNA
<213> ORGANISM: Zea mays;

<400> SEQUENCE: 594
agcatgttag tttaccaga                                          19

<210> SEQ ID NO 595
<211> LENGTH: 22
<212> TYPE: DNA
<213> ORGANISM: Zea mays;
```

-continued

```
<400> SEQUENCE: 595
tgtgccagtg ttatccaagg aa                                            22

<210> SEQ ID NO 596
<211> LENGTH: 21
<212> TYPE: DNA
<213> ORGANISM: Zea mays;

<400> SEQUENCE: 596
tccatgcttc agtcacacag t                                             21

<210> SEQ ID NO 597
<211> LENGTH: 20
<212> TYPE: DNA
<213> ORGANISM: Zea mays;

<400> SEQUENCE: 597
aagagtcaac actggagttg                                               20

<210> SEQ ID NO 598
<211> LENGTH: 23
<212> TYPE: DNA
<213> ORGANISM: Zea mays;

<400> SEQUENCE: 598
agggaagagt caacactaga gtt                                           23

<210> SEQ ID NO 599
<211> LENGTH: 22
<212> TYPE: DNA
<213> ORGANISM: Zea mays;

<400> SEQUENCE: 599
ccatgaaggc agagagcatg tg                                            22

<210> SEQ ID NO 600
<211> LENGTH: 20
<212> TYPE: DNA
<213> ORGANISM: Zea mays;

<400> SEQUENCE: 600
tctcggttgt gtggatggaa                                               20

<210> SEQ ID NO 601
<211> LENGTH: 15
<212> TYPE: DNA
<213> ORGANISM: Zea mays;

<400> SEQUENCE: 601
tactccctcc gtttt                                                    15

<210> SEQ ID NO 602
<211> LENGTH: 14
<212> TYPE: DNA
<213> ORGANISM: Zea mays;

<400> SEQUENCE: 602
actccctccg tttc                                                     14

<210> SEQ ID NO 603
<211> LENGTH: 21
<212> TYPE: DNA
```

-continued

```
<213> ORGANISM: Zea mays;

<400> SEQUENCE: 603
ggtcgaggag agtgaacctt g                                           21

<210> SEQ ID NO 604
<211> LENGTH: 21
<212> TYPE: DNA
<213> ORGANISM: Zea mays;

<400> SEQUENCE: 604
ggcagattgc caggatgaga t                                           21

<210> SEQ ID NO 605
<211> LENGTH: 22
<212> TYPE: DNA
<213> ORGANISM: Zea mays;

<400> SEQUENCE: 605
attctctatt atagaaagaa at                                          22

<210> SEQ ID NO 606
<211> LENGTH: 22
<212> TYPE: DNA
<213> ORGANISM: Zea mays;

<400> SEQUENCE: 606
attctctatt atagaaagaa ac                                          22

<210> SEQ ID NO 607
<211> LENGTH: 27
<212> TYPE: DNA
<213> ORGANISM: Zea mays;

<400> SEQUENCE: 607
ggtagcagat gaagttccaa tagtaaa                                     27

<210> SEQ ID NO 608
<211> LENGTH: 24
<212> TYPE: DNA
<213> ORGANISM: Zea mays;

<400> SEQUENCE: 608
gctatctagc cacttgttcc attc                                        24

<210> SEQ ID NO 609
<211> LENGTH: 17
<212> TYPE: DNA
<213> ORGANISM: Zea mays;

<400> SEQUENCE: 609
cacaacgtgg aagtagg                                                17

<210> SEQ ID NO 610
<211> LENGTH: 18
<212> TYPE: DNA
<213> ORGANISM: Zea mays;

<400> SEQUENCE: 610
ccacaacgtg gaagtaga                                               18

<210> SEQ ID NO 611
<211> LENGTH: 23
```

```
<212> TYPE: DNA
<213> ORGANISM: Zea mays;

<400> SEQUENCE: 611
gatcatcgga tcacttgaaa ggg                                                    23

<210> SEQ ID NO 612
<211> LENGTH: 19
<212> TYPE: DNA
<213> ORGANISM: Zea mays;

<400> SEQUENCE: 612
tggttcggcc aagtaacac                                                         19

<210> SEQ ID NO 613
<211> LENGTH: 13
<212> TYPE: DNA
<213> ORGANISM: Zea mays;

<400> SEQUENCE: 613
accgctgctg cca                                                               13

<210> SEQ ID NO 614
<211> LENGTH: 14
<212> TYPE: DNA
<213> ORGANISM: Zea mays;

<400> SEQUENCE: 614
aagaccgccg ctgc                                                              14

<210> SEQ ID NO 615
<211> LENGTH: 17
<212> TYPE: DNA
<213> ORGANISM: Zea mays;

<400> SEQUENCE: 615
tcctgctcgg cctgtga                                                           17

<210> SEQ ID NO 616
<211> LENGTH: 19
<212> TYPE: DNA
<213> ORGANISM: Zea mays;

<400> SEQUENCE: 616
gcgccaagca aatgtcgta                                                         19

<210> SEQ ID NO 617
<211> LENGTH: 16
<212> TYPE: DNA
<213> ORGANISM: Zea mays;

<400> SEQUENCE: 617
cgcggaacct tggatg                                                            16

<210> SEQ ID NO 618
<211> LENGTH: 16
<212> TYPE: DNA
<213> ORGANISM: Zea mays;

<400> SEQUENCE: 618
cgcggaagcc ttggat                                                            16

<210> SEQ ID NO 619
```

```
<211> LENGTH: 18
<212> TYPE: DNA
<213> ORGANISM: Zea mays;

<400> SEQUENCE: 619
aagaccgtcg cggactcg                                                   18

<210> SEQ ID NO 620
<211> LENGTH: 21
<212> TYPE: DNA
<213> ORGANISM: Zea mays;

<400> SEQUENCE: 620
gggcaaactc atgcgtagat g                                               21

<210> SEQ ID NO 621
<211> LENGTH: 17
<212> TYPE: DNA
<213> ORGANISM: Zea mays;

<400> SEQUENCE: 621
atcaaccatc tgtccat                                                    17

<210> SEQ ID NO 622
<211> LENGTH: 15
<212> TYPE: DNA
<213> ORGANISM: Zea mays;

<400> SEQUENCE: 622
caaccatctg cccat                                                      15

<210> SEQ ID NO 623
<211> LENGTH: 18
<212> TYPE: DNA
<213> ORGANISM: Zea mays;

<400> SEQUENCE: 623
cttcctaaac tcgtccct                                                   18

<210> SEQ ID NO 624
<211> LENGTH: 24
<212> TYPE: DNA
<213> ORGANISM: Zea mays;

<400> SEQUENCE: 624
tcaaatctaa gttattgagt gtta                                            24

<210> SEQ ID NO 625
<211> LENGTH: 20
<212> TYPE: DNA
<213> ORGANISM: Zea mays;

<400> SEQUENCE: 625
tgatagtcag tagtatggtt                                                 20

<210> SEQ ID NO 626
<211> LENGTH: 18
<212> TYPE: DNA
<213> ORGANISM: Zea mays;

<400> SEQUENCE: 626
agtcagtagt atggcttg                                                   18
```

-continued

```
<210> SEQ ID NO 627
<211> LENGTH: 24
<212> TYPE: DNA
<213> ORGANISM: Zea mays;

<400> SEQUENCE: 627
ggtcaattgg tagtcagagg acaa                                           24

<210> SEQ ID NO 628
<211> LENGTH: 21
<212> TYPE: DNA
<213> ORGANISM: Zea mays;

<400> SEQUENCE: 628
gtgctccaac gaggactagt g                                              21

<210> SEQ ID NO 629
<211> LENGTH: 16
<212> TYPE: DNA
<213> ORGANISM: Zea mays;

<400> SEQUENCE: 629
acccaagggc tcaaca                                                    16

<210> SEQ ID NO 630
<211> LENGTH: 16
<212> TYPE: DNA
<213> ORGANISM: Zea mays;

<400> SEQUENCE: 630
cacccaagag ctcaac                                                    16

<210> SEQ ID NO 631
<211> LENGTH: 19
<212> TYPE: DNA
<213> ORGANISM: Zea mays;

<400> SEQUENCE: 631
acagctcaaa gggcaggtt                                                 19

<210> SEQ ID NO 632
<211> LENGTH: 22
<212> TYPE: DNA
<213> ORGANISM: Zea mays;

<400> SEQUENCE: 632
ggcttgaaca gtgccaatag tc                                             22

<210> SEQ ID NO 633
<211> LENGTH: 19
<212> TYPE: DNA
<213> ORGANISM: Zea mays;

<400> SEQUENCE: 633
attgcgtctc gataaatca                                                 19

<210> SEQ ID NO 634
<211> LENGTH: 18
<212> TYPE: DNA
<213> ORGANISM: Zea mays;

<400> SEQUENCE: 634
ttgcgtctca ataaatca                                                  18
```

-continued

```
<210> SEQ ID NO 635
<211> LENGTH: 17
<212> TYPE: DNA
<213> ORGANISM: Zea mays;

<400> SEQUENCE: 635
tccgagttcg ctgtcca                                                  17

<210> SEQ ID NO 636
<211> LENGTH: 23
<212> TYPE: DNA
<213> ORGANISM: Zea mays;

<400> SEQUENCE: 636
cgttggcatt gaagggaagt cta                                           23

<210> SEQ ID NO 637
<211> LENGTH: 15
<212> TYPE: DNA
<213> ORGANISM: Zea mays;

<400> SEQUENCE: 637
attggcaatg ccgca                                                    15

<210> SEQ ID NO 638
<211> LENGTH: 16
<212> TYPE: DNA
<213> ORGANISM: Zea mays;

<400> SEQUENCE: 638
cattggcaat gccaca                                                   16

<210> SEQ ID NO 639
<211> LENGTH: 23
<212> TYPE: DNA
<213> ORGANISM: Zea mays;

<400> SEQUENCE: 639
tgcctgatct tttccttcac cat                                           23

<210> SEQ ID NO 640
<211> LENGTH: 20
<212> TYPE: DNA
<213> ORGANISM: Zea mays;

<400> SEQUENCE: 640
tgtaggccac ctaggattgg                                               20

<210> SEQ ID NO 641
<211> LENGTH: 17
<212> TYPE: DNA
<213> ORGANISM: Zea mays;

<400> SEQUENCE: 641
tttccattgt ttccatc                                                  17

<210> SEQ ID NO 642
<211> LENGTH: 18
<212> TYPE: DNA
<213> ORGANISM: Zea mays;

<400> SEQUENCE: 642
agtttccatt gtttccac                                                 18
```

-continued

```
<210> SEQ ID NO 643
<211> LENGTH: 29
<212> TYPE: DNA
<213> ORGANISM: Zea mays;

<400> SEQUENCE: 643
agttcctttt ctctactcct ataaagcac                                         29

<210> SEQ ID NO 644
<211> LENGTH: 23
<212> TYPE: DNA
<213> ORGANISM: Zea mays;

<400> SEQUENCE: 644
ggatgggatc atagccacag ttc                                               23

<210> SEQ ID NO 645
<211> LENGTH: 14
<212> TYPE: DNA
<213> ORGANISM: Zea mays;

<400> SEQUENCE: 645
cctccttgcg cgtg                                                         14

<210> SEQ ID NO 646
<211> LENGTH: 13
<212> TYPE: DNA
<213> ORGANISM: Zea mays;

<400> SEQUENCE: 646
ctcctcgcgc gtg                                                          13

<210> SEQ ID NO 647
<211> LENGTH: 16
<212> TYPE: DNA
<213> ORGANISM: Zea mays;

<400> SEQUENCE: 647
gcctgggacc gggaag                                                       16

<210> SEQ ID NO 648
<211> LENGTH: 18
<212> TYPE: DNA
<213> ORGANISM: Zea mays;

<400> SEQUENCE: 648
caccgacacc gacgaaga                                                     18

<210> SEQ ID NO 649
<211> LENGTH: 19
<212> TYPE: DNA
<213> ORGANISM: Zea mays;

<400> SEQUENCE: 649
tcacaaatca ataaagccc                                                    19

<210> SEQ ID NO 650
<211> LENGTH: 19
<212> TYPE: DNA
<213> ORGANISM: Zea mays;

<400> SEQUENCE: 650
```

-continued

```
ttcacaaatc aacaaagcc                                        19

<210> SEQ ID NO 651
<211> LENGTH: 22
<212> TYPE: DNA
<213> ORGANISM: Zea mays;

<400> SEQUENCE: 651
atggtacaag tcacaggtag gg                                    22

<210> SEQ ID NO 652
<211> LENGTH: 22
<212> TYPE: DNA
<213> ORGANISM: Zea mays;

<400> SEQUENCE: 652
gtcaagttag ggccggatca ta                                    22

<210> SEQ ID NO 653
<211> LENGTH: 22
<212> TYPE: DNA
<213> ORGANISM: Zea mays;

<400> SEQUENCE: 653
agtatggaac taatttgaca aa                                    22

<210> SEQ ID NO 654
<211> LENGTH: 24
<212> TYPE: DNA
<213> ORGANISM: Zea mays;

<400> SEQUENCE: 654
agagtatgga actaatttaa caaa                                  24

<210> SEQ ID NO 655
<211> LENGTH: 23
<212> TYPE: DNA
<213> ORGANISM: Zea mays;

<400> SEQUENCE: 655
aaacagttgg tgttggagtt gga                                   23

<210> SEQ ID NO 656
<211> LENGTH: 19
<212> TYPE: DNA
<213> ORGANISM: Zea mays;

<400> SEQUENCE: 656
tgtggatggc gtgttagca                                        19

<210> SEQ ID NO 657
<211> LENGTH: 20
<212> TYPE: DNA
<213> ORGANISM: Zea mays;

<400> SEQUENCE: 657
tccattactt attgaaacac                                       20

<210> SEQ ID NO 658
<211> LENGTH: 19
<212> TYPE: DNA
<213> ORGANISM: Zea mays;

<400> SEQUENCE: 658
```

-continued

```
ccattactta ctgaaacac                                                    19

<210> SEQ ID NO 659
<211> LENGTH: 21
<212> TYPE: DNA
<213> ORGANISM: Zea mays;

<400> SEQUENCE: 659
accacctcgg tctacacctt a                                                 21

<210> SEQ ID NO 660
<211> LENGTH: 21
<212> TYPE: DNA
<213> ORGANISM: Zea mays;

<400> SEQUENCE: 660
tgccagaaag catgggaagt c                                                 21

<210> SEQ ID NO 661
<211> LENGTH: 15
<212> TYPE: DNA
<213> ORGANISM: Zea mays;

<400> SEQUENCE: 661
taggcactga ccgga                                                        15

<210> SEQ ID NO 662
<211> LENGTH: 15
<212> TYPE: DNA
<213> ORGANISM: Zea mays;

<400> SEQUENCE: 662
taggcactga cccga                                                        15

<210> SEQ ID NO 663
<211> LENGTH: 17
<212> TYPE: DNA
<213> ORGANISM: Zea mays;

<400> SEQUENCE: 663
tggcgagacg aagcaga                                                      17

<210> SEQ ID NO 664
<211> LENGTH: 20
<212> TYPE: DNA
<213> ORGANISM: Zea mays;

<400> SEQUENCE: 664
gaccgaaccg aaccattagc                                                   20

<210> SEQ ID NO 665
<211> LENGTH: 17
<212> TYPE: DNA
<213> ORGANISM: Zea mays;

<400> SEQUENCE: 665
cttctgtgca tggatca                                                      17

<210> SEQ ID NO 666
<211> LENGTH: 16
<212> TYPE: DNA
<213> ORGANISM: Zea mays;
```

-continued

```
<400> SEQUENCE: 666
tctgtgcacg gatcat                                               16

<210> SEQ ID NO 667
<211> LENGTH: 22
<212> TYPE: DNA
<213> ORGANISM: Zea mays;

<400> SEQUENCE: 667
cgagaagttc ccatcagctc aa                                        22

<210> SEQ ID NO 668
<211> LENGTH: 22
<212> TYPE: DNA
<213> ORGANISM: Zea mays;

<400> SEQUENCE: 668
tggtgaacat tggttgcttg tg                                        22

<210> SEQ ID NO 669
<211> LENGTH: 21
<212> TYPE: DNA
<213> ORGANISM: Zea mays;

<400> SEQUENCE: 669
aaacaacaga atcttttag a                                          21

<210> SEQ ID NO 670
<211> LENGTH: 22
<212> TYPE: DNA
<213> ORGANISM: Zea mays;

<400> SEQUENCE: 670
aaacaacaga atctttttaa aa                                        22

<210> SEQ ID NO 671
<211> LENGTH: 24
<212> TYPE: DNA
<213> ORGANISM: Zea mays;

<400> SEQUENCE: 671
cagctctaaa ctcacagacg tttg                                      24

<210> SEQ ID NO 672
<211> LENGTH: 22
<212> TYPE: DNA
<213> ORGANISM: Zea mays;

<400> SEQUENCE: 672
agcgctctac catctgagct ac                                        22

<210> SEQ ID NO 673
<211> LENGTH: 22
<212> TYPE: DNA
<213> ORGANISM: Zea mays;

<400> SEQUENCE: 673
tcaaaataat gatatgaggg aa                                        22

<210> SEQ ID NO 674
<211> LENGTH: 22
<212> TYPE: DNA
<213> ORGANISM: Zea mays;
```

-continued

<400> SEQUENCE: 674
tcaaaataat gatatgagga aa                                          22

<210> SEQ ID NO 675
<211> LENGTH: 25
<212> TYPE: DNA
<213> ORGANISM: Zea mays;

<400> SEQUENCE: 675
aagactgaaa gcatgaataa acggt                                       25

<210> SEQ ID NO 676
<211> LENGTH: 20
<212> TYPE: DNA
<213> ORGANISM: Zea mays;

<400> SEQUENCE: 676
caggcgatct tgaccttggt                                             20

<210> SEQ ID NO 677
<211> LENGTH: 19
<212> TYPE: DNA
<213> ORGANISM: Zea mays;

<400> SEQUENCE: 677
ctaaatttaa gtgctgttg                                              19

<210> SEQ ID NO 678
<211> LENGTH: 22
<212> TYPE: DNA
<213> ORGANISM: Zea mays;

<400> SEQUENCE: 678
aagatctaaa tttaagtact gt                                          22

<210> SEQ ID NO 679
<211> LENGTH: 24
<212> TYPE: DNA
<213> ORGANISM: Zea mays;

<400> SEQUENCE: 679
ttctggataa agcaatgacc aaca                                        24

<210> SEQ ID NO 680
<211> LENGTH: 22
<212> TYPE: DNA
<213> ORGANISM: Zea mays;

<400> SEQUENCE: 680
gtgagtctgc ttcctctcca tt                                          22

<210> SEQ ID NO 681
<211> LENGTH: 18
<212> TYPE: DNA
<213> ORGANISM: Zea mays;

<400> SEQUENCE: 681
tggttgctct gcatgtat                                               18

<210> SEQ ID NO 682
<211> LENGTH: 18
<212> TYPE: DNA

-continued

<213> ORGANISM: Zea mays;

<400> SEQUENCE: 682
ttggttgctc tgcatata                                                      18

<210> SEQ ID NO 683
<211> LENGTH: 22
<212> TYPE: DNA
<213> ORGANISM: Zea mays;

<400> SEQUENCE: 683
gcctttgcga aggttttagc ag                                                 22

<210> SEQ ID NO 684
<211> LENGTH: 19
<212> TYPE: DNA
<213> ORGANISM: Zea mays;

<400> SEQUENCE: 684
aactccgtgg cagcatgtg                                                     19

<210> SEQ ID NO 685
<211> LENGTH: 15
<212> TYPE: DNA
<213> ORGANISM: Zea mays;

<400> SEQUENCE: 685
tgatctgggg catct                                                         15

<210> SEQ ID NO 686
<211> LENGTH: 17
<212> TYPE: DNA
<213> ORGANISM: Zea mays;

<400> SEQUENCE: 686
tgagtgatct gggacat                                                       17

<210> SEQ ID NO 687
<211> LENGTH: 22
<212> TYPE: DNA
<213> ORGANISM: Zea mays;

<400> SEQUENCE: 687
caccggtgcc aaggatatag ag                                                 22

<210> SEQ ID NO 688
<211> LENGTH: 20
<212> TYPE: DNA
<213> ORGANISM: Zea mays;

<400> SEQUENCE: 688
aggccgtcta acgaagtgtg                                                    20

<210> SEQ ID NO 689
<211> LENGTH: 18
<212> TYPE: DNA
<213> ORGANISM: Zea mays;

<400> SEQUENCE: 689
ttcatctatc cactagaa                                                      18

<210> SEQ ID NO 690
<211> LENGTH: 17

<212> TYPE: DNA
<213> ORGANISM: Zea mays;

<400> SEQUENCE: 690
tcatctatcc actacaa                                          17

<210> SEQ ID NO 691
<211> LENGTH: 22
<212> TYPE: DNA
<213> ORGANISM: Zea mays;

<400> SEQUENCE: 691
gtatgtaaaa caaggttcaa aa                                    22

<210> SEQ ID NO 692
<211> LENGTH: 21
<212> TYPE: DNA
<213> ORGANISM: Zea mays;

<400> SEQUENCE: 692
agggacaact atggatgaag t                                     21

<210> SEQ ID NO 693
<211> LENGTH: 17
<212> TYPE: DNA
<213> ORGANISM: Zea mays;

<400> SEQUENCE: 693
ccgtcctagt taagtgc                                          17

<210> SEQ ID NO 694
<211> LENGTH: 17
<212> TYPE: DNA
<213> ORGANISM: Zea mays;

<400> SEQUENCE: 694
tccgtcctag ctaagtg                                          17

<210> SEQ ID NO 695
<211> LENGTH: 20
<212> TYPE: DNA
<213> ORGANISM: Zea mays;

<400> SEQUENCE: 695
agtcggttct cttcgtctgc                                       20

<210> SEQ ID NO 696
<211> LENGTH: 23
<212> TYPE: DNA
<213> ORGANISM: Zea mays;

<400> SEQUENCE: 696
cgcatgcccg tgatttattt ctc                                   23

<210> SEQ ID NO 697
<211> LENGTH: 19
<212> TYPE: DNA
<213> ORGANISM: Zea mays;

<400> SEQUENCE: 697
ctgagagaat ggacacgaa                                        19

<210> SEQ ID NO 698

-continued

```
<211> LENGTH: 17
<212> TYPE: DNA
<213> ORGANISM: Zea mays;

<400> SEQUENCE: 698
ctgagagaat gggcaca                                                              17

<210> SEQ ID NO 699
<211> LENGTH: 20
<212> TYPE: DNA
<213> ORGANISM: Zea mays;

<400> SEQUENCE: 699
gtgttactag gatacagtga                                                           20

<210> SEQ ID NO 700
<211> LENGTH: 18
<212> TYPE: DNA
<213> ORGANISM: Zea mays;

<400> SEQUENCE: 700
tgcccttacc tgaagtct                                                             18

<210> SEQ ID NO 701
<211> LENGTH: 15
<212> TYPE: DNA
<213> ORGANISM: Zea mays;

<400> SEQUENCE: 701
tgctctgctt accgt                                                                15

<210> SEQ ID NO 702
<211> LENGTH: 14
<212> TYPE: DNA
<213> ORGANISM: Zea mays;

<400> SEQUENCE: 702
tgctctgcct accg                                                                 14

<210> SEQ ID NO 703
<211> LENGTH: 18
<212> TYPE: DNA
<213> ORGANISM: Zea mays;

<400> SEQUENCE: 703
gtgagcacca gccacttc                                                             18

<210> SEQ ID NO 704
<211> LENGTH: 19
<212> TYPE: DNA
<213> ORGANISM: Zea mays;

<400> SEQUENCE: 704
gaacacgacg gcattccaa                                                            19

<210> SEQ ID NO 705
<211> LENGTH: 21
<212> TYPE: DNA
<213> ORGANISM: Zea mays;

<400> SEQUENCE: 705
ataacacaag aatttgagca t                                                         21
```

-continued

```
<210> SEQ ID NO 706
<211> LENGTH: 21
<212> TYPE: DNA
<213> ORGANISM: Zea mays;

<400> SEQUENCE: 706
caataacaca agaatttaag c                                          21

<210> SEQ ID NO 707
<211> LENGTH: 18
<212> TYPE: DNA
<213> ORGANISM: Zea mays;

<400> SEQUENCE: 707
cctgctacag atttcaac                                              18

<210> SEQ ID NO 708
<211> LENGTH: 19
<212> TYPE: DNA
<213> ORGANISM: Zea mays;

<400> SEQUENCE: 708
ctgtttagga gccagatta                                             19

<210> SEQ ID NO 709
<211> LENGTH: 14
<212> TYPE: DNA
<213> ORGANISM: Zea mays;

<400> SEQUENCE: 709
cgacgggagt tggc                                                  14

<210> SEQ ID NO 710
<211> LENGTH: 14
<212> TYPE: DNA
<213> ORGANISM: Zea mays;

<400> SEQUENCE: 710
cgacgggagt aggc                                                  14

<210> SEQ ID NO 711
<211> LENGTH: 15
<212> TYPE: DNA
<213> ORGANISM: Zea mays;

<400> SEQUENCE: 711
agagccggga gccat                                                 15

<210> SEQ ID NO 712
<211> LENGTH: 15
<212> TYPE: DNA
<213> ORGANISM: Zea mays;

<400> SEQUENCE: 712
actcctccgc cttgg                                                 15

<210> SEQ ID NO 713
<211> LENGTH: 15
<212> TYPE: DNA
<213> ORGANISM: Zea mays;

<400> SEQUENCE: 713
cggcgccttc ttctg                                                 15
```

-continued

```
<210> SEQ ID NO 714
<211> LENGTH: 14
<212> TYPE: DNA
<213> ORGANISM: Zea mays;

<400> SEQUENCE: 714
cggcgcctcc ttct                                                      14

<210> SEQ ID NO 715
<211> LENGTH: 23
<212> TYPE: DNA
<213> ORGANISM: Zea mays;

<400> SEQUENCE: 715
gccgtgtcca tcaaacttca tct                                            23

<210> SEQ ID NO 716
<211> LENGTH: 19
<212> TYPE: DNA
<213> ORGANISM: Zea mays;

<400> SEQUENCE: 716
gggcttcttg cgcagagag                                                 19

<210> SEQ ID NO 717
<211> LENGTH: 22
<212> TYPE: DNA
<213> ORGANISM: Zea mays;

<400> SEQUENCE: 717
tattccaaga agtttatctt gt                                             22

<210> SEQ ID NO 718
<211> LENGTH: 19
<212> TYPE: DNA
<213> ORGANISM: Zea mays;

<400> SEQUENCE: 718
tccaagaagt ttaccttgt                                                 19

<210> SEQ ID NO 719
<211> LENGTH: 18
<212> TYPE: DNA
<213> ORGANISM: Zea mays;

<400> SEQUENCE: 719
agcacccagt cctccact                                                  18

<210> SEQ ID NO 720
<211> LENGTH: 18
<212> TYPE: DNA
<213> ORGANISM: Zea mays;

<400> SEQUENCE: 720
gctgcccagg atcgaact                                                  18

<210> SEQ ID NO 721
<211> LENGTH: 19
<212> TYPE: DNA
<213> ORGANISM: Zea mays;

<400> SEQUENCE: 721
ttccccagag aagggagtt                                                 19
```

-continued

<210> SEQ ID NO 722
<211> LENGTH: 20
<212> TYPE: DNA
<213> ORGANISM: Zea mays;

<400> SEQUENCE: 722
ttccccagag aaaggagtta                                                    20

<210> SEQ ID NO 723
<211> LENGTH: 20
<212> TYPE: DNA
<213> ORGANISM: Zea mays;

<400> SEQUENCE: 723
caggtagctt gccaaacgga                                                    20

<210> SEQ ID NO 724
<211> LENGTH: 23
<212> TYPE: DNA
<213> ORGANISM: Zea mays;

<400> SEQUENCE: 724
tgtctacacg aaggcaattg ttg                                                23

<210> SEQ ID NO 725
<211> LENGTH: 14
<212> TYPE: DNA
<213> ORGANISM: Zea mays;

<400> SEQUENCE: 725
tgttcgccgc agtc                                                          14

<210> SEQ ID NO 726
<211> LENGTH: 15
<212> TYPE: DNA
<213> ORGANISM: Zea mays;

<400> SEQUENCE: 726
tgttcgcagc agtcc                                                         15

<210> SEQ ID NO 727
<211> LENGTH: 16
<212> TYPE: DNA
<213> ORGANISM: Zea mays;

<400> SEQUENCE: 727
tgcccgggaa gatcca                                                        16

<210> SEQ ID NO 728
<211> LENGTH: 20
<212> TYPE: DNA
<213> ORGANISM: Zea mays;

<400> SEQUENCE: 728
ttaaccctga aggagacgga                                                    20

<210> SEQ ID NO 729
<211> LENGTH: 18
<212> TYPE: DNA
<213> ORGANISM: Zea mays;

<400> SEQUENCE: 729

```
acctccattc gcataaaa                                          18

<210> SEQ ID NO 730
<211> LENGTH: 20
<212> TYPE: DNA
<213> ORGANISM: Zea mays;

<400> SEQUENCE: 730
atgacctcca ttcacataaa                                        20

<210> SEQ ID NO 731
<211> LENGTH: 22
<212> TYPE: DNA
<213> ORGANISM: Zea mays;

<400> SEQUENCE: 731
ctggaacatg tcgaccattc ac                                     22

<210> SEQ ID NO 732
<211> LENGTH: 21
<212> TYPE: DNA
<213> ORGANISM: Zea mays;

<400> SEQUENCE: 732
ccctgaccac atgcatacac a                                      21

<210> SEQ ID NO 733
<211> LENGTH: 21
<212> TYPE: DNA
<213> ORGANISM: Zea mays;

<400> SEQUENCE: 733
ctagtaacca aatatgaatt a                                      21

<210> SEQ ID NO 734
<211> LENGTH: 21
<212> TYPE: DNA
<213> ORGANISM: Zea mays;

<400> SEQUENCE: 734
ctagtaacca aatatgaaat a                                      21

<210> SEQ ID NO 735
<211> LENGTH: 20
<212> TYPE: DNA
<213> ORGANISM: Zea mays;

<400> SEQUENCE: 735
ctgttatgat acctggtctt                                        20

<210> SEQ ID NO 736
<211> LENGTH: 17
<212> TYPE: DNA
<213> ORGANISM: Zea mays;

<400> SEQUENCE: 736
gactatgggc gtcttta                                           17

<210> SEQ ID NO 737
<211> LENGTH: 19
<212> TYPE: DNA
<213> ORGANISM: Zea mays;

<400> SEQUENCE: 737
```

-continued

```
aggcccattt taggatttt                                         19

<210> SEQ ID NO 738
<211> LENGTH: 19
<212> TYPE: DNA
<213> ORGANISM: Zea mays;

<400> SEQUENCE: 738
aggcccattt taggatatt                                         19

<210> SEQ ID NO 739
<211> LENGTH: 20
<212> TYPE: DNA
<213> ORGANISM: Zea mays;

<400> SEQUENCE: 739
agagcagtcc caccttggtt                                        20

<210> SEQ ID NO 740
<211> LENGTH: 20
<212> TYPE: DNA
<213> ORGANISM: Zea mays;

<400> SEQUENCE: 740
tgcttgaccg gagtgagaag                                        20

<210> SEQ ID NO 741
<211> LENGTH: 20
<212> TYPE: DNA
<213> ORGANISM: Zea mays;

<400> SEQUENCE: 741
aacaaatagg agaatcagat                                        20

<210> SEQ ID NO 742
<211> LENGTH: 18
<212> TYPE: DNA
<213> ORGANISM: Zea mays;

<400> SEQUENCE: 742
caaataggag aaccagat                                          18

<210> SEQ ID NO 743
<211> LENGTH: 23
<212> TYPE: DNA
<213> ORGANISM: Zea mays;

<400> SEQUENCE: 743
ggtggtgcct gcatataagt aaa                                    23

<210> SEQ ID NO 744
<211> LENGTH: 20
<212> TYPE: DNA
<213> ORGANISM: Zea mays;

<400> SEQUENCE: 744
atgtgccatg ctgcactaag                                        20

<210> SEQ ID NO 745
<211> LENGTH: 19
<212> TYPE: DNA
<213> ORGANISM: Zea mays;
```

<400> SEQUENCE: 745
tcgtaagatg ggaatgtgg                                                                 19

<210> SEQ ID NO 746
<211> LENGTH: 21
<212> TYPE: DNA
<213> ORGANISM: Zea mays;

<400> SEQUENCE: 746
tttcgtaaga tgagaatgtg g                                                              21

<210> SEQ ID NO 747
<211> LENGTH: 24
<212> TYPE: DNA
<213> ORGANISM: Zea mays;

<400> SEQUENCE: 747
acctttggtg tgtgctatgg tatg                                                           24

<210> SEQ ID NO 748
<211> LENGTH: 20
<212> TYPE: DNA
<213> ORGANISM: Zea mays;

<400> SEQUENCE: 748 accgtccct gctcaaaacc                                                                 20

<210> SEQ ID NO 749
<211> LENGTH: 19
<212> TYPE: DNA
<213> ORGANISM: Zea mays;

<400> SEQUENCE: 749
acatatttat agccctagg                                                                 19

<210> SEQ ID NO 750
<211> LENGTH: 19
<212> TYPE: DNA
<213> ORGANISM: Zea mays;

<400> SEQUENCE: 750
acatatttat agcccaagg                                                                 19

<210> SEQ ID NO 751
<211> LENGTH: 25
<212> TYPE: DNA
<213> ORGANISM: Zea mays;

<400> SEQUENCE: 751
caaacactac acaatgtcat accct                                                          25

<210> SEQ ID NO 752
<211> LENGTH: 25
<212> TYPE: DNA
<213> ORGANISM: Zea mays;

<400> SEQUENCE: 752
actgtcctct gtagtctctt tagca                                                          25

<210> SEQ ID NO 753
<211> LENGTH: 16
<212> TYPE: DNA
<213> ORGANISM: Zea mays;

-continued

```
<400> SEQUENCE: 753
accagcccta gtcatc                                                16

<210> SEQ ID NO 754
<211> LENGTH: 17
<212> TYPE: DNA
<213> ORGANISM: Zea mays;

<400> SEQUENCE: 754
cagccctact catcaaa                                               17

<210> SEQ ID NO 755
<211> LENGTH: 21
<212> TYPE: DNA
<213> ORGANISM: Zea mays;

<400> SEQUENCE: 755
ttgtccacaa cctcctactg a                                          21

<210> SEQ ID NO 756
<211> LENGTH: 21
<212> TYPE: DNA
<213> ORGANISM: Zea mays;

<400> SEQUENCE: 756
aaggctcaat tgcaacccat a                                          21

<210> SEQ ID NO 757
<211> LENGTH: 18
<212> TYPE: DNA
<213> ORGANISM: Zea mays;

<400> SEQUENCE: 757
ccacctcgaa tcagtata                                              18

<210> SEQ ID NO 758
<211> LENGTH: 18
<212> TYPE: DNA
<213> ORGANISM: Zea mays;

<400> SEQUENCE: 758
ccacctcgaa acagtata                                              18

<210> SEQ ID NO 759
<211> LENGTH: 25
<212> TYPE: DNA
<213> ORGANISM: Zea mays;

<400> SEQUENCE: 759
tctctattgg ctgagaacaa ttcac                                      25

<210> SEQ ID NO 760
<211> LENGTH: 21
<212> TYPE: DNA
<213> ORGANISM: Zea mays;

<400> SEQUENCE: 760
tcgttggatc aatcgcaact c                                          21

<210> SEQ ID NO 761
<211> LENGTH: 19
<212> TYPE: DNA
```

-continued

<213> ORGANISM: Zea mays;

<400> SEQUENCE: 761
ttggttgaac tttagtatc                                                          19

<210> SEQ ID NO 762
<211> LENGTH: 19
<212> TYPE: DNA
<213> ORGANISM: Zea mays;

<400> SEQUENCE: 762
ttggttgaac tttagaatc                                                          19

<210> SEQ ID NO 763
<211> LENGTH: 20
<212> TYPE: DNA
<213> ORGANISM: Zea mays;

<400> SEQUENCE: 763
ttgacactca ttactgtttg                                                         20

<210> SEQ ID NO 764
<211> LENGTH: 21
<212> TYPE: DNA
<213> ORGANISM: Zea mays;

<400> SEQUENCE: 764
ggagaatgac ttagaactta g                                                       21

<210> SEQ ID NO 765
<211> LENGTH: 13
<212> TYPE: DNA
<213> ORGANISM: Zea mays;

<400> SEQUENCE: 765
agcagcagcg ggg                                                                13

<210> SEQ ID NO 766
<211> LENGTH: 13
<212> TYPE: DNA
<213> ORGANISM: Zea mays;

<400> SEQUENCE: 766
cagcagcagg ggc                                                                13

<210> SEQ ID NO 767
<211> LENGTH: 18
<212> TYPE: DNA
<213> ORGANISM: Zea mays;

<400> SEQUENCE: 767
cacgcggtgg tggacatg                                                           18

<210> SEQ ID NO 768
<211> LENGTH: 20
<212> TYPE: DNA
<213> ORGANISM: Zea mays;

<400> SEQUENCE: 768
tccacgctca tctccttgtg                                                         20

<210> SEQ ID NO 769
<211> LENGTH: 20

-continued

<212> TYPE: DNA
<213> ORGANISM: Zea mays;

<400> SEQUENCE: 769
atgatgccag gagaggcaag                                                    20

<210> SEQ ID NO 770
<211> LENGTH: 16
<212> TYPE: DNA
<213> ORGANISM: Zea mays;

<400> SEQUENCE: 770
tgccaggaga cgcaag                                                        16

<210> SEQ ID NO 771
<211> LENGTH: 25
<212> TYPE: DNA
<213> ORGANISM: Zea mays;

<400> SEQUENCE: 771
gaacaagaag catgagcatt ctgac                                              25

<210> SEQ ID NO 772
<211> LENGTH: 21
<212> TYPE: DNA
<213> ORGANISM: Zea mays;

<400> SEQUENCE: 772
tcacggttgc tctcatcact t                                                  21

<210> SEQ ID NO 773
<211> LENGTH: 18
<212> TYPE: DNA
<213> ORGANISM: Zea mays;

<400> SEQUENCE: 773
cattcctatt caaggtta                                                      18

<210> SEQ ID NO 774
<211> LENGTH: 17
<212> TYPE: DNA
<213> ORGANISM: Zea mays;

<400> SEQUENCE: 774
ttcctattca aggctaa                                                       17

<210> SEQ ID NO 775
<211> LENGTH: 17
<212> TYPE: DNA
<213> ORGANISM: Zea mays;

<400> SEQUENCE: 775
aggcacgtgg atatctg                                                       17

<210> SEQ ID NO 776
<211> LENGTH: 15
<212> TYPE: DNA
<213> ORGANISM: Zea mays;

<400> SEQUENCE: 776
gtgtggagca accaa                                                         15

<210> SEQ ID NO 777

7,, 1 B2

7 B

US 12,653,119 B2

269                                                                    270

-continued

```
<211> LENGTH: 16
<212> TYPE: DNA
<213> ORGANISM: Zea mays;

<400> SEQUENCE: 777
ctgatagcgc gcagtg                                                      16

<210> SEQ ID NO 778
<211> LENGTH: 18
<212> TYPE: DNA
<213> ORGANISM: Zea mays;

<400> SEQUENCE: 778
ctgatagcga gcagtgac                                                    18

<210> SEQ ID NO 779
<211> LENGTH: 21
<212> TYPE: DNA
<213> ORGANISM: Zea mays;

<400> SEQUENCE: 779
gcacctcagt gaaacgacaa g                                                21

<210> SEQ ID NO 780
<211> LENGTH: 21
<212> TYPE: DNA
<213> ORGANISM: Zea mays;

<400> SEQUENCE: 780
tgaggaaggt gagtgatttg c                                                21

<210> SEQ ID NO 781
<211> LENGTH: 19
<212> TYPE: DNA
<213> ORGANISM: Zea mays;

<400> SEQUENCE: 781
cgatgcacac taagatgac                                                   19

<210> SEQ ID NO 782
<211> LENGTH: 17
<212> TYPE: DNA
<213> ORGANISM: Zea mays;

<400> SEQUENCE: 782
cgatgcacac caagatg                                                     17

<210> SEQ ID NO 783
<211> LENGTH: 20
<212> TYPE: DNA
<213> ORGANISM: Zea mays;

<400> SEQUENCE: 783
gaagggccaa actgaggcat                                                  20

<210> SEQ ID NO 784
<211> LENGTH: 19
<212> TYPE: DNA
<213> ORGANISM: Zea mays;

<400> SEQUENCE: 784
acttcccggt tgagcaaga                                                   19
```

-continued

```
<210> SEQ ID NO 785
<211> LENGTH: 18
<212> TYPE: DNA
<213> ORGANISM: Zea mays;

<400> SEQUENCE: 785
cctagttagg gttatgtg                                                 18

<210> SEQ ID NO 786
<211> LENGTH: 19
<212> TYPE: DNA
<213> ORGANISM: Zea mays;

<400> SEQUENCE: 786
cctagttagg gttatatgg                                                19

<210> SEQ ID NO 787
<211> LENGTH: 22
<212> TYPE: DNA
<213> ORGANISM: Zea mays;

<400> SEQUENCE: 787
tgcgtttacg tctgcaatta ga                                            22

<210> SEQ ID NO 788
<211> LENGTH: 23
<212> TYPE: DNA
<213> ORGANISM: Zea mays;

<400> SEQUENCE: 788
ctggcctctt tctcttctct gta                                           23

<210> SEQ ID NO 789
<211> LENGTH: 17
<212> TYPE: DNA
<213> ORGANISM: Zea mays;

<400> SEQUENCE: 789
ccttgtgcct gattcaa                                                  17

<210> SEQ ID NO 790
<211> LENGTH: 16
<212> TYPE: DNA
<213> ORGANISM: Zea mays;

<400> SEQUENCE: 790
ttgtgcccga ttcaac                                                   16

<210> SEQ ID NO 791
<211> LENGTH: 23
<212> TYPE: DNA
<213> ORGANISM: Zea mays;

<400> SEQUENCE: 791
cgcaagtcat tgttcgctgt ttg                                           23

<210> SEQ ID NO 792
<211> LENGTH: 23
<212> TYPE: DNA
<213> ORGANISM: Zea mays;

<400> SEQUENCE: 792
gtcgtcaccg tctttctttc aac                                           23
```

-continued

```
<210> SEQ ID NO 793
<211> LENGTH: 19
<212> TYPE: DNA
<213> ORGANISM: Zea mays;

<400> SEQUENCE: 793
agcaggctat gttttagtt                                              19

<210> SEQ ID NO 794
<211> LENGTH: 17
<212> TYPE: DNA
<213> ORGANISM: Zea mays;

<400> SEQUENCE: 794
agcaggctat gtttcag                                                17

<210> SEQ ID NO 795
<211> LENGTH: 19
<212> TYPE: DNA
<213> ORGANISM: Zea mays;

<400> SEQUENCE: 795
acttctcaag aggctaaac                                              19

<210> SEQ ID NO 796
<211> LENGTH: 18
<212> TYPE: DNA
<213> ORGANISM: Zea mays;

<400> SEQUENCE: 796
gctgtaacct gtggtcta                                               18

<210> SEQ ID NO 797
<211> LENGTH: 20
<212> TYPE: DNA
<213> ORGANISM: Zea mays;

<400> SEQUENCE: 797
ctgaggtagt atataagaag                                             20

<210> SEQ ID NO 798
<211> LENGTH: 20
<212> TYPE: DNA
<213> ORGANISM: Zea mays;

<400> SEQUENCE: 798
tctgaggtag tatataaaaa                                             20

<210> SEQ ID NO 799
<211> LENGTH: 20
<212> TYPE: DNA
<213> ORGANISM: Zea mays;

<400> SEQUENCE: 799
agagaatact tgagaaggct                                             20

<210> SEQ ID NO 800
<211> LENGTH: 18
<212> TYPE: DNA
<213> ORGANISM: Zea mays;

<400> SEQUENCE: 800
gtactgatgg gactggat                                               18
```

-continued

```
<210> SEQ ID NO 801
<211> LENGTH: 20
<212> TYPE: DNA
<213> ORGANISM: Zea mays;

<400> SEQUENCE: 801
atattttatt cctcgtttca                                              20

<210> SEQ ID NO 802
<211> LENGTH: 20
<212> TYPE: DNA
<213> ORGANISM: Zea mays;

<400> SEQUENCE: 802
atattttatt cctcatttca                                              20

<210> SEQ ID NO 803
<211> LENGTH: 21
<212> TYPE: DNA
<213> ORGANISM: Zea mays;

<400> SEQUENCE: 803
gaaactctac atttgggaga t                                            21

<210> SEQ ID NO 804
<211> LENGTH: 22
<212> TYPE: DNA
<213> ORGANISM: Zea mays;

<400> SEQUENCE: 804
ggacacaatt atatgacctc tt                                           22

<210> SEQ ID NO 805
<211> LENGTH: 16
<212> TYPE: DNA
<213> ORGANISM: Zea mays;

<400> SEQUENCE: 805
tttgggcggt caatgg                                                  16

<210> SEQ ID NO 806
<211> LENGTH: 13
<212> TYPE: DNA
<213> ORGANISM: Zea mays;

<400> SEQUENCE: 806
tgggcggcca atg                                                     13

<210> SEQ ID NO 807
<211> LENGTH: 18
<212> TYPE: DNA
<213> ORGANISM: Zea mays;

<400> SEQUENCE: 807
tgcgttccgg ccttactc                                                18

<210> SEQ ID NO 808
<211> LENGTH: 21
<212> TYPE: DNA
<213> ORGANISM: Zea mays;

<400> SEQUENCE: 808
```

-continued actgcgtttc tccctttgct t                                                    21

<210> SEQ ID NO 809
<211> LENGTH: 14
<212> TYPE: DNA
<213> ORGANISM: Zea mays;

<400> SEQUENCE: 809
ccgcgatgcc cttg                                                           14

<210> SEQ ID NO 810
<211> LENGTH: 13
<212> TYPE: DNA
<213> ORGANISM: Zea mays;

<400> SEQUENCE: 810
cgcgacgccc ttg                                                            13

<210> SEQ ID NO 811
<211> LENGTH: 20
<212> TYPE: DNA
<213> ORGANISM: Zea mays;

<400> SEQUENCE: 811
ggcaggtttc gtaccacatc                                                     20

<210> SEQ ID NO 812
<211> LENGTH: 21
<212> TYPE: DNA
<213> ORGANISM: Zea mays;

<400> SEQUENCE: 812
cgaggatccg tgctcttcta a                                                   21

<210> SEQ ID NO 813
<211> LENGTH: 17
<212> TYPE: DNA
<213> ORGANISM: Zea mays;

<400> SEQUENCE: 813
cagcagcctt gatctgt                                                        17

<210> SEQ ID NO 814
<211> LENGTH: 15
<212> TYPE: DNA
<213> ORGANISM: Zea mays;

<400> SEQUENCE: 814
cagcagcctc gatct                                                          15

<210> SEQ ID NO 815
<211> LENGTH: 22
<212> TYPE: DNA
<213> ORGANISM: Zea mays;

<400> SEQUENCE: 815
cctccaagat gtgctccatg at                                                  22

<210> SEQ ID NO 816
<211> LENGTH: 17
<212> TYPE: DNA
<213> ORGANISM: Zea mays;

<400> SEQUENCE: 816
tcgccgaggt cctgtct                                                      17

<210> SEQ ID NO 817
<211> LENGTH: 14
<212> TYPE: DNA
<213> ORGANISM: Zea mays;

<400> SEQUENCE: 817
cggcggtggg atga                                                        14

<210> SEQ ID NO 818
<211> LENGTH: 13
<212> TYPE: DNA
<213> ORGANISM: Zea mays;

<400> SEQUENCE: 818
cggcggcggg atg                                                         13

<210> SEQ ID NO 819
<211> LENGTH: 20
<212> TYPE: DNA
<213> ORGANISM: Zea mays;

<400> SEQUENCE: 819
gcgtgtgaga gggacaaagg                                                  20

<210> SEQ ID NO 820
<211> LENGTH: 18
<212> TYPE: DNA
<213> ORGANISM: Zea mays;

<400> SEQUENCE: 820
gtgcacaacg cactgttc                                                    18

<210> SEQ ID NO 821
<211> LENGTH: 13
<212> TYPE: DNA
<213> ORGANISM: Zea mays;

<400> SEQUENCE: 821
ccttggtgcc tgc                                                         13

<210> SEQ ID NO 822
<211> LENGTH: 14
<212> TYPE: DNA
<213> ORGANISM: Zea mays;

<400> SEQUENCE: 822
cccttggtgc ctac                                                        14

<210> SEQ ID NO 823
<211> LENGTH: 28
<212> TYPE: DNA
<213> ORGANISM: Zea mays;

<400> SEQUENCE: 823
cccaagatcc aagaagcgat atatatgc                                         28

<210> SEQ ID NO 824
<211> LENGTH: 19
<212> TYPE: DNA
<213> ORGANISM: Zea mays;

-continued

<400> SEQUENCE: 824
ggcgatcggg tgcaatttg                                              19

<210> SEQ ID NO 825
<211> LENGTH: 16
<212> TYPE: DNA
<213> ORGANISM: Zea mays;

<400> SEQUENCE: 825
ttaggccttg tttgtt                                                 16

<210> SEQ ID NO 826
<211> LENGTH: 14
<212> TYPE: DNA
<213> ORGANISM: Zea mays;

<400> SEQUENCE: 826
aggccttgtt cgtt                                                   14

<210> SEQ ID NO 827
<211> LENGTH: 18
<212> TYPE: DNA
<213> ORGANISM: Zea mays;

<400> SEQUENCE: 827
cagtggcagt aactgata                                               18

<210> SEQ ID NO 828
<211> LENGTH: 19
<212> TYPE: DNA
<213> ORGANISM: Zea mays;

<400> SEQUENCE: 828
aagcaatccg gttaggaat                                              19

<210> SEQ ID NO 829
<211> LENGTH: 18
<212> TYPE: DNA
<213> ORGANISM: Zea mays;

<400> SEQUENCE: 829
ccgacgatca tattcgta                                               18

<210> SEQ ID NO 830
<211> LENGTH: 17
<212> TYPE: DNA
<213> ORGANISM: Zea mays;

<400> SEQUENCE: 830
cgacgatcac attcgta                                                17

<210> SEQ ID NO 831
<211> LENGTH: 21
<212> TYPE: DNA
<213> ORGANISM: Zea mays;

<400> SEQUENCE: 831
ctgctgctgc aagcaattgt a                                           21

<210> SEQ ID NO 832
<211> LENGTH: 24
<212> TYPE: DNA
<213> ORGANISM: Zea mays;

-continued

```
<400> SEQUENCE: 832
tggcactgac taacagtcta acag                                      24

<210> SEQ ID NO 833
<211> LENGTH: 14
<212> TYPE: DNA
<213> ORGANISM: Zea mays;

<400> SEQUENCE: 833
ctgcagatcc ccag                                                 14

<210> SEQ ID NO 834
<211> LENGTH: 13
<212> TYPE: DNA
<213> ORGANISM: Zea mays;

<400> SEQUENCE: 834
tgcagacccc cag                                                  13

<210> SEQ ID NO 835
<211> LENGTH: 15
<212> TYPE: DNA
<213> ORGANISM: Zea mays;

<400> SEQUENCE: 835
ctgctccgac gactg                                                15

<210> SEQ ID NO 836
<211> LENGTH: 16
<212> TYPE: DNA
<213> ORGANISM: Zea mays;

<400> SEQUENCE: 836
ctgagctgct caaggt                                               16

<210> SEQ ID NO 837
<211> LENGTH: 20
<212> TYPE: DNA
<213> ORGANISM: Zea mays;

<400> SEQUENCE: 837
aaacgttacc tgataaatct                                           20

<210> SEQ ID NO 838
<211> LENGTH: 19
<212> TYPE: DNA
<213> ORGANISM: Zea mays;

<400> SEQUENCE: 838
aacgttacct gataaacct                                            19

<210> SEQ ID NO 839
<211> LENGTH: 19
<212> TYPE: DNA
<213> ORGANISM: Zea mays;

<400> SEQUENCE: 839
tgtttgcagc ccctctcaa                                            19

<210> SEQ ID NO 840
<211> LENGTH: 17
<212> TYPE: DNA
```

-continued

<210> ORGANISM: Zea mays;

<400> SEQUENCE: 840
ttctggcccg tgttgct                                                    17

<210> SEQ ID NO 841
<211> LENGTH: 16
<212> TYPE: DNA
<213> ORGANISM: Zea mays;

<400> SEQUENCE: 841
tcattctggt gctcat                                                     16

<210> SEQ ID NO 842
<211> LENGTH: 16
<212> TYPE: DNA
<213> ORGANISM: Zea mays;

<400> SEQUENCE: 842
tcattctggt gcacat                                                     16

<210> SEQ ID NO 843
<211> LENGTH: 22
<212> TYPE: DNA
<213> ORGANISM: Zea mays;

<400> SEQUENCE: 843
tctaggtttc ggctagtggt ta                                              22

<210> SEQ ID NO 844
<211> LENGTH: 25
<212> TYPE: DNA
<213> ORGANISM: Zea mays;

<400> SEQUENCE: 844
actattacac ttcgtctctg ggttt                                           25

<210> SEQ ID NO 845
<211> LENGTH: 20
<212> TYPE: DNA
<213> ORGANISM: Zea mays;

<400> SEQUENCE: 845
agctctcctt gatatgaacc                                                 20

<210> SEQ ID NO 846
<211> LENGTH: 17
<212> TYPE: DNA
<213> ORGANISM: Zea mays;

<400> SEQUENCE: 846
ctccttgata cgaaccc                                                    17

<210> SEQ ID NO 847
<211> LENGTH: 24
<212> TYPE: DNA
<213> ORGANISM: Zea mays;

<400> SEQUENCE: 847
tctcctaaac ccattgcaaa cagt                                            24

<210> SEQ ID NO 848
<211> LENGTH: 22

-continued

```
<212> TYPE: DNA
<213> ORGANISM: Zea mays;

<400> SEQUENCE: 848
tcaagacttg cacttgctca gt                                              22

<210> SEQ ID NO 849
<211> LENGTH: 19
<212> TYPE: DNA
<213> ORGANISM: Zea mays;

<400> SEQUENCE: 849
caagaaccga gattttact                                                  19

<210> SEQ ID NO 850
<211> LENGTH: 20
<212> TYPE: DNA
<213> ORGANISM: Zea mays;

<400> SEQUENCE: 850
caagaaccga gagtttactt                                                 20

<210> SEQ ID NO 851
<211> LENGTH: 22
<212> TYPE: DNA
<213> ORGANISM: Zea mays;

<400> SEQUENCE: 851
aggttgcatt gatgttggtt gt                                              22

<210> SEQ ID NO 852
<211> LENGTH: 20
<212> TYPE: DNA
<213> ORGANISM: Zea mays;

<400> SEQUENCE: 852
cagcactcct ggaattcaca                                                 20

<210> SEQ ID NO 853
<211> LENGTH: 13
<212> TYPE: DNA
<213> ORGANISM: Zea mays;

<400> SEQUENCE: 853
tgggcctctg gtc                                                        13

<210> SEQ ID NO 854
<211> LENGTH: 14
<212> TYPE: DNA
<213> ORGANISM: Zea mays;

<400> SEQUENCE: 854
ctgggcctct gatc                                                       14

<210> SEQ ID NO 855
<211> LENGTH: 18
<212> TYPE: DNA
<213> ORGANISM: Zea mays;

<400> SEQUENCE: 855
acaggactgt atctggtg                                                   18

<210> SEQ ID NO 856
```

```
<211> LENGTH: 17
<212> TYPE: DNA
<213> ORGANISM: Zea mays;

<400> SEQUENCE: 856
tgcagggtag ttagcat                                                17

<210> SEQ ID NO 857
<211> LENGTH: 20
<212> TYPE: DNA
<213> ORGANISM: Zea mays;

<400> SEQUENCE: 857
ttagtctctt ggatgcataa                                             20

<210> SEQ ID NO 858
<211> LENGTH: 18
<212> TYPE: DNA
<213> ORGANISM: Zea mays;

<400> SEQUENCE: 858
agtctcttgg acgcataa                                               18

<210> SEQ ID NO 859
<211> LENGTH: 24
<212> TYPE: DNA
<213> ORGANISM: Zea mays;

<400> SEQUENCE: 859
gaagctagta ttgtccacct cctt                                        24

<210> SEQ ID NO 860
<211> LENGTH: 25
<212> TYPE: DNA
<213> ORGANISM: Zea mays;

<400> SEQUENCE: 860
tcgagagagt tagatgagac agtga                                       25

<210> SEQ ID NO 861
<211> LENGTH: 16
<212> TYPE: DNA
<213> ORGANISM: Zea mays;

<400> SEQUENCE: 861
ataaatcccc atcggg                                                 16

<210> SEQ ID NO 862
<211> LENGTH: 16
<212> TYPE: DNA
<213> ORGANISM: Zea mays;

<400> SEQUENCE: 862
ataaatcccc aacggg                                                 16

<210> SEQ ID NO 863
<211> LENGTH: 19
<212> TYPE: DNA
<213> ORGANISM: Zea mays;

<400> SEQUENCE: 863
ggatccccac gaacgcttg                                              19
```

-continued

```
<210> SEQ ID NO 864
<211> LENGTH: 21
<212> TYPE: DNA
<213> ORGANISM: Zea mays;

<400> SEQUENCE: 864
gcacggacac tcagctagtt a                                                      21

<210> SEQ ID NO 865
<211> LENGTH: 13
<212> TYPE: DNA
<213> ORGANISM: Zea mays;

<400> SEQUENCE: 865
cggctacggc gag                                                               13

<210> SEQ ID NO 866
<211> LENGTH: 14
<212> TYPE: DNA
<213> ORGANISM: Zea mays;

<400> SEQUENCE: 866
agcggctacg acga                                                              14

<210> SEQ ID NO 867
<211> LENGTH: 20
<212> TYPE: DNA
<213> ORGANISM: Zea mays;

<400> SEQUENCE: 867
aggcacgagt caactaggga                                                        20

<210> SEQ ID NO 868
<211> LENGTH: 21
<212> TYPE: DNA
<213> ORGANISM: Zea mays;

<400> SEQUENCE: 868
cagcccatct gcatcctcat c                                                      21

<210> SEQ ID NO 869
<211> LENGTH: 21
<212> TYPE: DNA
<213> ORGANISM: Zea mays;

<400> SEQUENCE: 869
cttgtttgaa aggaaatgac c                                                      21

<210> SEQ ID NO 870
<211> LENGTH: 19
<212> TYPE: DNA
<213> ORGANISM: Zea mays;

<400> SEQUENCE: 870
tgtttgaaag caaatgacc                                                         19

<210> SEQ ID NO 871
<211> LENGTH: 24
<212> TYPE: DNA
<213> ORGANISM: Zea mays;

<400> SEQUENCE: 871
gtgtccgctt gaccctatat cttc                                                   24
```

-continued

```
<210> SEQ ID NO 872
<211> LENGTH: 20
<212> TYPE: DNA
<213> ORGANISM: Zea mays;

<400> SEQUENCE: 872
gcagcagcct ttccgttcag                                                  20

<210> SEQ ID NO 873
<211> LENGTH: 14
<212> TYPE: DNA
<213> ORGANISM: Zea mays;

<400> SEQUENCE: 873
cttcggcagg cacg                                                        14

<210> SEQ ID NO 874
<211> LENGTH: 15
<212> TYPE: DNA
<213> ORGANISM: Zea mays;

<400> SEQUENCE: 874
acgcttcgac aggca                                                       15

<210> SEQ ID NO 875
<211> LENGTH: 18
<212> TYPE: DNA
<213> ORGANISM: Zea mays;

<400> SEQUENCE: 875
acacggccac acggacac                                                    18

<210> SEQ ID NO 876
<211> LENGTH: 16
<212> TYPE: DNA
<213> ORGANISM: Zea mays;

<400> SEQUENCE: 876
tcgcgctccc gacaag                                                      16

<210> SEQ ID NO 877
<211> LENGTH: 18
<212> TYPE: DNA
<213> ORGANISM: Zea mays;

<400> SEQUENCE: 877
aaagggcgct atagtgga                                                    18

<210> SEQ ID NO 878
<211> LENGTH: 17
<212> TYPE: DNA
<213> ORGANISM: Zea mays;

<400> SEQUENCE: 878
agggcgctac agtggac                                                     17

<210> SEQ ID NO 879
<211> LENGTH: 25
<212> TYPE: DNA
<213> ORGANISM: Zea mays;

<400> SEQUENCE: 879
cttctaaatt ctgacgagca cgaaa                                            25
```

-continued

<210> SEQ ID NO 880
<211> LENGTH: 22
<212> TYPE: DNA
<213> ORGANISM: Zea mays;

<400> SEQUENCE: 880
ggctgcagtg attcagtttg ac                                              22

<210> SEQ ID NO 881
<211> LENGTH: 15
<212> TYPE: DNA
<213> ORGANISM: Zea mays;

<400> SEQUENCE: 881
acggtgtgtc cgtct                                                      15

<210> SEQ ID NO 882
<211> LENGTH: 15
<212> TYPE: DNA
<213> ORGANISM: Zea mays;

<400> SEQUENCE: 882
acggtgtgtc cgtca                                                      15

<210> SEQ ID NO 883
<211> LENGTH: 20
<212> TYPE: DNA
<213> ORGANISM: Zea mays;

<400> SEQUENCE: 883
gctctgccac tctgttgcat                                                 20

<210> SEQ ID NO 884
<211> LENGTH: 19
<212> TYPE: DNA
<213> ORGANISM: Zea mays;

<400> SEQUENCE: 884
ccacggtgtg gagtgtgag                                                  19

<210> SEQ ID NO 885
<211> LENGTH: 19
<212> TYPE: DNA
<213> ORGANISM: Zea mays;

<400> SEQUENCE: 885
cctcaatcga tatggatta                                                  19

<210> SEQ ID NO 886
<211> LENGTH: 18
<212> TYPE: DNA
<213> ORGANISM: Zea mays;

<400> SEQUENCE: 886
cacctcaatc gatatgaa                                                   18

<210> SEQ ID NO 887
<211> LENGTH: 15
<212> TYPE: DNA
<213> ORGANISM: Zea mays;

<400> SEQUENCE: 887

-continued

```
ctcactacgc ggcag                                                    15

<210> SEQ ID NO 888
<211> LENGTH: 19
<212> TYPE: DNA
<213> ORGANISM: Zea mays;

<400> SEQUENCE: 888
tcatgactgg atacgtatg                                                19

<210> SEQ ID NO 889
<211> LENGTH: 14
<212> TYPE: DNA
<213> ORGANISM: Zea mays;

<400> SEQUENCE: 889
aggcactggt cgtt                                                     14

<210> SEQ ID NO 890
<211> LENGTH: 16
<212> TYPE: DNA
<213> ORGANISM: Zea mays;

<400> SEQUENCE: 890
taggcactgg tcattg                                                   16

<210> SEQ ID NO 891
<211> LENGTH: 20
<212> TYPE: DNA
<213> ORGANISM: Zea mays;

<400> SEQUENCE: 891
gccagtacca ggtacaccat                                               20

<210> SEQ ID NO 892
<211> LENGTH: 25
<212> TYPE: DNA
<213> ORGANISM: Zea mays;

<400> SEQUENCE: 892
cctaagtcat taccttgcag ggata                                         25

<210> SEQ ID NO 893
<211> LENGTH: 21
<212> TYPE: DNA
<213> ORGANISM: Zea mays;

<400> SEQUENCE: 893
cttagtatgt ttttgtcatg a                                             21

<210> SEQ ID NO 894
<211> LENGTH: 23
<212> TYPE: DNA
<213> ORGANISM: Zea mays;

<400> SEQUENCE: 894
tacttagtat gtttttatca tga                                           23

<210> SEQ ID NO 895
<211> LENGTH: 25
<212> TYPE: DNA
<213> ORGANISM: Zea mays;

<400> SEQUENCE: 895
```

-continued

```
gtttaacttc tctttgctag ccgat                                          25

<210> SEQ ID NO 896
<211> LENGTH: 22
<212> TYPE: DNA
<213> ORGANISM: Zea mays;

<400> SEQUENCE: 896
ccggaatgct actgaacaac ac                                             22

<210> SEQ ID NO 897
<211> LENGTH: 15
<212> TYPE: DNA
<213> ORGANISM: Zea mays;

<400> SEQUENCE: 897
tgtcacacgg ctatc                                                     15

<210> SEQ ID NO 898
<211> LENGTH: 17
<212> TYPE: DNA
<213> ORGANISM: Zea mays;

<400> SEQUENCE: 898
caaatgtcac acagcta                                                   17

<210> SEQ ID NO 899
<211> LENGTH: 19
<212> TYPE: DNA
<213> ORGANISM: Zea mays;

<400> SEQUENCE: 899
gaactgatac gctactctt                                                 19

<210> SEQ ID NO 900
<211> LENGTH: 22
<212> TYPE: DNA
<213> ORGANISM: Zea mays;

<400> SEQUENCE: 900
accatattgg ataaaactct tg                                             22

<210> SEQ ID NO 901
<211> LENGTH: 15
<212> TYPE: DNA
<213> ORGANISM: Zea mays;

<400> SEQUENCE: 901
catgctttgc gcggt                                                     15

<210> SEQ ID NO 902
<211> LENGTH: 16
<212> TYPE: DNA
<213> ORGANISM: Zea mays;

<400> SEQUENCE: 902
tcatgctatg cgcggt                                                    16

<210> SEQ ID NO 903
<211> LENGTH: 16
<212> TYPE: DNA
<213> ORGANISM: Zea mays;
```

-continued

```
<400> SEQUENCE: 903
atcgtcgccg ccgtgt                                              16

<210> SEQ ID NO 904
<211> LENGTH: 21
<212> TYPE: DNA
<213> ORGANISM: Zea mays;

<400> SEQUENCE: 904
agctcccggt gtgatatcct t                                        21

<210> SEQ ID NO 905
<211> LENGTH: 16
<212> TYPE: DNA
<213> ORGANISM: Zea mays;

<400> SEQUENCE: 905
agtgtggcga tctcct                                              16

<210> SEQ ID NO 906
<211> LENGTH: 16
<212> TYPE: DNA
<213> ORGANISM: Zea mays;

<400> SEQUENCE: 906
agtgtggcga tctccc                                              16

<210> SEQ ID NO 907
<211> LENGTH: 20
<212> TYPE: DNA
<213> ORGANISM: Zea mays;

<400> SEQUENCE: 907
cgacactgct ctgctgaatc                                          20

<210> SEQ ID NO 908
<211> LENGTH: 23
<212> TYPE: DNA
<213> ORGANISM: Zea mays;

<400> SEQUENCE: 908
acggtcattc atctcatcga aca                                      23

<210> SEQ ID NO 909
<211> LENGTH: 20
<212> TYPE: DNA
<213> ORGANISM: Zea mays;

<400> SEQUENCE: 909
atttattaat aggctacgtt                                          20

<210> SEQ ID NO 910
<211> LENGTH: 21
<212> TYPE: DNA
<213> ORGANISM: Zea mays;

<400> SEQUENCE: 910
tgtatttatt aataggctac a                                        21

<210> SEQ ID NO 911
<211> LENGTH: 20
<212> TYPE: DNA
<213> ORGANISM: Zea mays;
```

-continued

```
<400> SEQUENCE: 911
agcaacagac gcctcacttc                                         20

<210> SEQ ID NO 912
<211> LENGTH: 23
<212> TYPE: DNA
<213> ORGANISM: Zea mays;

<400> SEQUENCE: 912
tccaagcaca ggagacaact aag                                     23

<210> SEQ ID NO 913
<211> LENGTH: 18
<212> TYPE: DNA
<213> ORGANISM: Zea mays;

<400> SEQUENCE: 913
tgagaacagt catgcctt                                           18

<210> SEQ ID NO 914
<211> LENGTH: 18
<212> TYPE: DNA
<213> ORGANISM: Zea mays;

<400> SEQUENCE: 914
agaacagtca cgcctttg                                           18

<210> SEQ ID NO 915
<211> LENGTH: 23
<212> TYPE: DNA
<213> ORGANISM: Zea mays;

<400> SEQUENCE: 915
tgttgaaata cgatgcgcta tgg                                     23

<210> SEQ ID NO 916
<211> LENGTH: 23
<212> TYPE: DNA
<213> ORGANISM: Zea mays;

<400> SEQUENCE: 916
gccaatgttg acaaccaaac agc                                     23

<210> SEQ ID NO 917
<211> LENGTH: 17
<212> TYPE: DNA
<213> ORGANISM: Zea mays;

<400> SEQUENCE: 917
aggtgtagtc gtcgtgt                                            17

<210> SEQ ID NO 918
<211> LENGTH: 17
<212> TYPE: DNA
<213> ORGANISM: Zea mays;

<400> SEQUENCE: 918
aggtgtagtc gtcctgt                                            17

<210> SEQ ID NO 919
<211> LENGTH: 24
<212> TYPE: DNA
```

-continued

<213> ORGANISM: Zea mays;

<400> SEQUENCE: 919
ctcaatcgat gttaaataag tatc                                                  24

<210> SEQ ID NO 920
<211> LENGTH: 17
<212> TYPE: DNA
<213> ORGANISM: Zea mays;

<400> SEQUENCE: 920
gagattggcg tagtcaa                                                          17

<210> SEQ ID NO 921
<211> LENGTH: 18
<212> TYPE: DNA
<213> ORGANISM: Zea mays;

<400> SEQUENCE: 921
ctatggccgg tatgtcat                                                         18

<210> SEQ ID NO 922
<211> LENGTH: 15
<212> TYPE: DNA
<213> ORGANISM: Zea mays;

<400> SEQUENCE: 922
tggccggtat gccat                                                            15

<210> SEQ ID NO 923
<211> LENGTH: 21
<212> TYPE: DNA
<213> ORGANISM: Zea mays;

<400> SEQUENCE: 923
tgcaggattt gttcaatcta t                                                     21

<210> SEQ ID NO 924
<211> LENGTH: 16
<212> TYPE: DNA
<213> ORGANISM: Zea mays;

<400> SEQUENCE: 924
gacgacgact tcatca                                                           16

<210> SEQ ID NO 925
<211> LENGTH: 16
<212> TYPE: DNA
<213> ORGANISM: Zea mays;

<400> SEQUENCE: 925
ttctcactcc ttactt                                                           16

<210> SEQ ID NO 926
<211> LENGTH: 15
<212> TYPE: DNA
<213> ORGANISM: Zea mays;

<400> SEQUENCE: 926
ctcactcctt acctt                                                            15

<210> SEQ ID NO 927
<211> LENGTH: 20

-continued

```
<212> TYPE: DNA
<213> ORGANISM: Zea mays;

<400> SEQUENCE: 927
agcgtgtttg gtttgaggaa                                           20

<210> SEQ ID NO 928
<211> LENGTH: 25
<212> TYPE: DNA
<213> ORGANISM: Zea mays;

<400> SEQUENCE: 928
gtggagtcac tttatgcttc atgag                                     25

<210> SEQ ID NO 929
<211> LENGTH: 17
<212> TYPE: DNA
<213> ORGANISM: Zea mays;

<400> SEQUENCE: 929
ctagctcctg tgggatg                                              17

<210> SEQ ID NO 930
<211> LENGTH: 16
<212> TYPE: DNA
<213> ORGANISM: Zea mays;

<400> SEQUENCE: 930
ctagctcccg tgggat                                               16

<210> SEQ ID NO 931
<211> LENGTH: 17
<212> TYPE: DNA
<213> ORGANISM: Zea mays;

<400> SEQUENCE: 931
cgagctgtgg gtcgtga                                              17

<210> SEQ ID NO 932
<211> LENGTH: 20
<212> TYPE: DNA
<213> ORGANISM: Zea mays;

<400> SEQUENCE: 932
gaaggcaacc gtctcggtat                                           20

<210> SEQ ID NO 933
<211> LENGTH: 13
<212> TYPE: DNA
<213> ORGANISM: Zea mays;

<400> SEQUENCE: 933
acttccgcct gct                                                  13

<210> SEQ ID NO 934
<211> LENGTH: 13
<212> TYPE: DNA
<213> ORGANISM: Zea mays;

<400> SEQUENCE: 934
acttccgcct gcc                                                  13

<210> SEQ ID NO 935
```

-continued

```
<211> LENGTH: 19
<212> TYPE: DNA
<213> ORGANISM: Zea mays;

<400> SEQUENCE: 935
ccttcgccgc gttacactg                                              19

<210> SEQ ID NO 936
<211> LENGTH: 21
<212> TYPE: DNA
<213> ORGANISM: Zea mays;

<400> SEQUENCE: 936
ggtgtggagt ggacgtgata c                                           21

<210> SEQ ID NO 937
<211> LENGTH: 15
<212> TYPE: DNA
<213> ORGANISM: Zea mays;

<400> SEQUENCE: 937
tggcccgaca tcagg                                                  15

<210> SEQ ID NO 938
<211> LENGTH: 16
<212> TYPE: DNA
<213> ORGANISM: Zea mays;

<400> SEQUENCE: 938
tgtggcccaa catcag                                                 16

<210> SEQ ID NO 939
<211> LENGTH: 18
<212> TYPE: DNA
<213> ORGANISM: Zea mays;

<400> SEQUENCE: 939
cggactgctc gactggaa                                               18

<210> SEQ ID NO 940
<211> LENGTH: 21
<212> TYPE: DNA
<213> ORGANISM: Zea mays;

<400> SEQUENCE: 940
gtcgagggtg agccaatact c                                           21

<210> SEQ ID NO 941
<211> LENGTH: 19
<212> TYPE: DNA
<213> ORGANISM: Zea mays;

<400> SEQUENCE: 941
tttggcaaaa cggtttata                                              19

<210> SEQ ID NO 942
<211> LENGTH: 19
<212> TYPE: DNA
<213> ORGANISM: Zea mays;

<400> SEQUENCE: 942
tttggcaaaa cggcttata                                              19
```

-continued

```
<210> SEQ ID NO 943
<211> LENGTH: 22
<212> TYPE: DNA
<213> ORGANISM: Zea mays;

<400> SEQUENCE: 943
ggtgcagcca cttctttaga tg                                          22

<210> SEQ ID NO 944
<211> LENGTH: 22
<212> TYPE: DNA
<213> ORGANISM: Zea mays;

<400> SEQUENCE: 944
cctagccacg tacaggagag at                                          22

<210> SEQ ID NO 945
<211> LENGTH: 18
<212> TYPE: DNA
<213> ORGANISM: Zea mays;

<400> SEQUENCE: 945
cagtgaccca tttctttt                                               18

<210> SEQ ID NO 946
<211> LENGTH: 19
<212> TYPE: DNA
<213> ORGANISM: Zea mays;

<400> SEQUENCE: 946
agtgacccat ttctttctt                                              19

<210> SEQ ID NO 947
<211> LENGTH: 24
<212> TYPE: DNA
<213> ORGANISM: Zea mays;

<400> SEQUENCE: 947
aaggacgaag tagcagctgg aaag                                        24

<210> SEQ ID NO 948
<211> LENGTH: 25
<212> TYPE: DNA
<213> ORGANISM: Zea mays;

<400> SEQUENCE: 948
agggctactt tgggaacctc aaatc                                       25

<210> SEQ ID NO 949
<211> LENGTH: 17
<212> TYPE: DNA
<213> ORGANISM: Zea mays;

<400> SEQUENCE: 949
tacaactcag cgagcta                                                17

<210> SEQ ID NO 950
<211> LENGTH: 18
<212> TYPE: DNA
<213> ORGANISM: Zea mays;

<400> SEQUENCE: 950
atgtacaact caccgagc                                               18
```

-continued

```
<210> SEQ ID NO 951
<211> LENGTH: 22
<212> TYPE: DNA
<213> ORGANISM: Zea mays;

<400> SEQUENCE: 951
agtgggcagt gcacatatga tg                                               22

<210> SEQ ID NO 952
<211> LENGTH: 22
<212> TYPE: DNA
<213> ORGANISM: Zea mays;

<400> SEQUENCE: 952
caactccaac cgccaataat gc                                               22

<210> SEQ ID NO 953
<211> LENGTH: 18
<212> TYPE: DNA
<213> ORGANISM: Zea mays;

<400> SEQUENCE: 953
ccttttggat tacttcac                                                    18

<210> SEQ ID NO 954
<211> LENGTH: 17
<212> TYPE: DNA
<213> ORGANISM: Zea mays;

<400> SEQUENCE: 954
ttttggatca cttcaca                                                     17

<210> SEQ ID NO 955
<211> LENGTH: 20
<212> TYPE: DNA
<213> ORGANISM: Zea mays;

<400> SEQUENCE: 955
gccgcagtaa agtacacgaa                                                  20

<210> SEQ ID NO 956
<211> LENGTH: 25
<212> TYPE: DNA
<213> ORGANISM: Zea mays;

<400> SEQUENCE: 956
atgggcctaa agaacaaatg cacaa                                            25

<210> SEQ ID NO 957
<211> LENGTH: 17
<212> TYPE: DNA
<213> ORGANISM: Zea mays;

<400> SEQUENCE: 957
actttggcta tgctttg                                                     17

<210> SEQ ID NO 958
<211> LENGTH: 19
<212> TYPE: DNA
<213> ORGANISM: Zea mays;

<400> SEQUENCE: 958
tgttactttg gctatgatt                                                   19
```

-continued

```
<210> SEQ ID NO 959
<211> LENGTH: 24
<212> TYPE: DNA
<213> ORGANISM: Zea mays;

<400> SEQUENCE: 959
acaatgaacg actcctgtca gaat                                          24

<210> SEQ ID NO 960
<211> LENGTH: 20
<212> TYPE: DNA
<213> ORGANISM: Zea mays;

<400> SEQUENCE: 960
ggctctaggg accatgaaca                                               20

<210> SEQ ID NO 961
<211> LENGTH: 18
<212> TYPE: DNA
<213> ORGANISM: Zea mays;

<400> SEQUENCE: 961
ttaaattgtc gagcttgt                                                 18

<210> SEQ ID NO 962
<211> LENGTH: 16
<212> TYPE: DNA
<213> ORGANISM: Zea mays;

<400> SEQUENCE: 962
aaattgtcga gcctgt                                                   16

<210> SEQ ID NO 963
<211> LENGTH: 25
<212> TYPE: DNA
<213> ORGANISM: Zea mays;

<400> SEQUENCE: 963
actcatgttt atccttagca gcaaa                                         25

<210> SEQ ID NO 964
<211> LENGTH: 25
<212> TYPE: DNA
<213> ORGANISM: Zea mays;

<400> SEQUENCE: 964
gcacattgat aatctcagct ccatt                                         25

<210> SEQ ID NO 965
<211> LENGTH: 18
<212> TYPE: DNA
<213> ORGANISM: Zea mays;

<400> SEQUENCE: 965
caactgagag actgtatg                                                 18

<210> SEQ ID NO 966
<211> LENGTH: 16
<212> TYPE: DNA
<213> ORGANISM: Zea mays;

<400> SEQUENCE: 966
```

-continued

```
ctgagagact gcatga                                                16

<210> SEQ ID NO 967
<211> LENGTH: 27
<212> TYPE: DNA
<213> ORGANISM: Zea mays;

<400> SEQUENCE: 967
gatggtgaat aattggcatg tataacc                                    27

<210> SEQ ID NO 968
<211> LENGTH: 23
<212> TYPE: DNA
<213> ORGANISM: Zea mays;

<400> SEQUENCE: 968
gtgcttggag aaccgaaaca tag                                        23

<210> SEQ ID NO 969
<211> LENGTH: 15
<212> TYPE: DNA
<213> ORGANISM: Zea mays;

<400> SEQUENCE: 969
ctgggcattc ggttt                                                 15

<210> SEQ ID NO 970
<211> LENGTH: 16
<212> TYPE: DNA
<213> ORGANISM: Zea mays;

<400> SEQUENCE: 970
ctgggcattc gatttt                                                16

<210> SEQ ID NO 971
<211> LENGTH: 20
<212> TYPE: DNA
<213> ORGANISM: Zea mays;

<400> SEQUENCE: 971
acaactgtat cttactgcta                                            20

<210> SEQ ID NO 972
<211> LENGTH: 16
<212> TYPE: DNA
<213> ORGANISM: Zea mays;

<400> SEQUENCE: 972
ccgaagttct cggttt                                                16

<210> SEQ ID NO 973
<211> LENGTH: 18
<212> TYPE: DNA
<213> ORGANISM: Zea mays;

<400> SEQUENCE: 973
agcagtcagt tgtccaac                                              18

<210> SEQ ID NO 974
<211> LENGTH: 18
<212> TYPE: DNA
<213> ORGANISM: Zea mays;

<400> SEQUENCE: 974
```

-continued

```
agcagtcagt agtccaac                                          18

<210> SEQ ID NO 975
<211> LENGTH: 23
<212> TYPE: DNA
<213> ORGANISM: Zea mays;

<400> SEQUENCE: 975
ggatgaagtt atcaagcctg tga                                    23

<210> SEQ ID NO 976
<211> LENGTH: 24
<212> TYPE: DNA
<213> ORGANISM: Zea mays;

<400> SEQUENCE: 976
tttgcaagag attctgtgaa ctgt                                   24

<210> SEQ ID NO 977
<211> LENGTH: 17
<212> TYPE: DNA
<213> ORGANISM: Zea mays;

<400> SEQUENCE: 977
ccgttccttc aatgcta                                           17

<210> SEQ ID NO 978
<211> LENGTH: 19
<212> TYPE: DNA
<213> ORGANISM: Zea mays;

<400> SEQUENCE: 978
tccgttcctt aaatgctac                                         19

<210> SEQ ID NO 979
<211> LENGTH: 21
<212> TYPE: DNA
<213> ORGANISM: Zea mays;

<400> SEQUENCE: 979
gtctgccagt ggttcctaac g                                      21

<210> SEQ ID NO 980
<211> LENGTH: 23
<212> TYPE: DNA
<213> ORGANISM: Zea mays;

<400> SEQUENCE: 980
tcaccccggg aattaggatg atg                                    23

<210> SEQ ID NO 981
<211> LENGTH: 17
<212> TYPE: DNA
<213> ORGANISM: Zea mays;

<400> SEQUENCE: 981
atcaccgagc cagatat                                           17

<210> SEQ ID NO 982
<211> LENGTH: 16
<212> TYPE: DNA
<213> ORGANISM: Zea mays;
```

-continued

```
<400> SEQUENCE: 982
accgagccag acatta                                              16

<210> SEQ ID NO 983
<211> LENGTH: 22
<212> TYPE: DNA
<213> ORGANISM: Zea mays;

<400> SEQUENCE: 983
ttgtttcctc ccccaagtac ag                                       22

<210> SEQ ID NO 984
<211> LENGTH: 21
<212> TYPE: DNA
<213> ORGANISM: Zea mays;

<400> SEQUENCE: 984
cgcaggcatg tctatgacaa c                                        21

<210> SEQ ID NO 985
<211> LENGTH: 19
<212> TYPE: DNA
<213> ORGANISM: Zea mays;

<400> SEQUENCE: 985
ttctggtttt gtatgtatg                                           19

<210> SEQ ID NO 986
<211> LENGTH: 20
<212> TYPE: DNA
<213> ORGANISM: Zea mays;

<400> SEQUENCE: 986
tagagttctg gttttgtata                                          20

<210> SEQ ID NO 987
<211> LENGTH: 24
<212> TYPE: DNA
<213> ORGANISM: Zea mays;

<400> SEQUENCE: 987
tgtttcctga tgttttggtt gaca                                     24

<210> SEQ ID NO 988
<211> LENGTH: 22
<212> TYPE: DNA
<213> ORGANISM: Zea mays;

<400> SEQUENCE: 988
ccactcatgt gggagttgtc tc                                        22

<210> SEQ ID NO 989
<211> LENGTH: 17
<212> TYPE: DNA
<213> ORGANISM: Zea mays;

<400> SEQUENCE: 989
aggaacaagg cctttcg                                             17

<210> SEQ ID NO 990
<211> LENGTH: 18
<212> TYPE: DNA
<213> ORGANISM: Zea mays;
```

-continued

```
<400> SEQUENCE: 990
aaggaacaag gccttacg                                              18

<210> SEQ ID NO 991
<211> LENGTH: 24
<212> TYPE: DNA
<213> ORGANISM: Zea mays;

<400> SEQUENCE: 991
cacctgaaat cgttccaccc aatt                                      24

<210> SEQ ID NO 992
<211> LENGTH: 22
<212> TYPE: DNA
<213> ORGANISM: Zea mays;

<400> SEQUENCE: 992
ttggcggaat cactagctgt tc                                        22

<210> SEQ ID NO 993
<211> LENGTH: 20
<212> TYPE: DNA
<213> ORGANISM: Zea mays;

<400> SEQUENCE: 993
ccacaattga aggaaatgga                                           20

<210> SEQ ID NO 994
<211> LENGTH: 20
<212> TYPE: DNA
<213> ORGANISM: Zea mays;

<400> SEQUENCE: 994
tgccacaatt gaaagaaatg                                           20

<210> SEQ ID NO 995
<211> LENGTH: 24
<212> TYPE: DNA
<213> ORGANISM: Zea mays;

<400> SEQUENCE: 995
gggatttata gagggttcga gacg                                      24

<210> SEQ ID NO 996
<211> LENGTH: 17
<212> TYPE: DNA
<213> ORGANISM: Zea mays;

<400> SEQUENCE: 996
tcctatgctg cggtcca                                              17

<210> SEQ ID NO 997
<211> LENGTH: 14
<212> TYPE: DNA
<213> ORGANISM: Zea mays;

<400> SEQUENCE: 997
cggactcggc tctc                                                 14

<210> SEQ ID NO 998
<211> LENGTH: 14
<212> TYPE: DNA
```

-continued

<213> ORGANISM: Zea mays;

<400> SEQUENCE: 998
cggactccgc tctc                                              14

<210> SEQ ID NO 999
<211> LENGTH: 21
<212> TYPE: DNA
<213> ORGANISM: Zea mays;

<400> SEQUENCE: 999
ggtttggaag gagcccgttc t                                      21

<210> SEQ ID NO 1000
<211> LENGTH: 17
<212> TYPE: DNA
<213> ORGANISM: Zea mays;

<400> SEQUENCE: 1000
agcttgccgc cggagta                                           17

<210> SEQ ID NO 1001
<211> LENGTH: 15
<212> TYPE: DNA
<213> ORGANISM: Zea mays;

<400> SEQUENCE: 1001
accctaccct accct                                             15

<210> SEQ ID NO 1002
<211> LENGTH: 15
<212> TYPE: DNA
<213> ORGANISM: Zea mays;

<400> SEQUENCE: 1002
caccctacac taccc                                             15

<210> SEQ ID NO 1003
<211> LENGTH: 20
<212> TYPE: DNA
<213> ORGANISM: Zea mays;

<400> SEQUENCE: 1003
gatcttggca ggaccaacac                                        20

<210> SEQ ID NO 1004
<211> LENGTH: 21
<212> TYPE: DNA
<213> ORGANISM: Zea mays;

<400> SEQUENCE: 1004
gcgaagcgat aagcacacat c                                      21

<210> SEQ ID NO 1005
<211> LENGTH: 18
<212> TYPE: DNA
<213> ORGANISM: Zea mays;

<400> SEQUENCE: 1005
tgttagtggg tatgggta                                          18

<210> SEQ ID NO 1006
<211> LENGTH: 18

-continued

```
<212> TYPE: DNA
<213> ORGANISM: Zea mays;

<400> SEQUENCE: 1006
ttagtgggta tggatacc                                              18

<210> SEQ ID NO 1007
<211> LENGTH: 20
<212> TYPE: DNA
<213> ORGANISM: Zea mays;

<400> SEQUENCE: 1007
ggtacttaca tttgcgattc                                            20

<210> SEQ ID NO 1008
<211> LENGTH: 15
<212> TYPE: DNA
<213> ORGANISM: Zea mays;

<400> SEQUENCE: 1008
cacgggtagc aggta                                                 15

<210> SEQ ID NO 1009
<211> LENGTH: 22
<212> TYPE: DNA
<213> ORGANISM: Zea mays;

<400> SEQUENCE: 1009
tattgagaat taatgtctaa gc                                         22

<210> SEQ ID NO 1010
<211> LENGTH: 19
<212> TYPE: DNA
<213> ORGANISM: Zea mays;

<400> SEQUENCE: 1010
tgagaattaa tggctaagc                                             19

<210> SEQ ID NO 1011
<211> LENGTH: 21
<212> TYPE: DNA
<213> ORGANISM: Zea mays;

<400> SEQUENCE: 1011
gtgtctgaga cagcagatcg a                                          21

<210> SEQ ID NO 1012
<211> LENGTH: 23
<212> TYPE: DNA
<213> ORGANISM: Zea mays;

<400> SEQUENCE: 1012
ggaggcttag atcgtcatat tgc                                        23

<210> SEQ ID NO 1013
<211> LENGTH: 15
<212> TYPE: DNA
<213> ORGANISM: Zea mays;

<400> SEQUENCE: 1013
tgggtggtct gctac                                                 15

<210> SEQ ID NO 1014
```

-continued

```
<211> LENGTH: 13
<212> TYPE: DNA
<213> ORGANISM: Zea mays;

<400> SEQUENCE: 1014
tggtccgcta cca                                                        13

<210> SEQ ID NO 1015
<211> LENGTH: 22
<212> TYPE: DNA
<213> ORGANISM: Zea mays;

<400> SEQUENCE: 1015
acattgcatt cttgaattta ga                                              22

<210> SEQ ID NO 1016
<211> LENGTH: 17
<212> TYPE: DNA
<213> ORGANISM: Zea mays;

<400> SEQUENCE: 1016
acttggtcgg acgtaag                                                    17

<210> SEQ ID NO 1017
<211> LENGTH: 21
<212> TYPE: DNA
<213> ORGANISM: Zea mays;

<400> SEQUENCE: 1017
aaattctggt atttatatat c                                               21

<210> SEQ ID NO 1018
<211> LENGTH: 18
<212> TYPE: DNA
<213> ORGANISM: Zea mays;

<400> SEQUENCE: 1018
ttctggtatt tagatatc                                                   18

<210> SEQ ID NO 1019
<211> LENGTH: 24
<212> TYPE: DNA
<213> ORGANISM: Zea mays;

<400> SEQUENCE: 1019
tgtacaatta tgccattcgg gttt                                            24

<210> SEQ ID NO 1020
<211> LENGTH: 22
<212> TYPE: DNA
<213> ORGANISM: Zea mays;

<400> SEQUENCE: 1020
ccgagacaat tcgagtgacc ta                                              22

<210> SEQ ID NO 1021
<211> LENGTH: 20
<212> TYPE: DNA
<213> ORGANISM: Zea mays;

<400> SEQUENCE: 1021
cttgcttatg gattatcata                                                 20
```

-continued

```
<210> SEQ ID NO 1022
<211> LENGTH: 20
<212> TYPE: DNA
<213> ORGANISM: Zea mays;

<400> SEQUENCE: 1022
cacttgctta tggattataa                                          20

<210> SEQ ID NO 1023
<211> LENGTH: 20
<212> TYPE: DNA
<213> ORGANISM: Zea mays;

<400> SEQUENCE: 1023
gaaaacttga aagggtagtg                                          20

<210> SEQ ID NO 1024
<211> LENGTH: 21
<212> TYPE: DNA
<213> ORGANISM: Zea mays;

<400> SEQUENCE: 1024
acaaacagtc cagcttattt g                                        21

<210> SEQ ID NO 1025
<211> LENGTH: 16
<212> TYPE: DNA
<213> ORGANISM: Zea mays;

<400> SEQUENCE: 1025
taggagggca tgggca                                              16

<210> SEQ ID NO 1026
<211> LENGTH: 15
<212> TYPE: DNA
<213> ORGANISM: Zea mays;

<400> SEQUENCE: 1026
agggcacggg caact                                               15

<210> SEQ ID NO 1027
<211> LENGTH: 22
<212> TYPE: DNA
<213> ORGANISM: Zea mays;

<400> SEQUENCE: 1027
tgtagcgggt atcttaccga ca                                       22

<210> SEQ ID NO 1028
<211> LENGTH: 24
<212> TYPE: DNA
<213> ORGANISM: Zea mays;

<400> SEQUENCE: 1028
tcacttcttt ctctgcacaa atcc                                     24

<210> SEQ ID NO 1029
<211> LENGTH: 13
<212> TYPE: DNA
<213> ORGANISM: Zea mays;

<400> SEQUENCE: 1029
ccgaacaggc agc                                                 13
```

-continued

```
<210> SEQ ID NO 1030
<211> LENGTH: 13
<212> TYPE: DNA
<213> ORGANISM: Zea mays;

<400> SEQUENCE: 1030
cgaacagcca gca                                                    13

<210> SEQ ID NO 1031
<211> LENGTH: 18
<212> TYPE: DNA
<213> ORGANISM: Zea mays;

<400> SEQUENCE: 1031
ttccagatat cgagagga                                               18

<210> SEQ ID NO 1032
<211> LENGTH: 18
<212> TYPE: DNA
<213> ORGANISM: Zea mays;

<400> SEQUENCE: 1032
acttgcgaag gtagacag                                               18

<210> SEQ ID NO 1033
<211> LENGTH: 13
<212> TYPE: DNA
<213> ORGANISM: Zea mays;

<400> SEQUENCE: 1033
tctcggccct ccg                                                    13

<210> SEQ ID NO 1034
<211> LENGTH: 15
<212> TYPE: DNA
<213> ORGANISM: Zea mays;

<400> SEQUENCE: 1034
cttctcgacc ctccg                                                  15

<210> SEQ ID NO 1035
<211> LENGTH: 16
<212> TYPE: DNA
<213> ORGANISM: Zea mays;

<400> SEQUENCE: 1035
tccgtcgcgc acatcg                                                 16

<210> SEQ ID NO 1036
<211> LENGTH: 25
<212> TYPE: DNA
<213> ORGANISM: Zea mays;

<400> SEQUENCE: 1036
gctgttgtta cagtgggaat ttacc                                       25

<210> SEQ ID NO 1037
<211> LENGTH: 21
<212> TYPE: DNA
<213> ORGANISM: Zea mays;

<400> SEQUENCE: 1037
taaattatta gtatctacta t                                           21
```

-continued

```
<210> SEQ ID NO 1038
<211> LENGTH: 21
<212> TYPE: DNA
<213> ORGANISM: Zea mays;

<400> SEQUENCE: 1038
ttttaaatta ttagtatata c                                                21

<210> SEQ ID NO 1039
<211> LENGTH: 25
<212> TYPE: DNA
<213> ORGANISM: Zea mays;

<400> SEQUENCE: 1039
tgcgacgttt attgaaacac agtta                                            25

<210> SEQ ID NO 1040
<211> LENGTH: 19
<212> TYPE: DNA
<213> ORGANISM: Zea mays;

<400> SEQUENCE: 1040
ccgcacggct tatgtacac                                                   19

<210> SEQ ID NO 1041
<211> LENGTH: 18
<212> TYPE: DNA
<213> ORGANISM: Zea mays;

<400> SEQUENCE: 1041
ttgtgaattg accggtat                                                    18

<210> SEQ ID NO 1042
<211> LENGTH: 16
<212> TYPE: DNA
<213> ORGANISM: Zea mays;

<400> SEQUENCE: 1042
tgaattgacc ggcatg                                                      16

<210> SEQ ID NO 1043
<211> LENGTH: 25
<212> TYPE: DNA
<213> ORGANISM: Zea mays;

<400> SEQUENCE: 1043
acccttgatg tttctcatac gatgc                                            25

<210> SEQ ID NO 1044
<211> LENGTH: 20
<212> TYPE: DNA
<213> ORGANISM: Zea mays;

<400> SEQUENCE: 1044
cgcggatatt cagcgtctac                                                  20

<210> SEQ ID NO 1045
<211> LENGTH: 13
<212> TYPE: DNA
<213> ORGANISM: Zea mays;

<400> SEQUENCE: 1045
```

-continued

```
cgatcccacc ggc                                                   13

<210> SEQ ID NO 1046
<211> LENGTH: 13
<212> TYPE: DNA
<213> ORGANISM: Zea mays;

<400> SEQUENCE: 1046
cgatcccacc cgc                                                   13

<210> SEQ ID NO 1047
<211> LENGTH: 17
<212> TYPE: DNA
<213> ORGANISM: Zea mays;

<400> SEQUENCE: 1047
aaaacagccg agtatcc                                               17

<210> SEQ ID NO 1048
<211> LENGTH: 16
<212> TYPE: DNA
<213> ORGANISM: Zea mays;

<400> SEQUENCE: 1048
gggtggtttt gttcgt                                                16

<210> SEQ ID NO 1049
<211> LENGTH: 16
<212> TYPE: DNA
<213> ORGANISM: Zea mays;

<400> SEQUENCE: 1049
tgtttccaga ctagtc                                                16

<210> SEQ ID NO 1050
<211> LENGTH: 15
<212> TYPE: DNA
<213> ORGANISM: Zea mays;

<400> SEQUENCE: 1050
ttccagacta gcctt                                                 15

<210> SEQ ID NO 1051
<211> LENGTH: 28
<212> TYPE: DNA
<213> ORGANISM: Zea mays;

<400> SEQUENCE: 1051
acaagggatt ctaatttttc caatgaaa                                   28

<210> SEQ ID NO 1052
<211> LENGTH: 26
<212> TYPE: DNA
<213> ORGANISM: Zea mays;

<400> SEQUENCE: 1052
cgctaatcat atataggcga ctcttc                                     26

<210> SEQ ID NO 1053
<211> LENGTH: 19
<212> TYPE: DNA
<213> ORGANISM: Zea mays;

<400> SEQUENCE: 1053
```

-continued

```
tgtggtccaa attttgtat                                          19

<210> SEQ ID NO 1054
<211> LENGTH: 17
<212> TYPE: DNA
<213> ORGANISM: Zea mays;

<400> SEQUENCE: 1054
tggtccaaat tttgcat                                           17

<210> SEQ ID NO 1055
<211> LENGTH: 21
<212> TYPE: DNA
<213> ORGANISM: Zea mays;

<400> SEQUENCE: 1055
acacgtcatg cttacctacg a                                      21

<210> SEQ ID NO 1056
<211> LENGTH: 21
<212> TYPE: DNA
<213> ORGANISM: Zea mays;

<400> SEQUENCE: 1056
gcttcactcg caagacagtt g                                      21

<210> SEQ ID NO 1057
<211> LENGTH: 16
<212> TYPE: DNA
<213> ORGANISM: Zea mays;

<400> SEQUENCE: 1057
cggttgccat tatcat                                            16

<210> SEQ ID NO 1058
<211> LENGTH: 14
<212> TYPE: DNA
<213> ORGANISM: Zea mays;

<400> SEQUENCE: 1058
cggttgccat tacc                                              14

<210> SEQ ID NO 1059
<211> LENGTH: 16
<212> TYPE: DNA
<213> ORGANISM: Zea mays;

<400> SEQUENCE: 1059
ggtggtcccc ctgacc                                            16

<210> SEQ ID NO 1060
<211> LENGTH: 22
<212> TYPE: DNA
<213> ORGANISM: Zea mays;

<400> SEQUENCE: 1060
gtggtcgacg tcgttcaatt tc                                      22

<210> SEQ ID NO 1061
<211> LENGTH: 15
<212> TYPE: DNA
<213> ORGANISM: Zea mays;
```

```
<400> SEQUENCE: 1061
cggccagttc acctt                                                  15

<210> SEQ ID NO 1062
<211> LENGTH: 14
<212> TYPE: DNA
<213> ORGANISM: Zea mays;

<400> SEQUENCE: 1062
ccggccaatt cacc                                                   14

<210> SEQ ID NO 1063
<211> LENGTH: 16
<212> TYPE: DNA
<213> ORGANISM: Zea mays;

<400> SEQUENCE: 1063
ggttcgccga atgcca                                                 16

<210> SEQ ID NO 1064
<211> LENGTH: 19
<212> TYPE: DNA
<213> ORGANISM: Zea mays;

<400> SEQUENCE: 1064
gcatggattc cgcactgaa                                              19

<210> SEQ ID NO 1065
<211> LENGTH: 20
<212> TYPE: DNA
<213> ORGANISM: Zea mays;

<400> SEQUENCE: 1065
cagaggacag aaagtatagg                                             20

<210> SEQ ID NO 1066
<211> LENGTH: 19
<212> TYPE: DNA
<213> ORGANISM: Zea mays;

<400> SEQUENCE: 1066
cagaggacag aaagtacag                                              19

<210> SEQ ID NO 1067
<211> LENGTH: 18
<212> TYPE: DNA
<213> ORGANISM: Zea mays;

<400> SEQUENCE: 1067
ccctggaggc tggagcag                                               18

<210> SEQ ID NO 1068
<211> LENGTH: 21
<212> TYPE: DNA
<213> ORGANISM: Zea mays;

<400> SEQUENCE: 1068
atctgttggc gccctaaac c                                            21

<210> SEQ ID NO 1069
<211> LENGTH: 18
<212> TYPE: DNA
<213> ORGANISM: Zea mays;
```

-continued

```
<400> SEQUENCE: 1069
actagttgtg tgcgaatt                                              18

<210> SEQ ID NO 1070
<211> LENGTH: 17
<212> TYPE: DNA
<213> ORGANISM: Zea mays;

<400> SEQUENCE: 1070
actagttgtg tgccaat                                               17

<210> SEQ ID NO 1071
<211> LENGTH: 18
<212> TYPE: DNA
<213> ORGANISM: Zea mays;

<400> SEQUENCE: 1071
ctactggttc ggtgtttc                                              18

<210> SEQ ID NO 1072
<211> LENGTH: 21
<212> TYPE: DNA
<213> ORGANISM: Zea mays;

<400> SEQUENCE: 1072
acctttgagg gaattatttc a                                          21

<210> SEQ ID NO 1073
<211> LENGTH: 20
<212> TYPE: DNA
<213> ORGANISM: Zea mays;

<400> SEQUENCE: 1073
atgtactaca gacatttgaa                                            20

<210> SEQ ID NO 1074
<211> LENGTH: 19
<212> TYPE: DNA
<213> ORGANISM: Zea mays;

<400> SEQUENCE: 1074
tgtactacag acatttcaa                                             19

<210> SEQ ID NO 1075
<211> LENGTH: 22
<212> TYPE: DNA
<213> ORGANISM: Zea mays;

<400> SEQUENCE: 1075
ggtgctacta caggtttgga ct                                         22

<210> SEQ ID NO 1076
<211> LENGTH: 22
<212> TYPE: DNA
<213> ORGANISM: Zea mays;

<400> SEQUENCE: 1076
actagcctag ctgcttccaa ct                                         22

<210> SEQ ID NO 1077
<211> LENGTH: 20
<212> TYPE: DNA
```

-continued

```
<213> ORGANISM: Zea mays;

<400> SEQUENCE: 1077
ctttctatta tacttgcatg                                               20

<210> SEQ ID NO 1078
<211> LENGTH: 18
<212> TYPE: DNA
<213> ORGANISM: Zea mays;

<400> SEQUENCE: 1078
ttctattata cttgcacg                                                 18

<210> SEQ ID NO 1079
<211> LENGTH: 18
<212> TYPE: DNA
<213> ORGANISM: Zea mays;

<400> SEQUENCE: 1079
ccctgcgtat gggctctg                                                 18

<210> SEQ ID NO 1080
<211> LENGTH: 21
<212> TYPE: DNA
<213> ORGANISM: Zea mays;

<400> SEQUENCE: 1080
gcgtgaacta cacggtgaaa g                                             21

<210> SEQ ID NO 1081
<211> LENGTH: 13
<212> TYPE: DNA
<213> ORGANISM: Zea mays;

<400> SEQUENCE: 1081
cacgtcgggg ccg                                                      13

<210> SEQ ID NO 1082
<211> LENGTH: 14
<212> TYPE: DNA
<213> ORGANISM: Zea mays;

<400> SEQUENCE: 1082
acgtcggggc cacg                                                     14

<210> SEQ ID NO 1083
<211> LENGTH: 16
<212> TYPE: DNA
<213> ORGANISM: Zea mays;

<400> SEQUENCE: 1083
gcacgcgccg tgaact                                                   16

<210> SEQ ID NO 1084
<211> LENGTH: 16
<212> TYPE: DNA
<213> ORGANISM: Zea mays;

<400> SEQUENCE: 1084
ggcccagcgt gcctat                                                   16

<210> SEQ ID NO 1085
<211> LENGTH: 19
```

-continued

```
<212> TYPE: DNA
<213> ORGANISM: Zea mays;

<400> SEQUENCE: 1085
aatctcaagt ttgtacatc                                          19

<210> SEQ ID NO 1086
<211> LENGTH: 19
<212> TYPE: DNA
<213> ORGANISM: Zea mays;

<400> SEQUENCE: 1086
aatctcaagt ttctacatc                                          19

<210> SEQ ID NO 1087
<211> LENGTH: 22
<212> TYPE: DNA
<213> ORGANISM: Zea mays;

<400> SEQUENCE: 1087
tgatagatct taggaaagtg at                                      22

<210> SEQ ID NO 1088
<211> LENGTH: 16
<212> TYPE: DNA
<213> ORGANISM: Zea mays;

<400> SEQUENCE: 1088
caaccacaag ggtgtc                                             16

<210> SEQ ID NO 1089
<211> LENGTH: 18
<212> TYPE: DNA
<213> ORGANISM: Zea mays;

<400> SEQUENCE: 1089
atcgaaccag ttctgtgc                                           18

<210> SEQ ID NO 1090
<211> LENGTH: 16
<212> TYPE: DNA
<213> ORGANISM: Zea mays;

<400> SEQUENCE: 1090
aaccagtcct gtgcac                                             16

<210> SEQ ID NO 1091
<211> LENGTH: 24
<212> TYPE: DNA
<213> ORGANISM: Zea mays;

<400> SEQUENCE: 1091
ggcgtagagg atatgtgaga acag                                    24

<210> SEQ ID NO 1092
<211> LENGTH: 20
<212> TYPE: DNA
<213> ORGANISM: Zea mays;

<400> SEQUENCE: 1092
gtgggaagga agccgacttt                                         20

<210> SEQ ID NO 1093
```

-continued

```
<211> LENGTH: 22
<212> TYPE: DNA
<213> ORGANISM: Zea mays;

<400> SEQUENCE: 1093
ccataatctc ctaatctaag aa                                              22

<210> SEQ ID NO 1094
<211> LENGTH: 20
<212> TYPE: DNA
<213> ORGANISM: Zea mays;

<400> SEQUENCE: 1094
ccataatctc ctaacctaag                                                 20

<210> SEQ ID NO 1095
<211> LENGTH: 23
<212> TYPE: DNA
<213> ORGANISM: Zea mays;

<400> SEQUENCE: 1095
tgcaatggtg tttataggca agt                                             23

<210> SEQ ID NO 1096
<211> LENGTH: 24
<212> TYPE: DNA
<213> ORGANISM: Zea mays;

<400> SEQUENCE: 1096
tggtgagccc tactgtattg ttac                                            24

<210> SEQ ID NO 1097
<211> LENGTH: 19
<212> TYPE: DNA
<213> ORGANISM: Zea mays;

<400> SEQUENCE: 1097
aagtttgtga tttctgttg                                                  19

<210> SEQ ID NO 1098
<211> LENGTH: 15
<212> TYPE: DNA
<213> ORGANISM: Zea mays;

<400> SEQUENCE: 1098
tgtgatttcc gttgg                                                      15

<210> SEQ ID NO 1099
<211> LENGTH: 21
<212> TYPE: DNA
<213> ORGANISM: Zea mays;

<400> SEQUENCE: 1099
aaattattgt catgcataca c                                               21

<210> SEQ ID NO 1100
<211> LENGTH: 20
<212> TYPE: DNA
<213> ORGANISM: Zea mays;

<400> SEQUENCE: 1100
ctcaaggcct atgaactatc                                                 20
```

-continued

```
<210> SEQ ID NO 1101
<211> LENGTH: 14
<212> TYPE: DNA
<213> ORGANISM: Zea mays;

<400> SEQUENCE: 1101
atccggcgga gtgg                                                     14

<210> SEQ ID NO 1102
<211> LENGTH: 13
<212> TYPE: DNA
<213> ORGANISM: Zea mays;

<400> SEQUENCE: 1102
atccggcgga gcg                                                      13

<210> SEQ ID NO 1103
<211> LENGTH: 15
<212> TYPE: DNA
<213> ORGANISM: Zea mays;

<400> SEQUENCE: 1103
tccgactccg ccagc                                                    15

<210> SEQ ID NO 1104
<211> LENGTH: 18
<212> TYPE: DNA
<213> ORGANISM: Zea mays;

<400> SEQUENCE: 1104
gttcgtggtg gacgagga                                                 18

<210> SEQ ID NO 1105
<211> LENGTH: 20
<212> TYPE: DNA
<213> ORGANISM: Zea mays;

<400> SEQUENCE: 1105
agtactacat agcatattac                                               20

<210> SEQ ID NO 1106
<211> LENGTH: 19
<212> TYPE: DNA
<213> ORGANISM: Zea mays;

<400> SEQUENCE: 1106
agtactacat agcacatta                                                19

<210> SEQ ID NO 1107
<211> LENGTH: 24
<212> TYPE: DNA
<213> ORGANISM: Zea mays;

<400> SEQUENCE: 1107
aaccatccat tcaacacacc aaag                                          24

<210> SEQ ID NO 1108
<211> LENGTH: 19
<212> TYPE: DNA
<213> ORGANISM: Zea mays;

<400> SEQUENCE: 1108
cccgctaacc cgtgggtat                                                19
```

-continued

```
<210> SEQ ID NO 1109
<211> LENGTH: 13
<212> TYPE: DNA
<213> ORGANISM: Zea mays;

<400> SEQUENCE: 1109
ccgcagcgaa ggc                                                      13

<210> SEQ ID NO 1110
<211> LENGTH: 13
<212> TYPE: DNA
<213> ORGANISM: Zea mays;

<400> SEQUENCE: 1110
ccgcagccaa ggc                                                      13

<210> SEQ ID NO 1111
<211> LENGTH: 19
<212> TYPE: DNA
<213> ORGANISM: Zea mays;

<400> SEQUENCE: 1111
tcccttccaa gagcacacg                                                19

<210> SEQ ID NO 1112
<211> LENGTH: 21
<212> TYPE: DNA
<213> ORGANISM: Zea mays;

<400> SEQUENCE: 1112
gtgctcaggt actacgccta c                                             21

<210> SEQ ID NO 1113
<211> LENGTH: 18
<212> TYPE: DNA
<213> ORGANISM: Zea mays;

<400> SEQUENCE: 1113
ccttcatact gggccaat                                                 18

<210> SEQ ID NO 1114
<211> LENGTH: 17
<212> TYPE: DNA
<213> ORGANISM: Zea mays;

<400> SEQUENCE: 1114
cttcataccg ggccaat                                                  17

<210> SEQ ID NO 1115
<211> LENGTH: 22
<212> TYPE: DNA
<213> ORGANISM: Zea mays;

<400> SEQUENCE: 1115
ggcctcttga caaatagcac aa                                            22

<210> SEQ ID NO 1116
<211> LENGTH: 23
<212> TYPE: DNA
<213> ORGANISM: Zea mays;

<400> SEQUENCE: 1116
cggagtacca gcaacatata gca                                           23
```

-continued

```
<210> SEQ ID NO 1117
<211> LENGTH: 14
<212> TYPE: DNA
<213> ORGANISM: Zea mays;

<400> SEQUENCE: 1117
cgggtacagg tggc                                                  14

<210> SEQ ID NO 1118
<211> LENGTH: 15
<212> TYPE: DNA
<213> ORGANISM: Zea mays;

<400> SEQUENCE: 1118
cgggtacaga tggcg                                                 15

<210> SEQ ID NO 1119
<211> LENGTH: 17
<212> TYPE: DNA
<213> ORGANISM: Zea mays;

<400> SEQUENCE: 1119
gcacagccgc gtcaagt                                               17

<210> SEQ ID NO 1120
<211> LENGTH: 18
<212> TYPE: DNA
<213> ORGANISM: Zea mays;

<400> SEQUENCE: 1120
cgttgcccac cagagtcg                                              18

<210> SEQ ID NO 1121
<211> LENGTH: 13
<212> TYPE: DNA
<213> ORGANISM: Zea mays;

<400> SEQUENCE: 1121
cgacgccgct gct                                                   13

<210> SEQ ID NO 1122
<211> LENGTH: 15
<212> TYPE: DNA
<213> ORGANISM: Zea mays;

<400> SEQUENCE: 1122
agagcgacac cgctg                                                 15

<210> SEQ ID NO 1123
<211> LENGTH: 19
<212> TYPE: DNA
<213> ORGANISM: Zea mays;

<400> SEQUENCE: 1123
gagctcgtca cagccttcc                                             19

<210> SEQ ID NO 1124
<211> LENGTH: 19
<212> TYPE: DNA
<213> ORGANISM: Zea mays;

<400> SEQUENCE: 1124
```

-continued

```
aacccgagcc tcgccgatt                                           19

<210> SEQ ID NO 1125
<211> LENGTH: 19
<212> TYPE: DNA
<213> ORGANISM: Zea mays;

<400> SEQUENCE: 1125
tgctgatact actcataca                                           19

<210> SEQ ID NO 1126
<211> LENGTH: 19
<212> TYPE: DNA
<213> ORGANISM: Zea mays;

<400> SEQUENCE: 1126
ctgatactgc tactcatac                                           19

<210> SEQ ID NO 1127
<211> LENGTH: 21
<212> TYPE: DNA
<213> ORGANISM: Zea mays;

<400> SEQUENCE: 1127
gaatctttgg ttgcagcttg c                                        21

<210> SEQ ID NO 1128
<211> LENGTH: 21
<212> TYPE: DNA
<213> ORGANISM: Zea mays;

<400> SEQUENCE: 1128
tctgtgtcga tcccatgtgt a                                        21

<210> SEQ ID NO 1129
<211> LENGTH: 18
<212> TYPE: DNA
<213> ORGANISM: Zea mays;

<400> SEQUENCE: 1129
accttttgat gagttcca                                            18

<210> SEQ ID NO 1130
<211> LENGTH: 17
<212> TYPE: DNA
<213> ORGANISM: Zea mays;

<400> SEQUENCE: 1130
accttttgat gagctcc                                             17

<210> SEQ ID NO 1131
<211> LENGTH: 19
<212> TYPE: DNA
<213> ORGANISM: Zea mays;

<400> SEQUENCE: 1131
aaacttgaat tggtggagc                                           19

<210> SEQ ID NO 1132
<211> LENGTH: 18
<212> TYPE: DNA
<213> ORGANISM: Zea mays;

<400> SEQUENCE: 1132
```

-continued

```
gtgcacgtgt ctctatac                                     18

<210> SEQ ID NO 1133
<211> LENGTH: 17
<212> TYPE: DNA
<213> ORGANISM: Zea mays;

<400> SEQUENCE: 1133
ttcatcagga aacaact                                      17

<210> SEQ ID NO 1134
<211> LENGTH: 17
<212> TYPE: DNA
<213> ORGANISM: Zea mays;

<400> SEQUENCE: 1134
ttcatcagga aacaaca                                      17

<210> SEQ ID NO 1135
<211> LENGTH: 17
<212> TYPE: DNA
<213> ORGANISM: Zea mays;

<400> SEQUENCE: 1135
ctcttgccaa ggctgca                                      17

<210> SEQ ID NO 1136
<211> LENGTH: 22
<212> TYPE: DNA
<213> ORGANISM: Zea mays;

<400> SEQUENCE: 1136
ttcaagcatt cgctgacttc tg                                22

<210> SEQ ID NO 1137
<211> LENGTH: 20
<212> TYPE: DNA
<213> ORGANISM: Zea mays;

<400> SEQUENCE: 1137
agtggtgaac cttgtgttat                                   20

<210> SEQ ID NO 1138
<211> LENGTH: 18
<212> TYPE: DNA
<213> ORGANISM: Zea mays;

<400> SEQUENCE: 1138
tggtgaacct cgtgttat                                     18

<210> SEQ ID NO 1139
<211> LENGTH: 20
<212> TYPE: DNA
<213> ORGANISM: Zea mays;

<400> SEQUENCE: 1139
gcgcacttga ttggcattct                                   20

<210> SEQ ID NO 1140
<211> LENGTH: 20
<212> TYPE: DNA
<213> ORGANISM: Zea mays;
```

-continued

```
<400> SEQUENCE: 1140
cgcacacaca caaccaagac                                              20

<210> SEQ ID NO 1141
<211> LENGTH: 20
<212> TYPE: DNA
<213> ORGANISM: Zea mays;

<400> SEQUENCE: 1141
acaacgttca ccactaacac                                             20

<210> SEQ ID NO 1142
<211> LENGTH: 20
<212> TYPE: DNA
<213> ORGANISM: Zea mays;

<400> SEQUENCE: 1142
acaaggttca ccactaacac                                             20

<210> SEQ ID NO 1143
<211> LENGTH: 20
<212> TYPE: DNA
<213> ORGANISM: Zea mays;

<400> SEQUENCE: 1143
agagtgcgaa gagcaacaca                                             20

<210> SEQ ID NO 1144
<211> LENGTH: 20
<212> TYPE: DNA
<213> ORGANISM: Zea mays;

<400> SEQUENCE: 1144
tagctgcctt ggggctataa                                             20

<210> SEQ ID NO 1145
<211> LENGTH: 17
<212> TYPE: DNA
<213> ORGANISM: Zea mays;

<400> SEQUENCE: 1145 tgcccccag gcggggt                                                 17

<210> SEQ ID NO 1146
<211> LENGTH: 17
<212> TYPE: DNA
<213> ORGANISM: Zea mays;

<400> SEQUENCE: 1146
tgctccccag gcggggt                                                17

<210> SEQ ID NO 1147
<211> LENGTH: 20
<212> TYPE: DNA
<213> ORGANISM: Zea mays;

<400> SEQUENCE: 1147
agcagtgctc aatcggtctt                                             20

<210> SEQ ID NO 1148
<211> LENGTH: 20
<212> TYPE: DNA
<213> ORGANISM: Zea mays;
```

-continued

```
<400> SEQUENCE: 1148
gacccctcca cctccttatc                                        20

<210> SEQ ID NO 1149
<211> LENGTH: 16
<212> TYPE: DNA
<213> ORGANISM: Zea mays;

<400> SEQUENCE: 1149
ctcaagcctg ctggta                                            16

<210> SEQ ID NO 1150
<211> LENGTH: 17
<212> TYPE: DNA
<213> ORGANISM: Zea mays;

<400> SEQUENCE: 1150
tcaagcctga tggtaca                                           17

<210> SEQ ID NO 1151
<211> LENGTH: 22
<212> TYPE: DNA
<213> ORGANISM: Zea mays;

<400> SEQUENCE: 1151
gtgggttgta agtgggtgtt ta                                     22

<210> SEQ ID NO 1152
<211> LENGTH: 25
<212> TYPE: DNA
<213> ORGANISM: Zea mays;

<400> SEQUENCE: 1152
ttctccttct ttctgagtat agcct                                  25

<210> SEQ ID NO 1153
<211> LENGTH: 23
<212> TYPE: DNA
<213> ORGANISM: Zea mays;

<400> SEQUENCE: 1153
tccaaaaact tgttgttctc cca                                    23

<210> SEQ ID NO 1154
<211> LENGTH: 23
<212> TYPE: DNA
<213> ORGANISM: Zea mays;

<400> SEQUENCE: 1154
tccaaaaaat tgttgttctc cca                                    23

<210> SEQ ID NO 1155
<211> LENGTH: 20
<212> TYPE: DNA
<213> ORGANISM: Zea mays;

<400> SEQUENCE: 1155
tcgtcttctc gtatgcatgg                                        20

<210> SEQ ID NO 1156
<211> LENGTH: 20
<212> TYPE: DNA
```

-continued

<213> ORGANISM: Zea mays;

<400> SEQUENCE: 1156
tgcgacaaaa ttgacgaaga                                                    20

<210> SEQ ID NO 1157
<211> LENGTH: 21
<212> TYPE: DNA
<213> ORGANISM: Zea mays;

<400> SEQUENCE: 1157
aatgggagaa caacaagttt t                                                  21

<210> SEQ ID NO 1158
<211> LENGTH: 19
<212> TYPE: DNA
<213> ORGANISM: Zea mays;

<400> SEQUENCE: 1158
tgggagaaca acacgtttt                                                     19

<210> SEQ ID NO 1159
<211> LENGTH: 19
<212> TYPE: DNA
<213> ORGANISM: Zea mays;

<400> SEQUENCE: 1159
cagtgcatcc acggtggtc                                                     19

<210> SEQ ID NO 1160
<211> LENGTH: 25
<212> TYPE: DNA
<213> ORGANISM: Zea mays;

<400> SEQUENCE: 1160
ctttgctttc ttgaacagac ttggt                                              25

<210> SEQ ID NO 1161
<211> LENGTH: 17
<212> TYPE: DNA
<213> ORGANISM: Zea mays;

<400> SEQUENCE: 1161
attcgtaaca ccagcct                                                       17

<210> SEQ ID NO 1162
<211> LENGTH: 14
<212> TYPE: DNA
<213> ORGANISM: Zea mays;

<400> SEQUENCE: 1162
cgtaacccca gcct                                                          14

<210> SEQ ID NO 1163
<211> LENGTH: 15
<212> TYPE: DNA
<213> ORGANISM: Zea mays;

<400> SEQUENCE: 1163
tgcgcatcgc agcag                                                         15

<210> SEQ ID NO 1164
<211> LENGTH: 19

<212> TYPE: DNA
<213> ORGANISM: Zea mays;

<400> SEQUENCE: 1164
acagacagca ggcctcaac                                                          19

<210> SEQ ID NO 1165
<211> LENGTH: 19
<212> TYPE: DNA
<213> ORGANISM: Zea mays;

<400> SEQUENCE: 1165
tgattaattc gtctgacca                                                          19

<210> SEQ ID NO 1166
<211> LENGTH: 20
<212> TYPE: DNA
<213> ORGANISM: Zea mays;

<400> SEQUENCE: 1166
ttgattaatt catctgacca                                                         20

<210> SEQ ID NO 1167
<211> LENGTH: 24
<212> TYPE: DNA
<213> ORGANISM: Zea mays;

<400> SEQUENCE: 1167
tgagatggtt gtgttatgac tcca                                                    24

<210> SEQ ID NO 1168
<211> LENGTH: 22
<212> TYPE: DNA
<213> ORGANISM: Zea mays;

<400> SEQUENCE: 1168
tccgacaccc agaatcaaat gg                                                      22

<210> SEQ ID NO 1169
<211> LENGTH: 17
<212> TYPE: DNA
<213> ORGANISM: Zea mays;

<400> SEQUENCE: 1169
cccgacacct gtccttc                                                            17

<210> SEQ ID NO 1170
<211> LENGTH: 17
<212> TYPE: DNA
<213> ORGANISM: Zea mays;

<400> SEQUENCE: 1170
cccgacagct gtccttc                                                            17

<210> SEQ ID NO 1171
<211> LENGTH: 20
<212> TYPE: DNA
<213> ORGANISM: Zea mays;

<400> SEQUENCE: 1171
ggagacgtca gcaaggactc                                                         20

<210> SEQ ID NO 1172

-continued

```
<211> LENGTH: 20
<212> TYPE: DNA
<213> ORGANISM: Zea mays;

<400> SEQUENCE: 1172
agccctggac cttcctttta                                                   20

<210> SEQ ID NO 1173
<211> LENGTH: 24
<212> TYPE: DNA
<213> ORGANISM: Zea mays;

<400> SEQUENCE: 1173
aaagatgaag aaacaatcaa tgta                                              24

<210> SEQ ID NO 1174
<211> LENGTH: 21
<212> TYPE: DNA
<213> ORGANISM: Zea mays;

<400> SEQUENCE: 1174
tgaagaaaca atccatgtat a                                                 21

<210> SEQ ID NO 1175
<211> LENGTH: 17
<212> TYPE: DNA
<213> ORGANISM: Zea mays;

<400> SEQUENCE: 1175
gtggtgcaag cgtggtc                                                      17

<210> SEQ ID NO 1176
<211> LENGTH: 24
<212> TYPE: DNA
<213> ORGANISM: Zea mays;

<400> SEQUENCE: 1176
gtgcaaaggt tgcttggaat tgag                                              24

<210> SEQ ID NO 1177
<211> LENGTH: 21
<212> TYPE: DNA
<213> ORGANISM: Zea mays;

<400> SEQUENCE: 1177
ttcaaggttt ttttgcaaat a                                                 21

<210> SEQ ID NO 1178
<211> LENGTH: 21
<212> TYPE: DNA
<213> ORGANISM: Zea mays;

<400> SEQUENCE: 1178
ttcaaggttc ttttgcaaat a                                                 21

<210> SEQ ID NO 1179
<211> LENGTH: 20
<212> TYPE: DNA
<213> ORGANISM: Zea mays;

<400> SEQUENCE: 1179
gtgcaaaggt tgcttggaat                                                   20
```

-continued

```
<210> SEQ ID NO 1180
<211> LENGTH: 20
<212> TYPE: DNA
<213> ORGANISM: Zea mays;

<400> SEQUENCE: 1180
ccaaaggaaa ggcatttgaa                                                    20

<210> SEQ ID NO 1181
<211> LENGTH: 21
<212> TYPE: DNA
<213> ORGANISM: Zea mays;

<400> SEQUENCE: 1181
catttacctt tgattatttg c                                                  21

<210> SEQ ID NO 1182
<211> LENGTH: 19
<212> TYPE: DNA
<213> ORGANISM: Zea mays;

<400> SEQUENCE: 1182
ttacctttga ctatttgca                                                     19

<210> SEQ ID NO 1183
<211> LENGTH: 25
<212> TYPE: DNA
<213> ORGANISM: Zea mays;

<400> SEQUENCE: 1183
ccaaaggaaa ggcatttgaa acagg                                              25

<210> SEQ ID NO 1184
<211> LENGTH: 19
<212> TYPE: DNA
<213> ORGANISM: Zea mays;

<400> SEQUENCE: 1184
gaccacgctt gcaccacat                                                     19

<210> SEQ ID NO 1185
<211> LENGTH: 18
<212> TYPE: DNA
<213> ORGANISM: Zea mays;

<400> SEQUENCE: 1185
tcagggcgag atgaaacg                                                      18

<210> SEQ ID NO 1186
<211> LENGTH: 18
<212> TYPE: DNA
<213> ORGANISM: Zea mays;

<400> SEQUENCE: 1186
atcagggcga gacgaaac                                                      18

<210> SEQ ID NO 1187
<211> LENGTH: 23
<212> TYPE: DNA
<213> ORGANISM: Zea mays;

<400> SEQUENCE: 1187
gggtagcttt gttcccaagg att                                                23
```

```
<210> SEQ ID NO 1188
<211> LENGTH: 22
<212> TYPE: DNA
<213> ORGANISM: Zea mays;

<400> SEQUENCE: 1188
tggagaggtg gacaggtagt ag                                        22

<210> SEQ ID NO 1189
<211> LENGTH: 17
<212> TYPE: DNA
<213> ORGANISM: Zea mays;

<400> SEQUENCE: 1189
cgactggatc agcgaag                                              17

<210> SEQ ID NO 1190
<211> LENGTH: 18
<212> TYPE: DNA
<213> ORGANISM: Zea mays;

<400> SEQUENCE: 1190
cacgactgga ttagcgaa                                             18

<210> SEQ ID NO 1191
<211> LENGTH: 17
<212> TYPE: DNA
<213> ORGANISM: Zea mays;

<400> SEQUENCE: 1191
gcgcacaagc cgtctac                                              17

<210> SEQ ID NO 1192
<211> LENGTH: 21
<212> TYPE: DNA
<213> ORGANISM: Zea mays;

<400> SEQUENCE: 1192
gacgcccttg ctgtatgtat g                                         21

<210> SEQ ID NO 1193
<211> LENGTH: 17
<212> TYPE: DNA
<213> ORGANISM: Zea mays;

<400> SEQUENCE: 1193
tcttggagtt gcttgac                                              17

<210> SEQ ID NO 1194
<211> LENGTH: 17
<212> TYPE: DNA
<213> ORGANISM: Zea mays;

<400> SEQUENCE: 1194
ctcttggagt ggcttga                                              17

<210> SEQ ID NO 1195
<211> LENGTH: 24
<212> TYPE: DNA
<213> ORGANISM: Zea mays;

<400> SEQUENCE: 1195
tgagtgtact tcgtttggct aatg                                      24
```

-continued

<210> SEQ ID NO 1196
<211> LENGTH: 25
<212> TYPE: DNA
<213> ORGANISM: Zea mays;

<400> SEQUENCE: 1196
aggatcatga cacagaaatt cgaga                                          25

<210> SEQ ID NO 1197
<211> LENGTH: 17
<212> TYPE: DNA
<213> ORGANISM: Zea mays;

<400> SEQUENCE: 1197
tcttggagtt gcttgac                                                  17

<210> SEQ ID NO 1198
<211> LENGTH: 17
<212> TYPE: DNA
<213> ORGANISM: Zea mays;

<400> SEQUENCE: 1198
ctcttggagg tgcttga                                                  17

<210> SEQ ID NO 1199
<211> LENGTH: 24
<212> TYPE: DNA
<213> ORGANISM: Zea mays;

<400> SEQUENCE: 1199
tgagtgtact tcgtttggct aatg                                          24

<210> SEQ ID NO 1200
<211> LENGTH: 25
<212> TYPE: DNA
<213> ORGANISM: Zea mays;

<400> SEQUENCE: 1200
aggatcatga cacagaaatt cgaga                                          25

<210> SEQ ID NO 1201
<211> LENGTH: 27
<212> TYPE: DNA
<213> ORGANISM: Zea mays;

<400> SEQUENCE: 1201
acttctagag aaaaaaaaaa aaataga                                        27

<210> SEQ ID NO 1202
<211> LENGTH: 27
<212> TYPE: DNA
<213> ORGANISM: Zea mays;

<400> SEQUENCE: 1202
acttctagag aaaaaataaa aaataga                                        27

<210> SEQ ID NO 1203
<211> LENGTH: 20
<212> TYPE: DNA
<213> ORGANISM: Zea mays;

<400> SEQUENCE: 1203

-continued

```
acctcctttt ggtccgtttt                                          20

<210> SEQ ID NO 1204
<211> LENGTH: 20
<212> TYPE: DNA
<213> ORGANISM: Zea mays;

<400> SEQUENCE: 1204
ggaggcaagt gaggagactg                                          20

<210> SEQ ID NO 1205
<211> LENGTH: 19
<212> TYPE: DNA
<213> ORGANISM: Zea mays;

<400> SEQUENCE: 1205
attaggttgt ttccagcaa                                           19

<210> SEQ ID NO 1206
<211> LENGTH: 16
<212> TYPE: DNA
<213> ORGANISM: Zea mays;

<400> SEQUENCE: 1206
aggttgttcc cagcaa                                              16

<210> SEQ ID NO 1207
<211> LENGTH: 22
<212> TYPE: DNA
<213> ORGANISM: Zea mays;

<400> SEQUENCE: 1207
tgttgggcaa tcaaacttca gg                                       22

<210> SEQ ID NO 1208
<211> LENGTH: 21
<212> TYPE: DNA
<213> ORGANISM: Zea mays;

<400> SEQUENCE: 1208
aggccacggt gaccatgtaa g                                        21

<210> SEQ ID NO 1209
<211> LENGTH: 19
<212> TYPE: DNA
<213> ORGANISM: Zea mays;

<400> SEQUENCE: 1209
tctactctga ggctgtatt                                           19

<210> SEQ ID NO 1210
<211> LENGTH: 21
<212> TYPE: DNA
<213> ORGANISM: Zea mays;

<400> SEQUENCE: 1210
tctactctga ggttgtattt g                                        21

<210> SEQ ID NO 1211
<211> LENGTH: 24
<212> TYPE: DNA
<213> ORGANISM: Zea mays;

<400> SEQUENCE: 1211
```

-continued

```
gcaacatgat ctcttcacca atga                                      24

<210> SEQ ID NO 1212
<211> LENGTH: 22
<212> TYPE: DNA
<213> ORGANISM: Zea mays;

<400> SEQUENCE: 1212
caaccagctc accagaacaa tg                                        22

<210> SEQ ID NO 1213
<211> LENGTH: 17
<212> TYPE: DNA
<213> ORGANISM: Zea mays;

<400> SEQUENCE: 1213
cgtcgagatc ctcattc                                              17

<210> SEQ ID NO 1214
<211> LENGTH: 19
<212> TYPE: DNA
<213> ORGANISM: Zea mays;

<400> SEQUENCE: 1214
acgtcgagat cttcattca                                            19

<210> SEQ ID NO 1215
<211> LENGTH: 19
<212> TYPE: DNA
<213> ORGANISM: Zea mays;

<400> SEQUENCE: 1215
tcggagcctt ggatcatca                                            19

<210> SEQ ID NO 1216
<211> LENGTH: 21
<212> TYPE: DNA
<213> ORGANISM: Zea mays;

<400> SEQUENCE: 1216
gcccgatctt ccgtgagata c                                         21

<210> SEQ ID NO 1217
<211> LENGTH: 15
<212> TYPE: DNA
<213> ORGANISM: Zea mays;

<400> SEQUENCE: 1217
accctccctc cgaaa                                                15

<210> SEQ ID NO 1218
<211> LENGTH: 15
<212> TYPE: DNA
<213> ORGANISM: Zea mays;

<400> SEQUENCE: 1218
accctcgctc cgaaa                                                15

<210> SEQ ID NO 1219
<211> LENGTH: 21
<212> TYPE: DNA
<213> ORGANISM: Zea mays;
```

<400> SEQUENCE: 1219
cgccttccag tccacaatct c                                               21

<210> SEQ ID NO 1220
<211> LENGTH: 21
<212> TYPE: DNA
<213> ORGANISM: Zea mays;

<400> SEQUENCE: 1220
gcggtctctc tctctctctc t                                               21

<210> SEQ ID NO 1221
<211> LENGTH: 20
<212> TYPE: DNA
<213> ORGANISM: Zea mays;

<400> SEQUENCE: 1221
aacagtagta tcttgtgcat                                                 20

<210> SEQ ID NO 1222
<211> LENGTH: 20
<212> TYPE: DNA
<213> ORGANISM: Zea mays;

<400> SEQUENCE: 1222
aacagtagta ttttgtgcat                                                 20

<210> SEQ ID NO 1223
<211> LENGTH: 25
<212> TYPE: DNA
<213> ORGANISM: Zea mays;

<400> SEQUENCE: 1223
agccgctcac tttgtggtat tcatc                                           25

<210> SEQ ID NO 1224
<211> LENGTH: 22
<212> TYPE: DNA
<213> ORGANISM: Zea mays;

<400> SEQUENCE: 1224
agtacggata gtcccatgtt ca                                              22

<210> SEQ ID NO 1225
<211> LENGTH: 17
<212> TYPE: DNA
<213> ORGANISM: Zea mays;

<400> SEQUENCE: 1225
cacaaagtga gcggctt                                                    17

<210> SEQ ID NO 1226
<211> LENGTH: 17
<212> TYPE: DNA
<213> ORGANISM: Zea mays;

<400> SEQUENCE: 1226
cacaaagtgt gcggctt                                                    17

<210> SEQ ID NO 1227
<211> LENGTH: 23
<212> TYPE: DNA
<213> ORGANISM: Zea mays;

-continued

<400> SEQUENCE: 1227
tctagcttca ttgtgcaggg atg                                                  23

<210> SEQ ID NO 1228
<211> LENGTH: 22
<212> TYPE: DNA
<213> ORGANISM: Zea mays;

<400> SEQUENCE: 1228
gagatcttga gggtgtccca aa                                                   22

<210> SEQ ID NO 1229
<211> LENGTH: 20
<212> TYPE: DNA
<213> ORGANISM: Zea mays;

<400> SEQUENCE: 1229
ccattgctca ggagttagaa                                                      20

<210> SEQ ID NO 1230
<211> LENGTH: 18
<212> TYPE: DNA
<213> ORGANISM: Zea mays;

<400> SEQUENCE: 1230
tgctcaggag ctagaaac                                                        18

<210> SEQ ID NO 1231
<211> LENGTH: 22
<212> TYPE: DNA
<213> ORGANISM: Zea mays;

<400> SEQUENCE: 1231
catcaaggga ctccgagctt ct                                                   22

<210> SEQ ID NO 1232
<211> LENGTH: 24
<212> TYPE: DNA
<213> ORGANISM: Zea mays;

<400> SEQUENCE: 1232
cagcttcctc ggcaacttta acag                                                 24

<210> SEQ ID NO 1233
<211> LENGTH: 18
<212> TYPE: DNA
<213> ORGANISM: Zea mays;

<400> SEQUENCE: 1233
catcctttgc tgatagca                                                        18

<210> SEQ ID NO 1234
<211> LENGTH: 16
<212> TYPE: DNA
<213> ORGANISM: Zea mays;

<400> SEQUENCE: 1234
tcctttgccg atagca                                                          16

<210> SEQ ID NO 1235
<211> LENGTH: 21
<212> TYPE: DNA

-continued

```
<213> ORGANISM: Zea mays;

<400> SEQUENCE: 1235
agctcggagt cccttgatgg t                                          21

<210> SEQ ID NO 1236
<211> LENGTH: 20
<212> TYPE: DNA
<213> ORGANISM: Zea mays;

<400> SEQUENCE: 1236
cgaagtgacc cgccttacac                                            20

<210> SEQ ID NO 1237
<211> LENGTH: 18
<212> TYPE: DNA
<213> ORGANISM: Zea mays;

<400> SEQUENCE: 1237
tgttggaatc tcggtaca                                              18

<210> SEQ ID NO 1238
<211> LENGTH: 17
<212> TYPE: DNA
<213> ORGANISM: Zea mays;

<400> SEQUENCE: 1238
tgttggaatc ccggtac                                               17

<210> SEQ ID NO 1239
<211> LENGTH: 19
<212> TYPE: DNA
<213> ORGANISM: Zea mays;

<400> SEQUENCE: 1239
tccaagatgg tcagcgagt                                             19

<210> SEQ ID NO 1240
<211> LENGTH: 19
<212> TYPE: DNA
<213> ORGANISM: Zea mays;

<400> SEQUENCE: 1240
cgcgacaacc tggacagat                                             19

<210> SEQ ID NO 1241
<211> LENGTH: 20
<212> TYPE: DNA
<213> ORGANISM: Zea mays;

<400> SEQUENCE: 1241
tcaggtactc tacaaactct                                            20

<210> SEQ ID NO 1242
<211> LENGTH: 19
<212> TYPE: DNA
<213> ORGANISM: Zea mays;

<400> SEQUENCE: 1242
caggtactct accaactct                                             19

<210> SEQ ID NO 1243
<211> LENGTH: 21
```

-continued

```
<212> TYPE: DNA
<213> ORGANISM: Zea mays;

<400> SEQUENCE: 1243
gaccagagag ctgacaggaa c                                          21

<210> SEQ ID NO 1244
<211> LENGTH: 22
<212> TYPE: DNA
<213> ORGANISM: Zea mays;

<400> SEQUENCE: 1244
gctctgtggc gtgagataga tg                                         22

<210> SEQ ID NO 1245
<211> LENGTH: 16
<212> TYPE: DNA
<213> ORGANISM: Zea mays;

<400> SEQUENCE: 1245
catatccggg cagtcc                                                16

<210> SEQ ID NO 1246
<211> LENGTH: 17
<212> TYPE: DNA
<213> ORGANISM: Zea mays;

<400> SEQUENCE: 1246
ccatatccgg acagtcc                                               17

<210> SEQ ID NO 1247
<211> LENGTH: 20
<212> TYPE: DNA
<213> ORGANISM: Zea mays;

<400> SEQUENCE: 1247
gagttggatg gtccagcgta                                            20

<210> SEQ ID NO 1248
<211> LENGTH: 19
<212> TYPE: DNA
<213> ORGANISM: Zea mays;

<400> SEQUENCE: 1248
ggaccgtccg ccatcttac                                             19

<210> SEQ ID NO 1249
<211> LENGTH: 20
<212> TYPE: DNA
<213> ORGANISM: Zea mays;

<400> SEQUENCE: 1249
aagccttttt cacctctttt                                            20

<210> SEQ ID NO 1250
<211> LENGTH: 20
<212> TYPE: DNA
<213> ORGANISM: Zea mays;

<400> SEQUENCE: 1250
aagccttttt cacttctttt                                            20

<210> SEQ ID NO 1251
```

-continued

```
<211> LENGTH: 21
<212> TYPE: DNA
<213> ORGANISM: Zea mays;

<400> SEQUENCE: 1251
gctgagtctt ggctgtacac a                                              21

<210> SEQ ID NO 1252
<211> LENGTH: 21
<212> TYPE: DNA
<213> ORGANISM: Zea mays;

<400> SEQUENCE: 1252
gagtgccaac acaagtgctt a                                              21

<210> SEQ ID NO 1253
<211> LENGTH: 21
<212> TYPE: DNA
<213> ORGANISM: Zea mays;

<400> SEQUENCE: 1253
aataatgtgt ggtgaatgcg a                                              21

<210> SEQ ID NO 1254
<211> LENGTH: 21
<212> TYPE: DNA
<213> ORGANISM: Zea mays;

<400> SEQUENCE: 1254
aataatgcgt ggtgaatgcg a                                              21

<210> SEQ ID NO 1255
<211> LENGTH: 20
<212> TYPE: DNA
<213> ORGANISM: Zea mays;

<400> SEQUENCE: 1255
aaatgcaatc gaggctgaac                                                20

<210> SEQ ID NO 1256
<211> LENGTH: 20
<212> TYPE: DNA
<213> ORGANISM: Zea mays;

<400> SEQUENCE: 1256
ttcatgccat ttgccagata                                                20

<210> SEQ ID NO 1257
<211> LENGTH: 16
<212> TYPE: DNA
<213> ORGANISM: Zea mays;

<400> SEQUENCE: 1257
tcttgtggga gaccca                                                    16

<210> SEQ ID NO 1258
<211> LENGTH: 19
<212> TYPE: DNA
<213> ORGANISM: Zea mays;

<400> SEQUENCE: 1258
caaggtcttg tgagagacc                                                 19
```

-continued

```
<210> SEQ ID NO 1259
<211> LENGTH: 25
<212> TYPE: DNA
<213> ORGANISM: Zea mays;

<400> SEQUENCE: 1259
gttcggacat ttatgggcac tattg                                         25

<210> SEQ ID NO 1260
<211> LENGTH: 25
<212> TYPE: DNA
<213> ORGANISM: Zea mays;

<400> SEQUENCE: 1260
cctaggatct catgatggat cttca                                         25

<210> SEQ ID NO 1261
<211> LENGTH: 16
<212> TYPE: DNA
<213> ORGANISM: Zea mays;

<400> SEQUENCE: 1261
agcaaagtgg gcgtcc                                                   16

<210> SEQ ID NO 1262
<211> LENGTH: 17
<212> TYPE: DNA
<213> ORGANISM: Zea mays;

<400> SEQUENCE: 1262
agcaaagtag gcgtcca                                                  17

<210> SEQ ID NO 1263
<211> LENGTH: 25
<212> TYPE: DNA
<213> ORGANISM: Zea mays;

<400> SEQUENCE: 1263
gctatctcaa ttctttggtc acatc                                         25

<210> SEQ ID NO 1264
<211> LENGTH: 21
<212> TYPE: DNA
<213> ORGANISM: Zea mays;

<400> SEQUENCE: 1264
aggtggcaac cagttgttag g                                             21

<210> SEQ ID NO 1265
<211> LENGTH: 21
<212> TYPE: DNA
<213> ORGANISM: Zea mays;

<400> SEQUENCE: 1265
ttggtatctt attattgtca a                                             21

<210> SEQ ID NO 1266
<211> LENGTH: 20
<212> TYPE: DNA
<213> ORGANISM: Zea mays;

<400> SEQUENCE: 1266
tggtatctta ttcttgtcaa                                               20
```

-continued

<210> SEQ ID NO 1267
<211> LENGTH: 22
<212> TYPE: DNA
<213> ORGANISM: Zea mays;

<400> SEQUENCE: 1267
ctttgagtag tgcggcagtg at                                          22

<210> SEQ ID NO 1268
<211> LENGTH: 20
<212> TYPE: DNA
<213> ORGANISM: Zea mays;

<400> SEQUENCE: 1268
ggtggtggac gcctactttg                                             20

<210> SEQ ID NO 1269
<211> LENGTH: 15
<212> TYPE: DNA
<213> ORGANISM: Zea mays;

<400> SEQUENCE: 1269
cctcgggggc taaaa                                                  15

<210> SEQ ID NO 1270
<211> LENGTH: 15
<212> TYPE: DNA
<213> ORGANISM: Zea mays;

<400> SEQUENCE: 1270
cctcgggggc tcaaa                                                  15

<210> SEQ ID NO 1271
<211> LENGTH: 20
<212> TYPE: DNA
<213> ORGANISM: Zea mays;

<400> SEQUENCE: 1271
cagctacgtc gcttctaccc                                             20

<210> SEQ ID NO 1272
<211> LENGTH: 20
<212> TYPE: DNA
<213> ORGANISM: Zea mays;

<400> SEQUENCE: 1272
acgtgtacct cgtcgtttcc                                             20

<210> SEQ ID NO 1273
<211> LENGTH: 17
<212> TYPE: DNA
<213> ORGANISM: Zea mays;

<400> SEQUENCE: 1273
tgtaaaatct ggccgta                                                17

<210> SEQ ID NO 1274
<211> LENGTH: 19
<212> TYPE: DNA
<213> ORGANISM: Zea mays;

<400> SEQUENCE: 1274
tgtaaaatct ggctgtaag                                              19

-continued

<210> SEQ ID NO 1275
<211> LENGTH: 20
<212> TYPE: DNA
<213> ORGANISM: Zea mays;

<400> SEQUENCE: 1275
caccagtttc gtgtcaagga                                                    20

<210> SEQ ID NO 1276
<211> LENGTH: 22
<212> TYPE: DNA
<213> ORGANISM: Zea mays;

<400> SEQUENCE: 1276
ttccgcccga gagatttaga ag                                                 22

<210> SEQ ID NO 1277
<211> LENGTH: 18
<212> TYPE: DNA
<213> ORGANISM: Zea mays;

<400> SEQUENCE: 1277
ttaccaggaa cagtaaac                                                      18

<210> SEQ ID NO 1278
<211> LENGTH: 18
<212> TYPE: DNA
<213> ORGANISM: Zea mays;

<400> SEQUENCE: 1278
taccaggaac aataaaca                                                      18

<210> SEQ ID NO 1279
<211> LENGTH: 17
<212> TYPE: DNA
<213> ORGANISM: Zea mays;

<400> SEQUENCE: 1279
ttccactatc gaccgaa                                                       17

<210> SEQ ID NO 1280
<211> LENGTH: 20
<212> TYPE: DNA
<213> ORGANISM: Zea mays;

<400> SEQUENCE: 1280
gggatttgag gttatgttct                                                    20

<210> SEQ ID NO 1281
<211> LENGTH: 17
<212> TYPE: DNA
<213> ORGANISM: Zea mays;

<400> SEQUENCE: 1281
ccgagcgtga gttactt                                                       17

<210> SEQ ID NO 1282
<211> LENGTH: 18
<212> TYPE: DNA
<213> ORGANISM: Zea mays;

<400> SEQUENCE: 1282

-continued

```
ccgagcgtga attacttt                                                 18

<210> SEQ ID NO 1283
<211> LENGTH: 21
<212> TYPE: DNA
<213> ORGANISM: Zea mays;

<400> SEQUENCE: 1283
ttcgtcggta gcagaatcac t                                             21

<210> SEQ ID NO 1284
<211> LENGTH: 23
<212> TYPE: DNA
<213> ORGANISM: Zea mays;

<400> SEQUENCE: 1284
acggatacct cactcatcac ctt                                           23

<210> SEQ ID NO 1285
<211> LENGTH: 19
<212> TYPE: DNA
<213> ORGANISM: Zea mays;

<400> SEQUENCE: 1285
tcacatcttg cataaataa                                                19

<210> SEQ ID NO 1286
<211> LENGTH: 19
<212> TYPE: DNA
<213> ORGANISM: Zea mays;

<400> SEQUENCE: 1286
cacatcttgc ataaagaat                                                19

<210> SEQ ID NO 1287
<211> LENGTH: 22
<212> TYPE: DNA
<213> ORGANISM: Zea mays;

<400> SEQUENCE: 1287
atgggacaaa gagtctagca tt                                            22

<210> SEQ ID NO 1288
<211> LENGTH: 19
<212> TYPE: DNA
<213> ORGANISM: Zea mays;

<400> SEQUENCE: 1288
ggttcaatca acaatcaca                                                19

<210> SEQ ID NO 1289
<211> LENGTH: 19
<212> TYPE: DNA
<213> ORGANISM: Zea mays;

<400> SEQUENCE: 1289
cttgattcag tccgagaag                                                19

<210> SEQ ID NO 1290
<211> LENGTH: 16
<212> TYPE: DNA
<213> ORGANISM: Zea mays;

<400> SEQUENCE: 1290
```

-continued

```
ttgattcagc ccgaga                                               16

<210> SEQ ID NO 1291
<211> LENGTH: 22
<212> TYPE: DNA
<213> ORGANISM: Zea mays;

<400> SEQUENCE: 1291
cagtatagct cggtgttgct ca                                        22

<210> SEQ ID NO 1292
<211> LENGTH: 19
<212> TYPE: DNA
<213> ORGANISM: Zea mays;

<400> SEQUENCE: 1292
cgcgtggaac agggtagag                                            19

<210> SEQ ID NO 1293
<211> LENGTH: 19
<212> TYPE: DNA
<213> ORGANISM: Zea mays;

<400> SEQUENCE: 1293
cctccataat gattagatc                                            19

<210> SEQ ID NO 1294
<211> LENGTH: 19
<212> TYPE: DNA
<213> ORGANISM: Zea mays;

<400> SEQUENCE: 1294
cctccataat gagtagatc                                            19

<210> SEQ ID NO 1295
<211> LENGTH: 25
<212> TYPE: DNA
<213> ORGANISM: Zea mays;

<400> SEQUENCE: 1295
cctacgatcg atttctaagc gtcta                                     25

<210> SEQ ID NO 1296
<211> LENGTH: 22
<212> TYPE: DNA
<213> ORGANISM: Zea mays;

<400> SEQUENCE: 1296
gcgacaactc tccaacaaca ac                                        22

<210> SEQ ID NO 1297
<211> LENGTH: 17
<212> TYPE: DNA
<213> ORGANISM: Zea mays;

<400> SEQUENCE: 1297
agtccattgg aggttcg                                              17

<210> SEQ ID NO 1298
<211> LENGTH: 17
<212> TYPE: DNA
<213> ORGANISM: Zea mays;
```

-continued

```
<400> SEQUENCE: 1298
agtccattgg agattcg                                              17

<210> SEQ ID NO 1299
<211> LENGTH: 21
<212> TYPE: DNA
<213> ORGANISM: Zea mays;

<400> SEQUENCE: 1299
tttgggcatc acttgtctca a                                        21

<210> SEQ ID NO 1300
<211> LENGTH: 19
<212> TYPE: DNA
<213> ORGANISM: Zea mays;

<400> SEQUENCE: 1300
gcgatgccac ggaacataa                                           19

<210> SEQ ID NO 1301
<211> LENGTH: 15
<212> TYPE: DNA
<213> ORGANISM: Zea mays;

<400> SEQUENCE: 1301
acgatcatgg cctgg                                               15

<210> SEQ ID NO 1302
<211> LENGTH: 15
<212> TYPE: DNA
<213> ORGANISM: Zea mays;

<400> SEQUENCE: 1302
acgatcatgg cgtgg                                               15

<210> SEQ ID NO 1303
<211> LENGTH: 18
<212> TYPE: DNA
<213> ORGANISM: Zea mays;

<400> SEQUENCE: 1303
cggcgtggca tacaagga                                            18

<210> SEQ ID NO 1304
<211> LENGTH: 20
<212> TYPE: DNA
<213> ORGANISM: Zea mays;

<400> SEQUENCE: 1304
caacgcggct cgttcatcag                                          20

<210> SEQ ID NO 1305
<211> LENGTH: 16
<212> TYPE: DNA
<213> ORGANISM: Zea mays;

<400> SEQUENCE: 1305
tgatgaccct gttggg                                              16

<210> SEQ ID NO 1306
<211> LENGTH: 15
<212> TYPE: DNA
<213> ORGANISM: Zea mays;
```

-continued

<400> SEQUENCE: 1306
tgatgacccc gttgg                                                                            15

<210> SEQ ID NO 1307
<211> LENGTH: 18
<212> TYPE: DNA
<213> ORGANISM: Zea mays;

<400> SEQUENCE: 1307
gcgtgtcggt acgtggat                                                                         18

<210> SEQ ID NO 1308
<211> LENGTH: 20
<212> TYPE: DNA
<213> ORGANISM: Zea mays;

<400> SEQUENCE: 1308
accatgctac gccaagttca                                                                       20

<210> SEQ ID NO 1309
<211> LENGTH: 20
<212> TYPE: DNA
<213> ORGANISM: Zea mays;

<400> SEQUENCE: 1309
ttttcaggca gcttttataa                                                                       20

<210> SEQ ID NO 1310
<211> LENGTH: 19
<212> TYPE: DNA
<213> ORGANISM: Zea mays;

<400> SEQUENCE: 1310
ttcaggcagc ttctataaa                                                                        19

<210> SEQ ID NO 1311
<211> LENGTH: 21
<212> TYPE: DNA
<213> ORGANISM: Zea mays;

<400> SEQUENCE: 1311
gcagactgca aaacacttag c                                                                     21

<210> SEQ ID NO 1312
<211> LENGTH: 25
<212> TYPE: DNA
<213> ORGANISM: Zea mays;

<400> SEQUENCE: 1312
ggtttgaccc tatttctctt tcaca                                                                 25

<210> SEQ ID NO 1313
<211> LENGTH: 13
<212> TYPE: DNA
<213> ORGANISM: Zea mays;

<400> SEQUENCE: 1313
cccggcggtg gaa                                                                              13

<210> SEQ ID NO 1314
<211> LENGTH: 13
<212> TYPE: DNA

-continued

```
<213> ORGANISM: Zea mays;

<400> SEQUENCE: 1314
tcgcccgacg gtg                                                   13

<210> SEQ ID NO 1315
<211> LENGTH: 16
<212> TYPE: DNA
<213> ORGANISM: Zea mays;

<400> SEQUENCE: 1315
tgtcggccgc cattgt                                                16

<210> SEQ ID NO 1316
<211> LENGTH: 22
<212> TYPE: DNA
<213> ORGANISM: Zea mays;

<400> SEQUENCE: 1316
gacgacagct acgacatgat ac                                         22

<210> SEQ ID NO 1317
<211> LENGTH: 18
<212> TYPE: DNA
<213> ORGANISM: Zea mays;

<400> SEQUENCE: 1317
attggatggc ctggaggc                                              18

<210> SEQ ID NO 1318
<211> LENGTH: 16
<212> TYPE: DNA
<213> ORGANISM: Zea mays;

<400> SEQUENCE: 1318
ttggatggcc cggagg                                                16

<210> SEQ ID NO 1319
<211> LENGTH: 25
<212> TYPE: DNA
<213> ORGANISM: Zea mays;

<400> SEQUENCE: 1319
gacgttagag accttgaagt tagga                                      25

<210> SEQ ID NO 1320
<211> LENGTH: 21
<212> TYPE: DNA
<213> ORGANISM: Zea mays;

<400> SEQUENCE: 1320
gtcgcgaaca tcgacaagaa g                                          21

<210> SEQ ID NO 1321
<211> LENGTH: 15
<212> TYPE: DNA
<213> ORGANISM: Zea mays;

<400> SEQUENCE: 1321
cttttcgcta cagct                                                 15

<210> SEQ ID NO 1322
<211> LENGTH: 17
```

-continued

<212> TYPE: DNA
<213> ORGANISM: Zea mays;

<400> SEQUENCE: 1322
ttcttttcgc tacaact                                                                17

<210> SEQ ID NO 1323
<211> LENGTH: 18
<212> TYPE: DNA
<213> ORGANISM: Zea mays;

<400> SEQUENCE: 1323
ggtagcacat tgcatagg                                                               18

<210> SEQ ID NO 1324
<211> LENGTH: 22
<212> TYPE: DNA
<213> ORGANISM: Zea mays;

<400> SEQUENCE: 1324
gctcaataca gtaattcctc at                                                          22

<210> SEQ ID NO 1325
<211> LENGTH: 15
<212> TYPE: DNA
<213> ORGANISM: Zea mays;

<400> SEQUENCE: 1325
caacgctcac ttacc                                                                  15

<210> SEQ ID NO 1326
<211> LENGTH: 14
<212> TYPE: DNA
<213> ORGANISM: Zea mays;

<400> SEQUENCE: 1326
aacgctcgct tacc                                                                   14

<210> SEQ ID NO 1327
<211> LENGTH: 23
<212> TYPE: DNA
<213> ORGANISM: Zea mays;

<400> SEQUENCE: 1327
caagcagagg aagggacatt cat                                                         23

<210> SEQ ID NO 1328
<211> LENGTH: 27
<212> TYPE: DNA
<213> ORGANISM: Zea mays;

<400> SEQUENCE: 1328
gggtagctgt ccgaatttaa tagaaga                                                     27

<210> SEQ ID NO 1329
<211> LENGTH: 18
<212> TYPE: DNA
<213> ORGANISM: Zea mays;

<400> SEQUENCE: 1329
tttatttgaa tggctata                                                               18

<210> SEQ ID NO 1330

-continued

```
<211> LENGTH: 20
<212> TYPE: DNA
<213> ORGANISM: Zea mays;

<400> SEQUENCE: 1330
tttatttgaa tgactatata                                           20

<210> SEQ ID NO 1331
<211> LENGTH: 24
<212> TYPE: DNA
<213> ORGANISM: Zea mays;

<400> SEQUENCE: 1331
agggcagtca gcacaagtta gaag                                      24

<210> SEQ ID NO 1332
<211> LENGTH: 18
<212> TYPE: DNA
<213> ORGANISM: Zea mays;

<400> SEQUENCE: 1332
atgtggccgg tgaagtgt                                             18

<210> SEQ ID NO 1333
<211> LENGTH: 15
<212> TYPE: DNA
<213> ORGANISM: Zea mays;

<400> SEQUENCE: 1333
ctgccgtcat cgtcg                                                15

<210> SEQ ID NO 1334
<211> LENGTH: 13
<212> TYPE: DNA
<213> ORGANISM: Zea mays;

<400> SEQUENCE: 1334
ccgtcaccgt cgc                                                  13

<210> SEQ ID NO 1335
<211> LENGTH: 18
<212> TYPE: DNA
<213> ORGANISM: Zea mays;

<400> SEQUENCE: 1335
ccggtcgtca ccgtcatc                                             18

<210> SEQ ID NO 1336
<211> LENGTH: 22
<212> TYPE: DNA
<213> ORGANISM: Zea mays;

<400> SEQUENCE: 1336
tggactctcc gactcctcta ag                                        22

<210> SEQ ID NO 1337
<211> LENGTH: 17
<212> TYPE: DNA
<213> ORGANISM: Zea mays;

<400> SEQUENCE: 1337
ctaaggtccg tcaaagc                                              17
```

-continued

```
<210> SEQ ID NO 1338
<211> LENGTH: 19
<212> TYPE: DNA
<213> ORGANISM: Zea mays;

<400> SEQUENCE: 1338
aactaaggtc catcaaagc                                                    19

<210> SEQ ID NO 1339
<211> LENGTH: 25
<212> TYPE: DNA
<213> ORGANISM: Zea mays;

<400> SEQUENCE: 1339
cgaggcccac taaatataga ctcag                                             25

<210> SEQ ID NO 1340
<211> LENGTH: 24
<212> TYPE: DNA
<213> ORGANISM: Zea mays;

<400> SEQUENCE: 1340
aggtattggt tctcgaaggc ttat                                              24

<210> SEQ ID NO 1341
<211> LENGTH: 23
<212> TYPE: DNA
<213> ORGANISM: Zea mays;

<400> SEQUENCE: 1341
taaatgagac aacgatagat ata                                               23

<210> SEQ ID NO 1342
<211> LENGTH: 20
<212> TYPE: DNA
<213> ORGANISM: Zea mays;

<400> SEQUENCE: 1342
tgagacaacg acagatataa                                                   20

<210> SEQ ID NO 1343
<211> LENGTH: 20
<212> TYPE: DNA
<213> ORGANISM: Zea mays;

<400> SEQUENCE: 1343
accatagctc ttgctcacga                                                   20

<210> SEQ ID NO 1344
<211> LENGTH: 22
<212> TYPE: DNA
<213> ORGANISM: Zea mays;

<400> SEQUENCE: 1344
ccacttgtta tgaggcaggt ca                                                22

<210> SEQ ID NO 1345
<211> LENGTH: 12
<212> TYPE: DNA
<213> ORGANISM: Zea mays;

<400> SEQUENCE: 1345
cggcagacgc gc                                                           12
```

-continued

```
<210> SEQ ID NO 1346
<211> LENGTH: 13
<212> TYPE: DNA
<213> ORGANISM: Zea mays;

<400> SEQUENCE: 1346
cggcagacgc acc                                                          13

<210> SEQ ID NO 1347
<211> LENGTH: 16
<212> TYPE: DNA
<213> ORGANISM: Zea mays;

<400> SEQUENCE: 1347
cgggttcggc gagacg                                                       16

<210> SEQ ID NO 1348
<211> LENGTH: 18
<212> TYPE: DNA
<213> ORGANISM: Zea mays;

<400> SEQUENCE: 1348
tggcctcacg gttctgaa                                                     18

<210> SEQ ID NO 1349
<211> LENGTH: 17
<212> TYPE: DNA
<213> ORGANISM: Zea mays;

<400> SEQUENCE: 1349
agagttcttt gggtctc                                                      17

<210> SEQ ID NO 1350
<211> LENGTH: 20
<212> TYPE: DNA
<213> ORGANISM: Zea mays;

<400> SEQUENCE: 1350
agagttcttt gagtctcttt                                                   20

<210> SEQ ID NO 1351
<211> LENGTH: 25
<212> TYPE: DNA
<213> ORGANISM: Zea mays;

<400> SEQUENCE: 1351
tgtcagtatt gttccatgca cagtt                                             25

<210> SEQ ID NO 1352
<211> LENGTH: 22
<212> TYPE: DNA
<213> ORGANISM: Zea mays;

<400> SEQUENCE: 1352
tgatgccact accacgattg tc                                                22

<210> SEQ ID NO 1353
<211> LENGTH: 18
<212> TYPE: DNA
<213> ORGANISM: Zea mays;

<400> SEQUENCE: 1353
agaggtaccg tccgtttc                                                     18
```

<210> SEQ ID NO 1354
<211> LENGTH: 18
<212> TYPE: DNA
<213> ORGANISM: Zea mays;

<400> SEQUENCE: 1354
caagaggtac catccgtt                                          18

<210> SEQ ID NO 1355
<211> LENGTH: 19
<212> TYPE: DNA
<213> ORGANISM: Zea mays;

<400> SEQUENCE: 1355
gacgcgactt cgtcaccat                                         19

<210> SEQ ID NO 1356
<211> LENGTH: 18
<212> TYPE: DNA
<213> ORGANISM: Zea mays;

<400> SEQUENCE: 1356
gcgggtcgaa gctgaatc                                          18

<210> SEQ ID NO 1357
<211> LENGTH: 23
<212> TYPE: DNA
<213> ORGANISM: Zea mays;

<400> SEQUENCE: 1357
cgaataacag aatagttgag aac                                    23

<210> SEQ ID NO 1358
<211> LENGTH: 23
<212> TYPE: DNA
<213> ORGANISM: Zea mays;

<400> SEQUENCE: 1358
cgaataacag aatacttgag aac                                    23

<210> SEQ ID NO 1359
<211> LENGTH: 24
<212> TYPE: DNA
<213> ORGANISM: Zea mays;

<400> SEQUENCE: 1359
gggcaactga atatacaacc ttga                                   24

<210> SEQ ID NO 1360
<211> LENGTH: 21
<212> TYPE: DNA
<213> ORGANISM: Zea mays;

<400> SEQUENCE: 1360
gacacctttg ggcatattgg a                                      21

<210> SEQ ID NO 1361
<211> LENGTH: 19
<212> TYPE: DNA
<213> ORGANISM: Zea mays;

<400> SEQUENCE: 1361
tgcgttaagg tttatttct                                                          19

<210> SEQ ID NO 1362
<211> LENGTH: 18
<212> TYPE: DNA
<213> ORGANISM: Zea mays;

<400> SEQUENCE: 1362
tgcgttaagg tttagttc                                                           18

<210> SEQ ID NO 1363
<211> LENGTH: 25
<212> TYPE: DNA
<213> ORGANISM: Zea mays;

<400> SEQUENCE: 1363
tcacgatttt gaagtagtcg agtca                                                   25

<210> SEQ ID NO 1364
<211> LENGTH: 18
<212> TYPE: DNA
<213> ORGANISM: Zea mays;

<400> SEQUENCE: 1364
tgcagcccaa aacagcaa                                                           18

<210> SEQ ID NO 1365
<211> LENGTH: 15
<212> TYPE: DNA
<213> ORGANISM: Zea mays;

<400> SEQUENCE: 1365
cacagccctg ccttg                                                              15

<210> SEQ ID NO 1366
<211> LENGTH: 14
<212> TYPE: DNA
<213> ORGANISM: Zea mays;

<400> SEQUENCE: 1366
acagccccgc cttg                                                               14

<210> SEQ ID NO 1367
<211> LENGTH: 19
<212> TYPE: DNA
<213> ORGANISM: Zea mays;

<400> SEQUENCE: 1367
atagacggcc tccggtcac                                                          19

<210> SEQ ID NO 1368
<211> LENGTH: 24
<212> TYPE: DNA
<213> ORGANISM: Zea mays;

<400> SEQUENCE: 1368
tgctacggca caataaatga atga                                                    24

<210> SEQ ID NO 1369
<211> LENGTH: 19
<212> TYPE: DNA
<213> ORGANISM: Zea mays;

<400> SEQUENCE: 1369
aatcccttaa tgtgtcttc                                          19

<210> SEQ ID NO 1370
<211> LENGTH: 18
<212> TYPE: DNA
<213> ORGANISM: Zea mays;

<400> SEQUENCE: 1370
aatcccttaa tgcgtctt                                           18

<210> SEQ ID NO 1371
<211> LENGTH: 18
<212> TYPE: DNA
<213> ORGANISM: Zea mays;

<400> SEQUENCE: 1371
ttgcatcgcc aataccca                                           18

<210> SEQ ID NO 1372
<211> LENGTH: 25
<212> TYPE: DNA
<213> ORGANISM: Zea mays;

<400> SEQUENCE: 1372
tttgtgaaca ttactccttt gtgtc                                   25

<210> SEQ ID NO 1373
<211> LENGTH: 20
<212> TYPE: DNA
<213> ORGANISM: Zea mays;

<400> SEQUENCE: 1373
cattgtttat tacagttcct                                         20

<210> SEQ ID NO 1374
<211> LENGTH: 21
<212> TYPE: DNA
<213> ORGANISM: Zea mays;

<400> SEQUENCE: 1374
cattgtttat taaagttcct a                                       21

<210> SEQ ID NO 1375
<211> LENGTH: 20
<212> TYPE: DNA
<213> ORGANISM: Zea mays;

<400> SEQUENCE: 1375
agccgagcaa gggtaatggt                                         20

<210> SEQ ID NO 1376
<211> LENGTH: 25
<212> TYPE: DNA
<213> ORGANISM: Zea mays;

<400> SEQUENCE: 1376
ggaagtaaag gaccctctga aatgt                                   25

<210> SEQ ID NO 1377
<211> LENGTH: 18
<212> TYPE: DNA
<213> ORGANISM: Zea mays;

-continued

<400> SEQUENCE: 1377
aatccgtgtc ttctctgt                                                    18

<210> SEQ ID NO 1378
<211> LENGTH: 19
<212> TYPE: DNA
<213> ORGANISM: Zea mays;

<400> SEQUENCE: 1378
aaatccgtgt attctctgt                                                   19

<210> SEQ ID NO 1379
<211> LENGTH: 15
<212> TYPE: DNA
<213> ORGANISM: Zea mays;

<400> SEQUENCE: 1379
cggcgcccgt ggttt                                                       15

<210> SEQ ID NO 1380
<211> LENGTH: 25
<212> TYPE: DNA
<213> ORGANISM: Zea mays;

<400> SEQUENCE: 1380
gagagataga gggagtcagg gagat                                            25

<210> SEQ ID NO 1381
<211> LENGTH: 14
<212> TYPE: DNA
<213> ORGANISM: Zea mays;

<400> SEQUENCE: 1381
cgtctgcagc tgac                                                        14

<210> SEQ ID NO 1382
<211> LENGTH: 13
<212> TYPE: DNA
<213> ORGANISM: Zea mays;

<400> SEQUENCE: 1382
cgtctgcagc cga                                                         13

<210> SEQ ID NO 1383
<211> LENGTH: 20
<212> TYPE: DNA
<213> ORGANISM: Zea mays;

<400> SEQUENCE: 1383
acactcgaca aggcgtcgtc                                                  20

<210> SEQ ID NO 1384
<211> LENGTH: 22
<212> TYPE: DNA
<213> ORGANISM: Zea mays;

<400> SEQUENCE: 1384
ctcgagactc acaagctatc ac                                               22

<210> SEQ ID NO 1385
<211> LENGTH: 14
<212> TYPE: DNA
<213> ORGANISM: Zea mays;

-continued

```
<400> SEQUENCE: 1385
acagtccggt gcac                                                  14

<210> SEQ ID NO 1386
<211> LENGTH: 14
<212> TYPE: DNA
<213> ORGANISM: Zea mays;

<400> SEQUENCE: 1386
cggacagtcc gctg                                                  14

<210> SEQ ID NO 1387
<211> LENGTH: 16
<212> TYPE: DNA
<213> ORGANISM: Zea mays;

<400> SEQUENCE: 1387
cgagagcagc aagttc                                                16

<210> SEQ ID NO 1388
<211> LENGTH: 18
<212> TYPE: DNA
<213> ORGANISM: Zea mays;

<400> SEQUENCE: 1388
gaagagatgg ccttgttc                                              18

<210> SEQ ID NO 1389
<211> LENGTH: 18
<212> TYPE: DNA
<213> ORGANISM: Zea mays;

<400> SEQUENCE: 1389
ccaaaaggta ctgtccgt                                              18

<210> SEQ ID NO 1390
<211> LENGTH: 17
<212> TYPE: DNA
<213> ORGANISM: Zea mays;

<400> SEQUENCE: 1390
caaaaggtac cgtccgt                                               17

<210> SEQ ID NO 1391
<211> LENGTH: 18
<212> TYPE: DNA
<213> ORGANISM: Zea mays;

<400> SEQUENCE: 1391
acgcgacttc accaccgt                                              18

<210> SEQ ID NO 1392
<211> LENGTH: 21
<212> TYPE: DNA
<213> ORGANISM: Zea mays;

<400> SEQUENCE: 1392
ttggtggatc gaagctgaat c                                          21
```

GENETIC LOCI ASSOCIATED WITH EAR ROT RESISTANCE IN MAIZE

CROSS-REFERENCE TO RELATED APPLICATIONS

This application is a 371 National Stage application of International Application No. PCT/US2020/045854 filed Aug. 12, 2020, which claims the priority to PCT/CN2019/100801, filed Aug. 15, 2019, the disclosure of which is incorporated herein in its entirety.

FIELD OF DISCLOSURE

The current disclosure relates to compositions and methods for identifying, selecting, and producing enhanced disease and/or pathogen resistant maize plants.

SEQUENCE LISTING

This application is accompanied by a sequence listing entitled 81918-WO-Seq_ST25.txt, created 10 Aug. 2020, which is approximately 192 kb in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

Maize ear rot is one of the most devastating fungal diseases which threatens global maize production. After being reported firstly in the United States in 1946 (Ullstrup 1946), maize ear rot has been detected in many other countries, such as South Africa, Mexico, Brazil, Canada, Germany, India, and so on (Logrieco et al. 2002; Van, et al. 2007). Since then, maize ear rot is becoming increasingly serious worldwide owing to the deployment of susceptible varieties, high-humidity at both filing and late storage periods, and etc. In China, ear rot was first reported in Henan province (Pan et al. 1987), and then spread to all maize-growing areas of the country. It is estimated that ear rot generally reduces the yield by 10-20%, even reaches 50% or more in some severely infected regions (REN 1993). Even worse, *Fusarium* spp. can produce an array of mycotoxins, like deoxynivalenol, nivalenol, zearalenone, ochratoxin, aflatoxins and fumonisins. Acting as carcinogens, the myco-toxins can be fatal to human health, and cause neural tube birth defects to livestock (Rheeder et al. 1992; Chu, et al 1994; Missmer et al. 2006).

More than ten *Fusarium* spp. can cause maize ear rot, and a certain fungus has its own favorable infection environments. For instance, *F. verticillioides* prefers a low rainfall, high humidity environment; while *F. graminearum* prefers a high rainfall and cool environment (Munkvold 2003). So far, *Aspergillus* ear rot (AER), *Fusarium* ear rot (FER), and *Gibberella* ear rot (GER) are among the most serious and prevalent ear rot diseases around the world (Mesterhazy et al. 2012; Chen et al. 2009; Li et al. 2007). In the field, occurrence of ear rot is generally caused by mixed fungi, rather than a single fungus. In addition to ear rot, *F. graminearum* is also the causal pathogen for other diseases, like *Fusarium* head blight (FHB) in small-grain cereals (Sutton 1982). With the large-scale application of mechanical harvesting, ear rot has become one of the key inhibitory factors since the infected ears could not be automatically removed during harvesting and thus cause contamination of maize kernels with fumonisin mycotoxins.

Resistance to maize ear rot is controlled by multiple small-effect quantitative trait loci (QTL), exhibiting additive, dominant and additive/dominant interaction genetic effects, of which the additive/dominant plays a key role in resistance performance in the field (Boling et al. 1965; Robertson et al. 2006; Ding et al. 2008; Chen et al. 2012). Numbers of OIL analyses have been performed in the past few decades, and resistance QTLs were found to scatter on all ten maize chromosomes. Three resistance QTLs were identified on chrs. 4, 5 and 10, and the major one on chr. 4 could explain 17.95% of the total phenotypic variation (Chen et al. 2012). By using two F2:3 populations sharing the common susceptible parent, nine and seven resistance QTL against *Fusarium* ear rot have been identified, totally explaining 11-44% of the cumulative phenotypic variation. Of them, three were consistently detected in two populations, with one on chr. 3 and two on chr. 6 (Perez et al. 2001). With a RIL population from the cross between 87-1 and Zong 3 inbred lines, the QTL were detected on chrs. 3, 5, 8 and 10, on which two QTLs in bin 3.04, each explaining 13-22% of the phenotypic variation, were consistently detected across all environments (Ding et al. 2008). Among 15 QTL for *Fusarium* ear rot and 17 QTLs for Fumonisin B1, eight common QTLs between them were found to be localized on chrs. 1, 2, 3, 6, 7 and 9, making it possible to select genotypes with both low disease severity and fumonisin contamination (Valentina et al. 2017). Recently, an auxin regulatory protein gene, ZmAuxRP1, was found to enhance maize resistance to both stalk rot and ear rot by regulating the balance between root growth and disease resistance (Ye et al. 2018).

High-density molecular markers can be generated to detect small-effect QTL. Similarly, high-density markers are important in genome-wide association study (GWAS) to identify numerous alleles. With a core panel of 267 diverse maize inbred lines and 47,445 SNPs, three SNPs were found in GWAS to be significantly associated with ear rot resistance, which could explain 3-12% of the total genotypic variation. Of them, two were related to genes responsible for programmed cell death (Zila et al. 2013). One year later in 2014, a large-scale GWAS was conducted by the same group with 1,687 diverse inbred lines and 200,978 SNPs, and 7 significant SNPs were identified in both populations. All SNPs are localized in exons and the associated genes are related to a variety of cellular process (Zila et al. 2014). Recently, GWAS was performed in a panel of 818 tropical inbred lines with 43,424 SNPs. A total of 45 SNPs were significantly associated with *Fusarium* ear rot, and located within or adjacent to 38 candidate genes. Six loci in bins 3.06, 4.04, 4.08, 5.03, 5.04, and 10.03 are in regions that have previously been reported to be associated with *Fusarium* ear rot resistance, and another two loci in bins 4.04 and 9.01 contain the genes of unknown function (Chen et al. 2016).

Plants need to manipulate complex defense strategies to defend pathogen invasion. After *fusarium* inoculation, transcriptome reprogramming reportedly occurs in both resistant and susceptible maize lines. The differentially expressed genes (DEGs) could be classified into more than ten categories, and most were assigned into "cell rescue, defense, and virulence", encoding for PR proteins, detoxification enzymes and β-glucosidases etc. (Alessandra et al. 2010). By analyzing large-scale DEGs in the bract of resistant and susceptible lines, genes associated with defense responses, such as pathogenesis-related protein 1 (PR-1), osmotin (PR-5), RAB GTP binding (RAB), small ubiquitin-like modifier (SUM), ethylene-responsive protein (ERF), S-adenosylmethionine synthase (SAMS), abscisic stress protein (ABA), MYB family transcription factor (MYB), were greatly induced in the resistant genotype (Yuan et al. 2013). Following inoculation, genes related to the secondary metabolism categories, like shikimate, lignin, flavonoid and terpenoid, were highly expressed in the resistant line (Lanu-bile et al. 2014). The 15 lipoxygenase (LOX) pathway genes were strongly induced in the resistant line at 3 or 7 days post inoculation (dpi), while reduced or delayed in the suscep-tible line at 14 dpi. The resistant line restricted the fungal growth and fumonisin accumulation, and this may be asso-ciated with the activation of genes for jasmonic acid bio-synthesis (Maschietto et al. 2015). Moreover, the expression levels of PR genes were constitutively higher in the resistant lines (C0441 and C0433) than in the susceptible lines (C0354 and C0389) before and after inoculation (Maschietto et al. 2016). Interestingly, it was also reported that the fungal infection did induce considerable transcriptome changes in the susceptible line, but not in the resistant line, especially in the pathways related to carbon and amino acid metabo-lism (Campos-Bermudez et al. 2013).

Collection and evaluation of resistant germplasm are critical to breeding of ear rot resistant maize. Thus far, hundreds of resistant maize lines have been identified by different institutes, such as C0387, C0388, C0441 (Canadian Department of Agriculture) (Duan et al. 2015), GE440 and NC300 (North Carolina State University) (Clements et al. 2004), 87-1 (China Agriculture University) (Ding et al. 2008) and BT-1 (Henan Agricultural University) (Chen et al. 2002). These resistant lines have been used to breed disease-resistant hybrids, which has remarkedly accelerated in the last decade (Santiago et al. 2013). Because of the small effects and easily influenced by environmental conditions, it is very difficult to fine-map resistance QTL.

Thus far, no resistance gene has been cloned to maize ear rot except for ZmAuxRP1 (Ye et al. 2018). Nevertheless, genetic control of maize ear rot is an effective way to reduce ear rot disease, thus, applicants desire tools for the devel-opment of as many resistant QTLs as possible for, for example, pyramiding of multiple resistance genes via marker-assisted selection to improve maize resistance to ear rot. Further, applicants desire plants having increased resis-tance to ear rot.

SUMMARY

Compositions and methods for identifying, selecting and producing maize plants with enhanced ear rot resistance are provided. Ear rot resistance maize plants and germplasms are also provided.

In some embodiments, methods of identifying an ear rot resistance maize plant or germplasm are provided. Such methods may comprise detecting, in the plant or germplasm, a marker associated with enhanced ear rot resistance.

In some embodiments, methods of producing an ear rot resistance plant are provided. Such methods may comprise detecting, in a maize germplasm, the presence of a marker associated with enhanced ear rot resistance and producing a progeny plant from said maize germplasm.

In some embodiments, methods of selecting an ear rot resistance maize plant or germplasm are provided. Such methods may comprise crossing a first maize plant or germplasm with a second maize plant or germplasm, wherein the first maize plant or germplasm comprises a marker associated with enhanced ear rot resistance, and selecting a progeny plant or germplasm that possesses the marker.

In some embodiments, methods of introgressing an allele associated with enhanced ear rot resistance into a maize plant or germplasm are provided. Such methods may com-prise crossing a first maize plant or germplasm comprising an allele associated with enhanced ear rot resistance with a second maize plant or germplasm that lacks said allele and optionally repeatedly backcrossing progeny plants compris-ing said allele with the second plant or germplasm to produce an ear rot resistance plant or germplasm comprising the allele associated with enhanced ear rot resistance. Prog-eny comprising the allele associated with enhanced ear rot resistance may be identified by detecting, in their genomes, the presence of a marker associated with said allele.

Maize plants and/or germplasms identified, produced or selected by the methods of this invention are also provided, as are any progeny and/or seeds derived from a maize plant or germplasm identified, produced or selected by these methods.

Non-naturally occurring maize seeds, plants and/or germ-plasms comprising one or more markers associated with enhanced ear rot resistance are also provided.

A marker associated with enhanced ear rot resistance may comprise, consist essentially of or consist of a single allele or a combination of alleles at one or more genetic loci.

Additionally, some embodiments encompass the combi-nation of maize plants selected, identified or produced by the use of the markers described herein in combination with commercial fungicides for the control of a pathogen (e.g. a *Fusarium* spp.).

The foregoing and other objects and aspects of the present invention are explained in more detail below.

BRIEF DESCRIPTION OF THE SEQUENCE LISTING

Primers and probes useful for detecting intervals and alleles of the present disclosure are set forth in Table XI, Table XII, and Table XIII.

BRIEF DESCRIPTION OF THE FIGURES

FIG. 1 is a distribution of disease severity index (DSI) estimated with BLUP among the GWAS population.

FIG. 2A shows quantile-quantile and manhattan plots for maize ear rot in Beijing in 2017 summer (A, B).

FIG. 2B shows quantile-quantile and manhattan plots for maize ear rot in Hainan in 2017 winter (C, D).

FIG. 2C shows quantile-quantile and manhattan plots for maize ear rot in Beijing in 2018 summer (E, F).

FIG. 2D shows quantile-quantile and manhattan plots for maize ear rot in BLUP (G, H).

FIG. 3 shows dynamic expression patterns of genes in the early time post inoculation. The genes in the resistant line CIMBL47 were transiently induced by pathogen and reached their expression peaks at 0.5 hpi (A-F) and 1.5 hpi (G-L).

FIG. 4 shows differentially expressed genes (DEGs) involved in plant hormone signal transduction pathways. Red and blue colors separately mark the up- and down-regulated DEGs in CIMBL47 compared with SY1035; while green colors indicate mixed (both up and down) regulated DEGs.

FIG. 5 shows the differentially expressed genes (DEGs) involved in Phenylpropanoid biosynthesis. Only up-regu-lated DEGs (marked as red colors) were detected at 1.5 hpi in CIMBL47 compared with SY1035.

FIG. 6 shows distribution of disease severity index (DSI) of the GWAS population under three environmental conditions.

FIG. 7 shows functional categories of the potential resistance genes revealed by GWAS.

FIGS. 8A-8E shows GO enrichment of differentially expressed genes (DEGs) between resistant CIMBL47 (R) and susceptible SY1035 (S) lines. Scatter plots of enriched GO terms of R vs S at 0 (A), 0.5 (B), 1.5 (C), 3 (D), and 6 (E) hours post inoculation. The enriched GO terms were listed in the ordinate; while numbers of DEGs were indicated in the abscissa. Differential colors are used to distinguish biological processes, cellular components, and molecular functions.

FIGS. 9A-9E show KEGG enrichment of differentially expressed genes (DEGs) between the resistant CIMBL47 (R) and susceptible SY1035 (S) lines at from 0 to 6 hpi.

FIGS. 10A-10E show distribution of DEGs for differential pathways between the resistant CIMBL47 (R) and susceptible SY1035 (S) lines. Percentages of DEGs were estimated for differential pathways of R vs S at 0 (A), 0.5 (B), 1.5 (C), 3 (D), and 6 (E) hours post inoculation.

FIG. 11 shows dynamic expression patterns of genes in the early time post inoculation. The genes in the susceptible line SY1035 were downregulated to their lowest points at 1.5 hpi.

FIG. 12 shows dynamic expression patterns of genes in the early time post inoculation. Genes were highly expressed in the resistant line CIMBL47 compared to susceptible line SY1035.

FIG. 13 shows dynamic expression patterns of genes in the early time post inoculation. Genes were highly expressed in the susceptible line SY1035 compared to resistant line CIMBL47.

Figure 14C:
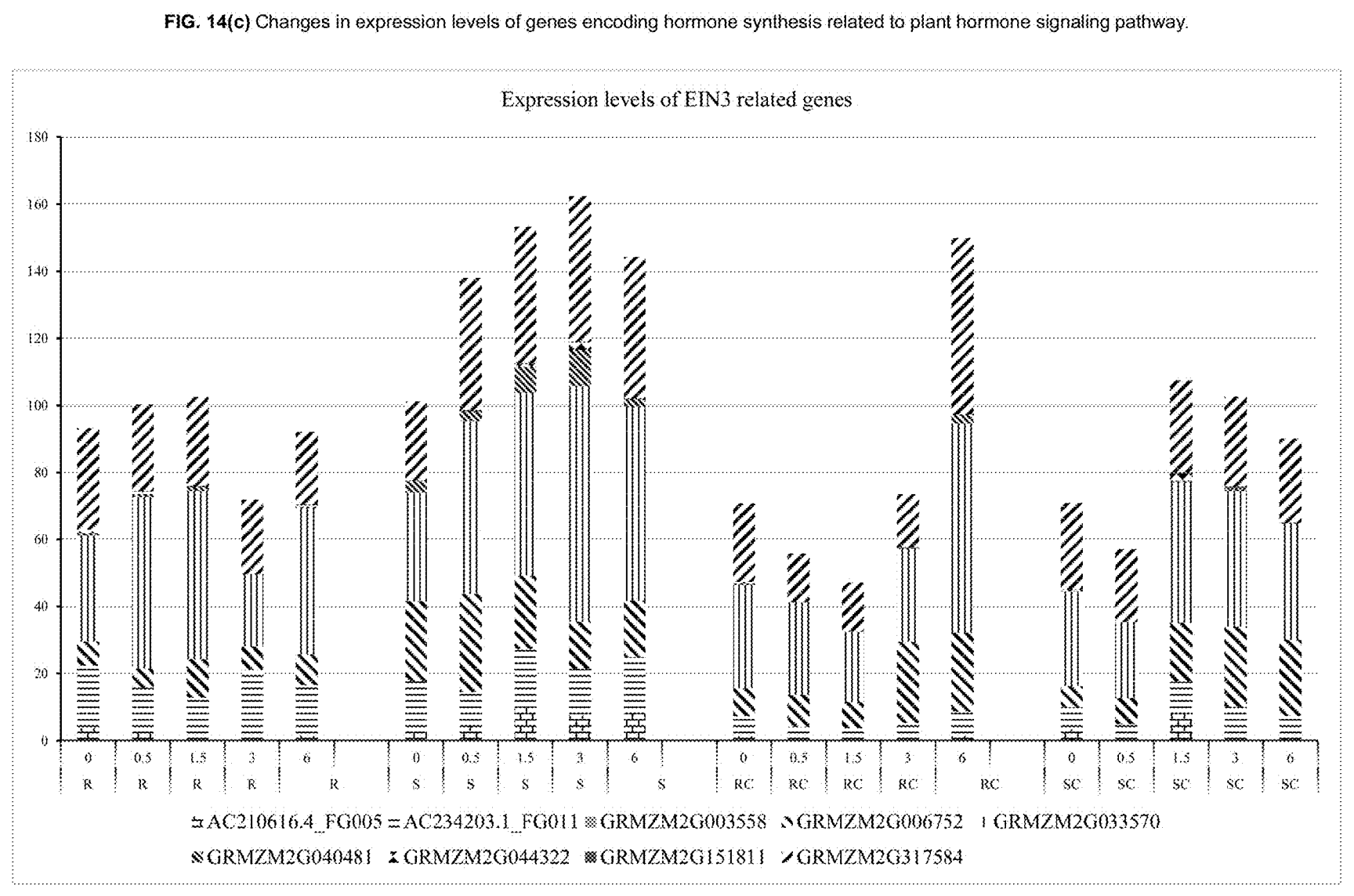
Figure 15A:
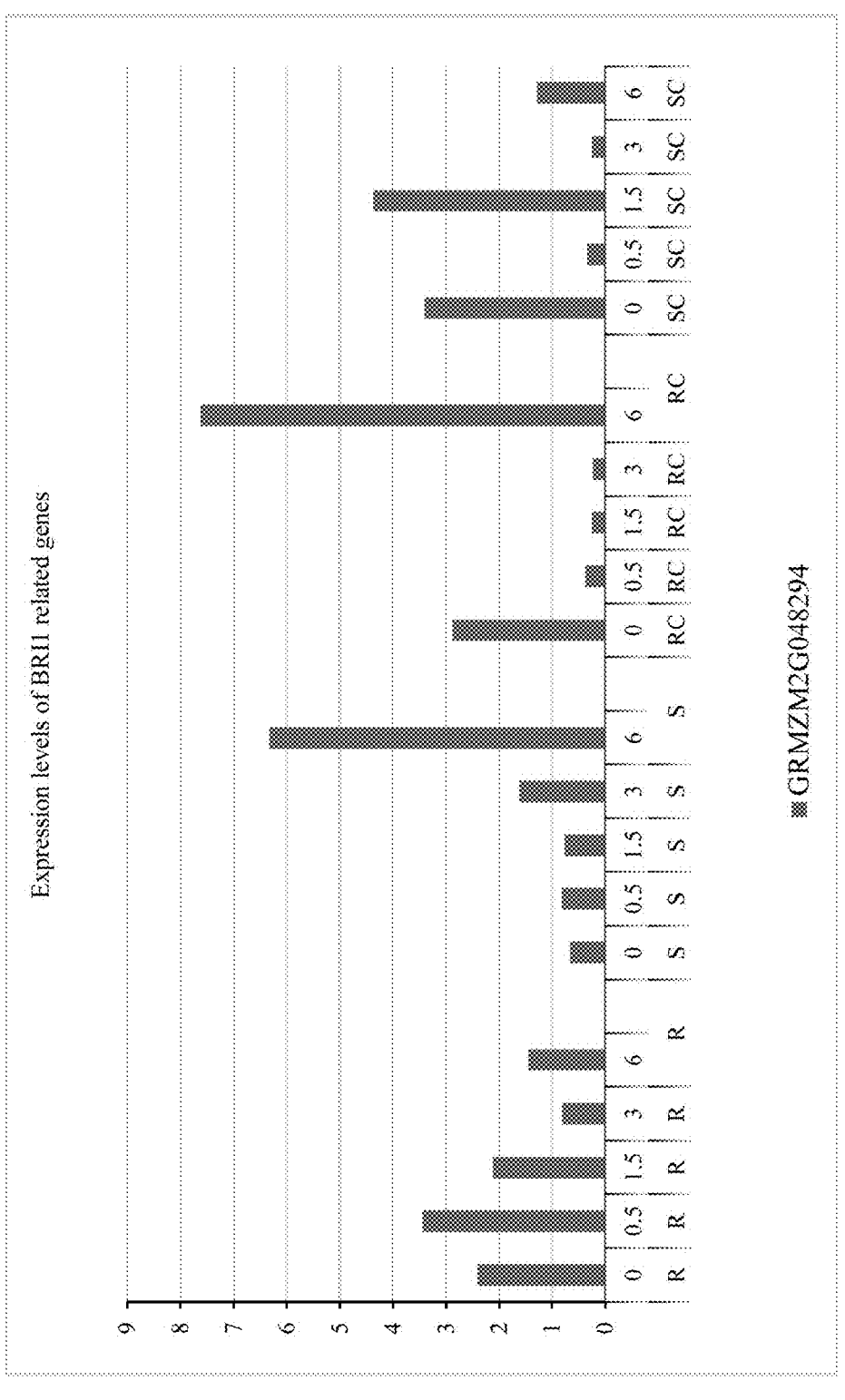
Figure 15B:
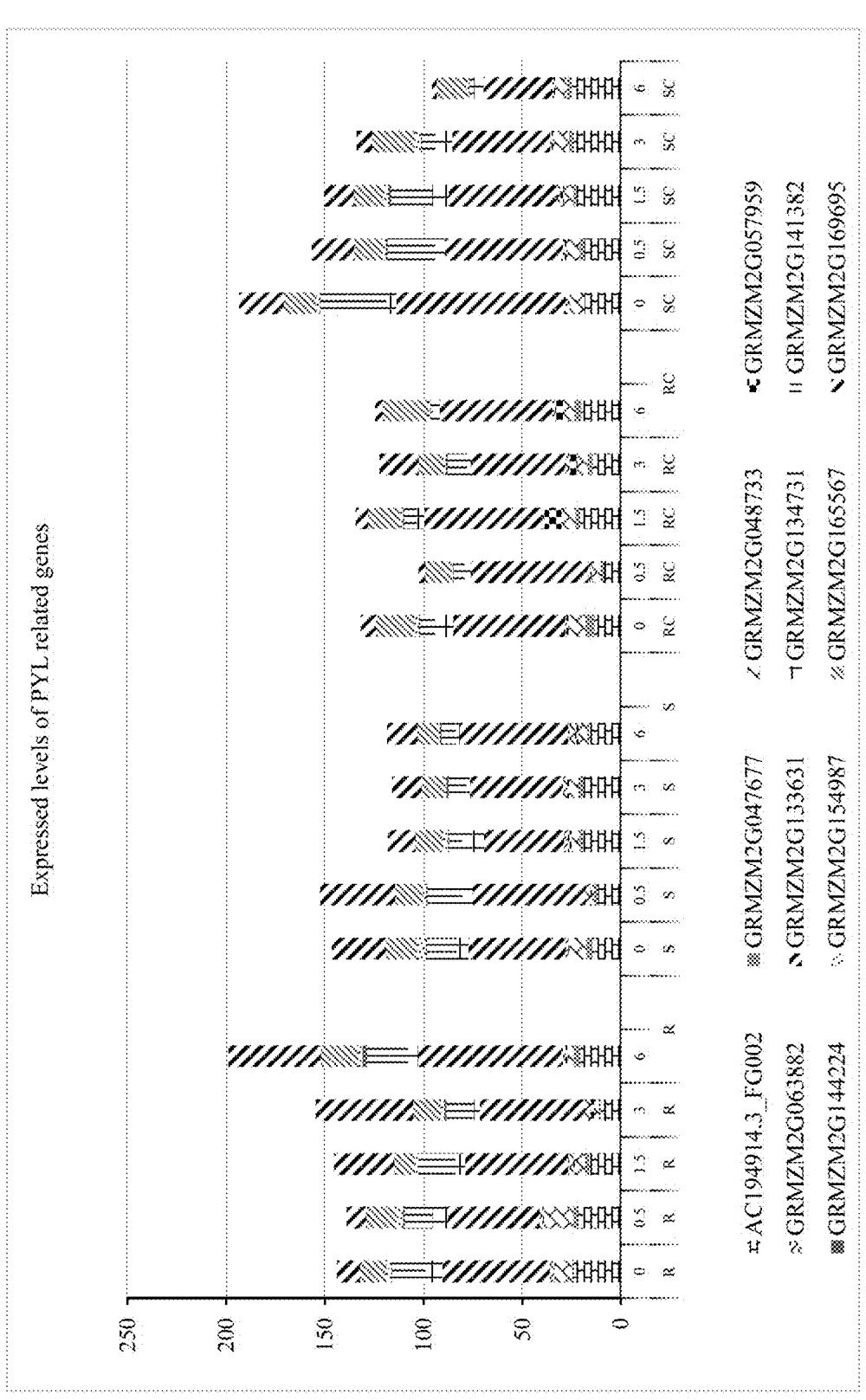
Figure 15C:
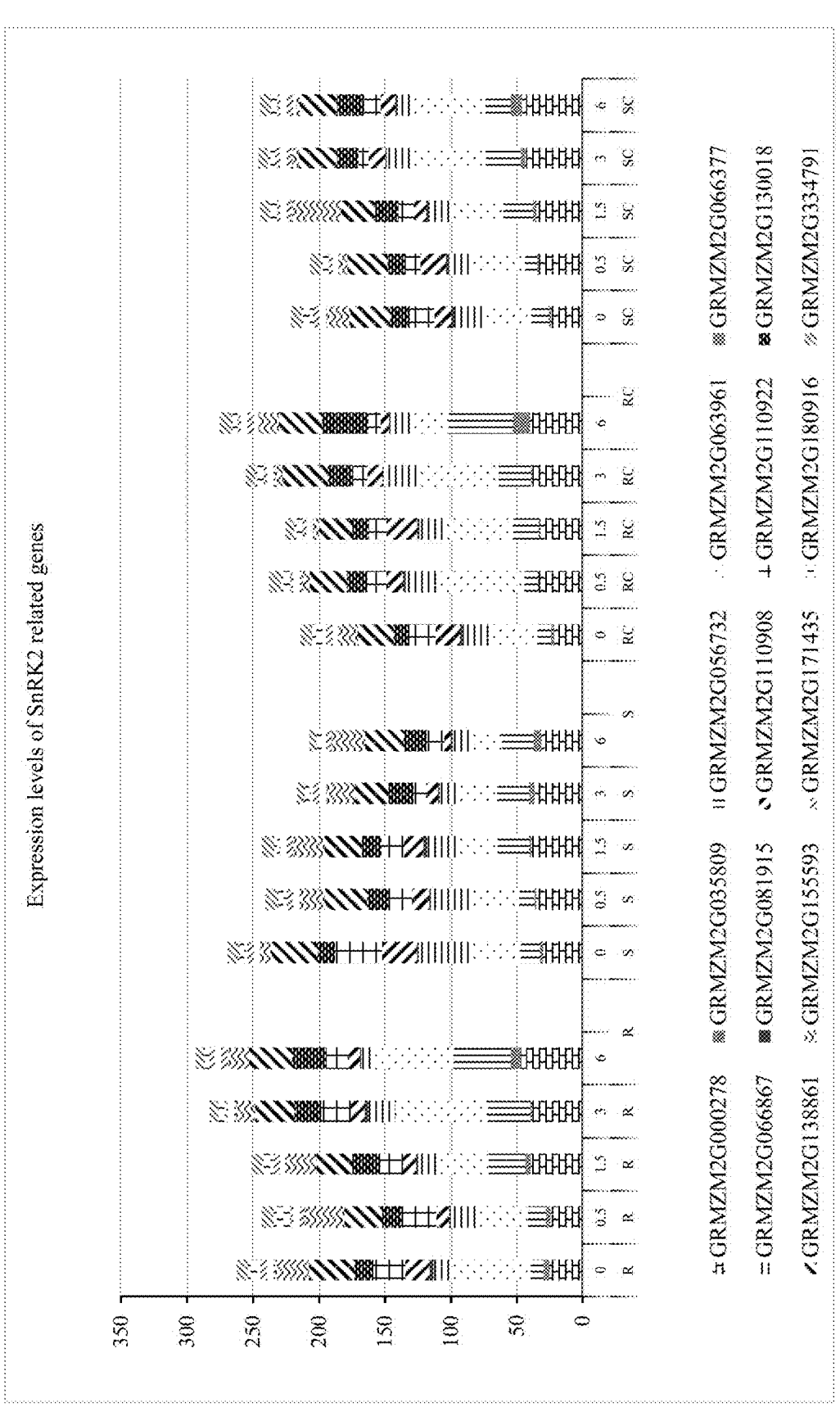
Figure 15D:
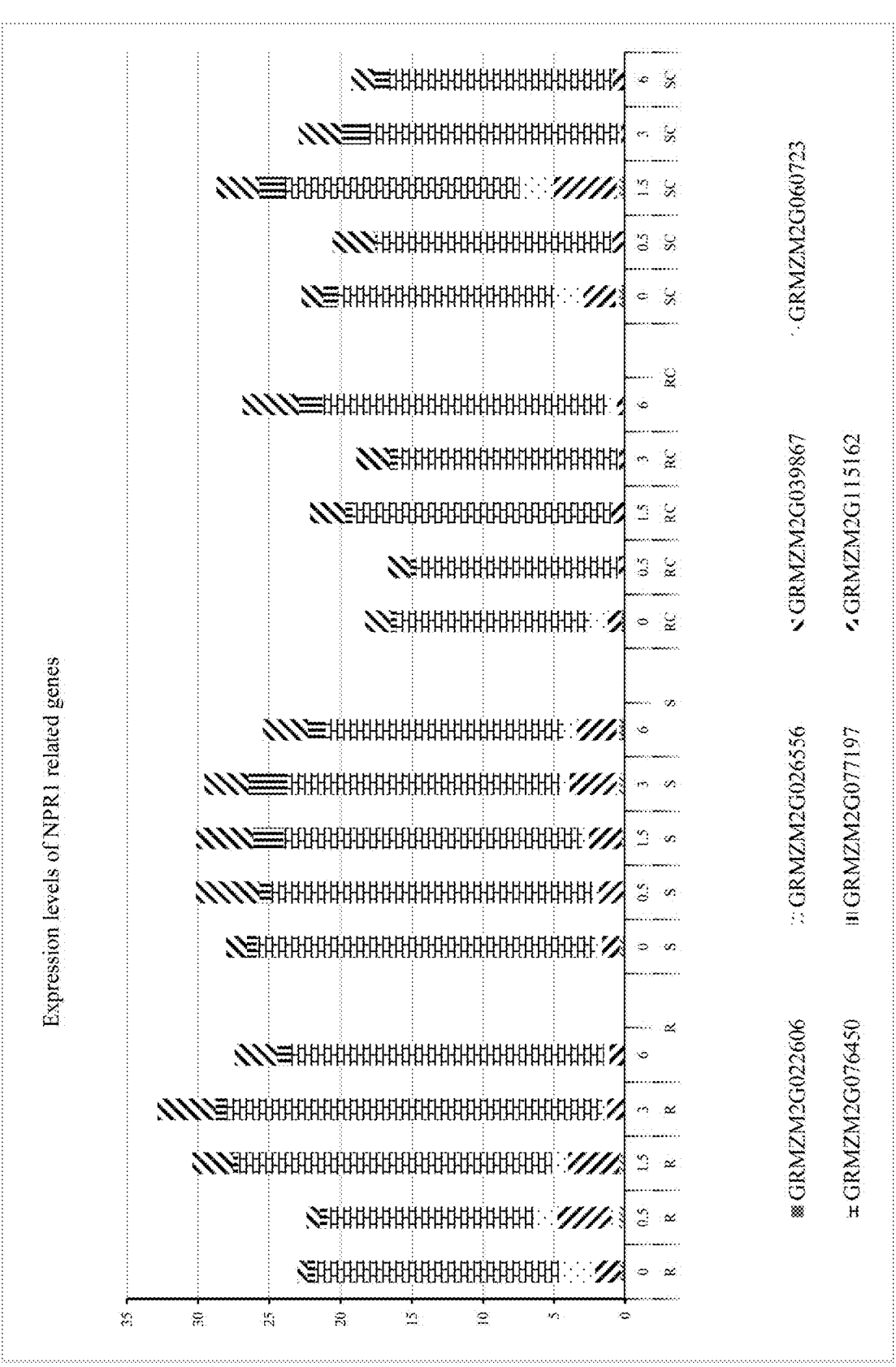

FIG. 14 and 15 shows changes in expression levels of genes encoding hormone synthesis related to plant hormone signaling pathway.

FIG. 16 shows maize half-kernels used in the RNA-seq analysis.

DETAILED DESCRIPTION

The present disclosure provides compositions and methods for identifying, selecting and/or producing maize plants with enhanced ear rot resistance, as well as maize plants identified, selected and/or produced by a method of this invention. In addition, the present invention provides maize plants and/or germplasms having within their genome one or more markers associated with enhanced ear rot resistance.

Definitions

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" marker can mean one marker or a plurality of markers.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

The term "consists essentially of" (and grammatical variants thereof), as applied to a polynucleotide sequence of this invention, means a polynucleotide sequence that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together. The term "materially altered," as applied to polynucleotides of the invention, refers to an increase or decrease in ability to express the polynucleotide sequence of at least about 50% or more as compared to the expression level of a polynucleotide sequence consisting of the recited sequence.

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced ear rot resistance" refers to a marker whose presence or absence can be used to predict whether and/or to what extent a plant will display an ear rot resistance phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the phrase "introduced into a genome" refers to any known method one may employ to insert a given nucleotide sequence into the genome of an organism. For example, "introduced into the genome" of a soy plant would encompass traditional plant breeding methods, transgenic expression of a gene or gene editing methods (i.e. CRISPR, TALEN, etc) wherein said plant did not have said nucleotide sequence in its genome prior to said introduction.

As used herein, the terms "cultivar" and "variety" refer to a group of similar plants that by structural or genetic features and/or performance can be distinguished from other varieties within the same species.

As used herein, the terms "desired allele", "allele of interest" and "favorable allele" are used interchangeably to refer to an allele associated with a desired trait. In some embodiments, a "desired allele" and/or "allele of interest" may be associated with either an increase or a decrease of or in a given trait, depending on the nature of the desired phenotype. In some embodiments, a "desired allele" and/or "allele of interest" may be associated with a change in morphology, color, etc.

As used herein, the term "enhanced ear rot resistance" refers to an improvement, enhancement, or increase in a plant's ability to endure and/or thrive despite being infected with *Fusarium verticillioides* as compared to one or more control plants (e.g., one or both of the parents, or a plant lacking a marker associated with enhanced ear rot resistance). Enhanced ear rot resistance includes any mechanism (other than whole-plant immunity or resistance) that reduces the expression of symptoms indicative of infection.

As used herein, the terms "elite" and "elite line" refer to any line that has resulted from breeding and selection for desirable agronomic performance. An elite line may be substantially homozygous. Numerous elite lines are available and known to those of skill in the art.

As used herein, the term "elite germplasm" refers to any germplasm that is derived from or is capable of giving rise to an elite plant.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" refers to a seed and/or plant produced when at least two genetically dissimilar parents are crossed.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ear rot resistance may be introgressed from a donor into a recurrent parent that is not ear rot resistant. The resulting offspring could then be repeatedly backcrossed and selected until the progeny possess the ear rot resistance allele(s) in the recurrent parent background.

As used herein, the term "linkage" refers to the degree with which one marker locus is associated with another marker locus or some other locus (for example, an SDS tolerance locus). The linkage relationship between a molecular marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

In some aspects of the present invention, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) may also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome may be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., SDS tolerance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, Theor. Appl. Genet. 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., Nature Reviews Genetics 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker or allele is located. In some embodiments, a locus may encompass one or more nucleotides.

As used herein, the terms "marker" and "genetic marker" are used interchangeably to refer to a nucleotide and/or a nucleotide sequence that has been associated with a phenotype, trait or trait form. In some embodiments, a marker may be associated with an allele or alleles of interest and may be indicative of the presence or absence of the allele or alleles of interest in a cell or organism. A marker may be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138: 255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), a chromosome interval, or an RNA cleavage product (such as a Lynx tag). A marker may be present in genomic or expressed nucleic acids (e.g., ESTs). The term marker may also refer to nucleic acids used as probes or primers (e.g., primer pairs) for use in amplifying, hybridizing to and/or detecting nucleic acid molecules according to methods well known in the art.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. In some embodiments, marker genotypes are used to identify plants that will be selected for a breeding program or for planting. In some embodiments, marker genotypes are used to identify plants that will not be selected for a breeding program or for planting (i.e., counter-selected plants), allowing them to be removed from the breeding/planting population.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology is used in the examples provided herein.

A "non-naturally occurring variety of maize" is any variety of maize that does not naturally exist in nature. A "non-naturally occurring variety of maize" may be produced by any method known in the art, including, but not limited to, transforming a maize plant or germplasm, transfecting a maize plant or germplasm and crossing a naturally occurring variety of maize with a non-naturally occurring variety of maize. In some embodiments, a "non-naturally occurring variety of maize" may comprise one of more heterologous nucleotide sequences. In some embodiments, a "non-natu-rally occurring variety of maize" may comprise one or more non-naturally occurring copies of a naturally occurring nucleotide sequence (i.e., extraneous copies of a gene that naturally occurs in maize). In some embodiments, a "non-naturally occurring variety of maize" may comprise a non-natural combination of two or more naturally occurring nucleotide sequences (i.e., two or more naturally occurring genes that do not naturally occur in the same maize).

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "ear rot resistant phenotype" takes into account environmental conditions that might affect ear rot resistance such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, kernels, ears, etc.), plant tissues, seeds and/or plant cells. A plant cell is a cell of a plant, taken from a plant, or derived through culture from a cell taken from a plant. Thus, the term "maize plant" may refer to a whole maize plant, one or more parts of a maize plant (e.g., roots, root tips, stems, leaves, buds, flowers, seeds, cotyledons, etc.), maize plant cells, maize plant protoplasts and/or maize plant calli.

As used herein, the term "polymorphism" refers to a variation in the nucleotide sequence at a locus, where said variation is too common to be due merely to a spontaneous mutation. A polymorphism can be a single nucleotide poly-morphism (SNP) or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "population" refers to a geneti-cally heterogeneous collection of plants sharing a common genetic derivation.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

As used herein, the term "reference sequence" refers to a defined nucleotide sequence used as a basis for nucleotide sequence comparison. The reference sequence for a marker, for example, is obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism;

however, it is useful for designing primers and probes for actual polymorphisms in the locus or loci.

As used herein, the term "parental line" refers to a line for which a given plant is derived from. A "parental line" encompasses multiple generations.

As used herein, the terms "ear rot resistance" and "ear rot resistant" refer to a plant's ability to endure and/or thrive despite being infected with *Fusarium* spp., e.g. *F. verticillioides*. When used in reference to germplasm, the terms refer to the ability of a plant that arises from that germplasm to endure and/or thrive despite being infected with *Fusarium* spp., e.g. *F. verticillioides*. In some embodiments, infected ear rot resistant plants may yield as well (or nearly as well) as uninfected soybean plants. In general, a plant or germplasm is labeled as "ear rot resistant" if it displays "enhanced ear rot resistance."

An "unfavorable allele" of a marker is a marker allele that segregates with the unfavorable plant phenotype, therefore providing the benefit of identifying plants that can be removed from a breeding program or planting.

Genetic Mapping

Genetic loci correlating with particular phenotypes, such as ear rot resistance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides, inter alia, markers associated with enhanced ear rot resistance. Detection of these markers and/or other linked markers can be used to identify, select and/or produce ear rot resistant plants and/or to eliminate plants that are not ear rot resistant from breeding programs or planting.

Markers Associated with Enhanced Ear Rot Resistance

Markers associated with enhanced ear rot resistance are identified herein. A marker of the present invention may comprise a single allele or a combination of alleles at one or more genetic loci. For example, the marker may comprise one or more marker alleles located within a first chromosomal interval and one or more marker alleles located within a second chromosomal interval.

Markers of the present invention are described herein with respect to the positions of marker loci in a public build of the maize B73 reference genome (AGPv4).

Marker-Assisted Selection

Markers can be used in a variety of plant breeding applications. See, e.g., Staub et al., *Hortscience* 31: 729 (1996); Tanksley, *Plant Molecular Biology Reporter* 1: 3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. An ideal situation is to have a marker in the gene itself, so that recombination cannot occur between the marker and the gene. Such a marker is called a "perfect marker."

When a gene is introgressed by MAS, it is not only the gene that is introduced but also the flanking regions. Gepts, *Crop Sci* 42:1780 (2002). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints. Young et al., *Genetics* 120:579 (1998). In classical breeding, it is usually only by chance that recombinations that contribute to a reduction in the size of the donor segment are selected. Tanksley et al., *Biotechnology* 7: 257 (1989). Even after 20 backcrosses, one might find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS.

Of all the molecular marker types, SNPs are the most abundant and have the potential to provide the highest genetic map resolution. Bhattramakki et al., *Plant Molec. Biol.* 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); *Shi, Clin. Chem.* 47:164 (2001); *Kwok, Pharmacogenomics* 1:95 (2000); Bhattramakki and Rafalski, Discovery and application of single nucleotide polymorphism markers in plants, in Plant Genotyping: The DNA Fingerprinting of Plants, *CABI Publishing, Wallingford* (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

A number of SNP alleles together within a sequence, or across linked sequences, can be used to describe a haplotype for any particular genotype. Ching et al., *BMC Genet.* 3:19 (2002); Gupta et al., (2001), *Rafalski, Plant ScL* 162:329 (2002b). Haplotypes can be more informative than single SNPs and can be more descriptive of any particular genotype. For example, a single SNP may be allele "T" for a specific ear rot resistance line or variety, but the allele "T" might also occur in the maize breeding population being utilized for recurrent parents. In this case, a combination of alleles at linked SNPs may be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the present invention can be used in marker-assisted selection protocols to identify and/or select progeny with enhanced ear rot resistance. Such methods can comprise, consist essentially of or consist of crossing a first maize plant or germplasm with a second maize plant or germplasm, wherein the first maize plant or germplasm comprises a marker associated with enhanced ear rot resistance, and selecting a progeny plant that possesses the marker. Either of the first and second maize plants, or both, may be of a non-naturally occurring variety of maize. In some embodiments, the second maize plant or germplasm is of an elite variety. In some embodiments, the genome of the second maize plant or germplasm is at least about 50%, 55%, 60%, 65%, 70%, 75%, 80%, 85%, 90%, 95%, 97%, 99% or 100% identical to that of an elite variety of maize.

Methods for identifying and/or selecting an ear rot resistant plant or germplasm may comprise, consist essentially of or consist of detecting the presence of a marker associated with enhanced ear rot resistance. The marker may be detected in any sample taken from the plant or germplasm, including, but not limited to, the whole plant or germplasm, a portion of said plant or germplasm (e.g., a seed chip, a leaf punch disk or a cell from said plant or germplasm) or a nucleotide sequence from said plant or germplasm. Such a sample may be taken from the plant or germplasm using any present or future method known in the art, including, but not limited to, automated methods of removing a portion of endosperm with a sharp blade, drilling a small hole in the seed and collecting the resultant powder, cutting the seed with a laser and punching a leaf disk. The maize plant may be of a non-naturally occurring variety. In some embodiments, the genome of the maize plant or germplasm is at least about 50%, 55%, 60%, 65%, 70%, 75%, 80%, 85%, 90%, 95%, 97%, 99% or 100% identical to that of an elite variety of maize.

Suitable markers may comprise, consist essentially of or consist of one or more marker alleles located within a chromosomal interval shown in Table X (all physical positions in Tables X, XI, XII, and XIII correspond to the B73 genome (AGPv4)).

In one embodiment, a method of identifying or selecting a maize plant having enhanced ear rot resistance comprises a) isolating a nucleic acid from a maize cell or plant part; b) detecting, in said cell or plant part the presence of a marker associated with increased ear rot resistance, wherein said marker is located within at least one chromosomal interval of selected from the group consisting of (aa) maize chromosome 1 corresponding to physical positions 3,225,079 to 4,188,653;

(bb) maize chromosome 1 corresponding to physical positions 221,604,561 to 222,599,974;

(cc) maize chromosome 2 corresponding to physical positions 8,618,657 to 9,599,938;

(dd) maize chromosome 3 corresponding to physical positions 14,511,390 to 215,165,758;

(ee) maize chromosome 4 corresponding to physical positions 242,101,915 to 243,081,515;

(ff) maize chromosome 5 corresponding to physical positions 186,344,944 to 187,256,786;

(gg) maize chromosome 5 corresponding to physical positions 207,001,816 to 215,694,297;

(hh) maize chromosome 6 corresponding to physical positions 85,714,579 to 86,684,841;

(ii) maize chromosome 7 corresponding to physical positions 136,237,488 to 137,181,700;

(jj) maize chromosome 8 corresponding to physical positions 3,624,919 to 4,585,283;

(kk) maize chromosome 8 corresponding to physical positions 9,535,964 to 10,493,645;

(ll) maize chromosome 8 corresponding to physical positions 164,507,475 to 172,699,565;

(mm) maize chromosome 9 corresponding to physical positions 11,507,069 to 135,985,429;

(nn) maize chromosome 9 corresponding to physical positions 151,907,512 to 152,897,067; and (oo) maize chromosome 10 corresponding to physical positions 128,310,945 to 129,283,212; and c) identifying or selecting said plant on the basis of the presence of the marker detected in b).

In many examples, the above-referenced intervals will also include at least one of the resistance alleles set forth in Table XII. For example, maize chromosome 1 corresponding to physical positions 3,225,079 to 4,188,653 will comprise at least one of an A allele at a position corresponding to physical position 3702462 and a C allele at a position corresponding to physical position 3702464; maize chromosome 1 corresponding to physical positions 221,604,561 to 222,599,974 will comprise a C allele at a position corresponding to physical position 222146924; maize chromosome 2 corresponding to physical positions 8,618,657 to 9,599,938 will comprise a C allele at a position corresponding to physical position 9122256; maize chromosome 3 corresponding to physical positions 14,511,390 to 215,165, 758 will comprise at least one of a C allele at a position corresponding to physical position 19344196, a T allele at a position corresponding to physical position 19344197, an A allele at a position corresponding to physical position 19826372, a G allele ata position corresponding to physical position 151251885, a C allele ata position corresponding to physical position 199952894, a T allele at a position corresponding to physical position 214794069, and an A allele at a position corresponding to physical position 214794170; maize chromosome 4 corresponding to physical positions 242,101,915 to 243,081,515 will comprise an A allele at a position corresponding to physical position 242643396; maize chromosome 5 corresponding to physical positions 186,344,944 to 187,256,786 will comprise a C allele at a position corresponding to physical position 186795332; maize chromosome 5 corresponding to physical positions 207,001,816 to 215,694,297 comprises at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; maize chromosome 6 corresponding to physical positions 85,714,579 to 86,684,841 will comprise a C allele at a position corresponding to physical position 86282196; maize chromosome 7 corresponding to physical positions 136,237,488 to 137,181,700 will comprise a C allele at a position corresponding to physical position 136725791; maize chromosome 8 corresponding to physical positions 3,624,919 to 4,585,283 will comprise at least one of a G allele at a position corresponding to physical position 4128809 and an A allele at a position corresponding to physical position 4128860; maize chromosome 8 corresponding to physical positions 9,535,964 to 10,493,645 will comprise at least one of an A allele at a position corresponding to physical position 10122708, a T allele at a position corresponding to physical position 10122766, and a T allele at a position corresponding to physical position 10122892; maize chromosome 8 corresponding to physical positions 164,507,475 to 172,699,565 will comprise at least one of an A allele at a position corresponding to physical position 164990912 and a C allele at a position corresponding to physical position 172218916; maize chromosome 9 corresponding to physical positions 11,507,069 to 135,985,429 will comprise at least one of a C allele at a position corresponding to physical position 11929493, a T allele at a position corresponding to physical position 135483968, and a G allele at a position corresponding to physical position 135483999; maize chromosome 9 corresponding to physical positions 151,907,512 to 152,897,067 will comprise at least one of a C allele at a position corresponding to physical position 152415102 and a T allele at a position corresponding to physical position 152415196; and maize chromosome 10 corresponding to physical positions 128,310,945 to 129,283,212 will comprise an A allele at a position corresponding to physical position 128812208.

It should be clear that multiple resistance alleles may be present in the above-mentioned intervals. For example, the interval corresponding to maize chromosome 1 physical positions 3,225,079 to 4,188,653 may comprise both of an A allele at a position corresponding to physical position 3702462 and a C allele at a position corresponding to physical position 3702464; the maize chromosome 3 corresponding to physical positions 14,511,390 to 215,165,758 may comprise two or three or more of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; etc.

Detection of the referenced markers and or interval boundaries may be determined by PCR amplification, e.g. using at least one probe or primer listed in Table XI, Table XII, or Table XIII.

Further, some may prefer to detect within a subset of the above referenced intervals. In some such examples detecting in interval (aa) includes detecting on chromosome 1 within 400K bp upstream or downstream from of an A allele at a position corresponding to physical position 3702462 or a C allele at a position corresponding to physical position 3702464; detecting in interval (cc) includes detecting on chromosome 2 within 300K bp upstream or downstream from a C allele at a position corresponding to physical position 9122256; detecting in interval (dd) includes detecting on chromosome 3 within 300K bp upstream or downstream from at least one of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; detecting in interval (ee) includes detecting on chromosome 4 within 300K bp upstream or downstream from an A allele at a position corresponding to physical position 242643396; detecting in interval (ff) includes detecting on chromosome 5 within 300K bp upstream or downstream from a C allele at a position corresponding to physical position 186795332; detecting in interval (gg) includes detecting on chromosome 5 within 100K bp upstream or downstream from at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; detecting in interval (hh) includes detecting on chromosome 6 within 300K bp upstream or downstream from a C allele at a position corresponding to physical position 86282196; detecting in interval (ii) includes detecting on chromosome 7 within 400K bp upstream or downstream of a C allele at a position corresponding to physical position 136725791; detecting in interval (jj) includes detecting on chromosome 8 within 300K bp upstream or downstream of at least one of a G allele at a position corresponding to physical position 4128809 and an A allele at a position corresponding to physical position 4128860; detecting in interval (kk) includes detecting on chromosome 8 within 300K bp upstream or downstream of at least one of an A allele at a position corresponding to physical position 10122708, a T allele at a position corresponding to physical position 10122766, and a T allele at a position corresponding to physical position 10122892; detecting in interval (ll) includes detecting on chromosome 8 within 400K bp upstream or downstream of at least one of an A allele at a position corresponding to physical position 164990912 and a C allele at a position corresponding to physical position 172218916; detecting in interval (mm) includes detecting on chromosome 9 within 300K bp upstream or downstream of at least one of a C allele at a position corresponding to physical position 11929493, a T allele at a position corresponding to physical position 135483968, and a G allele at a position corresponding to physical position 135483999; detecting in interval (nn) includes detecting on chromosome 9 within 300K bp upstream or downstream of at least one of a C allele at a position corresponding to physical position 152415102 and a T allele at a position corresponding to physical position 152415196; and detecting in interval (oo) includes detecting on chromosome 10 within 300K bp upstream or downstream of an A allele at a position corresponding to physical position 128812208. Additional intervals may be further defined by any of the markers identified in Table XI.

Methods may also include additional steps. For example, method as disclosed herein may further comprise (a) crossing the progeny maize plant that comprises said marker within its genome with itself or another maize plant to yield additional progeny maize plants comprising the marker within their genome. Additional crossing may be performed, for example, (b) repeating the crossing step of (a) at least 2 times to generate further progeny maize plants comprising the marker within their genome.

TABLE X

| CHR | Physical Position | |
| --- | --- | --- |
| | Start | Stop |
| 1 | 3,225,079 | 4,188,653 |
| 1 | 221,604,561 | 222,599,974 |

TABLE X-continued

| CHR | Physical Position | |
| --- | --- | --- |
| | Start | Stop |
| 2 | 8,618,657 | 9,599,938 |
| 3 | 14,511,390 | 215,165,758 |
| 4 | 242,101,915 | 243,081,515 |
| 5 | 186,344,944 | 187,256,786 |
| 5 | 207,001,816 | 215,694,297 |
| 6 | 85,714,579 | 86,684,841 |
| 7 | 136,237,488 | 137,181,700 |
| 8 | 3,624,919 | 4,585,283 |
| 8 | 9,535,964 | 10,493,645 |
| 8 | 164,507,475 | 172,699,565 |
| 9 | 11,507,069 | 135,985,429 |
| 9 | 151,907,512 | 152,897,067 |
| 10 | 128,310,945 | 129,283,212 |

Exemplary markers and assays within the intervals are listed in Table XI below:

TABLE XI

| CHR # | Physical position | SNP | probe 1 sequence | probe 2 sequence | primer 1 sequence | primer 2 sequence |
| --- | --- | --- | --- | --- | --- | --- |
| 1 | 3231967 | A/G | AGACCAATTCGTTCTTTTTCT (SEQ ID NO: 1) | ACCAATTCGTTCCTTTTCT (SEQ ID NO: 2) | TTTGTACATGTTTCGCGGAGATTTC (SEQ ID NO: 3) | TGGCTGGTACACGCAGAAG (SEQ ID NO: 4) |
| 1 | 3279861 | A/G | CAGGTCCAGTTCTGCA (SEQ ID NO: 5) | CAGGTCCAGTCCTGCA (SEQ ID NO: 6) | GCATGATGCTGATGGGAAAGATTA (SEQ ID NO: 7) | GCCCCTTTCAGTCATCGAAC (SEQ ID NO: 8) |
| 1 | 3282427 | A/G | TCCCGCAACCAAAT (SEQ ID NO: 9) | TCCCGCAACCAAAC (SEQ ID NO: 10) | TCCCCAGTTATCCCTCAAAATTGG (SEQ ID NO: 11) | TGAAGCCACGCAACCACTTAG (SEQ ID NO: 12) |
| 1 | 3286654 | A/G | TCAACTTGAATGGATTGG (SEQ ID NO: 13) | CAACTTGAATGGACTGG (SEQ ID NO: 14) | TTTATCTGAATTTGGAAGTCCT (SEQ ID NO: 15) | CATGGGTCCTAGTATTCGT (SEQ ID NO: 16) |
| 1 | 3292226 | A/T | AGCGGGAAATGCCACAT (SEQ ID NO: 17) | TAGCGGGAAAAGCCACAT (SEQ ID NO: 18) | GAATCAGGTAGTCCAATAGTAGAGC (SEQ ID NO: 19) | TCTGCAGTCGCCTTCCG (SEQ ID NO: 20) |
| 1 | 3316669 | A/G | CATCATGTGCCTAGAAAG (SEQ ID NO: 21) | CATCATGTGCCTAGAAAA (SEQ ID NO: 22) | GCATGATAGAGATATGCCTAGGAGAAG (SEQ ID NO: 23) | TGCCCCTAATTTCCTAGCAAC (SEQ ID NO: 24) |
| 1 | 3369969 | A/C | TCATTGTATATCTCGGC (SEQ ID NO: 25) | CATATTCATTGTAGATCTCGG (SEQ ID NO: 26) | ACCTAGAATGCTCAAAAGGGAACA (SEQ ID NO: 27) | CATGCTGCGTCATCAATCATCTG (SEQ ID NO: 28) |
| 1 | 3379725 | A/G | CGGCGCTAGCTGCAG (SEQ ID NO: 29) | CCGGCGCCAGCTG (SEQ ID NO: 30) | AGGTCGCAGGACGCGAAG (SEQ ID NO: 31) | GGCGACTCCATCTGTAAGCA (SEQ ID NO: 32) |
| 1 | 3381814 | A/G | CTGATGTTCAGGCC (SEQ ID NO: 33) | CTGATGTTCAAGCCT (SEQ ID NO: 34) | CCACGAGGAACATTCGACCAT (SEQ ID NO: 35) | TCTCGTCAAGTCCGCTCTTATTG (SEQ ID NO: 36) |
| 1 | 3441846 | A/G | ACTCCTCGCCTGC (SEQ ID NO: 37) | AAGTACTCCCCGCCT (SEQ ID NO: 38) | TCCTGACTCCGGATCCAC (SEQ ID NO: 39) | AGGCACAGGCTGGCAGTG (SEQ ID NO: 40) |
| 1 | 3450399 | A/G | CCGAACACGCCCT (SEQ ID NO: 41) | CGAACACGCCCC (SEQ ID NO: 42) | CTGCAACAGTGTCGGCTTGTAG (SEQ ID NO: 43) | GCTCCAAGAGCGAGGGATAC (SEQ ID NO: 44) |
| 1 | 3480456 | A/G | AAGTTTCAAATTATAATGGTA (SEQ ID NO: 45) | TTTCAAATTATAATGATAGAGT (SEQ ID NO: 46) | TGACTGATGGAGGTTCGAAGTTG (SEQ ID NO: 47) | CGACTAATAAAAGAAACGGAGGGAGTA (SEQ ID NO: 48) |
| 1 | 3481816 | A/G | TGGGTAATTTCTAGGAAAC (SEQ ID NO: 49) | TGGTGGGTAATTTCTAAGA (SEQ ID NO: 50) | CGATTCGGTGGATTATAATGGCA (SEQ ID NO: 51) | GCTTTCGTTAGGGCCTGTTTG (SEQ ID NO: 52) |
| 1 | 3486296 | A/T | ATAGAACTCCTAGCAGGCA (SEQ ID NO: 53) | AACTCCTTGCAGGCAA (SEQ ID NO: 54) | GGGATGTTGCAAGCAAGAGAA (SEQ ID NO: 55) | GTCACGAGCCGTGTGAAA (SEQ ID NO: 56) |
| 1 | 3490045 | A/C | CATCTTGAGTGATGTAAATG (SEQ ID NO: 57) | CATCTTGAGTGATGTACAT (SEQ ID NO: 58) | GGCAGGGCTAAATCAACTTGC (SEQ ID NO: 59) | CAACAGATTGGTGAGATCAAGAGCTG (SEQ ID NO: 60) |
| 1 | 3529830 | A/G | ACGGACCCACCTTG (SEQ ID NO: 61) | ACGGACCCACCTTAA (SEQ ID NO: 62) | ACGGTCCTGTATATGACAAGCAG (SEQ ID NO: 63) | TGGGCTGAGTGGTGAAGC (SEQ ID NO: 64) |

TABLE XI-continued

| CHR # | Physical position | SNP | probe 1 sequence | probe 2 sequence | primer 1 sequence | primer 2 sequence |
|---|---|---|---|---|---|---|
| 1 | 3532636 | C/G | TGCAGTTGCAGGTACG (SEQ ID NO: 65) | ATTGCAGTTGCAGGTACC (SEQ ID NO: 66) | ACAGCCACTGGTGGTTGGT C (SEQ ID NO: 67) | GGCGTACGTGCCACTTATATA GTC (SEQ ID NO: 68) |
| 1 | 3542679 | A/G | TGGAGCGTCTACACC (SEQ ID NO: 69) | CATGGAGCATCTACACC (SEQ ID NO: 70) | CTTGTTCTAAGCGCCTCCTG AT (SEQ ID NO: 71) | TGGTGACTCTTGATGGAGTT CA (SEQ ID NO: 72) |
| 1 | 3550747 | A/G | TTCTGTAATTTTATCAATT (SEQ ID NO: 73) | TTCTGTAATTTTACCA (SEQ ID NO: 74) | CTGCCTACATGCAGTTT (SEQ ID NO: 75) | TGCCACGATAAGAAAGG (SEQ ID NO: 76) |
| 1 | 3588126 | A/G | TCTCCAGGAGTTCGAG (SEQ ID NO: 77) | CTCCAGGAGTTCAAGG (SEQ ID NO: 78) | CCTTTGGTGCAATCTATGAT CAGGT (SEQ ID NO: 79) | CGAAACGTAGCCAACGTAAA CAAC (SEQ ID NO: 80) |
| 1 | 3650079 | A/G | CGCGGAAATCCGAGTAG (SEQ ID NO: 81) | CGGAAATCCGAGCAG (SEQ ID NO: 82) | GGGTGGACTCACTCCGAAT G (SEQ ID NO: 83) | GAGCCCCTCTCTCCTCGTT (SEQ ID NO: 84) |
| 1 | 3654086 | A/G | CTGCGCCGCGT (SEQ ID NO: 85) | CTGCGCCGCATG (SEQ ID NO: 86) | CGTCGCCCTGAGCCTAC (SEQ ID NO: 87) | TGCGACGGTGATAGACGATG (SEQ ID NO: 88) |
| 1 | 3771238 | A/T | CCCTATACCCCACTAC (SEQ ID NO: 89) | CCTATACCCCACAAC (SEQ ID NO: 90) | TCCACCCTGTACAATGGTTC C (SEQ ID NO: 91) | GCGTACACCAGTATTTGTCAG TTC (SEQ ID NO: 92) |
| 1 | 3776990 | C/G | TCCTTGTCAGGATCATC (SEQ ID NO: 93) | TCCTTGTCAGCATCATC (SEQ ID NO: 94) | CGCCATTAATTCATGCTTGTC TCTG (SEQ ID NO: 95) | ACACGCTGCGTTGGAGAATC C (SEQ ID NO: 96) |
| 1 | 3798340 | A/G | CAGCCAAAATCGAACCA (SEQ ID NO: 97) | CAGCCAAAACCGAACC (SEQ ID NO: 98) | GAGCGAGCCGCCTGA (SEQ ID NO: 99) | CCGTGGCAACTGGTCCTG (SEQ ID NO: 100) |
| 1 | 3800924 | C/G | CCCTGCGAACGCC (SEQ ID NO: 101) | CCCTGCCAACGCC (SEQ ID NO: 102) | TGGAGGCCAAGTCGAACG (SEQ ID NO: 103) | GGCTCGGGTCCAGCA (SEQ ID NO: 104) |
| 1 | 3802621 | A/G | CTGCTTGTGATAGAAATA AA (SEQ ID NO: 105) | CTTGTGATAGAAACAAAGATG (SEQ ID NO: 106) | ATGAAGGGAAGACCGCAT (SEQ ID NO: 107) | TGGGACATATTAGACCATC (SEQ ID NO: 108) |
| 1 | 3845897 | C/G | CTTTCTCTAGCCGTACTA (SEQ ID NO: 109) | CTTTCTCTAGCCCTACTA (SEQ ID NO: 110) | AGCTTTGCTTCCTGGGTGCT T (SEQ ID NO: 111) | TCGGCATCACCTGTATCAGA (SEQ ID NO: 112) |
| 1 | 3897684 | A/C | CATGAAAGTTAATCCTCA A (SEQ ID NO: 113) | TTCATGAAAGTTAATCATCA (SEQ ID NO: 114) | CAGCTTTTTGGTCGTTTTTC TTTGATTG (SEQ ID NO: 115) | GGTGAGCTTGTGTTATGTTCT CA (SEQ ID NO: 116) |
| 1 | 3924419 | C/G | CGCTAGACCGTGATGGT (SEQ ID NO: 117) | CGCTAGACCCTGATGGT (SEQ ID NO: 118) | TGCAACCAGTGAATGTCCTT G (SEQ ID NO: 119) | GTCGTTTGGAGCTAGTAGTT GAC (SEQ ID NO: 120) |
| 1 | 3964537 | A/C | ATGGCTGCTGCTTCATAC (SEQ ID NO: 121) | ATGGCTGCTGCGTCATA (SEQ ID NO: 122) | GTTGGACCTTCTCTCTGTAA GTCA (SEQ ID NO: 123) | TGCTTGCCTCGCTGTGAT (SEQ ID NO: 124) |
| 1 | 3974478 | A/G | ATTTTATTATTCGTCCGTCT A (SEQ ID NO: 125) | TATTATTCGCCCGTCTA (SEQ ID NO: 126) | TCCAAGGTTACCTGAACCCT AA (SEQ ID NO: 127) | GAGCATGGACATTACATGGC ATAA (SEQ ID NO: 128) |
| 1 | 4040167 | A/G | AATTGATCACGCACTA (SEQ ID NO: 129) | AATTGATCACACACTATC (SEQ ID NO: 130) | AGGCAAGCTCGATGGTTCA C (SEQ ID NO: 131) | CCATGTGGTCGTGGGTTCAA G (SEQ ID NO: 132) |
| 1 | 4110584 | A/G | CGCAAAGGGCGTGTG (SEQ ID NO: 133) | ACGCAAAGAGCGTGTGG (SEQ ID NO: 134) | ACCCGCGGCAACCGTAAA (SEQ ID NO: 135) | CGTCGTCGTCGGAGACA (SEQ ID NO: 136) |
| 1 | 4113871 | A/T | TCTTTCAAGATTAATGAA G (SEQ ID NO: 137) | CTTTCAAGATTAAAGAAGG (SEQ ID NO: 138) | GCAGTGGGTTGACATCAAC AATG (SEQ ID NO: 139) | GTTTAGCAAGCTGAAAGGGT GA (SEQ ID NO: 140) |
| 1 | 221997255 | A/G | CAGGTATTCGTGTGCATC (SEQ ID NO: 141) | CAGGTATTCGCGTGCAT (SEQ ID NO: 142) | AGGGCACTCAGGCACATGA T (SEQ ID NO: 143) | CCACCACTCGCACTAGGAAA (SEQ ID NO: 144) |
| 1 | 222025570 | A/G | AGGTTAGTCGTTCGAATT GGA (SEQ ID NO: 145) | AAGGTTAGTCGTTCAAATTGG (SEQ ID NO: 146) | GTTTGGTTTGTGGCTAAATG TGC (SEQ ID NO: 147) | AGGTGAGTGTGACGTGCATA G (SEQ ID NO: 148) |
| 1 | 222201946 | A/C | CATGCTGCGGTCGC (SEQ ID NO: 149) | ATGCGGCGGTCGC (SEQ ID NO: 150) | ACATGTAGATGATGCGGTCG TG (SEQ ID NO: 151) | ACCAGCTCCCGTTTCTGC (SEQ ID NO: 152) |
| 1 | 222224260 | A/G | CCCCGCCTTCGAA (SEQ ID NO: 153) | TGCCCCACCTTCG (SEQ ID NO: 154) | GGGCCATCAGCGTTCGTC (SEQ ID NO: 155) | AGATGGCGTGCTCGGTGTTC (SEQ ID NO: 156) |
| 1 | 222412787 | A/G | CCATCCAATGTATCAATTG (SEQ ID NO: 157) | CATCCAATGTATCAACTGA (SEQ ID NO: 158) | GAACTTGATATGTAGCTAAA GAC (SEQ ID NO: 159) | TCATGTTGAAGTTGAATTGGT (SEQ ID NO: 160) |
| 2 | 8912449 | A/G | CGAGAGGATGACACTATA A (SEQ ID NO: 161) | AGAGGATGACACTACAAGT (SEQ ID NO: 162) | GCTATCGCCCACCAATAAAG TG (SEQ ID NO: 163) | ATGTGTCCTCAACCCTTAGAT GA (SEQ ID NO: 164) |

TABLE XI-continued

| CHR # | Physical position | SNP | probe 1 sequence | probe 2 sequence | primer 1 sequence | primer 2 sequence |
|---|---|---|---|---|---|---|
| 2 | 8974708 | A/T | TCAACTGGACTAAATAA (SEQ ID NO: 165) | AAGTCAACTGGACAAA (SEQ ID NO: 166) | TCCAAGCAGCTATCAGATCC A (SEQ ID NO: 167) | GCTCTTGCCTTCTGTTCTTCA C (SEQ ID NO: 168) |
| 2 | 8984389 | A/G | AACAGGACTACTCAGATT ATA (SEQ ID NO: 169) | CAGGACTACTCAGACTA (SEQ ID NO: 170) | GAGGGCATTCTTGTCTTCCT CATAC (SEQ ID NO: 171) | GCTTCGGGCCTGTTTGTTTAC (SEQ ID NO: 172) |
| 2 | 8988981 | A/C | CCCGATGCGACGTC (SEQ ID NO: 173) | CCCGAGGCGACGTC (SEQ ID NO: 174) | CGCCTTGGCGGCCTT (SEQ ID NO: 175) | CCGCGTCAAGTGTTTCATCA (SEQ ID NO: 176) |
| 2 | 9058510 | A/G | AGCATGGAAATCTTGTCT TC (SEQ ID NO: 177) | TAGCATGGAAATCCTGTCTT (SEQ ID NO: 178) | TCCACCCAAAAGATATCATC CGA (SEQ ID NO: 179) | CCACCTGGGAATGCAAGGAA T (SEQ ID NO: 180) |
| 2 | 9066199 | A/G | CAAAGCATGTACCATTAAT (SEQ ID NO: 181) | AAAGCATGTACCATCAAT (SEQ ID NO: 182) | ACGTATCCCGGCCGTCTAC (SEQ ID NO: 183) | GCGGTGAAGGAAGATCATG GTT (SEQ ID NO: 184) |
| 2 | 9081820 | C/G | TCCAGGAAGGGCCAAAG (SEQ ID NO: 185) | CCAGGAAGGCCCAAAGAT (SEQ ID NO: 186) | GCAGACGTGATCCTGAAGC A (SEQ ID NO: 187) | TCAGGCACGGGCTGAAC (SEQ ID NO: 188) |
| 2 | 9096620 | A/G | CCCCGGTTGTCACAT (SEQ ID NO: 189) | CCCGGTTATCACATGC (SEQ ID NO: 190) | GGCAAAGAGGGATTGCTAC ACTT (SEQ ID NO: 191) | CATCCACAACACAAACACTG ACATC (SEQ ID NO: 192) |
| 2 | 9172431 | —/ CGG TAT | TCTTCGTAGAGAAAGTAT GT (SEQ ID NO: 193) | CGTAGAGAAAGATACCGTAT (SEQ ID NO: 194) | TGTTCAGGTAACACGAG (SEQ ID NO: 195) | CACTCAATACTCCAAACAGT (SEQ ID NO: 196) |
| 2 | 9194560 | A/G | TCCAATTTCTGGTTCACAT (SEQ ID NO: 197) | CCAATTTCTGGCTCACA (SEQ ID NO: 198) | CCTCCAGGCCAAAGATGCA AT (SEQ ID NO: 199) | CCCGCTCTATCCGTTACACTT CT (SEQ ID NO: 200) |
| 2 | 9199551 | A/G | TAACTAATAGCAATGC (SEQ ID NO: 201) | TAATAACTAATAGCAATAC (SEQ ID NO: 202) | ATGAACCATATATCCTAGGA A (SEQ ID NO: 203) | GAGGTGCTCCAATCTTC (SEQ ID NO: 204) |
| 2 | 9275574 | C/G | CAGTAGGTTGGGCAAC (SEQ ID NO: 205) | CCAGTAGGTTGCGC (SEQ ID NO: 206) | TGTTAGTCCAGGCCTTCTGA ATC (SEQ ID NO: 207) | ACAGCAGAGGTTAAAGTAGC ATAGC (SEQ ID NO: 208) |
| 2 | 9302515 | A/G | TGGCTTTGGATCGGGT (SEQ ID NO: 209) | TTGGCTTTGGATCGAGTT (SEQ ID NO: 210) | TTGACGTATCGGGTCGGATT (SEQ ID NO: 211) | CGGGCTAAGTACAAGCCATG AT (SEQ ID NO: 212) |
| 2 | 9309689 | A/G | TCCGACGGCTAGAGA (SEQ ID NO: 213) | CAATATCCGACAGCTAGA (SEQ ID NO: 214) | CAGACTACCATGAAGAGAG TTGTGA (SEQ ID NO: 215) | GGTAGTTGATTCTTGTCCGC TGAT (SEQ ID NO: 216) |
| 2 | 9317525 | A/C | CGTTTAGGAATCTCTGG (SEQ ID NO: 217) | CGTTTAGGAATATCTGGG (SEQ ID NO: 218) | GGCGAGAATGACTGC (SEQ ID NO: 219) | AATGACATGTGATCTTTGTTT (SEQ ID NO: 220) |
| 2 | 9431202 | A/C | CGAGAGTGTATTATGGTA G (SEQ ID NO: 221) | CGAGAGTGTATTATGGGAG (SEQ ID NO: 222) | TCCTGGCAACCGAGACC (SEQ ID NO: 223) | ACAGGCCAGCAGGCAGATA G (SEQ ID NO: 224) |
| 2 | 9436735 | A/G | TGTTGGTCTGCGAGGT (SEQ ID NO: 225) | TGTGTTGGTCTACGAGGT (SEQ ID NO: 226) | CGTCAGGTGCTTCACCGA (SEQ ID NO: 227) | GAGGGTGGAGACGCAAGAT AC (SEQ ID NO: 228) |
| 2 | 9441334 | A/G | TCACATTCCATTGGTTGG (SEQ ID NO: 229) | CACATTCCATCGGTTGG (SEQ ID NO: 230) | GGTGGAGGCGCATAGGTT (SEQ ID NO: 231) | ACGGCAGGAGAGGAAGGAA (SEQ ID NO: 232) |
| 2 | 9544415 | A/G | ATACTATCCTCTCCGGGA (SEQ ID NO: 233) | TATCCCCTCCGGGA (SEQ ID NO: 234) | TGATTTGGATTTGGGAATTG GGA (SEQ ID NO: 235) | AAACGAGCAGGTGTTTAGCC A (SEQ ID NO: 236) |
| 2 | 9548957 | A/G | AATGACACCCCCTTCC (SEQ ID NO: 237) | ATGACACCCCTCCC (SEQ ID NO: 238) | CCAACCATTTCTTGCTGCCA (SEQ ID NO: 239) | TTGAGAGCTCCGCGAAATGA G (SEQ ID NO: 240) |
| 3 | 14519017 | A/G | TCACCAAGTACTCCCTA (SEQ ID NO: 241) | CACCAAGTACTCCCCA (SEQ ID NO: 242) | AGCAAAGGTGCGGATGCCA TT (SEQ ID NO: 243) | GCTTCCAAATCGCTACCTTGT TTC (SEQ ID NO: 244) |
| 3 | 14537670 | A/G | CTCGTATGCCGTTTTGTT (SEQ ID NO: 245) | TCGTATGCCATTTTGTTC (SEQ ID NO: 246) | TCCATCATCAAACCCTAAAC ACCAG (SEQ ID NO: 247) | GAATGCCAACCATCAGAAGT CAAC (SEQ ID NO: 248) |
| 3 | 14740954 | A/G | CCATGTATGTTGATAATTT CTAAA (SEQ ID NO: 249) | ACCATGTATGTTGATAACTTC TA (SEQ ID NO: 250) | GCAGTATGGCCTATGTTTGT TGC (SEQ ID NO: 251) | CCGGTACCCTGGTGTCGTT (SEQ ID NO: 252) |
| 3 | 14755567 | A/G | TTGAAGGAGAGAGGACA GA (SEQ ID NO: 253) | TTTGAAGGAGAGAGGACAAA (SEQ ID NO: 254) | AGGAGCACCTCATTTGGTTA GAAA (SEQ ID NO: 255) | CCGAGCGAAGTCGAGAACC (SEQ ID NO: 256) |
| 3 | 15018789 | A/G | CTGAGGAACGATCGATTC (SEQ ID NO: 257) | TGAGGAACGACCGATTCT (SEQ ID NO: 258) | GCTAGTCAACACACACCCAC AAG (SEQ ID NO: 259) | GGAGCCAGGCTCATCACATA C (SEQ ID NO: 260) |

TABLE XI-continued

| CHR # | Physical position | SNP | probe 1 sequence | probe 2 sequence | primer 1 sequence | primer 2 sequence |
|---|---|---|---|---|---|---|
| 3 | 15130444 | A/G | CAGTCGGAGCGGG (SEQ ID NO: 261) | AGTCGGAGCAGGGC (SEQ ID NO: 262) | AACTCGGTTGTTGTCAGTCT TACC (SEQ ID NO: 263) | CTGACCGACCTGACAGGAAA (SEQ ID NO: 264) |
| 3 | 15230570 | A/G | CGGATTCTCTCTGAATGAT G (SEQ ID NO: 265) | ACGGATTCTCTCCGAATGA (SEQ ID NO: 266) | GATTTGTGTTCGACAGTGG GATG (SEQ ID NO: 267) | GCAAGCCCGAACCAATATAAT AACC (SEQ ID NO: 268) |
| 3 | 15812104 | C/G | CAGTGCTTTGACCTCG (SEQ ID NO: 269) | CAGTGCTTTCACCTCG (SEQ ID NO: 270) | CAGTGCTTTCACCTCG (SEQ ID NO: 271) | TGTCCGCCATCTCCAGCAT (SEQ ID NO: 272) |
| 3 | 15919138 | A/C | CACATTGACGTTGATGAC (SEQ ID NO: 273) | CATTGACGTTGAGGACA (SEQ ID NO: 274) | GTTGACAATGGAAGGAGA (SEQ ID NO: 275) | CCGGATATGTATATGATGCTG (SEQ ID NO: 276) |
| 3 | 15959205 | A/T | AGTATTATAGCTAAAAATA GAC (SEQ ID NO: 277) | CATAAGTATTATAGCTAAA AA (SEQ ID NO: 278) | ACACATATCACAAGTCAGAA TGCTC (SEQ ID NO: 279) | ACGGTTAATTGGTAGGCACG GTAA (SEQ ID NO: 280) |
| 3 | 16008114 | A/G | CGACATTGTGCGCTT (SEQ ID NO: 281) | TTCGACATTGTACGCTT (SEQ ID NO: 282) | TTTATGTCAGAAAGCTTGAG GCA (SEQ ID NO: 283) | TGTCGGCTAATCATCTCAAGG A (SEQ ID NO: 284) |
| 3 | 16066986 | A/C | TTCACTAACGATGTAATT (SEQ ID NO: 285) | TCACTAACGATGGAAT (SEQ ID NO: 286) | AGTCCCTATGGGTTTCCAA (SEQ ID NO: 287) | CCTCTTCCCATGAGAACT (SEQ ID NO: 288) |
| 3 | 16410918 | A/T | TTTATGCTAGTCAAACTTT (SEQ ID NO: 289) | TTTATGCTAGTCAAACATT (SEQ ID NO: 290) | TCAGTTAAGTATCGTCTAGA TTT (SEQ ID NO: 291) | ACCGCGATACATCATTGG (SEQ ID NO: 292) |
| 3 | 16529552 | A/T | TTGAGAACCTTCAGTAC (SEQ ID NO: 293) | TTGAGAACCATCAGTAC (SEQ ID NO: 294) | CGTTGTCAGCATTGGTGGA C (SEQ ID NO: 295) | GATCGTCGCACGGATGTCTA (SEQ ID NO: 296) |
| 3 | 16639711 | A/G | CAAACCATCGAATCTGTA AC (SEQ ID NO: 297) | ACCATCGAATCCGTAACAA (SEQ ID NO: 298) | TTGCCAGAGTTGATTCCACC TAA (SEQ ID NO: 299) | CTGCGACATTGCCTCTAACCA (SEQ ID NO: 300) |
| 3 | 16790156 | A/G | ATCGGACTCTCGGCT (SEQ ID NO: 2301) | AATCGGACTCTCAGC (SEQ ID NO: 302) | CAATCCGGTCTCAGTGGTTG G (SEQ ID NO: 303) | CCTGAGCTGGCTACTGATGA (SEQ ID NO: 304) |
| 3 | 16937055 | A/T | ATAGCATTAGATTCTGAGC ATT (SEQ ID NO: 305) | AGCATTAGATTCTGAGCATA (SEQ ID NO: 306) | TTCGGCGTCTACTTCCTGTAT C (SEQ ID NO: 307) | TGCTTTGTGTTCGTATGCATG AATA (SEQ ID NO: 308) |
| 3 | 16974560 | A/G | CTGCTGCTGTTTGCA (SEQ ID NO: 309) | TGCTGCTGCTATTTGC (SEQ ID NO: 310) | CCAAGACAAACTCTCCCTGT ATGC (SEQ ID NO: 311) | GGCTCGGAAGGTCTCAAAG AAG (SEQ ID NO: 312) |
| 3 | 17143814 | A/C | TGGTTGTAGTATTGCAA (SEQ ID NO: 313) | TTGGTTGTAGTATTGAAAA (SEQ ID NO: 314) | GGTTTGCTCTTGCTGATCGA TATGT (SEQ ID NO: 315) | GCTCAGCTACTCCCTCTGTTC (SEQ ID NO: 316) |
| 3 | 17172687 | C/G | CGAGGTGGTGACGATGT (SEQ ID NO: 317) | CGAGGTGGTCACGATG (SEQ ID NO: 318) | CGGGTCAAGTTCTGCTGTG A (SEQ ID NO: 319) | ATCATACGGCGGAAGTAGTT CA (SEQ ID NO: 320) |
| 3 | 17289544 | A/G | AAACATGAATACTCGATCT GC (SEQ ID NO: 321) | CAAACATGAATACCCGATCT (SEQ ID NO: 322) | TGGCTTGAGCCATTACCTGA T (SEQ ID NO: 323) | GAAACTGCAAGAGGCATGA AAC (SEQ ID NO: 324) |
| 3 | 17384151 | A/C | TGATGCGATTTCGTTGAAT (SEQ ID NO: 325) | CGTGATGCGATTTAGTTGAA (SEQ ID NO: 326) | CGGATTACAACTCTCTGTTG CC (SEQ ID NO: 327) | CACACTCAAGGTGACTTAGA CCAA (SEQ ID NO: 328) |
| 3 | 17995981 | A/G | CAGTTGTTTGTATAGACA (SEQ ID NO: 329) | ATACAGTTGTTTGTATAAAC (SEQ ID NO: 330) | GGATTGGACCAGCAGAT (SEQ ID NO: 331) | GTGAGACAAGGCTACATAC (SEQ ID NO: 332) |
| 3 | 18373437 | A/G | CCGGCCGCAGT (SEQ ID NO: 333) | CCGCAGCGGTGAT (SEQ ID NO: 334) | CGTCGCGGTCCTCTCTGAT (SEQ ID NO: 335) | CTGCGAATCGTCCATCCTGTA (SEQ ID NO: 336) |
| 3 | 18558341 | A/G | CCTTGTGAGAAAACTCTA (SEQ ID NO: 337) | CTTGTGAGAAAACCCTAG (SEQ ID NO: 338) | GTGCAATGGCTGACTC (SEQ ID NO: 339) | GCACGATTATGCATGATTAG (SEQ ID NO: 340) |
| 3 | 18829864 | A/C | TCAAAGCTAGGTTTATGC (SEQ ID NO: 341) | TCAAAGCTAGGTTTAGGC (SEQ ID NO: 342) | AGGGTTAGGGTTTCACTTC CA (SEQ ID NO: 343) | AGCACTGGCGAGGCTACAG (SEQ ID NO: 344) |
| 3 | 18853840 | A/G | AGATCTGATTGGTATAGG GCA (SEQ ID NO: 345) | CTGATTGGTACAGGGCA (SEQ ID NO: 346) | AAGGCAGAGGTGCTTCGGT (SEQ ID NO: 347) | GTGCTGCATTTCTAAGGTGTC AAG (SEQ ID NO: 348) |
| 3 | 18867240 | A/G | CTAGGGAAGTTGTCGTTT GAAA (SEQ ID NO: 349) | AGGGAAGTTGTCGCTTGAA (SEQ ID NO: 350) | GGTGCAGGCAAGAGAGCAT TT (SEQ ID NO: 351) | TGGATTATATGGAAGGTCCG AAGGT (SEQ ID NO: 352) |
| 3 | 18928655 | C/G | AGGCGGCGACCAACT (SEQ ID NO: 353) | AGGCGGCCACCAACT (SEQ ID NO: 354) | ACGTTCGCCGACGAGGAG (SEQ ID NO: 355) | CGCAGCATGTCGACGATCTC (SEQ ID NO: 356) |

TABLE XI-continued

| CHR # | Physical position | SNP | probe 1 sequence | probe 2 sequence | primer 1 sequence | primer 2 sequence |
|---|---|---|---|---|---|---|
| 3 | 19119372 | A/G | AGCGGAGCAATGACTACT T (SEQ ID NO: 357) | CGGAGCAACGACTACTT (SEQ ID NO: 358) | GGTGCACACCGGACTGT (SEQ ID NO: 359) | CAACTGCGCGTCCTCTGTC (SEQ ID NO: 360) |
| 3 | 19238886 | A/G | CCAGTTTCTTCTGTGAGT G (SEQ ID NO: 361) | CAGTTTCTTCCGTGAGTG (SEQ ID NO: 362) | TGCATCTGAGTTCCTGATTG TTG (SEQ ID NO: 363) | CCGCAGCACGACATCCTT (SEQ ID NO: 364) |
| 3 | 19481264 | C/G | CCATATATAGGTTAGTTGA TCGA (SEQ ID NO: 365) | CCATATATAGGTTAGTTCATC GAT (SEQ ID NO: 366) | GCGGTGAGTACAAGTTAAT CCAA (SEQ ID NO: 367) | GCCGTCACTTGACTTGATTCT TC (SEQ ID NO: 368) |
| 3 | 19663796 | A/C | ACCCAGCCCCCT (SEQ ID NO: 369) | ACCCAGCCCCCG (SEQ ID NO: 370) | TGATCTGGCTCACGTGGGTA G (SEQ ID NO: 371) | CGCATGAACGTCCATGGAAG (SEQ ID NO: 372) |
| 3 | 19726656 | A/G | CACATGCACAGTGCTATA (SEQ ID NO: 373) | CCACATGCACAGTACTATA (SEQ ID NO: 374) | GAGACCCAGCTAGAGAGTT GAC (SEQ ID NO: 375) | TGGGCACATAGGCCAGTAG (SEQ ID NO: 376) |
| 3 | 19814765 | A/G | TGCAAACAGGAGCATG (SEQ ID NO: 377) | AAATGCAAACAGGAACATG (SEQ ID NO: 378) | GTTGCTGAAATGCTAATGG (SEQ ID NO: 379) | GTGTCGTCGTCTTCTC (SEQ ID NO: 380) |
| 3 | 19823458 | C/G | CCACCACCGGAATT (SEQ ID NO: 381) | CACCACCGCAATTG (SEQ ID NO: 382) | GAGTTCATCAAGTAGCTCGT (SEQ ID NO: 383) | TGCACATCAGCATTCTC (SEQ ID NO: 384) |
| 3 | 19826701 | A/G | CGGTTACCATTGTTGTGTA (SEQ ID NO: 385) | TCGGTTACCATTATTGTGTA (SEQ ID NO: 386) | CCTTGTTTGAAACCTCCTTG TGTTG (SEQ ID NO: 387) | GTCCAGGTCGCCTTACTGA (SEQ ID NO: 388) |
| 3 | 19829343 | A/T | TACAAAGCCGGGTTG (SEQ ID NO: 389) | TACAAAGCCGGGATGT (SEQ ID NO: 390) | GAACTGATTCATCTGGGTAA (SEQ ID NO: 391) | CTCCTGCTGTGGTCAC (SEQ ID NO: 392) |
| 3 | 19994319 | A/G | CAAGTGAAATGGTATATA ATAC (SEQ ID NO: 393) | AAGTGAAATGGTATATAACAC (SEQ ID NO: 394) | CATGCCACAATTGCAGAAG CA (SEQ ID NO: 395) | GCATAGCTCAACATGTGAACT CA (SEQ ID NO: 396) |
| 3 | 20165823 | A/T | CCGGCTCAAGCCTA (SEQ ID NO: 397) | CCGGCACAAGCCTA (SEQ ID NO: 398) | CGCCCTAGTGCTGGGAATC (SEQ ID NO: 399) | GGACCGACACGATCCAATAA AG (SEQ ID NO: 400) |
| 3 | 20310707 | C/G | CGGGCGGAGTACGTG (SEQ ID NO: 401) | CGGGCGGACTACGT (SEQ ID NO: 402) | AGAGGGCGCGGTCTGA (SEQ ID NO: 403) | TGGTCGCACTTCCTTCTTC (SEQ ID NO: 404) |
| 3 | 20351131 | A/G | CGACAGCGGAGGAG (SEQ ID NO: 405) | CGACAGCGGAAGAGG (SEQ ID NO: 406) | CTCGTGCTTGCTTTACG (SEQ ID NO: 407) | CGCAAGAGGTTGATAGG (SEQ ID NO: 408) |
| 3 | 20395987 | A/C | ACCAGCTACTGCAGC (SEQ ID NO: 409) | CCAGCGACTGCAGC (SEQ ID NO: 410) | GTCCCTGCCCGTTTTGTCT (SEQ ID NO: 411) | ACACCTCTCCGTCGTATCAAG (SEQ ID NO: 412) |
| 4 | 242123154 | A/G | TCATTGTAATCCATATTAC GT (SEQ ID NO: 413) | CATTGTAATCCATACTACGT (SEQ ID NO: 414) | GCCAACAGTTCACTCCCAGT A (SEQ ID NO: 415) | ACTTGTTACCTTTCCTTGCTA GACA (SEQ ID NO: 416) |
| 4 | 242134237 | A/C | TTACTGGTACTTAGATATA TG (SEQ ID NO: 417) | TACTGGTACTTAGATAGATG (SEQ ID NO: 418) | AGATACATGAAGTAACATGC T (SEQ ID NO: 419) | GGTACTCAAGAACAATTAAC C (SEQ ID NO: 420) |
| 4 | 242143841 | A/G | TCAAAGAATCTCCGGTCA (SEQ ID NO: 421) | CAAAGAATCCCCGGTCA (SEQ ID NO: 422) | GGACTGTGCGTAGTATGAG C (SEQ ID NO: 423) | GTCACGTCTATCCTCCAGTTC A (SEQ ID NO: 424) |
| 4 | 242180041 | A/G | ACCCCGACACTGCT (SEQ ID NO: 425) | CACCCCAACACTGC (SEQ ID NO: 426) | GTCGACGACGGTGAAGC (SEQ ID NO: 427) | CACGCTCGAGGTGATCCA (SEQ ID NO: 428) |
| 4 | 242210603 | A/G | AAGTTATCTTCCATTGTAG TG (SEQ ID NO: 429) | AGTTATCTTCCATTGCAG (SEQ ID NO: 430) | CATGTTTATTTTGAGAGCCA (SEQ ID NO: 431) | GAAACGTGTTGCTGAAG (SEQ ID NO: 432) |
| 4 | 242225286 | A/G | CGACAGCCTTCGAT (SEQ ID NO: 433) | CGACAGCCTTCAAT (SEQ ID NO: 434) | CTAGCCGAACTGTCCTA (SEQ ID NO: 435) | CACACCAACGGATCAAG (SEQ ID NO: 436) |
| 4 | 242281050 | A/G | CGGTGACGAATACTGAT (SEQ ID NO: 437) | CGGTGACGAATACTGAC (SEQ ID NO: 438) | GAAACATCCCAACAACATC (SEQ ID NO: 439) | AGCCTTGCTAGTGCTG (SEQ ID NO: 440) |
| 4 | 242290671 | A/C | CATCAGAGGGAATATAAT TT (SEQ ID NO: 441) | CATCAGAGGGAATAGAATT (SEQ ID NO: 442) | AGCTATATTTTAGAGACCGT GTT (SEQ ID NO: 443) | GCACGATGACGATGA (SEQ ID NO: 444) |
| 4 | 242393156 | A/G | CGGTAACATGTAGAATGC A (SEQ ID NO: 445) | CGGTAACATGTAGAACGC (SEQ ID NO: 446) | TGAATGCTCTCAGATGCCAC AT (SEQ ID NO: 447) | AGCAGCTTCAAGAAACAAAG GA (SEQ ID NO: 448) |
| 4 | 242401749 | A/G | ACTGCGCGTTGCAA (SEQ ID NO: 449) | CTACTGCGCATTGCAA (SEQ ID NO: 450) | GGCCGCCAAGGTGCT (SEQ ID NO: 451) | GCCTGGTCGATCCTGATGAC (SEQ ID NO: 452) |
| 4 | 242495406 | A/G | CATGGGCCGTGACCT (SEQ ID NO: 453) | ATGGGCCGCGACCT (SEQ ID NO: 454) | CCTTTAACAGGTTGTACTCA TGCC (SEQ ID NO: 455) | TCGAGTCAGCACGGTTCG (SEQ ID NO: 456) |

TABLE XI-continued

| CHR # | Physical position SNP | probe 1 sequence | probe 2 sequence | primer 1 sequence | primer 2 sequence |
|---|---|---|---|---|---|
| 4 | 242564204 A/G | CAACCTCACGAACCT (SEQ ID NO: 457) | CGGCAACCTCACAAA (SEQ ID NO: 458) | CAACCTGAGCTTCAACAGC CT (SEQ ID NO: 459) | GGCGGTTGCTGGACA (SEQ ID NO: 460) |
| 4 | 242569684 A/G | ATTCTCAAAGCCGTAGA (SEQ ID NO: 461) | AGATTCTCAAAACCGTAGA (SEQ ID NO: 462) | GGCAGTTTCCGATGTCCAG A (SEQ ID NO: 463) | GAACCTGACCACGCTTCTTC (SEQ ID NO: 464) |
| 4 | 242573653 A/G | CACACACCGAGAGAGAG (SEQ ID NO: 465) | CCACACACCGAGAAAG (SEQ ID NO: 466) | AGCACACGTTCTCTTCCAAA (SEQ ID NO: 467) | CGGGTTCATCCTCTTCGTGGT (SEQ ID NO: 468) |
| 4 | 242636783 A/G | CTGAAGCTGCCTCAA (SEQ ID NO: 469) | TGAAGCTGCCCCA (SEQ ID NO: 470) | AGCAAATAAATTTAGATGGA ACA (SEQ ID NO: 471) | GTCAAGGTGAATATGTCCTA (SEQ ID NO: 472) |
| 4 | 242710102 A/G | AGCCAGAAAACGGGCA (SEQ ID NO: 473) | ACAAGCCAGAAAACGGACA (SEQ ID NO: 474) | GCGCGTACCTGATTCACA (SEQ ID NO: 475) | AGCCAGCAGCTGAAGAGAA GAC (SEQ ID NO: 476) |
| 4 | 242870532 C/G | CCGCCAGGTCCGAT (SEQ ID NO: 477) | CGCCACGTCCGATG (SEQ ID NO: 478) | TGGGCAGCCTCACCGT (SEQ ID NO: 479) | CGGAGCTGGAAAGGATGGA (SEQ ID NO: 480) |
| 4 | 242886246 A/G | CAATAGTGAATATTGTAGT TT (SEQ ID NO: 481) | CAATAGTGAATATTGTAATTT (SEQ ID NO: 482) | AGCAGAAAAACATTGGGAC TGTAC (SEQ ID NO: 483) | AGCCTGAAGCTGTGGATCTT C (SEQ ID NO: 484) |
| 4 | 242973043 A/C | CTCACCGTGGACCG (SEQ ID NO: 485) | CCTCACAGTGGACCG (SEQ ID NO: 486) | CATCCGCAAGGTCCTGCTC (SEQ ID NO: 487) | GGGCGATCGAGTTGTGCTTT G (SEQ ID NO: 488) |
| 4 | 243041588 A/G | CCTAAACAGATGTATTATA TA (SEQ ID NO: 489) | CCTAAACAGATGTACTATA (SEQ ID NO: 490) | AGTTGTGCCAAGGGCTAGT TG (SEQ ID NO: 491) | GGAGTCATGCACATTTGAGA AGAAAC (SEQ ID NO: 492) |
| 4 | 243050445 A/G | AATGGCACCATTAG (SEQ ID NO: 493) | TAATGGCACCATCAG (SEQ ID NO: 494) | TGGTTGCTTCGGAAGAGTT C (SEQ ID NO: 495) | AGGGTTGCGCTCCTAGTTCT (SEQ ID NO: 496) |
| 5 | 186387089 A/G | CCTAAAGAAAGGTGTAGC CT (SEQ ID NO: 497) | TTCCTAAAGAAAGGTATAGCC T (SEQ ID NO: 498) | CAAGACCAGGTCTAACAGA GCATA (SEQ ID NO: 499) | GGACCCGTAAATTATCATTGC TTCA (SEQ ID NO: 500) |
| 5 | 186616138 A/T | ACGTCTAAGAGATTAAAA G (SEQ ID NO: 501) | AAATACGTCTAAGAGATAAAA (SEQ ID NO: 502) | GTCTGCAAATAAATTATCTT GGT (SEQ ID NO: 503) | GACACAAGATGGTCTCAA (SEQ ID NO: 504) |
| 5 | 186620278 A/G | CTGGGAGTCAATTTCATT G (SEQ ID NO: 505) | CTGGGAGTCAATTCCATTG (SEQ ID NO: 506) | TGGCCGGTAAACAAACAAA GTC (SEQ ID NO: 507) | TCAGTGGGTGATCCGGTAAC (SEQ ID NO: 508) |
| 5 | 186643531 A/G | CTGCAGGTGAAGACC (SEQ ID NO: 509) | CTGCAGGTGAAAACC (SEQ ID NO: 510) | GGGCGCAGCCGTGTAG (SEQ ID NO: 511) | CACGACTCCACAGGCACTCT (SEQ ID NO: 512) |
| 5 | 186652796 A/G | AGCAAGAGAAGCAGCTG (SEQ ID NO: 513) | TGAGCAAGAGAAGCAACT (SEQ ID NO: 514) | GTAGTAGCCTCAGTAGGA (SEQ ID NO: 515) | TTTGATAGTTTCATGATAGAT AC (SEQ ID NO: 516) |
| 5 | 186716755 A/G | CGCGTATCTCGATTCC (SEQ ID NO: 517) | CGCGTATCTCAATTCCA (SEQ ID NO: 518) | CATTACAAACGCAGCCAAG GTA (SEQ ID NO: 519) | GCGCCCATCTCCAGCAA (SEQ ID NO: 520) |
| 5 | 186771763 A/G | TACAACAAAGGTCAATAA GTAA (SEQ ID NO: 521) | CAACAAAGGTCAACAAGTAA (SEQ ID NO: 522) | GCAAGTGGAGAGAAGAAC TAAGGA (SEQ ID NO: 523) | CCTGGGCATATCAGTGGTGTT (SEQ ID NO: 524) |
| 5 | 186794253 A/G | TTCAGCAGTACTTGACGT (SEQ ID NO: 525) | TCAGCAGTACCTGACG (SEQ ID NO: 526) | CCGCAGGAAATCAAACATG GGT (SEQ ID NO: 527) | ACGTGGTCTCCGTCGATGAG (SEQ ID NO: 528) |
| 5 | 186866016 A/G | CGAGGCGATGGTGCC (SEQ ID NO: 529) | AGGCGACGGTGCCA (SEQ ID NO: 530) | GACGTCAGGTCCAGGGT (SEQ ID NO: 531) | AGCCTCATCTCCTACACTTAC TAC (SEQ ID NO: 532) |
| 5 | 187068361 A/G | TCAGTATTAGTAAGGTGC (SEQ ID NO: 533) | AAATCAGTATTAGTAAGATGC (SEQ ID NO: 534) | GATGTAGTTAACAAGCGAG CGTCT (SEQ ID NO: 535) | GCCTGCACTCTTTATGCTTCA (SEQ ID NO: 536) |
| 5 | 187133585 C/G | AGCCGGTTCGGGTACT (SEQ ID NO: 537) | AGCCGGTTCCGGTACT (SEQ ID NO: 538) | CGTCGGGCCTGTGCTG (SEQ ID NO: 539) | CACGGACGCGTTGTTGGT (SEQ ID NO: 540) |
| 5 | 187219122 A/C | CAGATCCGATCTCTGTTAG (SEQ ID NO: 541) | AGATCCGATCGCTGTTAGT (SEQ ID NO: 542) | GGGAGGATACATCCCTTCAT CA (SEQ ID NO: 543) | AACAACGACTGTGAGGGTTC A (SEQ ID NO: 544) |
| 5 | 207085360 A/G | CAGCCATAGTGTGTGGAA (SEQ ID NO: 545) | AGCCATAGTGCGTGGAAA (SEQ ID NO: 546) | GGGCACTGCTGGCGTT (SEQ ID NO: 547) | CCCTCACCTATGCAACAGAAC (SEQ ID NO: 548) |
| 5 | 207092087 A/G | TGGCTACACTTTAATCGA A (SEQ ID NO: 549) | TGGCTACACTTCAATCG (SEQ ID NO: 550) | GACAGCTCTCATCACTGCAT CAG (SEQ ID NO: 551) | GCACTGCTTTCAGAGTTCTG GT (SEQ ID NO: 552) |

TABLE XI-continued

| CHR # | Physical position | SNP | probe 1 sequence | probe 2 sequence | primer 1 sequence | primer 2 sequence |
|---|---|---|---|---|---|---|
| 5 | 207145010 | A/G | AAAGGTTTGTTTTATTTATTG (SEQ ID NO: 553) | TAAAGGTTTGTTTTATTTATC (SEQ ID NO: 554) | CACGTCAGGAAAGGATGCAAA (SEQ ID NO: 555) | GCGGATCATCACTCCCATCTTC (SEQ ID NO: 556) |
| 5 | 207290101 | A/C | CAGCCATCTTGCTGATA (SEQ ID NO: 557) | CAGCCATCGTGCTGAT (SEQ ID NO: 558) | CGTGTCGTTGAAATATGCATGGTT (SEQ ID NO: 559) | TCACGGTCCTCCATCATCTAAC (SEQ ID NO: 560) |
| 5 | 207374213 | A/G | CTAAAAGTGACTAACTAAAGT (SEQ ID NO: 561) | CTAAAAGTGACTAACTAAAATT (SEQ ID NO: 562) | GTCACTCTCTTAAACTCTAGTC (SEQ ID NO: 563) | GCTATCGCATTGTACTAGTAG (SEQ ID NO: 564) |
| 5 | 207411122 | A/T | TCATAAGCTGTCTCCAAA (SEQ ID NO: 565) | TTCATAAGCTGACTCCAAA (SEQ ID NO: 566) | TGTGGGTGTTTGATTCAATGGATG (SEQ ID NO: 567) | TCCAAGGCTCAGCTCGAAA (SEQ ID NO: 568) |
| 5 | 207484313 | A/G | CATCGATGTACTTCAAAAG (SEQ ID NO: 569) | CATCGATGTACTTCAAAAA (SEQ ID NO: 570) | GCCCAAGTGATCCAGAACTAATACAC (SEQ ID NO: 571) | TGCAGTTCATTTTTGCACTATTTGAC (SEQ ID NO: 572) |
| 5 | 207511495 | A/G | TGGTGGCAGTTTAGGT (SEQ ID NO: 573) | TGGTGGCAGTTCAGG (SEQ ID NO: 574) | CCTTGAGGCTTGGTTTAGATTGGT (SEQ ID NO: 575) | CTCACCCACATCTTTCGCACTATT (SEQ ID NO: 576) |
| 5 | 207524612 | A/G | TTAAACGCTTTGTTGA (SEQ ID NO: 577) | AAACGCTTTGCTGAT (SEQ ID NO: 578) | TGGAACTCTTCAGTCTTG (SEQ ID NO: 579) | GAACGGTGTTCTAGGG (SEQ ID NO: 580) |
| 5 | 207646561 | A/T | TGATGTCCATATTGAAGC (SEQ ID NO: 581) | TTGATGTCCATATAGAAGC (SEQ ID NO: 582) | TGAAGTGTTAGAAGAAGTTGCACA (SEQ ID NO: 583) | AAGCACCCTTGAGGCAGT (SEQ ID NO: 584) |
| 5 | 207743659 | C/G | CGGCTGGGCGACTT (SEQ ID NO: 585) | CGGCTCGGCGACTT (SEQ ID NO: 586) | TCATGCTGGACTCGTCGTTC (SEQ ID NO: 587) | GTCCGTGTAGGAGGTCTTGTC (SEQ ID NO: 588) |
| 5 | 207750678 | A/G | CAGTAGCTGTGATAGAC (SEQ ID NO: 589) | CAGTAGCTGTGACAGA (SEQ ID NO: 590) | TTGCAAGGAAAATGGAAGA (SEQ ID NO: 591) | ATCGTGATGGGCTGCT (SEQ ID NO: 592) |
| 5 | 207862632 | A/C | CATGTTAGTTTACCCGAAA (SEQ ID NO: 593) | AGCATGTTAGTTTACCAGA (SEQ ID NO: 594) | TGTGCCAGTGTTATCCAGGAA (SEQ ID NO: 595) | TCCATGCTTCAGTCACACAGT (SEQ ID NO: 596) |
| 5 | 211702290 | A/G | AAGAGTCAACACTGGAGTTG (SEQ ID NO: 597) | AGGGAAGAGTCAACACTAGAGTT (SEQ ID NO: 598) | CCATGAAGGCAGAGAGCATGTG (SEQ ID NO: 599) | TCTCGGTTGTGTGGATGAA (SEQ ID NO: 600) |
| 5 | 211818656 | A/G | TACTCCCTCCGTTTT (SEQ ID NO: 601) | ACTCCCTCCGTTTC (SEQ ID NO: 602) | GGTCGAGGAGAGTGAACCTTG (SEQ ID NO: 603) | GGCAGATTGCCAGGATGAGAT (SEQ ID NO: 604) |
| 5 | 212009058 | A/G | ATTCTCTATTATAGAAAGAAAT (SEQ ID NO: 605) | ATTCTCTATTATAGAAAGAAAC (SEQ ID NO: 606) | GGTAGCAGATGAAGTTCCAATAGTAAA (SEQ ID NO: 607) | GCTATCTAGCCACTTGTTCCATTC (SEQ ID NO: 608) |
| 5 | 212182157 | A/G | CACAACGTGGAAGTAGG (SEQ ID NO: 609) | CCACAACGTGGAAGTAGA (SEQ ID NO: 610) | GATCATCGGATCACTTGAAAGGG (SEQ ID NO: 611) | TGGTTCGGCCAAGTAACAC (SEQ ID NO: 612) |
| 5 | 212254866 | A/G | ACCGCTGCTGCCA (SEQ ID NO: 613) | AAGACCGCCGCTGC (SEQ ID NO: 614) | TCCTGCTCGGCCTGTGA (SEQ ID NO: 615) | GCGCCAAGCAAATGTCGTA (SEQ ID NO: 616) |
| 5 | 212483325 | —/G | CGCGGAACCTTGGATG (SEQ ID NO: 617) | CGCGGAAGCCTTGGAT (SEQ ID NO: 618) | AAGACCGTCGCGGACTCG (SEQ ID NO: 619) | GGGCAAACTCATGCGTAGATG (SEQ ID NO: 620) |
| 5 | 212585339 | A/G | ATCAACCATCTGTCCAT (SEQ ID NO: 621) | CAACCATCTGCCCAT (SEQ ID NO: 622) | CTTCCTAAACTCGTCCCT (SEQ ID NO: 623) | TCAAATCTAAGTTATTGAGTGTTA (SEQ ID NO: 624) |
| 5 | 212627813 | A/G | TGATAGTCAGTAGTATGGTT (SEQ ID NO: 625) | AGTCAGTAGTATGGCTTG (SEQ ID NO: 626) | GGTCAATTGGTAGTCAGAGGACAA (SEQ ID NO: 627) | GTGCTCCAACGAGGACTAGTG (SEQ ID NO: 628) |
| 5 | 212687514 | A/G | ACCCAAGGGCTCAACA (SEQ ID NO: 629) | CACCCAAGAGCTCAAC (SEQ ID NO: 630) | ACAGCTCAAAGGGCAGGTT (SEQ ID NO: 631) | GGCTTGAACAGTGCCAATAGTC (SEQ ID NO: 632) |
| 5 | 214806851 | A/G | ATTGCGTCTCGATAAATCA (SEQ ID NO: 633) | TTGCGTCTCAATAAATCA (SEQ ID NO: 634) | TCCGAGTTCGCTGTCCA (SEQ ID NO: 635) | CGTTGGCATTGAAGGGAAGTCTA (SEQ ID NO: 636) |
| 5 | 214958658 | A/G | ATTGGCAATGCCGCA (SEQ ID NO: 637) | CATTGGCAATGCCACA (SEQ ID NO: 638) | TGCCTGATCTTTTCCTTCACCAT (SEQ ID NO: 639) | TGTAGGCCACCTAGGATTGG (SEQ ID NO: 640) |
| 6 | 85812814 | A/G | TTTCCATTGTTTCCATC (SEQ ID NO: 641) | AGTTTCCATTGTTTCCAC (SEQ ID NO: 642) | AGTTCCTTTTCTCTACTCCTATAAAGCAC (SEQ ID NO: 643) | GGATGGGATCATAGCCACAGTTC (SEQ ID NO: 644) |
| 6 | 86008900 | A/G | CCTCCTTGCGCGTG (SEQ ID NO: 645) | CTCCTCGCGCGTG (SEQ ID NO: 646) | GCCTGGGACCGGGAAG (SEQ ID NO: 647) | CACCGACACCGACGAAGA (SEQ ID NO: 648) |

TABLE XI-continued

| CHR # | Physical position | SNP | probe 1 sequence | probe 2 sequence | primer 1 sequence | primer 2 sequence |
|---|---|---|---|---|---|---|
| 6 | 86116579 | A/G | TCACAAATCAATAAAGCC C (SEQ ID NO: 649) | TTCACAAATCAACAAAGCC (SEQ ID NO: 650) | ATGGTACAAGTCACAGGTA GGG (SEQ ID NO: 651) | GTCAAGTTAGGGCCGGATCA TA (SEQ ID NO: 652) |
| 6 | 86300786 | A/G | AGTATGGAACTAATTTGA CAAA (SEQ ID NO: 653) | AGAGTATGGAACTAATTTAA CAAA (SEQ ID NO: 654) | AAACAGTTGGTGTTGGAGT TGGA (SEQ ID NO: 655) | TGTGGATGGCGTGTTAGCA (SEQ ID NO: 656) |
| 6 | 86335319 | A/G | TCCATTACTTATTGAAACA C (SEQ ID NO: 657) | CCATTACTTACTGAAACAC (SEQ ID NO: 658) | ACCACCTCGGTCTACACCTT A (SEQ ID NO: 659) | TGCCAGAAAGCATGGGAAGT C (SEQ ID NO: 660) |
| 6 | 86351479 | C/G | TAGGCACTGACCGGA (SEQ ID NO: 661) | TAGGCACTGACCCGA (SEQ ID NO: 662) | TGGCGAGACGAAGCAGA (SEQ ID NO: 663) | GACCGAACCGAACCATTAGC (SEQ ID NO: 664) |
| 6 | 86551985 | A/G | CTTCTGTGCATGGATCA (SEQ ID NO: 665) | TCTGTGCACGGATCAT (SEQ ID NO: 666) | CGAGAAGTTCCCATCAGCTC AA (SEQ ID NO: 667) | TGGTGAACATTGGTTGCTTG TG (SEQ ID NO: 668) |
| 6 | 86658904 | A/G | AAACAACAGAATCTTTTT AGA (SEQ ID NO: 669) | AAACAACAGAATCTTTTTAA AA (SEQ ID NO: 670) | CAGCTCTAAACTCACAGAC GTTTG (SEQ ID NO: 671) | AGCGCTCTACCATCTGAGCTA C (SEQ ID NO: 672) |
| 7 | 136240277 | A/G | TCAAAATAATGATATGAG GGAA (SEQ ID NO: 673) | TCAAAATAATGATATGAGGA AA (SEQ ID NO: 674) | AAGACTGAAAGCATGAATA AACGGT (SEQ ID NO: 675) | CAGGCGATCTTGACCTTGGT (SEQ ID NO: 676) |
| 7 | 136241408 | A/G | CTAAATTTAAGTGCTGTTG (SEQ ID NO: 677) | AAGATCTAAATTTAAGTACT GT (SEQ ID NO: 678) | TTCTGGATAAAGCAATGACC AACA (SEQ ID NO: 679) | GTGAGTCTGCTTCCTCTCCAT T (SEQ ID NO: 680) |
| 7 | 136250893 | A/G | TGGTTGCTCTGCATGTAT (SEQ ID NO: 681) | TTGGTTGCTCTGCATATA (SEQ ID NO: 682) | GCCTTTGCGAAGGTTTTAG CAG (SEQ ID NO: 683) | AACTCCGTGGCAGCATGTG (SEQ ID NO: 684) |
| 7 | 136281854 | A/G | TGATCTGGGGCATCT (SEQ ID NO: 685) | TGAGTGATCTGGGACAT (SEQ ID NO: 686) | CACCGGTGCCAAGGATATA GAG (SEQ ID NO: 687) | AGGCCGTCTAACGAAGTGTG (SEQ ID NO: 688) |
| 7 | 136602547 | C/G | TTCATCTATCCACTAGAA (SEQ ID NO: 689) | TCATCTATCCACTACAA (SEQ ID NO: 690) | GTATGTAAACAAGGTTCAA AA (SEQ ID NO: 691) | AGGGACAACTATGGATGAAG T (SEQ ID NO: 692) |
| 7 | 136688931 | A/G | CCGTCCTAGTTAAGTGC (SEQ ID NO: 693) | TCCGTCCTAGCTAAGTG (SEQ ID NO: 694) | AGTCGGTTCTCTTCGTCTGC (SEQ ID NO: 695) | CGCATGCCCGTGATTTATTTC TC (SEQ ID NO: 696) |
| 7 | 136722650 | −/GC | CTGAGAGAATGGACACG AA (SEQ ID NO: 697) | CTGAGAGAATGGGCACA (SEQ ID NO: 698) | GTGTTACTAGGATACAGTGA (SEQ ID NO: 699) | TGCCCTTACCTGAAGTCT (SEQ ID NO: 700) |
| 7 | 136903521 | A/G | TGCTCTGCTTACCGT (SEQ ID NO: 701) | TGCTCTGCCTACCG (SEQ ID NO: 702) | GTGAGCACCAGCCACTTC (SEQ ID NO: 703) | GAACACGACGGCATTCCAA (SEQ ID NO: 704) |
| 7 | 137020340 | A/G | ATAACACAAGAATTTGAG CAT (SEQ ID NO: 705) | CAATAACACAAGAATTTAAGC (SEQ ID NO: 706) | CCTGCTACAGATTTCAAC (SEQ ID NO: 707) | CTGTTTAGGAGCCAGATTA (SEQ ID NO: 708) |
| 7 | 137150767 | A/T | CGACGGGAGTTGGC (SEQ ID NO: 709) | CGACGGGAGTAGGC (SEQ ID NO: 710) | AGAGCCGGGAGCCAT (SEQ ID NO: 711) | ACTCCTCCGCCTTGG (SEQ ID NO: 712) |
| 8 | 3732302 | A/G | CGGCGCCTTCTTCTG (SEQ ID NO: 713) | CGGCGCCTCCTTCT (SEQ ID NO: 714) | GCCGTGTCCATCAAACTTCA TCT (SEQ ID NO: 715) | GGGCTTCTTGCGCAGAGAG (SEQ ID NO: 716) |
| 8 | 3858710 | A/G | TATTCCAAGAAGTTTATCT TGT (SEQ ID NO: 717) | TCCAAGAAGTTTACCTTGT (SEQ ID NO: 718) | AGCACCCAGTCCTCCACT (SEQ ID NO: 719) | GCTGCCCAGGATCGAACT (SEQ ID NO: 720) |
| 8 | 3987539 | A/G | TTCCCCAGAGAAGGGAG TT (SEQ ID NO: 721) | TTCCCCAGAGAAAGGAGTTA (SEQ ID NO: 722) | CAGGTAGCTTGCCAAACGG A (SEQ ID NO: 723) | TGTCTACACGAAGGCAATTG TTG (SEQ ID NO: 724) |
| 8 | 4081677 | A/C | TGTTCGCCGCAGTC (SEQ ID NO: 725) | TGTTCGCAGCAGTCC (SEQ ID NO: 726) | TGCCCGGGAAGATCCA (SEQ ID NO: 727) | TTAACCCTGAAGGAGACGGA (SEQ ID NO: 728) |
| 8 | 4178632 | A/G | ACCTCCATTCGCATAAAA (SEQ ID NO: 729) | ATGACCTCCATTCACATAAA (SEQ ID NO: 730) | CTGGAACATGTCGACCATTC AC (SEQ ID NO: 731) | CCCTGACCACATGCATACACA (SEQ ID NO: 732) |
| 8 | 4379574 | A/T | CTAGTAACCAAATATGAAT TA (SEQ ID NO: 733) | CTAGTAACCAAATATGAAATA (SEQ ID NO: 734) | CTGTTATGATACCTGGTCTT (SEQ ID NO: 735) | GACTATGGGCGTCTTTA (SEQ ID NO: 736) |
| 8 | 4471335 | A/T | AGGCCCATTTTAGGATTT T (SEQ ID NO: 737) | AGGCCCATTTTAGGATATT (SEQ ID NO: 738) | AGAGCAGTCCCACCTTGGT T (SEQ ID NO: 739) | TGCTTGACCGGAGTGAGAAG (SEQ ID NO: 740) |
| 8 | 4497449 | A/G | AACAAATAGGAGAATCAG AT (SEQ ID NO: 741) | CAAATAGGAGAACCAGAT (SEQ ID NO: 742) | GGTGGTGCCTGCATATAAGT AAA (SEQ ID NO: 743) | ATGTGCCATGCTGCACTAAG (SEQ ID NO: 744) |
| 8 | 4566630 | A/G | TCGTAAGATGGGAATGTG G (SEQ ID NO: 745) | TTTCGTAAGATGAGAATGTGG (SEQ ID NO: 746) | ACCTTTGGTGTGTGCTATGG TATG (SEQ ID NO: 747) | ACCGTCCCCTGCTCAAAACC (SEQ ID NO: 748) |

TABLE XI-continued

| CHR # | Physical position | SNP | probe 1 sequence | probe 2 sequence | primer 1 sequence | primer 2 sequence |
|---|---|---|---|---|---|---|
| 8 | 9625854 | A/T | ACATATTTATAGCCCTAGG (SEQ ID NO: 749) | ACATATTTATAGCCCAAGG (SEQ ID NO: 750) | CAAACACTACACAATGTCAT ACCCT (SEQ ID NO: 751) | ACTGTCCTCTGTAGTCTCTTT AGCA (SEQ ID NO: 752) |
| 8 | 9820514 | C/G | ACCAGCCCTAGTCATC (SEQ ID NO: 753) | CAGCCCTACTCATCAAA (SEQ ID NO: 754) | TTGTCCACAACCTCCTACTG A (SEQ ID NO: 755) | AAGGCTCAATTGCAACCCATA (SEQ ID NO: 756) |
| 8 | 10001339 | A/T | CCACCTCGAATCAGTATA (SEQ ID NO: 757) | CCACCTCGAAACAGTATA (SEQ ID NO: 758) | TCTCTATTGGCTGAGAACAA TTCAC (SEQ ID NO: 759) | TCGTTGGATCAATCGCAACTC (SEQ ID NO: 760) |
| 8 | 10205544 | A/T | TTGGTTGAACTTTAGTATC (SEQ ID NO: 761) | TTGGTTGAACTTTAGAATC (SEQ ID NO: 762) | TTGACACTCATTACTGTTTG (SEQ ID NO: 763) | GGAGAATGACTTAGAACTTA G (SEQ ID NO: 764) |
| 8 | 10383181 | A/G | AGCAGCAGCGGGG (SEQ ID NO: 765) | CAGCAGCAGGGGC (SEQ ID NO: 766) | CACGCGGTGGTGGACATG (SEQ ID NO: 767) | TCCACGCTCATCTCCTTGTG (SEQ ID NO: 768) |
| 8 | 10486043 | C/G | ATGATGCCAGGAGAGGC AAG (SEQ ID NO: 769) | TGCCAGGAGACGCAAG (SEQ ID NO: 770) | GAACAAGAAGCATGAGCAT TCTGAC (SEQ ID NO: 771) | TCACGGTTGCTCTCATCACTT (SEQ ID NO: 772) |
| 8 | 164546096 | A/G | CATTCCTATTCAAGGTTA (SEQ ID NO: 773) | TTCCTATTCAAGGCTAA (SEQ ID NO: 774) | AGGCACGTGGATATCTG (SEQ ID NO: 775) | GTGTGGAGCAACCAA (SEQ ID NO: 776) |
| 8 | 164679493 | A/C | CTGATAGCGCGCAGTG (SEQ ID NO: 777) | CTGATAGCGAGCAGTGAC (SEQ ID NO: 778) | GCACCTCAGTGAAACGACA AG (SEQ ID NO: 779) | TGAGGAAGGTGAGTGATTTG C (SEQ ID NO: 780) |
| 8 | 164886047 | A/G | CGATGCACACTAAGATGA C (SEQ ID NO: 781) | CGATGCACACCAAGATG (SEQ ID NO: 782) | GAAGGGCCAAACTGAGGC AT (SEQ ID NO: 783) | ACTTCCCGGTTGAGCAAGA (SEQ ID NO: 784) |
| 8 | 164963082 | A/G | CCTAGTTAGGGTTATGTG (SEQ ID NO: 785) | CCTAGTTAGGGTTATATGG (SEQ ID NO: 786) | TGCGTTTACGTCTGCAATTA GA (SEQ ID NO: 787) | CTGGCCTCTTTCTCTTCTCTG TA (SEQ ID NO: 788) |
| 8 | 164993163 | A/G | CCTTGTGCCTGATTCAA (SEQ ID NO: 789) | TTGTGCCCGATTCAAC (SEQ ID NO: 790) | CGCAAGTCATTGTTCGCTGT TTG (SEQ ID NO: 791) | GTCGTCACCGTCTTTCTTTCA AC (SEQ ID NO: 792) |
| 8 | 165151326 | A/G | AGCAGGCTATGTTTTAGT T (SEQ ID NO: 793) | AGCAGGCTATGTTTCAG (SEQ ID NO: 794) | ACTTCTCAAGAGGCTAAAC (SEQ ID NO: 795) | GCTGTAACCTGTGGTCTA (SEQ ID NO: 796) |
| 8 | 165269767 | A/G | CTGAGGTAGTATATAAGA AG (SEQ ID NO: 797) | TCTGAGGTAGTATATAAAAA (SEQ ID NO: 798) | AGAGAATACTTGAGAAGGC T (SEQ ID NO: 799) | GTACTGATGGGACTGGAT (SEQ ID NO: 800) |
| 8 | 165290988 | A/G | ATATTTTATTCCTCGTTTCA (SEQ ID NO: 801) | ATATTTTATTCCTCATTTCA (SEQ ID NO: 802) | GAAACTCTACATTTGGGAG AT (SEQ ID NO: 803) | GGACACAATTATATGACCTCT T (SEQ ID NO: 804) |
| 8 | 165309200 | A/G | TTTGGGCGGTCAATGG (SEQ ID NO: 805) | TGGGCGGCCAATG (SEQ ID NO: 806) | TGCGTTCCGGCCTTACTC (SEQ ID NO: 807) | ACTGCGTTTCTCCCTTTGCTT (SEQ ID NO: 808) |
| 8 | 165343030 | A/G | CCGCGATGCCCTTG (SEQ ID NO: 809) | CGCGACGCCCTTG (SEQ ID NO: 810) | GGCAGGTTTCGTACCACATC (SEQ ID NO: 811) | CGAGGATCCGTGCTCTTCTAA (SEQ ID NO: 812) |
| 8 | 165482649 | A/G | CAGCAGCCTTGATCTGT (SEQ ID NO: 813) | CAGCAGCCTCGATCT (SEQ ID NO: 814) | CCTCCAAGATGTGCTCCATG AT (SEQ ID NO: 815) | TCGCCGAGGTCCTGTCT (SEQ ID NO: 816) |
| 8 | 171781842 | A/G | CGGCGGTGGGATGA (SEQ ID NO: 817) | CGGCGGCGGGATG (SEQ ID NO: 818) | GCGTGTGAGAGGGACAAA GG (SEQ ID NO: 819) | GTGCACAACGCACTGTTC (SEQ ID NO: 820) |
| 8 | 171833160 | A/G | CCTTGGTGCCTGC (SEQ ID NO: 821) | CCCTTGGTGCCTAC (SEQ ID NO: 822) | CCCAAGATCCAAGAAGCGA TATATATGC (SEQ ID NO: 823) | GGCGATCGGGTGCAATTTG (SEQ ID NO: 824) |
| 8 | 171863486 | A/G | TTAGGCCTTGTTTGTT (SEQ ID NO: 825) | AGGCCTTGTTCGTT (SEQ ID NO: 826) | CAGTGGCAGTAACTGATA (SEQ ID NO: 827) | AAGCAATCCGGTTAGGAAT (SEQ ID NO: 828) |
| 8 | 172025007 | A/G | CCGACGATCATATTCGTA (SEQ ID NO: 829) | CGACGATCACATTCGTA (SEQ ID NO: 830) | CTGCTGCTGCAAGCAATTGT A (SEQ ID NO: 831) | TGGCACTGACTAACAGTCTA ACAG (SEQ ID NO: 832) |
| 8 | 172040252 | A/G | CTGCAGATCCCCAG (SEQ ID NO: 833) | TGCAGACCCCCAG (SEQ ID NO: 834) | CTGCTCCGACGACTG (SEQ ID NO: 835) | CTGAGCTGCTCAAGGT (SEQ ID NO: 836) |
| 8 | 172131684 | A/G | AAACGTTACCTGATAAATC T (SEQ ID NO: 837) | AACGTTACCTGATAAACCT (SEQ ID NO: 838) | TGTTTGCAGCCCCTCTCAA (SEQ ID NO: 839) | TTCTGGCCCGTGTTGCT (SEQ ID NO: 840) |
| 8 | 172155970 | A/T | TCATTCTGGTGCTCAT (SEQ ID NO: 841) | TCATTCTGGTGCACAT (SEQ ID NO: 842) | TCTAGGTTTCGGCTAGTGGT TA (SEQ ID NO: 843) | ACTATTACACTTCGTCTCTGG GTTT (SEQ ID NO: 844) |

TABLE XI-continued

| CHR # | Physical position | SNP | probe 1 sequence | probe 2 sequence | primer 1 sequence | primer 2 sequence |
|---|---|---|---|---|---|---|
| 8 | 172336136 | A/G | AGCTCTCCTTGATATGAAC C (SEQ ID NO: 845) | CTCCTTGATACGAACCC (SEQ ID NO: 846) | TCTCCTAAACCCATTGCAAA CAGT (SEQ ID NO: 847) | TCAAGACTTGCACTTGCTCA GT (SEQ ID NO: 848) |
| 8 | 172367654 | A/C | CAAGAACCGAGATTTTAC T (SEQ ID NO: 849) | CAAGAACCGAGAGTTTACTT (SEQ ID NO: 850) | AGGTTGCATTGATGTTGGTT GT (SEQ ID NO: 851) | CAGCACTCCTGGAATTCACA (SEQ ID NO: 852) |
| 8 | 172434600 | A/G | TGGGCCTCTGGTC (SEQ ID NO: 853) | CTGGGCCTCTGATC (SEQ ID NO: 854) | ACAGGACTGTATCTGGTG (SEQ ID NO: 855) | TGCAGGGTAGTTAGCAT (SEQ ID NO: 856) |
| 8 | 172502859 | A/G | TTAGTCTCTTGGATGCATA A (SEQ ID NO: 857) | AGTCTCTTGGACGCATAA (SEQ ID NO: 858) | GAAGCTAGTATTGTCCACCT CCTT (SEQ ID NO: 859) | TCGAGAGAGTTAGATGAGAC AGTGA (SEQ ID NO: 860) |
| 8 | 172532270 | A/T | ATAAATCCCCATCGGG (SEQ ID NO: 861) | ATAAATCCCCAACGGG (SEQ ID NO: 862) | GGATCCCCACGAACGCTTG (SEQ ID NO: 863) | GCACGGACACTCAGCTAGTT A (SEQ ID NO: 864) |
| 8 | 172693261 | A/G | CGGCTACGGCGAG (SEQ ID NO: 865) | AGCGGCTACGACGA (SEQ ID NO: 866) | AGGCACGAGTCAACTAGGG A (SEQ ID NO: 867) | CAGCCCATCTGCATCCTCATC (SEQ ID NO: 868) |
| 9 | 11555029 | C/G | CTTGTTTGAAAGGAAATG ACC (SEQ ID NO: 869) | TGTTTGAAAGCAAATGACC (SEQ ID NO: 870) | GTGTCCGCTTGACCCTATAT CTTC (SEQ ID NO: 871) | GCAGCAGCCTTTCCGTTCAG (SEQ ID NO: 872) |
| 9 | 11747146 | A/G | CTTCGGCAGGCACG (SEQ ID NO: 873) | ACGCTTCGACAGGCA (SEQ ID NO: 874) | ACACGGCCACACGGACAC (SEQ ID NO: 875) | TCGCGCTCCCGACAAG (SEQ ID NO: 876) |
| 9 | 11779406 | A/G | AAAGGGCGCTATAGTGG A (SEQ ID NO: 877) | AGGGCGCTACAGTGGAC (SEQ ID NO: 878) | CTTCTAAATTCTGACGAGCA CGAAA (SEQ ID NO: 879) | GGCTGCAGTGATTCAGTTTG AC (SEQ ID NO: 880) |
| 9 | 11789752 | A/T | ACGGTGTGTCCGTCT (SEQ ID NO: 881) | ACGGTGTGTCCGTCA (SEQ ID NO: 882) | GCTCTGCCACTCTGTTGCAT (SEQ ID NO: 883) | CCACGGTGTGGAGTGTGAG (SEQ ID NO: 884) |
| 9 | 11803298 | A/G | CCTCAATCGATATGGATTA (SEQ ID NO: 885) | CACCTCAATCGATATGAA (SEQ ID NO: 886) | CTCACTACGCGGCAG (SEQ ID NO: 887) | TCATGACTGGATACGTATG (SEQ ID NO: 888) |
| 9 | 11817256 | A/G | AGGCACTGGTCGTT (SEQ ID NO: 889) | TAGGCACTGGTCATTG (SEQ ID NO: 890) | GCCAGTACCAGGTACACCAT (SEQ ID NO: 891) | CCTAAGTCATTACCTTGCAGG GATA (SEQ ID NO: 892) |
| 9 | 11999858 | A/G | CTTAGTATGTTTTTGTCAT GA (SEQ ID NO: 893) | TACTTAGTATGTTTTTATCAT GA (SEQ ID NO: 894) | GTTTAACTTCTCTTTGCTAG CCGAT (SEQ ID NO: 895) | CCGGAATGCTACTGAACAAC AC (SEQ ID NO: 896) |
| 9 | 12050694 | A/G | TGTCACACGGCTATC (SEQ ID NO: 897) | CAAATGTCACACAGCTA (SEQ ID NO: 898) | GAACTGATACGCTACTCTT (SEQ ID NO: 899) | ACCATATTGGATAAAACTCTT G (SEQ ID NO: 900) |
| 9 | 12076924 | A/T | CATGCTTTGCGCGGT (SEQ ID NO: 901) | TCATGCTATGCGCGGT (SEQ ID NO: 902) | ATCGTCGCCGCCGTGT (SEQ ID NO: 903) | AGCTCCCGGTGTGATATCCTT (SEQ ID NO: 904) |
| 9 | 12198353 | A/G | AGTGTGGCGATCTCCT (SEQ ID NO: 905) | AGTGTGGCGATCTCCC (SEQ ID NO: 906) | CGACACTGCTCTGCTGAATC (SEQ ID NO: 907) | ACGGTCATTCATCTCATCGAA CA (SEQ ID NO: 908) |
| 9 | 12261852 | A/G | ATTTATTAATAGGCTACGT T (SEQ ID NO: 909) | TGTATTTATTAATAGGCTACA (SEQ ID NO: 910) | AGCAACAGACGCCTCACTT C (SEQ ID NO: 911) | TCCAAGCACAGGAGACAACT AAG (SEQ ID NO: 912) |
| 9 | 12386096 | A/G | TGAGAACAGTCATGCCTT (SEQ ID NO: 913) | AGAACAGTCACGCCTTTG (SEQ ID NO: 914) | TGTTGAAATACGATGCGCTA TGG (SEQ ID NO: 915) | GCCAATGTTGACAACCAAAC AGC (SEQ ID NO: 916) |
| 9 | 12440999 | C/G | AGGTGTAGTCGTCGTGT (SEQ ID NO: 917) | AGGTGTAGTCGTCCTGT (SEQ ID NO: 918) | CTCAATCGATGTTAAATAAG TATC (SEQ ID NO: 919) | GAGATTGGCGTAGTCAA (SEQ ID NO: 920) |
| 9 | 12498968 | A/G | CTATGGCCGGTATGTCAT (SEQ ID NO: 921) | TGGCCGGTATGCCAT (SEQ ID NO: 922) | TGCAGGATTTGTTCAATCTA T (SEQ ID NO: 923) | GACGACGACTTCATCA (SEQ ID NO: 924) |
| 9 | 135116166 | A/G | TTCTCACTCCTTACTT (SEQ ID NO: 925) | CTCACTCCTTACCTT (SEQ ID NO: 926) | AGCGTGTTTGGTTTGAGGA A (SEQ ID NO: 927) | GTGGAGTCACTTTATGCTTCA TGAG (SEQ ID NO: 928) |
| 9 | 135268376 | A/G | CTAGCTCCTGTGGGATG (SEQ ID NO: 929) | CTAGCTCCCGTGGGAT (SEQ ID NO: 930) | CGAGCTGTGGGTCGTGA (SEQ ID NO: 931) | GAAGGCAACCGTCTCGGTAT (SEQ ID NO: 932) |
| 9 | 135492874 | A/G | ACTTCCGCCTGCT (SEQ ID NO: 933) | ACTTCCGCCTGCC (SEQ ID NO: 934) | CCTTCGCCGCGTTACACTG (SEQ ID NO: 935) | GGTGTGGAGTGGACGTGATA C (SEQ ID NO: 936) |
| 9 | 135608295 | A/G | TGGCCCGACATCAGG (SEQ ID NO: 937) | TGTGGCCCAACATCAG (SEQ ID NO: 938) | CGGACTGCTCGACTGGAA (SEQ ID NO: 939) | GTCGAGGGTGAGCCAATACT C (SEQ ID NO: 940) |

TABLE XI-continued

| CHR # | Physical position | SNP | probe 1 sequence | probe 2 sequence | primer 1 sequence | primer 2 sequence |
|---|---|---|---|---|---|---|
| 9 | 135746812 | A/G | TTTGGCAAAACGGTTTATA (SEQ ID NO: 941) | TTTGGCAAAACGGCTTATA (SEQ ID NO: 942) | GGTGCAGCCACTTCTTTAGATG (SEQ ID NO: 943) | CCTAGCCACGTACAGGAGAGAT (SEQ ID NO: 944) |
| 9 | 135895337 | A/G | CAGTGACCCATTTCTTTT (SEQ ID NO: 945) | AGTGACCCATTTCTTTCTT (SEQ ID NO: 946) | AAGGACGAAGTAGCAGCTGGAAAG (SEQ ID NO: 947) | AGGGCTACTTTGGGAACCTCAAATC (SEQ ID NO: 948) |
| 9 | 135978006 | C/G | TACAACTCAGCGAGCTA (SEQ ID NO: 949) | ATGTACAACTCACCGAGC (SEQ ID NO: 950) | AGTGGGCAGTGCACATATGATG (SEQ ID NO: 951) | CAACTCCAACCGCCAATAATGC (SEQ ID NO: 952) |
| 9 | 152012085 | A/G | CCTTTTGGATTACTTCAC (SEQ ID NO: 953) | TTTTGGATCACTTCACA (SEQ ID NO: 954) | GCCGCAGTAAAGTACACGAA (SEQ ID NO: 955) | ATGGGCCTAAAGAACAAATGCACAA (SEQ ID NO: 956) |
| 9 | 152023195 | A/C | ACTTTGGCTATGCTTTG (SEQ ID NO: 957) | TGTTACTTTGGCTATGATT (SEQ ID NO: 958) | ACAATGAACGACTCCTGTCAGAAT (SEQ ID NO: 959) | GGCTCTAGGGACCATGAACA (SEQ ID NO: 960) |
| 9 | 152140312 | A/G | TTAAATTGTCGAGCTTGT (SEQ ID NO: 961) | AAATTGTCGAGCCTGT (SEQ ID NO: 962) | ACTCATGTTTATCCTTAGCAGCAAA (SEQ ID NO: 963) | GCACATTGATAATCTCAGCTCCATT (SEQ ID NO: 964) |
| 9 | 152147083 | A/G | CAACTGAGAGACTGTATG (SEQ ID NO: 965) | CTGAGAGACTGCATGA (SEQ ID NO: 966) | GATGGTGAATAATTGGCATGTATAACC (SEQ ID NO: 967) | GTGCTTGGAGAACCGAAACATAG (SEQ ID NO: 968) |
| 9 | 152166993 | A/G | CTGGGCATTCGGTTT (SEQ ID NO: 969) | CTGGGCATTCGATTTT (SEQ ID NO: 970) | ACAACTGTATCTTACTGCTA (SEQ ID NO: 971) | CCGAAGTTCTCGGTTT (SEQ ID NO: 972) |
| 9 | 152188515 | A/T | AGCAGTCAGTTGTCCAAC (SEQ ID NO: 973) | AGCAGTCAGTAGTCCAAC (SEQ ID NO: 974) | GGATGAAGTTATCAAGCCTGTGA (SEQ ID NO: 975) | TTTGCAAGAGATTCTGTGAACTGT (SEQ ID NO: 976) |
| 9 | 152247427 | A/C | CCGTTCCTTCAATGCTA (SEQ ID NO: 977) | TCCGTTCCTTAAATGCTAC (SEQ ID NO: 978) | GTCTGCCAGTGGTTCCTAACG (SEQ ID NO: 979) | TCACCCCGGGAATTAGGATGATG (SEQ ID NO: 980) |
| 9 | 152292640 | A/G | ATCACCGAGCCAGATAT (SEQ ID NO: 981) | ACCGAGCCAGACATTA (SEQ ID NO: 982) | TTGTTTCCTCCCCCAAGTACAG (SEQ ID NO: 983) | CGCAGGCATGTCTATGACAAC (SEQ ID NO: 984) |
| 9 | 152295588 | A/G | TTCTGGTTTTGTATGTATG (SEQ ID NO: 985) | TAGAGTTCTGGTTTTGTATA (SEQ ID NO: 986) | TGTTTCCTGATGTTTTGGTTGACA (SEQ ID NO: 987) | CCACTCATGTGGGAGTTGTCTC (SEQ ID NO: 988) |
| 9 | 152299814 | A/T | AGGAACAAGGCCTTTCG (SEQ ID NO: 989) | AAGGAACAAGGCCTTACG (SEQ ID NO: 990) | CACCTGAAATCGTTCCACCCAATT (SEQ ID NO: 991) | TTGGCGGAATCACTAGCTGTTC (SEQ ID NO: 992) |
| 9 | 152369485 | A/G | CCACAATTGAAGGAAATGGA (SEQ ID NO: 993) | TGCCACAATTGAAAGAAATG (SEQ ID NO: 994) | GGGATTTATAGAGGGTTCGAGACG (SEQ ID NO: 995) | TCCTATGCTGCGGTCCA (SEQ ID NO: 996) |
| 9 | 152377422 | C/G | CGGACTCGGCTCTC (SEQ ID NO: 997) | CGGACTCCGCTCTC (SEQ ID NO: 998) | GGTTTGGAAGGAGCCCGTTCT (SEQ ID NO: 999) | AGCTTGCCGCCGGAGTA (SEQ ID NO: 1000) |
| 9 | 152400200 | A/C | ACCCTACCCTACCCT (SEQ ID NO: 1001) | CACCCTACACTACCC (SEQ ID NO: 1002) | GATCTTGGCAGGACCAACAC (SEQ ID NO: 1003) | GCGAAGCGATAAGCACACATC (SEQ ID NO: 1004) |
| 9 | 152516032 | A/G | TGTTAGTGGGTATGGGTA (SEQ ID NO: 1005) | TTAGTGGGTATGGATACC (SEQ ID NO: 1006) | GGTACTTACATTTGCGATTC (SEQ ID NO: 1007) | CACGGGTAGCAGGTA (SEQ ID NO: 1008) |
| 9 | 152574700 | A/C | TATTGAGAATTAATGTCTAAGC (SEQ ID NO: 1009) | TGAGAATTAATGGCTAAGC (SEQ ID NO: 1010) | GTGTCTGAGACAGCAGATCGA (SEQ ID NO: 1011) | GGAGGCTTAGATCGTCATATTGC (SEQ ID NO: 1012) |
| 9 | 152583226 | A/G | TGGGTGGTCTGCTAC (SEQ ID NO: 1013) | TGGTCCGCTACCA (SEQ ID NO: 1014) | ACATTGCATTCTTGAATTTAGA (SEQ ID NO: 1015) | ACTTGGTCGGACGTAAG (SEQ ID NO: 1016) |
| 9 | 152591115 | A/C | AAATTCTGGTATTTATATATC (SEQ ID NO: 1017) | TTCTGGTATTTAGATATC (SEQ ID NO: 1018) | TGTACAATTATGCCATTCGGGTTT (SEQ ID NO: 1019) | CCGAGACAATTCGAGTGACCTA (SEQ ID NO: 1020) |
| 9 | 152614701 | A/C | CTTGCTTATGGATTATCATA (SEQ ID NO: 1021) | CACTTGCTTATGGATTATAA (SEQ ID NO: 1022) | GAAAACTTGAAAGGGTAGTG (SEQ ID NO: 1023) | ACAAACAGTCCAGCTTATTTG (SEQ ID NO: 1024) |
| 9 | 152660560 | A/G | TAGGAGGGCATGGGCA (SEQ ID NO: 1025) | AGGGCACGGGCAACT (SEQ ID NO: 1026) | TGTAGCGGGTATCTTACCGACA (SEQ ID NO: 1027) | TCACTTCTTTCTCTGCACAAATCC (SEQ ID NO: 1028) |
| 9 | 152668964 | C/G | CCGAACAGGCAGC (SEQ ID NO: 1029) | CGAACAGCCAGCA (SEQ ID NO: 1030) | TTCCAGATATCGAGAGGA (SEQ ID NO: 1031) | ACTTGCGAAGGTAGACAG (SEQ ID NO: 1032) |

TABLE XI-continued

| CHR # | Physical position | SNP | probe 1 sequence | probe 2 sequence | primer 1 sequence | primer 2 sequence |
|---|---|---|---|---|---|---|
| 9 | 152674493 | A/G | TCTCGGCCCTCCG (SEQ ID NO: 1033) | CTTCTCGACCCTCCG (SEQ ID NO: 1034) | TCCGTCGCGCACATCG (SEQ ID NO: 1035) | GCTGTTGTTACAGTGGGAAT TTACC (SEQ ID NO: 1036) |
| 9 | 152686468 | A/C | TAAATTATTAGTATCTACTA T (SEQ ID NO: 1037) | TTTTAAATTATTAGTATATAC (SEQ ID NO: 1038) | TGCGACGTTTATTGAAACAC AGTTA (SEQ ID NO: 1039) | CCGCACGGCTTATGTACAC (SEQ ID NO: 1040) |
| 9 | 152727140 | A/G | TTGTGAATTGACCGGTAT (SEQ ID NO: 1041) | TGAATTGACCGGCATG (SEQ ID NO: 1042) | ACCCTTGATGTTTCTCATAC GATGC (SEQ ID NO: 1043) | CGCGGATATTCAGCGTCTAC (SEQ ID NO: 1044) |
| 9 | 152805126 | C/G | CGATCCCACCGGC (SEQ ID NO: 1045) | CGATCCCACCCGC (SEQ ID NO: 1046) | AAAACAGCCGAGTATCC (SEQ ID NO: 1047) | GGGTGGTTTTGTTCGT (SEQ ID NO: 1048) |
| 9 | 152862803 | A/G | TGTTTCCAGACTAGTC (SEQ ID NO: 1049) | TTCCAGACTAGCCTT (SEQ ID NO: 1050) | ACAAGGGATTCTAATTTTTC CAATGAAA (SEQ ID NO: 1051) | CGCTAATCATATATAGGCGAC TCTTC (SEQ ID NO: 1052) |
| 9 | 152874462 | A/G | TGTGGTCCAAATTTTGTAT (SEQ ID NO: 1053) | TGGTCCAAATTTTGCAT (SEQ ID NO: 1054) | ACACGTCATGCTTACCTACG A (SEQ ID NO: 1055) | GCTTCACTCGCAAGACAGTT G (SEQ ID NO: 1056) |
| 9 | 152890683 | A/G | CGGTTGCCATTATCAT (SEQ ID NO: 1057) | CGGTTGCCATTACC (SEQ ID NO: 1058) | GGTGGTCCCCCTGACC (SEQ ID NO: 1059) | GTGGTCGACGTCGTTCAATTT C (SEQ ID NO: 1060) |
| 9 | 152894385 | A/G | CGGCCAGTTCACCTT (SEQ ID NO: 1061) | CCGGCCAATTCACC (SEQ ID NO: 1062) | GGTTCGCCGAATGCCA (SEQ ID NO: 1063) | GCATGGATTCCGCACTGAA (SEQ ID NO: 1064) |
| 10 | 128376614 | A/G | CAGAGGACAGAAAGTAT AGG (SEQ ID NO: 1065) | CAGAGGACAGAAAGTACAG (SEQ ID NO: 1066) | CCCTGGAGGCTGGAGCAG (SEQ ID NO: 1067) | ATCTGTTGGCGCCCCTAAACC (SEQ ID NO: 1068) |
| 10 | 128388069 | C/G | ACTAGTTGTGTGCGAATT (SEQ ID NO: 1069) | ACTAGTTGTGTGCCAAT (SEQ ID NO: 1070) | CTACTGGTTCGGTGTTTC (SEQ ID NO: 1071) | ACCTTTGAGGGAATTATTTCA (SEQ ID NO: 1072) |
| 10 | 128394181 | C/G | ATGTACTACAGACATTTGA A (SEQ ID NO: 1073) | TGTACTACAGACATTTCAA (SEQ ID NO: 1074) | GGTGCTACTACAGGTTTGG ACT (SEQ ID NO: 1075) | ACTAGCCTAGCTGCTTCCAAC T (SEQ ID NO: 1076) |
| 10 | 128399735 | A/G | CTTTCTATTATACTTGCATG (SEQ ID NO: 1077) | TTCTATTATACTTGCACG (SEQ ID NO: 1078) | CCCTGCGTATGGGCTCTG (SEQ ID NO: 1079) | GCGTGAACTACACGGTGAAA G (SEQ ID NO: 1080) |
| 10 | 128415372 | A/G | CACGTCGGGGCCG (SEQ ID NO: 1081) | ACGTCGGGGCCACG (SEQ ID NO: 1082) | GCACGCGCCGTGAACT (SEQ ID NO: 1083) | GGCCCAGCGTGCCTAT (SEQ ID NO: 1084) |
| 10 | 128573259 | C/G | AATCTCAAGTTTGTACATC (SEQ ID NO: 1085) | AATCTCAAGTTTCTACATC (SEQ ID NO: 1086) | TGATAGATCTTAGGAAAGTG AT (SEQ ID NO: 1087) | CAACCACAAGGGTGTC (SEQ ID NO: 1088) |
| 10 | 128601227 | A/G | ATCGAACCAGTTCTGTGC (SEQ ID NO: 1089) | AACCAGTCCTGTGCAC (SEQ ID NO: 1090) | GGCGTAGAGGATATGTGAG AACAG (SEQ ID NO: 1091) | GTGGGAAGGAAGCCGACTT T (SEQ ID NO: 1092) |
| 10 | 128608139 | A/G | CCATAATCTCCTAATCTAA GAA (SEQ ID NO:) 1093 | CCATAATCTCCTAACCTAAG (SEQ ID NO: 1094) | TGCAATGGTGTTTATAGGCA AGT (SEQ ID NO: 1095) | TGGTGAGCCCTACTGTATTGT TAC (SEQ ID NO: 1096) |
| 10 | 128632607 | A/G | AAGTTTGTGATTTCTGTT G (SEQ ID NO: 1097) | TGTGATTTCCGTTGG (SEQ ID NO: 1098) | AAATTATTGTCATGCATACAC (SEQ ID NO: 1099) | CTCAAGGCCTATGAACTATC (SEQ ID NO: 1100) |
| 10 | 128640250 | A/G | ATCCGGCGGAGTGG (SEQ ID NO: 1101) | ATCCGGCGGAGCG (SEQ ID NO: 1102) | TCCGACTCCGCCAGC (SEQ ID NO: 1103) | GTTCGTGGTGGACGAGGA (SEQ ID NO: 1104) |
| 10 | 128644223 | A/G | AGTACTACATAGCATTTA C (SEQ ID NO: 1105) | AGTACTACATAGCACATTA (SEQ ID NO: 1106) | AACCATCCATTCAACACACC AAAG (SEQ ID NO: 1107) | CCCGCTAACCCGTGGGTAT (SEQ ID NO: 1108) |
| 10 | 128649900 | C/G | CCGCAGCGAAGGC (SEQ ID NO: 1109) | CCGCAGCCAAGGC (SEQ ID NO: 1110) | TCCCTTCCAAGAGCACACG (SEQ ID NO: 1111) | GTGCTCAGGTACTACGCCTAC (SEQ ID NO: 1112) |
| 10 | 128655287 | A/G | CCTTCATACTGGGCCAAT (SEQ ID NO: 1113) | CTTCATACCGGGCCAAT (SEQ ID NO: 1114) | GGCCTCTTGACAAATAGCAC AA (SEQ ID NO: 1115) | CGGAGTACCAGCAACATATA GCA (SEQ ID NO: 1116) |
| 10 | 128934579 | A/G | CGGGTACAGGTGGC (SEQ ID NO: 1117) | CGGGTACAGATGGCG (SEQ ID NO: 1118) | GCACAGCCGCGTCAAGT (SEQ ID NO: 1119) | CGTTGCCCACCAGAGTCG (SEQ ID NO: 1120) |
| 10 | 129045229 | A/G | CGACGCCGCTGCT (SEQ ID NO: 1121) | AGAGCGACACCGCTG (SEQ ID NO: 1122) | GAGCTCGTCACAGCCTTCC (SEQ ID NO: 1123) | AACCCGAGCCTCGCCGATT (SEQ ID NO: 1124) |

TABLE XI-continued

| CHR # | Physical position | SNP | probe 1 sequence | probe 2 sequence | primer 1 sequence | primer 2 sequence |
|---|---|---|---|---|---|---|
| 10 | 129063699 | −/GCT | TGCTGATACTACTCATACA (SEQ ID NO: 1125) | CTGATACTGCTACTCATAC (SEQ ID NO: 1126) | GAATCTTTGGTTGCAGCTTG C (SEQ ID NO: 1127) | TCTGTGTCGATCCCATGTGTA (SEQ ID NO: 1128) |
| 10 | 129133123 | A/G | ACCTTTTGATGAGTTCCA (SEQ ID NO: 1129) | ACCTTTTGATGAGCTCC (SEQ ID NO: 1130) | AAACTTGAATTGGTGGAGC (SEQ ID NO: 1131) | GTGCACGTGTCTCTATAC (SEQ ID NO: 1132) |
| 10 | 129149080 | A/T | TTCATCAGGAAACAACT (SEQ ID NO: 1133) | TTCATCAGGAAACAACA (SEQ ID NO: 1134) | CTCTTGCCAAGGCTGCA (SEQ ID NO: 1135) | TTCAAGCATTCGCTGACTTCT G (SEQ ID NO: 1136) |

Preferred markers and assays are listed in Table XII below:

TABLE XII

| CHR# | Physical position on CHR | R/S | Probe for Resistant allele | Probe for Susceptible allele | primer 1 sequence | primer 2 sequence |
|---|---|---|---|---|---|---|
| 1 | 3702462 | A/G | AGTGGTGAACCTT GTGTTAT (SEQ ID NO: 1137) | TGGTGAACCTCGTGTTAT (SEQ ID NO: 1138) | GCGCACTTGATTGGCATTCT (SEQ ID NO: 1139) | CGCACACACACAACCAAGAC (SEQ ID NO: 1140) |
| 1 | 3702464 | C/G | ACAACGTTCACCA CTAACAC (SEQ ID NO: 1141) | ACAAGGTTCACCACTAACA C (SEQ ID NO: 1142) | AGAGTGCGAAGAGCAACACA (SEQ ID NO: 1143) | TAGCTGCCTTGGGGCTATAA (SEQ ID NO: 1144) |
| 1 | 222146924 | C/T | TGCCCCCCAGGCG GGGT (SEQ ID NO: 1145) | TGCTCCCCAGGCGGGGT (SEQ ID NO: 1146) | AGCAGTGCTCAATCGGTCTT (SEQ ID NO: 1147) | GACCCCTCCACCTCCTTATC (SEQ ID NO: 1148) |
| 2 | 9122256 | C/A | CTCAAGCCTGCTG GTA (SEQ ID NO: 1149) | TCAAGCCTGATGGTACA (SEQ ID NO: 1150) | GTGGGTTGTAAGTGGGTGTT TA (SEQ ID NO: 1151) | TTCTCCTTCTTTCTGAGTATAG CCT (SEQ ID NO: 1152) |
| 3 | 19344196 | C/A | TCCAAAAACTTGT TGTTCTCCCA (SEQ ID NO: 1153) | TCCAAAAAATTGTTGTTCTC CCA (SEQ ID NO: 1154) | TCGTCTTCTCGTATGCATGG (SEQ ID NO: 1155) | TGCGACAAAATTGACGAAGA (SEQ ID NO: 1156) |
| 3 | 19344197 | T/G | AATGGGAGAACAACA AGTTTT (SEQ ID NO: 1157) | TGGGAGAACAACACGTTTT (SEQ ID NO: 1158) | CAGTGCATCCACGGTGGTC (SEQ ID NO: 1159) | CTTTGCTTTCTTGAACAGACTT GGT (SEQ ID NO: 1160) |
| 3 | 19826372 | A/C | ATTCGTAACACCAGC CT (SEQ ID NO: 1161) | CGTAACCCCAGCCT (SEQ ID NO: 1162) | TGCGCATCGCAGCAG (SEQ ID NO: 1163) | ACAGACAGCAGGCCTCAAC (SEQ ID NO: 1164) |
| 3 | 151251885 | G/A | TGATTAATTCGTCTG ACCA (SEQ ID NO: 1165) | TTGATTAATTCATCTGACCA (SEQ ID NO: 1166) | TGAGATGGTTGTGTTAT GACTCCA (SEQ ID NO: 1167) | TCCGACACCCAGAATCAAA TGG (SEQ ID NO: 1168) |
| 3 | 199952894 | C/G | CCCGACACCTGTCCT TC (SEQ ID NO: 1169) | CCCGACAGCTGTCCTTC (SEQ ID NO: 1170) | GGAGACGTCAGCAAGGACTC (SEQ ID NO: 1171) | AGCCCTGGACCTTCCTTTTA (SEQ ID NO: 1172) |
| 3 | 214794069 | T/G | AAAGATGAAGAAACA ATCAATGTA (SEQ ID NO: 1173) | TGAAGAAACAATCCATGTAT A (SEQ ID NO: 1174) | GTGGTGCAAGCGTGGTC (SEQ ID NO: 1175) | GTGCAAAGGTTGCTTGGAATTG AG (SEQ ID NO: 1176) |
| 3 | 214794158 | T/C | TTCAAGGTTTTTTTG CAAATA (SEQ ID NO: 1177) | TTCAAGGTTCTTTTGCAAAT A (SEQ ID NO: 1178) | GTGCAAAGGTTGCTTGGAAT (SEQ ID NO: 1179) | CCAAAGGAAAGGCATTTGAA (SEQ ID NO: 1180) |
| 3 | 214794170 | A/G | CATTTACCTTTGATT ATTTGC (SEQ ID NO: 1181) | TTACCTTTGACTATTTGCA (SEQ ID NO: 1182) | CCAAAGGAAAGGCATTTGAA ACAGG (SEQ ID NO: 1183) | GACCACGCTTGCACCACAT (SEQ ID NO: 1184) |
| 4 | 242643396 | A/G | TCAGGGCGAGATGAA ACG (SEQ ID NO: 1185) | ATCAGGGCGAGACGAAAC (SEQ ID NO: 1186) | GGGTAGCTTGTTCCCAAGG ATT (SEQ ID NO: 1187) | TGGAGAGGTGGACAGGTAGTAG (SEQ ID NO: 1188) |
| 5 | 186795332 | C/T | CGACTGGATCAGCGA AG (SEQ ID NO: 1189) | CACGACTGGATTAGCGAA (SEQ ID NO: 1190) | GCGCACAAGCCGTCTAC (SEQ ID NO: 1191) | GACGCCCTTGCTGTATGTATG (SEQ ID NO: 1192) |

TABLE XII-continued

| CHR# | Physical position on CHR | R/S | Probe for Resistant allele | Probe for Susceptible allele | primer 1 sequence | primer 2 sequence |
|---|---|---|---|---|---|---|
| 5 | 207505420 | A/C | TCTTGGAGTTGCTTG AC (SEQ ID NO: 1193) | CTCTTGGAGTTGCTTGA (SEQ ID NO: 1194) | TGAGTGTACTTCGTTTGGCT AATG (SEQ ID NO: 1195) | AGGATCATGACACAGAAATTCG AGA (SEQ ID NO: 1196) |
| 5 | 207505421 | C/A | TCTTGGAGTTGCTTG AC (SEQ ID NO: 1197) | CTCTTGGAGGTGCTTGA (SEQ ID NO: 1198) | TGAGTGTACTTCGTTTGGCT AATG (SEQ ID NO: 1199) | AGGATCATGACACAGAAATTCG AGA (SEQ ID NO: 1200) |
| 5 | 212254755 | A/T | ACTTCTAGAGAAAAA AAAAAAATAGA (SEQ ID NO: 1201) | ACTTCTAGAGAAAAATAAA AAATAGA (SEQ ID NO: 1202) | ACCTCCTTTTGGTCCGTTTT (SEQ ID NO: 1203) | GGAGGCAAGTGAGGAGACTG (SEQ ID NO: 1204) |
| 5 | 215392749 | A/G | ATTAGGTTGTTTCCA GCAA (SEQ ID NO: 1205) | AGGTTGTTCCCAGCAA (SEQ ID NO: 1206) | TGTTGGGCAATCAAACTTCA GG (SEQ ID NO: 1207) | AGGCCACGGTGACCATGTAAG (SEQ ID NO: 1208) |
| 5 | 215500881 | C/T | TCTACTCTGAGGCTG TATT (SEQ ID NO: 1209) | TCTACTCTGAGGTTGTATTT G (SEQ ID NO: 1210) | GCAACATGATCTCTTCACCA ATGA (SEQ ID NO: 1211) | CAACCAGCTCACCAGAACAATG (SEQ ID NO: 1212) |
| 6 | 86282196 | C/T | CGTCGAGATCCTCATTC (SEQ ID NO: 1213) | ACGTCGAGATCTTCATTCA (SEQ ID NO: 1214) | TCGGAGCCTTGGATCATCA (SEQ ID NO: 1215) | GCCCGATCTTCCGTGAGATAC (SEQ ID NO: 1216) |
| 7 | 136725791 | C/G | ACCCTCCCTCCGAAA (SEQ ID NO: 1217) | ACCCTCGCTCCGAAA (SEQ ID NO: 1218) | CGCCTTCCAGTCCACAATCT C (SEQ ID NO: 1219) | GCGGTCTCTCTCTCTCTCT (SEQ ID NO: 1220) |
| 8 | 4128809 | G/A | AACAGTAGTATCTTGT GCAT (SEQ ID NO: 1221) | AACAGTAGTATTTTGTGCAT (SEQ ID NO: 1222) | AGCCGCTCACTTTGTGGTAT TCATC (SEQ ID NO: 1223) | AGTACGGATAGTCCCATGTTCA (SEQ ID NO: 1224) |
| 8 | 4128860 | A/T | CACAAAGTGAGCGGCTT (SEQ ID NO: 1225) | CACAAAGTGTGCGGCTT (SEQ ID NO: 1226) | TCTAGCTTCATTGTGCAGGG ATG (SEQ ID NO: 1227) | GAGATCTTGAGGGTGTCCCAAA (SEQ ID NO: 1228) |
| 8 | 10122708 | A/G | CCATTGCTCAGGAGTT AGAA (SEQ ID NO: 1229) | TGCTCAGGAGCTAGAAAC (SEQ ID NO: 1230) | CATCAAGGGACTCCGAGCTT CT (SEQ ID NO: 1231) | CAGCTTCCTCGGCAACTTTAAC AG (SEQ ID NO: 1232) |
| 8 | 10122766 | T/C | CATCCTTTGCTGATAG CA (SEQ ID NO: 1233) | TCCTTTGCCGATAGCA (SEQ ID NO: 1234) | AGCTCGGAGTCCCTTGATGG T (SEQ ID NO: 1235) | CGAAGTGACCCGCCTTACAC (SEQ ID NO: 1236) |
| 8 | 10122892 | T/C | TGTTGGAATCTCGGTA CA (SEQ ID NO: 1237) | TGTTGGAATCCCGGTAC (SEQ ID NO: 1238) | TCCAAGATGGTCAGCGAGT (SEQ ID NO: 1239) | CGCGACAACCTGGACAGAT (SEQ ID NO: 1240) |
| 8 | 164990912 | A/C | TCAGGTACTCTACAAAC TCT (SEQ ID NO: 1241) | CAGGTACTCTACCAACTCT (SEQ ID NO: 1242) | GACCAGAGAGCTGACAGGAA C (SEQ ID NO: 1243) | GCTCTGTGGCGTGAGATAGATG (SEQ ID NO: 1244) |
| 8 | 172218916 | C/T | CATATCCGGGCAGTCC (SEQ ID NO: 1245) | CCATATCCGGACAGTCC (SEQ ID NO: 1246) | GAGTTGGATGGTCCAGCGTA (SEQ ID NO: 1247) | GGACCGTCCGCCATCTTAC (SEQ ID NO: 1248) |
| 9 | 11929493 | C/T | AAGCCTTTTTCACCTC TTTT (SEQ ID NO: 1249) | AAGCCTTTTTCACTTCTTTT (SEQ ID NO: 1250) | GCTGAGTCTTGGCTGTACAC A (SEQ ID NO: 1251) | GAGTGCCAACACAAGTGCTTA (SEQ ID NO: 1252) |
| 9 | 135483968 | T/C | AATAATGTGTGGTGAA TGCGA (SEQ ID NO: 1253) | AATAATGCGTGGTGAATGC GA (SEQ ID NO: 1254) | AAATGCAATCGAGGCTGAAC (SEQ ID NO: 1255) | TTCATGCCATTTGCCAGATA (SEQ ID NO: 1256) |
| 9 | 135483999 | G/A | TCTTGTGGGAGACCCA (SEQ ID NO: 1257) | CAAGGTCTTGTGAGAGAC C (SEQ ID NO: 1258) | GTTCGGACATTTATGGGCAC TATTG (SEQ ID NO: 1259) | CCTAGGATCTCATGATGGAT CTTCA (SEQ ID NO: 1260) |
| 9 | 152415102 | C/T | AGCAAAGTGGGCGTCC (SEQ ID NO: 1261) | AGCAAAGTAGGCGTCCA (SEQ ID NO: 1262) | GCTATCTCAATTCTTTGGTC ACATC (SEQ ID NO: 1263) | AGGTGGCAACCAGTTGTTAGG (SEQ ID NO: 1264) |
| 9 | 152415196 | T/G | TTGGTATCTTATTATT GTCAA (SEQ ID NO: 1265) | TGGTATCTTATTCTTGTCAA (SEQ ID NO: 1266) | CTTTGAGTAGTGCGGCAGTG AT (SEQ ID NO: 1267) | GGTGGTGGACGCCTACTTTG (SEQ ID NO: 1268) |

TABLE XII-continued

| CHR# | Physical position on CHR | R/S | Probe for Resistant allele | Probe for Susceptible allele | primer 1 sequence | primer 2 sequence |
|---|---|---|---|---|---|---|
| 10 | 12881228 | A/C | CCTCGGGGGCTAAAA (SEQ ID NO: 1269) | CCTCGGGGGCTCAAA (SEQ ID NO: 1270) | CAGCTACGTCGCTTCTACCC (SEQ ID NO: 1271) | ACGTGTACCTCGTCGTTTCC (SEQ ID NO: 1272) |

(R/S = Resistance/Susceptible)

Table XIII lists probes and primers that can be used to identify the interval locations of Table X.

TABLE XIII

| CHR# | Physical position | SNP | probe 1 sequence | probe 2 sequence | primer 1 sequence | primer 2 sequence |
|---|---|---|---|---|---|---|
| 1 | 3225079 | A/G | TGTAAAATCTGGCCGTA (SEQ ID NO: 1273) | TGTAAAATCTGGCTGT (SEQ ID NO: 1274) | CACCAGTTTCGTGTCAAG GA (SEQ ID NO: 1275) | TTCCGCCCGAG AGATTTAGAAG (SEQ ID NO: 1276) |
| 1 | 4188653 | A/G | TTACCAGGAACAGTAAAC (SEQ ID NO: 1277) | TACCAGGAACAATAAACA (SEQ ID NO: 1278) | TTCCACTATCGACCGAA (SEQ ID NO: 1279) | GGGATTTGAGG TTATGTTCT (SEQ ID NO: 1280) |
| 1 | 221604561 | A/G | CCGAGCGTGAGTTACTT (SEQ ID NO: 1281) | CCGAGCGTGAATTACTTT (SEQ ID NO: 1282) | TTCGTCGGTAGCAGAATC ACT (SEQ ID NO: 1283) | ACGGATACCTCA CTCATCACCTT (SEQ ID NO: 1284) |
| 1 | 222599974 | A/C | TCACATCTTGCATAAATAA (SEQ ID NO: 1285) | CACATCTTGCATAAAGAAT (SEQ ID NO: 1286) | ATGGGACAAAGAGTCTAG CATT (SEQ ID NO: 1287) | GGTTCAATCAAC AATCACA (SEQ ID NO: 1288) |
| 2 | 8618657 | A/G | CTTGATTCAGTCCGAGAAG (SEQ ID NO: 1289) | TTGATTCAGCCCGAGA (SEQ ID NO: 1290) | CAGTATAGCTCGGTGTTG CTCA (SEQ ID NO: 1291) | CGCGTGGAACAG GGTAGAG (SEQ ID NO: 1292) |
| 2 | 9599938 | A/C | CCTCCATAATGATTAGATC (SEQ ID NO: 1293) | CCTCCATAATGAGTAGATC (SEQ ID NO: 1294) | CCTACGATCGATTTCTAAG CGTCTA (SEQ ID NO: 1295) | GCGACAACTCTC CAACAACAAC (SEQ ID NO: 1296) |
| 3 | 14511390 | A/G | AGTCCATTGGAGGTTCG (SEQ ID NO: 1297) | AGTCCATTGGAGATTCG (SEQ ID NO: 1298) | TTTGGGCATCACTTGTCTC AA (SEQ ID NO: 1299) | GCGATGCCACGG AACATAA (SEQ ID NO: 1300) |
| 3 | 215165758 | C/G | ACGATCATGGCCTGG (SEQ ID NO: 1301) | ACGATCATGGCGTGG (SEQ ID NO: 1302) | CGGCGTGGCATACAAGGA (SEQ ID NO: 1303) | CAACGCGGCTCG TTCATCAG (SEQ ID NO: 1304) |
| 4 | 242101915 | A/G | TGATGACCCTGTTGGG (SEQ ID NO: 1305) | TGATGACCCCGTTGG (SEQ ID NO: 1306) | GCGTGTCGGTACGTGGAT (SEQ ID NO: 1307) | ACCATGCTACGC CAAGTTCA (SEQ ID NO: 1308) |
| 4 | 243081515 | A/G | TTTTCAGGCAGCTTTTAT AA (SEQ ID NO: 1309) | TTCAGGCAGCTTCTATAAA (SEQ ID NO: 1310) | GCAGACTGCAAAACACTT AGC (SEQ ID NO: 1311) | GGTTTGACCCTAT TTCTCTTTCACA (SEQ ID NO: 1312) |
| 5 | 186344944 | A/G | CCCGGCGGTGGAA (SEQ ID NO: 1313) | TCGCCCGACGGTG (SEQ ID NO: 1314) | TGTCGGCCGCCATTGT (SEQ ID NO: 1315) | GACGACAGCTACG ACATGATAC (SEQ ID NO: 1316) |
| 5 | 187256786 | A/G | ATTGGATGGCCTGGAGGC (SEQ ID NO: 1317) | TTGGATGGCCCGGAGG (SEQ ID NO: 1318) | GACGTTAGAGACCTTGAA GTTAGGA (SEQ ID NO: 1319) | GTCGCGAACATCG ACAAGAAG (SEQ ID NO: 1320) |
| 5 | 207001816 | A/G | CTTTTCGCTACAGCT (SEQ ID NO: 1321) | TTCTTTTCGCTACAACT (SEQ ID NO: 1322) | GGTAGCACATTGCATAGG (SEQ ID NO: 1323) | GCTCAATACAGT AATTCCTCAT (SEQ ID NO: 1324) |

TABLE XIII-continued

| CHR# | Physical position | SNP | probe 1 sequence | probe 2 sequence | primer 1 sequence | primer 2 sequence |
|---|---|---|---|---|---|---|
| 5 | 215694297 | A/G | CAACGCTCACTTACC (SEQ ID NO: 1325) | AACGCTCGCTTACC (SEQ ID NO: 1326) | CAAGCAGAGGAAGGGAC ATTCAT (SEQ ID NO: 1327) | GGGTAGCTGTCC GAATTTAATAGA AGA (SEQ ID NO: 1328) |
| 6 | 85714579 | A/G | TTTATTTGAATGGCTATA (SEQ ID NO: 1329) | TTTATTTGAATGACTATATA (SEQ ID NO: 1330) | AGGGCAGTCAGCACAAGT TAGAAG (SEQ ID NO: 1331) | ATGTGGCCGGTG AAGTGT (SEQ ID NO: 1332) |
| 6 | 86684841 | A/G | CTGCCGTCATCGTCG (SEQ ID NO: 1333) | CCGTCACCGTCGC (SEQ ID NO: 1334) | CCGGTCGTCACCGTCATC (SEQ ID NO: 1335) | TGGACTCTCCGA CTCCTCTAAG (SEQ ID NO: 1336) |
| 7 | 136237488 | A/G | CTAAGGTCCGTCAAAGC (SEQ ID NO: 1337) | AACTAAGGTCCATCAAAGC (SEQ ID NO: 1338) | CGAGGCCCACTAAATATA GACTCAG (SEQ ID NO: 1339) | AGGTATTGGTTC TCGAAGGCTTAT (SEQ ID NO: 1340) |
| 7 | 137181700 | A/G | TAAATGAGACAACGATAG ATATA (SEQ ID NO: 1341) | TGAGACAACGACAGATATAA (SEQ ID NO: 1342) | ACCATAGCTCTTGCTCACG A (SEQ ID NO: 1343) | CCACTTGTTATG AGGCAGGTCA (SEQ ID NO: 1344) |
| 8 | 3624919 | A/G | CGGCAGACGCGC (SEQ ID NO: 1345) | CGGCAGACGCACC (SEQ ID NO: 1346) | CGGGTTCGGCGAGACG (SEQ ID NO: 1347) | TGGCCTCACGGT TCTGAA (SEQ ID NO: 1348) |
| 8 | 4585283 | A/G | AGAGTTCTTTGGGTCTC (SEQ ID NO: 1349) | AGAGTTCTTTGAGTCTCTTT (SEQ ID NO: 1350) | TGTCAGTATTGTTCCATGC ACAGTT (SEQ ID NO: 1351) | TGATGCCACTAC CACGATTGTC (SEQ ID NO: 1352) |
| 8 | 9535964 | A/G | AGAGGTACCGTCCGTTTC (SEQ ID NO: 1353) | CAAGAGGTACCATCCGTT (SEQ ID NO: 1354) | GACGCGACTTCGTCACCA T (SEQ ID NO: 1355) | GCGGGTCGAAGC TGAATC (SEQ ID NO: 1356) |
| 8 | 10493645 | C/G | CGAATAACAGAATAGTTG AGAAC (SEQ ID NO: 1357) | CGAATAACAGAATACTTGAG AAC (SEQ ID NO: 1358) | GGGCAACTGAATATACAA CCTTGA (SEQ ID NO: 1359) | GACACCTTTGGG CATATTGGA (SEQ ID NO: 1360) |
| 8 | 164507475 | A/C | TGCGTTAAGGTTTATTTCT (SEQ ID NO: 1361) | TGCGTTAAGGTTTAGTTC (SEQ ID NO: 1362) | TCACGATTTTGAAGTAGTC GAGTCA (SEQ ID NO: 1363) | TGCAGCCCAAAA CAGCAA (SEQ ID NO: 1364) |
| 8 | 172699565 | A/G | CACAGCCCTGCCTTG (SEQ ID NO: 1365) | ACAGCCCCGCCTTG (SEQ ID NO: 1366) | ATAGACGGCCTCCGGTCA C (SEQ ID NO: 1367) | TGCTACGGCACA ATAAATGAATGA (SEQ ID NO: 1368) |
| 9 | 11507069 | A/G | AATCCCTTAATGTGTCTTC (SEQ ID NO: 1369) | AATCCCTTAATGCGTCTT (SEQ ID NO: 1370) | TTGCATCGCCAATACCCA (SEQ ID NO: 1371) | TTTGTGAACATT ACTCCTTTGTGT C (SEQ ID NO: 1372) |
| 9 | 135985429 | A/C | CATTGTTTATTACAGTTC CT (SEQ ID NO: 1373) | CATTGTTTATTAAAGTTCCTA (SEQ ID NO: 1374) | AGCCGAGCAAGGGTAATG GT (SEQ ID NO: 1375) | GGAAGTAAAGGA CCCTCTGAAATG T (SEQ ID NO: 1376) |
| 9 | 151907512 | A/C | AATCCGTGTCTTCTCTGT (SEQ ID NO: 1377) | AAATCCGTGTATTCTCTGT (SEQ ID NO: 1378) | CGGCGCCCGTGGTTT (SEQ ID NO: 1379) | GAGAGATAGAGG GAGTCAGGGAGA T (SEQ ID NO: 1380) |
| 9 | 152897067 | A/G | CGTCTGCAGCTGAC (SEQ ID NO: 1381) | CGTCTGCAGCCGA (SEQ ID NO: 1382) | ACACTCGACAAGGCGTCG TC (SEQ ID NO: 1383) | CTCGAGACTCAC AAGCTATCAC (SEQ ID NO: 1384) |
| 10 | 128310945 | C/G | ACAGTCCGGTGCAC (SEQ ID NO: 1385) | CGGACAGTCCGCTG (SEQ ID NO: 1386) | CGAGAGCAGCAAGTTC (SEQ ID NO: 1387) | GAAGAGATGGCC TTGTTC (SEQ ID NO: 1388) |

TABLE XIII-continued

| CHR# | Physical position | SNP | probe 1 sequence | probe 2 sequence | primer 1 sequence | primer 2 sequence |
|---|---|---|---|---|---|---|
| 10 | 129283212 | A/G | CCAAAAGGTACTGTCCGT (SEQ ID NO: 1389) | CAAAAGGTACCGTCCGT (SEQ ID NO: 1390) | ACGCGACTTCACCACCGT (SEQ ID NO: 1391) | TTGGTGGATCGA AGCTGAAATC (SEQ ID NO: 1392) |

Using the teachings contained herein, those of ordinary skill in the art will be able to locate other marker alleles within the intervals of Table X.

Methods for producing an ear rot resistance plant may comprise, consist essentially of or consist of detecting, in a germplasm, a marker associated with enhanced ear rot resistance and producing a maize plant from said germplasm. The marker may be detected in any sample taken from the germplasm, including, but not limited to, a portion of said germplasm (e.g., a seed chip or a cell from said germplasm) or a nucleotide sequence from said germplasm. Such a sample may be taken from the germplasm using any present or future method known in the art, including, but not limited to, automated methods of removing a portion of endosperm with a sharp blade, drilling a small hole in the seed and collecting the resultant powder, cutting the seed with a laser and punching a leaf disk. The germplasm may be of a non-naturally occurring variety of maize. In some embodiments, the genome of the germplasm is at least about 50%, 55%, 60%, 65%, 70%, 75%, 80%, 85%, 90%, 95%, 97%, 99% or 100% identical to that of an elite variety of maize. An ear rot resistant plant is then produced from the germplasm identified as having the marker associated with enhanced ear rot resistance according to methods well known in the art for breeding and producing plants from germplasm.

Methods for producing and/or selecting an ear rot resistant maize plant or germplasm may comprise crossing a first maize plant or germplasm with a second maize plant or germplasm, wherein said first soybean plant or germplasm comprises a marker associated with enhanced ear rot resistance, and selecting a progeny plant or germplasm comprising said marker associated with enhanced ear rot resistance. Either the first or second maize plant or germplasm, or both, may be of a non-naturally occurring variety of soybean. In some embodiments, the second maize plant or germplasm is of an elite variety of maize.

In some embodiments, the genome of the second maize plant or germplasm is at least about 50%, 55%, 60%, 65%, 70%, 75%, 80%, 85%, 90%, 95%, 97%, 99% or 100% identical to that of an elite variety of maize.

In one example, a method of producing a maize plant having enhanced ear rot resistance comprises the steps of a) isolating a nucleic acid from a maize cell or plant part; b) detecting, in said cell or plant part the presence of a marker associated with increased ear rot resistance, wherein said marker is located within at least one chromosomal interval of selected from the group consisting of (aa) maize chromosome 1 corresponding to physical positions 3,225,079 to 4,188,653; (bb) maize chromosome 1 corresponding to physical positions 221,604,561 to 222,599,974; (cc) maize chromosome 2 corresponding to physical positions 8,618, 657 to 9,599,938; (dd) maize chromosome 3 corresponding to physical positions 14,511,390 to 215,165,758; (ee) maize chromosome 4 corresponding to physical positions 242,101, 915 to 243,081,515; (ff) maize chromosome 5 corresponding to physical positions 186,344,944 to 187,256,786; (gg) maize chromosome 5 corresponding to physical positions 207,001,816 to 215,694,297; (hh) maize chromosome 6 corresponding to physical positions 85,714,579 to 86,684, 841; (ii) maize chromosome 7 corresponding to physical positions 136,237,488 to 137,181,700; (jj) maize chromosome 8 corresponding to physical positions 3,624,919 to 4,585,283; (kk) maize chromosome 8 corresponding to physical positions 9,535,964 to 10,493,645; (ll) maize chromosome 8 corresponding to physical positions 164,507,475 to 172,699,565; (mm) maize chromosome 9 corresponding to physical positions 11,507,069 to 135,985,429; (nn) maize chromosome 9 corresponding to physical positions 151,907, 512 to 152,897,067; and (oo) maize chromosome 10 corresponding to physical positions 128,310,945 to 129,283,212; and c) crossing a maize plant that comprises said marker within its genome with another maize plant that does not comprise said marker to yield a progeny maize plant comprising the marker within its genome.

In many such examples, the maize chromosome 1 corresponding to physical positions 3,225,079 to 4,188,653 comprises at least one of an A allele at a position corresponding to physical position 3702462 and a C allele at a position corresponding to physical position 3702464; the maize chromosome 1 corresponding to physical positions 221,604, 561 to 222,599,974 comprises a C allele at a position corresponding to physical position 222146924; the maize chromosome 2 corresponding to physical positions 8,618, 657 to 9,599,938 comprises a C allele at a position corresponding to physical position 9122256; the maize chromosome 3 corresponding to physical positions 14,511,390 to 215,165,758 comprises at least one of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; the maize chromosome 4 corresponding to physical positions 242,101,915 to 243,081,515 comprises an A allele at a position corresponding to physical position 242643396; the maize chromosome 5 corresponding to physical positions 186,344,944 to 187,256,786 comprises a C allele at a position corresponding to physical position 186795332; the maize chromosome 5 corresponding to physical positions 207,001,816 to 215,694,297 comprises at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; the maize chromosome 6 corresponding to physical positions 85,714,579 to 86,684, 841 comprises a C allele at a position corresponding to physical position 86282196; the maize chromosome 7 corresponding to physical positions 136,237,488 to 137,181,700 comprises a C allele at a position corresponding to physical position 136725791; the maize chromosome 8 corresponding to physical positions 3,624,919 to 4,585,283 comprises at least one of a G allele at a position corresponding to physical position 4128809 and an A allele at a position corresponding to physical position 4128860; the maize chromosome 8 corresponding to physical positions 9,535,964 to 10,493,645 comprises at least one of an A allele at a position corresponding to physical position 10122708, a T allele at a position corresponding to physical position 10122766, and a T allele at a position corresponding to physical position 10122892; the maize chromosome 8 corresponding to physical positions 164,507,475 to 172,699,565 comprises at least one of an A allele at a position corresponding to physical position 164990912 and a C allele at a position corresponding to physical position 172218916; the maize chromosome 9 corresponding to physical positions 11,507,069 to 135,985,429 comprises at least one of a C allele at a position corresponding to physical position 11929493, a T allele at a position corresponding to physical position 135483968, and a G allele at a position corresponding to physical position 135483999; the maize chromosome 9 corresponding to physical positions 151,907,512 to 152,897,067 comprises at least one of a C allele at a position corresponding to physical position 152415102 and a T allele at a position corresponding to physical position 152415196; and the maize chromosome 10 corresponding to physical positions 128,310,945 to 129,283,212 comprises an A allele at a position corresponding to physical position 128812208.

Methods may further include detecting any of the above alleles, using PCR for 122 example. For example, detecting may include: in said maize chromosome 1 123 corresponding to physical positions 3,225,079 to 4,188,653, detecting at least one of an A allele at a position corresponding to physical position 3702462 and a C allele at a position corresponding to physical position 3702464; in said maize chromosome 1 corresponding to physical positions 221,604,561 to 222,599,974, detecting a C allele at a position corresponding to physical position 222146924; in said maize chromosome 2 corresponding to physical positions 8,618,657 to 9,599,938, detecting a C allele at a position corresponding to physical position 9122256; in said maize chromosome 3 corresponding to physical positions 14,511,390 to 215,165,758, detecting at least one of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; in said maize chromosome 4 corresponding to physical positions 242,101,915 to 243,081,515, detecting an A allele at a position corresponding to physical position 242643396; in said maize chromosome 5 corresponding to physical positions 186,344,944 to 187,256,786, detecting a C allele at a position corresponding to physical position 186795332; in said maize chromosome 5 corresponding to physical positions 207,001,816 to 215,694,297, detecting at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; in said maize chromosome 6 corresponding to physical positions 85,714,579 to 86,684,841, detecting a C allele at a position corresponding to physical position 86282196; in said maize chromosome 7 corresponding to physical positions 136,237,488 to 137,181,700, detecting a C allele at a position corresponding to physical position 136725791; in said maize chromosome 8 corresponding to physical positions 3,624,919 to 4,585,283, detecting at least one of a G allele at a position corresponding to physical position 4128809 and an A allele at a position corresponding to physical position 4128860; in said maize chromosome 8 corresponding to physical positions 9,535,964 to 10,493,645, detecting at least one of an A allele at a position corresponding to physical position 10122708, a T allele at a position corresponding to physical position 10122766, and a T allele at a position corresponding to physical position 10122892; in said maize chromosome 8 corresponding to physical positions 164,507,475 to 172,699,565, detecting at least one of an A allele at a position corresponding to physical position 164990912 and a C allele at a position corresponding to physical position 172218916; in said maize chromosome 9 corresponding to physical positions 11,507,069 to 135,985,429, detecting at least one of a C allele at a position corresponding to physical position 11929493, a T allele at a position corresponding to physical position 135483968, and a G allele at a position corresponding to physical position 135483999; in said maize chromosome 9 corresponding to physical positions 151,907,512 to 152,897,067, detecting at least one of a C allele at a position corresponding to physical position 152415102 and a T allele at a position corresponding to physical position 152415196; and in said maize chromosome 10 corresponding to physical positions 128,310,945 to 129,283,212, detecting an A allele at a position corresponding to physical position 128812208. Exemplary probes and primers for detecting these alleles are set forth in Table XII.

Also provided herein is a method of introgressing an allele associated with enhanced ear rot resistance into a maize plant. Such methods for introgressing an allele associated with enhanced ear rot resistance into a maize plant or germplasm may comprise, consist essentially of or consist of crossing a first maize plant or germplasm comprising said allele (the donor) with a second maize plant or germplasm that lacks said allele (the recurrent parent) and repeatedly backcrossing progeny comprising said allele with the recurrent parent. Progeny comprising said allele may be identified by detecting, in their genomes, the presence of a marker associated with enhanced ear rot resistance. The marker may be detected in any sample taken from the progeny, including, but not limited to, a portion of said progeny (e.g., a seed chip, a leaf punch disk or a cell from said plant or germplasm) or a nucleotide sequence from said progeny. Such a sample may be taken from the progeny using any present or future method known in the art, including, but not limited to, automated methods of removing a portion of endosperm with a sharp blade, drilling a small hole in the seed and collecting the resultant powder, cutting the seed with a laser and punching a leaf disk. Either the donor or the recurrent parent, or both, may be of a non-naturally occurring variety of maize. In some embodiments, the recurrent parent is of an elite variety of maize. In some embodiments, the genome of the recurrent parent is at least about 50%, 55%, 60%, 65%, 70%, 75%, 80%, 85%, 90%, 95%, 97%, 99% or 100% identical to that of an elite variety of maize.

In some embodiments, the marker used to identify progeny comprising an allele associated with enhanced ear rot resistance may comprise, consist essentially of or consist of one or more marker alleles located within a chromosomal interval selected from the group consisting of those in Table X. For example, at least one marker on chromosome 1 between physical positions 3,225,079 and 4,188,653; at least one marker on chromosome 1 between physical positions 221,604,561 and 222,599,974; at least one marker on chromosome 2 between physical positions 8,618,657 and 9,599,938; at least one marker on chromosome 3 between physical positions 14,511,390 and 215,165,758; at least one marker on chromosome 4 between physical positions 242,101,915 and 243,081,515; at least one marker on chromosome 5 between physical positions 186,344,944 and 187,256,786; at least one marker on chromosome 5 between physical positions 207,001,816 and 215,694,297; at least one marker on chromosome 6 between physical positions 85,714,579 and 86,684,841; at least one marker on chromosome 7 between physical positions 136,237,488 and 137,181,700; at least one marker on chromosome 8 between physical positions 3,624,919 and 4,585,283; at least one marker on chromosome 8 between physical positions 9,535,964 and 10,493,645; at least one marker on chromosome 8 between physical positions 164,507,475 and 172,699,565; at least one marker on chromosome 9 between physical positions 11,507,069 and 135,985,429; at least one marker on chromosome 9 between physical positions 151,907,512 and 152,897,067; and at least one marker on chromosome 10 between physical positions 128,310,945 and 129,283,212. Markers may also include any of the other markers listed above.

In some embodiments, the marker may comprise, consist essentially of or consist of marker alleles located in at least two different chromosomal intervals. For example, the marker may comprise one or more alleles located in the chromosomal interval of chromosome 2 between physical positions 8,618,657 and 9,599,938, and one or more alleles located in the chromosomal interval defined by and including at least one or more marker alleles on chromosome 8 between physical positions 3,624,919 and 4,585,283 (with interval boundaries including the alleles set forth in in Table XIII for example). In other embodiments the marker may comprise, consist essentially of or consist of marker alleles located in at least three different chromosomal intervals of Table X, in at least four different chromosomal intervals of Table X, in at least five different chromosomal intervals of Table X, in at least six different chromosomal intervals of Table X, in at least seven different chromosomal intervals of Table X, in at least eight different chromosomal intervals of Table X, in at least nine different chromosomal intervals of Table X, in at least 10 different chromosomal intervals of Table X, in at least eleven different chromosomal intervals of Table X, in at least twelve different chromosomal intervals of Table X, in at least thirteen different chromosomal intervals of Table X, in at least fourteen different chromosomal intervals of Table X, or in all of the intervals of Table X.

In some embodiments, the marker used to identify progeny comprising an allele associated with enhanced ear rot resistance may comprise, consist essentially of or consist of one or more marker alleles within Table XI, Table XII, or those within any of the intervals of Table X.

Ear Rot Resistant Maize Plants and Germplasms

The present invention provides ear rot resistant maize plants and germplasms. As discussed above, the methods of the present invention may be utilized to identify, produce and/or select an ear rot resistant maize plant or germplasm.

In addition to the methods described above, an ear rot resistant maize plant or germplasm may be produced by any method whereby a marker associated with enhanced ear rot resistance is introduced into the maize plant or germplasm, including, but not limited to, transformation, protoplast transformation or fusion, a double haploid technique, embryo rescue, and/or by any other nucleic acid transfer system.

In some embodiments, the maize plant or germplasm comprises a non-naturally occurring variety of maize. In some embodiments, the maize plant or germplasm is at least about 50%, 55%, 60%, 65%, 70%, 75%, 80%, 85%, 90%, 95%, 97%, 99% or 100% identical to that of an elite variety of maize.

The ear rot resistant maize plant or germplasm may be the progeny of a cross between an elite variety of maize and a variety of maize that comprises an allele associated with enhanced ear rot resistance.

The ear rot resistant maize plant or germplasm may be the progeny of an introgression wherein the recurrent parent is an elite variety of maize and the donor comprises an allele associated with enhanced ear rot resistance.

The ear rot resistant maize plant or germplasm may be the progeny of a cross between a first elite variety of maize (e.g., a tester line) and the progeny of a cross between a second elite variety of maize (e.g., a recurrent parent) and a variety of maize that comprises an allele associated with enhanced ear rot resistance (e.g., a donor).

The ear rot resistant plant or germplasm may be the progeny of a cross between a first elite variety of maize and the progeny of an introgression wherein the recurrent parent is a second elite variety of maize and the donor comprises an allele associated with enhanced ear rot resistance.

An ear rot resistant maize plant and germplasm of the present invention may comprise one or more markers of the present invention.

In some embodiments, the ear rot resistant maize plant or germplasm may comprise within its genome, a marker associated with enhanced ear rot resistance, wherein said marker is located within a chromosomal interval of Table X. Exemplary markers include those of Table XI or those of Table XII.

In some embodiments, the ear rot resistant maize plant or germplasm may comprise within its genome a marker that comprises, consists essentially of or consists of marker alleles located in at least two different chromosomal intervals.

Embodiments also include maize plants having in their parental pedigree a plant selected based on the presence of a marker associated with increased ear rot resistance, wherein said marker is located within at least one chromosomal interval of selected from the group consisting of (aa) maize chromosome 1 corresponding to physical positions 3,225,079 to 4,188,653; (bb) maize chromosome 1 corresponding to physical positions 221,604,561 to 222,599,974; (cc) maize chromosome 2 corresponding to physical positions 8,618,657 to 9,599,938; (dd) maize chromosome 3 corresponding to physical positions 14,511,390 to 215,165,758; (ee) maize chromosome 4 corresponding to physical positions 242,101,915 to 243,081,515; (ff) maize chromosome 5 corresponding to physical positions 186,344,944 to 187,256,786; (gg) maize chromosome 5 corresponding to physical positions 207,001,816 to 215,694,297; (hh) maize chromosome 6 corresponding to physical positions 85,714,579 to 86,684,841; (ii) maize chromosome 7 corresponding to physical positions 136,237,488 to 137,181,700; (jj) maize chromosome 8 corresponding to physical positions 3,624, 919 to 4,585,283; (kk) maize chromosome 8 corresponding to physical positions 9,535,964 to 10,493,645; (ll) maize chromosome 8 corresponding to physical positions 164,507, 475 to 172,699,565; (mm) maize chromosome 9 corresponding to physical positions 11,507,069 to 135,985,429; (nn) maize chromosome 9 corresponding to physical positions 151,907,512 to 152,897,067; and (oo) maize chromosome 10 corresponding to physical positions 128,310,945 to 129, 283,212. In some embodiments, said maize chromosome 1 corresponding to physical positions 3,225,079 to 4,188,653 comprises at least one of an A allele at a position corresponding to physical position 3702462 and a C allele at a position corresponding to physical position 3702464; said maize chromosome 1 corresponding to physical positions 221,604,561 to 222,599,974 comprises a C allele at a position corresponding to physical position 222146924; said maize chromosome 2 corresponding to physical positions 8,618,657 to 9,599,938 comprises a C allele at a position corresponding to physical position 9122256; said maize chromosome 3 corresponding to physical positions 14,511, 390 to 215,165,758 comprises at least one of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; said maize chromosome 4 corresponding to physical positions 242,101,915 to 243,081,515 comprises an A allele at a position corresponding to physical position 242643396; said maize chromosome 5 corresponding to physical positions 186,344,944 to 187,256,786 comprises a C allele at a position corresponding to physical position 186795332; said maize chromosome 5 corresponding to physical positions 207,001,816 to 215,694,297 comprises at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; said maize chromosome 6 corresponding to physical positions 85,714,579 to 86,684, 841 comprises a C allele at a position corresponding to physical position 86282196; said maize chromosome 7 corresponding to physical positions 136,237,488 to 137,181, 700 comprises a C allele at a position corresponding to physical position 136725791; said maize chromosome 8 corresponding to physical positions 3,624,919 to 4,585,283 comprises at least one of a G allele at a position corresponding to physical position 4128809 and an A allele at a position corresponding to physical position 4128860; said maize chromosome 8 corresponding to physical positions 9,535, 964 to 10,493,645 comprises at least one of an A allele at a position corresponding to physical position 10122708, a T allele at a position corresponding to physical position 10122766, and a T allele at a position corresponding to physical position 10122892; said maize chromosome 8 corresponding to physical positions 164,507,475 to 172,699, 565 comprises at least one of an A allele at a position corresponding to physical position 164990912 and a C allele at a position corresponding to physical position 172218916; said maize chromosome 9 corresponding to physical positions 11,507,069 to 135,985,429 comprises at least one of a C allele at a position corresponding to physical position 11929493, a T allele at a position corresponding to physical position 135483968, and a G allele at a position corresponding to physical position 135483999; said maize chromosome 9 corresponding to physical positions 151,907,512 to 152, 897,067 comprises at least one of a C allele at a position corresponding to physical position 152415102 and a T allele at a position corresponding to physical position 152415196; and said maize chromosome 10 corresponding to physical positions 128,310,945 to 129,283,212 comprises an A allele at a position corresponding to physical position 128812208. In some embodiments, said maize chromosome 1 corresponding to physical positions 3,225,079 to 4,188,653 comprises all of an A allele at a position corresponding to physical position 3702462 and a C allele at a position corresponding to physical position 3702464; said maize chromosome 3 corresponding to physical positions 14,511, 390 to 215,165,758 comprises at least three of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; said maize chromosome 5 corresponding to physical positions 207,001,816 to 215,694,297 comprises all of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; said maize chromosome 8 corresponding to physical positions 3,624,919 to 4,585,283 comprises all of a G allele at a position corresponding to physical position 4128809 and an A allele at a position corresponding to physical position 4128860; said maize chromosome 8 corresponding to physical positions 9,535,964 to 10,493,645 comprises all of an A allele at a position corresponding to physical position 10122708, a T allele at a position corresponding to physical position 10122766, and a T allele at a position corresponding to physical position 10122892; said maize chromosome 8 corresponding to physical positions 164,507,475 to 172,699,565 comprises all of an A allele at a position corresponding to physical position 164990912 and a C allele at a position corresponding to physical position 172218916; said maize chromosome 9 corresponding to physical positions 11,507,069 to 135,985,429 comprises all of a C allele at a position corresponding to physical position 11929493, a T allele at a position corresponding to physical position 135483968, and a G allele at a position corresponding to physical position 135483999; said maize chromosome 9 corresponding to physical positions 151,907, 512 to 152,897,067 comprises all of a C allele at a position corresponding to physical position 152415102 and a T allele at a position corresponding to physical position 152415196; and said maize chromosome 10 corresponding to physical positions 128,310,945 to 129,283,212 comprises an A allele at a position corresponding to physical position 128812208.

In some embodiments, selecting includes: in said maize chromosome 1 corresponding to physical positions 3,225, 079 to 4,188,653, detecting at least one of an A allele at a position corresponding to physical position 3702462 and a C allele at a position corresponding to physical position 3702464; in said maize chromosome 1 corresponding to physical positions 221,604,561 to 222,599,974, detecting a C allele at a position corresponding to physical position 222146924; in said maize chromosome 2 corresponding to physical positions 8,618,657 to 9,599,938, detecting a C allele at a position corresponding to physical position 9122256; in said maize chromosome 3 corresponding to physical positions 14,511,390 to 215,165,758, detecting at least one of a C allele at a position corresponding to physical position 19344196, a T allele at a position corresponding to physical position 19344197, an A allele at a position corresponding to physical position 19826372, a G allele at a position corresponding to physical position 151251885, a C allele at a position corresponding to physical position 199952894, a T allele at a position corresponding to physical position 214794069, and an A allele at a position corresponding to physical position 214794170; in said maize chromosome 4 corresponding to physical positions 242,101, 915 to 243,081,515, detecting an A allele at a position corresponding to physical position 242643396; in said maize chromosome 5 corresponding to physical positions 186,344,944 to 187,256,786, detecting a C allele at a position corresponding to physical position 186795332; in said maize chromosome 5 corresponding to physical positions 207,001,816 to 215,694,297, detecting at least one of an A allele at a position corresponding to physical position 207505420, a C allele at a position corresponding to physical position 207505421, an A allele at a position corresponding to physical position 212254755, an A allele at a position corresponding to physical position 215392749, and a C allele at a position corresponding to physical position 215500881; in said maize chromosome 6 corresponding to physical positions 85,714,579 to 86,684,841, detecting a C allele at a position corresponding to physical position 86282196; in said maize chromosome 7 corresponding to physical positions 136,237,488 to 137,181,700, detecting a C allele at a position corresponding to physical position 136725791; in said maize chromosome 8 corresponding to physical positions 3,624,919 to 4,585,283, detecting at least one of a G allele at a position corresponding to physical position 4128809 and an A allele at a position corresponding to physical position 4128860; in said maize chromosome 8 corresponding to physical positions 9,535,964 to 10,493, 645, detecting at least one of an A allele at a position corresponding to physical position 10122708, a T allele at a position corresponding to physical position 10122766, and a T allele at a position corresponding to physical position 10122892; in said maize chromosome 8 corresponding to physical positions 164,507,475 to 172,699,565, detecting at least one of an A allele at a position corresponding to physical position 164990912 and a C allele at a position corresponding to physical position 172218916; in said maize chromosome 9 corresponding to physical positions 11,507,069 to 135,985,429, detecting at least one of a C allele at a position corresponding to physical position 11929493, a T allele at a position corresponding to physical position 135483968, and a G allele at a position corresponding to physical position 135483999; in said maize chromosome 9 corresponding to physical positions 151,907,512 to 152,897,067, detecting at least one of a C allele at a position corresponding to physical position 152415102 and a T allele at a position corresponding to physical position 152415196; and in said maize chromosome 10 corresponding to physical positions 128,310,945 to 129,283,212, detecting an A allele at a position corresponding to physical position 128812208. In various embodiments, detecting can include at least one probe or primer listed in Table XI, Table XII, or Table XIII.

Ear Rot Resistant Seeds

The present invention provides ear rot resistant maize seeds. As discussed above, the methods of the present invention may be utilized to identify, produce and/or select an ear rot resistant maize seed. In addition to the methods described above, an ear rot resistant seed may be produced by any method whereby a marker associated with enhanced ear rot resistance is introduced into the maize seed, including, but not limited to, transformation, protoplast transformation or fusion, a double haploid technique, embryo rescue, and/or by any other nucleic acid transfer system.

In some embodiments, the ear rot resistant maize seed comprises a non-naturally occurring variety of maize. In some embodiments, the maize seed is at least about 50%, 55%, 60%, 65%, 70%, 75%, 80%, 85%, 90%, 95%, 97%, 99% or 100% identical to that of an elite variety of maize.

The ear rot resistant maize seed may be produced by an ear rot resistant plant identified, produced or selected by the methods of the present invention. In some embodiments, the ear rot resistant maize seed is produced by an ear rot resistant maize plant of the present invention.

An ear rot resistant seed of the present invention may comprise one or more markers of the present invention. For example, an ear rot resistant seed may comprise any of the markers within Table XI, Table XII, or at least one marker within the intervals of Table X.

In some embodiments, the ear rot resistant seed may comprise within its genome a marker that comprises, consists essentially of or consists of marker alleles located in at least two different chromosomal intervals.

Examples

Detection of Potential Resistance Genes to *Fusarium* Ear Rot by GWAS

A panel of 508 maize lines were grown in Beijing (2017 and 2018) and Hainan (2017) to investigate their resistance to *Fusarium* ear rot disease. Under the long-day conditions in Beijing, most tropical lines showed severely delayed flowering time, and they were then removed for further analysis. From three field tests, we selected the same set of 309 lines to perform GWAS analysis. The filtered GWAS population showed a normal distribution of disease severity index (DSI) of *Fusarium* ear rot in Beijing, while a left-skewed distribution towards resistance in Hainan (FIG. 6). This is in consistent with the fact that ear rot may be influenced by environmental conditions. We then perform a best linear unbiased prediction (BLUP) of the data from three field trials to obtain the joint distribution of ear rot severity (FIG. 1). The whole GWAS population could be divided into Tang Si Ping Tou (TSPT), Stiff Stalk (SS), non-Stiff Stalk (NSS), and Mixed heterotic groups (Mixed) based on their pedigrees, and no significant difference in DSI was detected between any two of them (Table 1). Within the GWAS population, the resistant inbred lines are CIMBL4, CML225, DAN599, CML304, and CIMBL47; while the susceptible inbred lines are RY737, CIMBL55, Ye478, GEMS45, and GEMS39.

TABLE 1

| The average DSIs for four heterotic groups within the GWAS population | | | |
|---|---|---|---|
| sub-population | mixed | NSS | TSPT | SS |
| Individuals | 92 | 106 | 79 | 25 |
| DSI (%) | 51.4 | 48.6 | 47.8 | 49.9 |

We conducted the GWAS by using a mixed linear model. Consequently, tens of SNPs were found to be significantly associated with ear rot resistance, and these SNPs included 6 in Beijing (2017), 20 in Hainan (2017), 7 in Beijing (2018) and 1 in BLUP data, as shown in the quantile-quantile and Manhattan plots (FIG. 2). After comparison of the SNPs detected from three different environments, we found four chromosomal regions, bins 3.04, 5.05/09, 8.01/02, and 8.06/08, enriched in significant SNPs, and each of them could explain 7.73-11.22% of the total phenotypic variation. The SNP chr8.S_4128809 with the highest significance (P=1.65× $10^{-7}$) was found in bin 8.01 and this SNP could account for 11.22% of the total phenotypic variation.

According to the B73 genome (AGPv4), genes that cover or locate adjacent to the significant SNPs were identified, and this revealed 4 in Beijing (2017), 40 in Hainan (2017), 24 in Beijing (2018), and 2 in BLUP data (Table S1). These genes were classified into different categories according to their functions, and most of them were related to defense response signaling pathway, binding activity, plant growth and development, enzymes related to catabolizes, transport activity, and drug metabolism (FIG. 7).

TABLE S1

| | chr | pos | P-Value | Allele | Bin | Gene | Predicted Function |
|---|---|---|---|---|---|---|---|
| The list of significant SNPs identified by GWAS and their corresponding genes under three field trails | | | | | | | |
| BJ | 1 | 3702462 | 9.58E−06 | A/G | 1.01 | GRMZM2G029824 | peroxisomal membrane protein homolog1 |
| 2017 | 1 | 3702464 | 9.58E−06 | C/G | 1.01 | GRMZM2G062210 | fusca homolog |
| | 5 | 186795332 | 4.33E−06 | G/A | 5.05 | GRMZM2G001033 | CMP-sialic acid transporter 3 |
| | 8 | 10122708 | 1.86E−07 | T/C | 8.02 | GRMZM2G313128 | no description |
| | 8 | 10122766 | 1.86E−07 | T/C | 8.02 | | |
| | 8 | 10122892 | 1.44E−06 | T/C | 8.02 | | |
| HN | 3 | 19344196 | 9.34E−06 | G/T | 3.04 | GRMZM2G169152 | cytochrome P450 family 77 subfamily A polypeptide 5 pseudogene |
| 2017 | 3 | 19344197 | 9.34E−06 | A/C | 304 | GRMZM2G169121 | DUF789 family protein |
| | | | | | | GRMZM2G467671 | PR5-like receptor kinase |
| | | | | | | GRMZM2G169182 | Octicosapeptide/Phox/Bem1p family protein |
| | 3 | 19826372 | 6.20E−06 | A/C | 3.04 | GRMZM2G013884 | unknown |
| | | | | | | GRMZM2G013790 | Leaf rust 10 disease-resistance locus receptor-like kinase-like 1.1 |
| | | | | | | GRMZM2G437100 | 16.9 kDa class I heat shock protein 1 |
| | | | | | | GRMZM2G422240 | heat shock protein17.2 |
| | 3 | 151251885 | 1.06E−05 | C/T | 3.05 | GRMZM2G039867 | tassels replace upper ears1 |
| | 3 | 199952894 | 1.54E−06 | C/G | 3.07 | GRMZM5G154165 | Dolichyl-diphosphooligosaccharide-protein glycosyltransferase subunit STT3A |
| | 3 | 214794069 | 4.25E−06 | A/C | 3.08 | GRMZM2G031400 | Protein kinase superfamily protein |
| | 3 | 214794158 | 7.50E−06 | A/G | 3.08 | GRMZM2G336225 | unknown |
| | 3 | 214794170 | 7.50E−06 | A/G | 3.08 | GRMZM2G122362 | SCP1-like small phosphatase 4b |
| | | | | | | GRMZM2G122335 | Mitogen-activated protein kinase 20 |
| | 5 | 207505420 | 1.51E−06 | A/C | 5.07 | GRMZM2G020040 | Heat shock 70 kDa protein 17 |
| | 5 | 207505421 | 3.81E−06 | G/T | 5.07 | GRMZM2G180983 | P-loop containing nucleoside triphosphate hydrolases superfamily protein |
| | | | | | | GRMZM2G481604 | Pentatricopeptide repeat (PPR) superfamily protein |
| | | | | | | GRMZM2G481605 | 17.4 kDa class I heat shock protein 3 |
| | | | | | | GRMZM2G315127 | unknown |
| | 6 | 86282196 | 3.35E−06 | C/T | 6.01 | GRMZM2G857090 | Transcription factor bHLH93 |
| | 8 | 4128809 | 1.65E−07 | C/T | 8.01 | GRMZM2G153434 | PQ-loop repeat family protein/transmembrane family protein |
| | 8 | 4128860 | 1.65E−06 | A/T | 8.01 | GRMZM2G050325 | Phenazine biosynthesis PhzC/PhzF protein |
| | | | | | | GRMZM2G050384 | unknown |
| | | | | | | GRMZM2G139952 | La-related protein 1A |
| | 8 | 172218916 | 1.01E−06 | C/T | 8.08 | GRMZM2G146437 | Undecaprenyl pyrophosphate synthetase |
| | | | | | | GRMZM2G447876 | CDP-diacylglycerol-serine O-phosphatidyl transferase 1 |
| | | | | | | GRMZM2G133029 | Eukaryotic aspartyl protease family protein |
| | | | | | | GRMZM2G074462 | Carbohydrate-binding-like fold |
| | 9 | 11929493 | 5.01E−06 | C/T | 9.02 | GRMZM2G032214 | Probable folate-biopterin transporter 2 |
| | 9 | 135483968 | 1.01E−05 | A/G | 9.05 | GRMZM2G402341 | RING/U-box superfamily protein |
| | 9 | 135483999 | 7.77E−06 | C/T | 9.05 | GRMZM2G162481 | Putative homeobox DNA-binding domain superfamily protein |
| | 9 | 152415102 | 7.78E−06 | C/T | 9.07 | GRMZM2G004528 | Inositol-3-phosphate synthase isozyme 1 |
| | 9 | 152415196 | 7.78E−06 | A/C | 9.07 | GRMZM2G004466 | Putative bifunctional inhibitor/LTP/seed storage protein family |
| | | | | | | GRMZM2G004377 | Probable protein phosphatase 2C BIPP2C1 |
| | | | | | | GRMZM2G004172 | NADH-ubiquinone oxidoreductase B16.6 subunit |
| | | | | | | GRMZM2G004157 | RING/U-box superfamily protein |
| | | | | | | GRMZM2G004119 | RING/U-box superfamily protein |
| | | 128812208 | 7.20E−06 | A/C | 10.04 | GRMZM2G066162 | Endoglucanase 7 |
| | | | | | | GRMZM2G066059 | Autophagy 10 variant 1% 3B Autophagy-related 10 variant 1 |
| | | | | | | GRMZM2G096705 | La protein 1 |
| BJ | 2 | 9122256 | 1.70E−06 | G/T | 2.02 | GRMZM2G076239 | Peroxisomal (S)-2-hydroxy-acid oxidase GLO1 |
| 2018 | | | | | | GRMZM2G148998 | unknown |
| | | | | | | GRMZM5G853854 | Peroxisomal (S)-2-hydroxy-acid oxidase GLO1 |
| | | | | | | GRMZM2G076539 | Signal recognition particle 14 kDa protein |
| | | | | | | GRMZM5G876898 | Aminomethyl transferase |
| | | | | | | GRMZM2G076826 | Autophagy-related protein 8c |

TABLE S1-continued

| | chr | pos | P-Value | Allele | Bin | Gene | Predicted Function |
|---|---|---|---|---|---|---|---|
| | 4 | 242643396 | 5.04E−06 | A/G | 4.11 | GRMZM2G153797 | DNA-directed RNA polymerase V subunit 1 |
| | | | | | | GRMZM2G153899 | unknown |
| | | | | | | GRMZM5G851807 | DNA-directed RNA polymerase V subunit 1 |
| | 5 | 212254755 | 9.57E−06 | A/T | 5.08 | GRMZM2G351832 | unknown |
| | | | | | | GRMZM2G053396 | Putative pentatricopeptide repeat-containing protein |
| | | | | | | GRMZM2G053420 | 23-bisphosphoglycerate-independent phosphoglycerate mutase 1 |
| | | | | | | GRMZM2G074267 | PIN-formed protein2 |
| | 5 | 215392749 | 4.08E−06 | A/G | 5.08 | GRMZM2G046885 | MADS-box protein SVP |
| | | | | | | GRMZM2G012178 | ARM repeat superfamily protein |
| | 5 | 215500881 | 1.62E−05 | C/T | 5.09 | GRMZM2G072861 | Presequence protease 2 chloroplastic/mitochondrial |
| | | | | | | GRMZM2G101463 | Phenylalanine-tRNA ligase alpha subunit cytoplasmic |
| | | | | | | GRMZM2G101271 | Presequence protease 2 chloroplastic/mitochondrial |
| | | | | | | GRMZM2G101412 | Methionine aminopeptidase 1D chloroplastic/mitochondrial |
| | | | | | | GRMZM2G402242 | Cytoplasmic tRNA 2-thiolation protein 1 |
| | 7 | 136725791 | 2.40E−06 | C/G | 7.03 | GRMZM2G084014 | Zinc finger protein |
| | | | | | | GRMZM2G083932 | BCR/ABL-regulated protein |
| | | | | | | GRMZM2G083894 | AN15 |
| | 8 | 164990912 | 4.95E−06 | A/C | 8.06 | GRMZM2G116557 | Auxin response factor 2 |
| BLUP data | 1 | 222146924 | 5.47E−06 | C/T | 1.07 | GRMZM5G895175 | splicing factor PWI domain-containing protein |
| | | | | | | GRMZM2G066757 | unknown |

Comparison of the Transcriptomes of Resistant CIMBL47 and Susceptible SY1035 Lines Among the 309 lines tested in the three field trials, CIMBL47 (DSI=7.5%) and SY1035 (DSI=83.4%) were proved to be the most resistant and susceptible lines, respectively. It was speculated that CIMBL47 has the highest and SY1035 the lowest numbers of resistance alleles within the GWAS population. To identify those genes potentially involved in resistance to ear rot, we used both lines to conduct RNA-seq on the 15-day-old kernels to reveal reprogramming of transcriptome at 0, 0.5, 1.5, 3, and 6 hours post inoculation (hpi). Totally, 1,020,525,460 clean reads were obtained and on average 76.6% of the reads were mapped to the B73 reference genome (AGPv4) (Table S2). The differentially expressed genes (DEGs) were identified with the criterion of q≤21.05 and $\log_2$ fold-change≥1c. Surprisingly, numerous DEGs appeared as early as Ohpi (immediately after 5-min pathogen challenge) (Table 2). The resistant line CIMBL47 showed a total of 645 DEGs, and nearly two-thirds of them were up-regulated. By contrast, the susceptible line SY1035 showed only 364 DEGs, and the numbers of up- and down-regulated DEGs are close to each other. The resistant CIMBL47 and susceptible SY1035 lines did show great difference in basal transcriptome as thousands of DEGs appeared when treated with water control as observed in RC vs SC. Upon challenge with the pathogen, CIMBL47 showed even more up-regulated and less down-regulated DEGs as compared with SY1035 (R vs S). It seems that CIMBL47 could react very strongly to the pathogen invasion as compared with SY1035. We assumed CIMBL47 may have numerous resistant-related genes which primed to give a quick response to the pathogen infection. For the other sampling times after inoculation, CIMBL47 still had more up-regulated than down-regulated DEGs at 0.5 hpi, how-ever, this trend did not continue thereafter (Table 2). The susceptible line SY1035 had much more down-regulated DEGs than the resistant line CIMBL47, peaking at 1.5 hpi.

TABLE S2

The clean reads of RNA-Seq data and their mapping percentages

| Samples | Total reads | Total mapped | Mapping ratio |
|---|---|---|---|
| R-0 h | 40138492 | 31757125 | 79.12% |
| R-0.5 h | 59506018 | 45161847 | 75.89% |
| R-1.5 h | 59418878 | 45479188 | 76.54% |
| R-3 h | 45692262 | 34133864 | 74.70% |
| R-6 h | 42002100 | 31752856 | 75.60% |
| RC-0 h | 44651208 | 33304846 | 74.59% |
| RC-0.5 h | 57663994 | 43793807 | 75.95% |
| RC-1.5 h | 57731170 | 44548513 | 77.17% |
| RC-3 h | 61003842 | 45814929 | 75.10% |
| RC-6 h | 42379698 | 33074729 | 78.04% |
| S-0 h | 50631858 | 40507159 | 80.00% |
| S-0.5 h | 55985810 | 44946471 | 80.28% |
| S-1.5 h | 65265720 | 51599022 | 79.06% |
| S-3 h | 44721856 | 35333559 | 79.01% |
| S-6 h | 43353898 | 33970591 | 78.36% |
| SC-0 h | 41423772 | 33120569 | 79.96% |
| SC-0.5 h | 60599592 | 47560249 | 78.48% |
| SC-1.5 h | 61738392 | 37788098 | 61.21% |
| SC-3 h | 42741632 | 33843466 | 79.18% |
| SC-6 h | 43875268 | 33814163 | 77.07% |

TABLE 2

Numbers of up- and down-regulated DEGs at differential time points after inoculation

| | 0 hpi | | 0.5 hpi | | 1.5 hpi | | 3 hpi | | 6 hpi | |
|---|---|---|---|---|---|---|---|---|---|---|
| Comparisom | Up | Down | Up | Down | Up | Down | Up | Down | Up | Down |
| RC VS R | 405 | 240 | 189 | 79 | 630 | 763 | 183 | 620 | 588 | 705 |
| SC VS S | 188 | 176 | 193 | 304 | 944 | 2112 | 933 | 1102 | 921 | 831 |

TABLE 2-continued

Numbers of up- and down-regulated DEGs at differential time points after inoculation

| Comparisom | 0 hpi | | 0.5 hpi | | 1.5 hpi | | 3 hpi | | 6 hpi | |
|---|---|---|---|---|---|---|---|---|---|---|
| | Up | Down | Up | Down | Up | Down | Up | Down | Up | Down |
| RC VS SC | 1633 | 711 | 994 | 1316 | 1023 | 906 | 842 | 765 | 661 | 664 |
| R VS S | 1801 | 162 | 1473 | 2671 | 2320 | 2657 | 1000 | 1669 | 644 | 972 |

R and RC: the resistant line CIMBL47 were challenged with pathogen (R) and treated with water (RC);
S and SC: the susceptible line SY1035 were challenged with pathogen (S) and treated with water (SC).

Gene ontology (GO) analysis revealed remarkable enrichment of DEGs in several functional categories, including catalytic activity, binding activity, metabolic process, cellular process, biological regulation, response to stimulation, developmental process and so on (FIG. 8). KEGG analysis indicated that the pathways enriched in DEGs were those down-regulated DEGs at the same time points after pathogen inoculation. It is obvious that genes cover or locate adjacent to the significant SNPs showed much higher rate of DEGs than the genome-wide genes in the very early responses to pathogen invasion. (Table 3).

TABLE 3

The ratios of up- and down-regulated DEGs at differential time points after inoculation

| Comparisons | 0 hpi (%) | | 0.5 hpi (%) | | 1.5 hpi (%) | | 3 hpi (%) | | 6 hpi (%) | |
|---|---|---|---|---|---|---|---|---|---|---|
| | Up | Down | Up | Down | Up | Down | Up | Down | Up | Down |
| RC VS R | 1.27 | 0.75 | 0.59 | 0.24 | 1.96 | 2.38 | 0.57 | 1.94 | 1.83 | 2.2 |
| | 21.42 | 10 | 25.71 | 5.71 | 25.71 | 5.71 | 11.42 | 20 | 14.3 | 17.14 |
| SC VS S | 0.59 | 0.55 | 0.6 | 0.95 | 2.95 | 6.6 | 2.92 | 3.44 | 2.87 | 2.59 |
| | 18.57 | 12.85 | 15.71 | 15.71 | 8.57 | 22.85 | 12.85 | 18.57 | 22.9 | 8.57 |
| RC VS SC | 5.1 | 2.22 | 3.1 | 4.11 | 3.2 | 2.83 | 3.12 | 5.21 | 4.56 | 5.2 |
| | 12.85 | 18.57 | 28.57 | 2.85 | 18.57 | 12.85 | 14.28 | 17.14 | 24.3 | 7.14 |
| R VS S | 5.63 | 2.7 | 4.6 | 8.34 | 7.25 | 8.3 | 2.63 | 2.39 | 2.01 | 3.03 |
| | 22.85 | 8.57 | 28.57 | 2.85 | 28.57 | 2.85 | 25.71 | 5.71 | 16.1 | 14.28 |

R and RC: the resistant line CIMBL47 were challenged with pathogen (R) and treated with water (RC);
S and SC: the susceptible line SY1035 were challenged with pathogen (S) and treated with water (SC).

closely related to stress and pathogen defenses, such as plant hormone signal transduction, phenylpropanoid biosynthesis, drug metabolism by cytochrome P450, platinum drug resistance, and starch/sucrose metabolism (FIG. 9; Scatter plots of enriched pathway terms of R vs S at 0 (A), 0.5 (B), 1.5 (C), 3 (D), and 6 (E) hours post inoculation. The vertical axis represents the pathway terms, and the horizontal axis represents the Rich factor. The size of the dot indicates the number of DEGs in the corresponding pathway, and the color of the dot corresponds to a different Qvalue range. KEGG: Kyoto Encyclopedia of Genes and Genomes.) Within the period of 6 hours after the pathogen infection, the plant hormone signal transduction was ranked as the top pathway enriched in DEGs, followed by phenylpropanoid biosynthesis (FIG. 10). At 3 hpi and 6 hpi, other pathways, such as glutathione metabolism, drug metabolism by cytochrome P450, and glyoxylate and dicarboxylate metabolism, were also appeared as major pathways enriched in DEGs.

Integration of Data from GWAS and Transcriptome

We evaluated candidate genes which were detected in the GWAS and showed differential expression levels after pathogen inoculation. Of 70 genes detected in the GWAS, 59 were found to express in 15-day-old kernels from transcriptome data, in which 22 showed differential expression after pathogen inoculation and thus are more likely to be involved in maize resistance to *Fusarium* ear rot. For more detail on the dynamic changes of DEGs, we calculated the rates of up- and down-regulated DEGs at 0, 0.5, 1.5, 3, and 6 hpi. In parallel, we estimated the rates of genome-wide up- and A: The ratios of genome-wide DEGs estimated from RNA-seq data; B: the ratios of DEGs from the 70 potential resistance genes detected by GWAS.

Of the 22 DEGs, 12 were found to be highly induced shortly after inoculation in the resistant line CIMBL47, but not the susceptible line SY1035, and reached their highest expression levels either at 0.5 hpi (6 genes) or 1.5 hpi (6 genes) (FIG. 3). Interestingly, five of them are located on bin 3.04/05, a hotspot region clustered with numerous resistance genes. These five genes encode two heat shock proteins, one PR-like receptor kinase, one DUF 789 family protein, and one regulatory protein NPR5. The other seven genes were scatted on bins 1.01, 5.08, 5.09, 9.05/07, and 10.04, of which three genes, encoding peroxisomal membrane protein homolog (bin 1.01), Inositol-3-phosphate synthase isozyme (bin 9.07), and endoglucanase 7 (bin 10.04), were reported to be associated with disease resistance (Table 4).

Five of the 22 DEGs exhibit distinct expression profiles in which the alleles of the susceptible line SY1035 were down-regulated by the pathogen, reaching to the lowest point at 1.5 hpi, and then upregulated to high expression levels at 6 hpi (FIG. 11). So far, two of them, encoding auxin component-related protein and pentatricopeptide repeat-containing protein, were known to engage in biotic or abiotic stress (Table S3).

TABLE S3

The list of genes in the susceptible line SY1035 which
were reduced by pathogen to the lowest at 1.5 hpi.

| gene | chr | bin | Description |
| --- | --- | --- | --- |
| GRMZM2G169182 | 3 | 3.04 | Octicosapeptide/Phox/Bem1p family protein |
| GRMZM2G053396 | 5 | 5.08 | Putative pentatricopeptide repeat-containing protein |
| GRMZM2G101271 | 5 | 5.09 | Presequence protease 2 chloroplastic/mitochondrial |
| GRMZM2G074267 | 5 | 5.08 | Auxin efflux carrier component |
| GRMZM2G116557 | 8 | 8.06 | Auxin response factor 2 |

Three of the 22 DEGs expressed highly in the resistant line CIMBL47 compared with the susceptible line SY1035, and could also induced by pathogen inoculation (FIG. 12). The first gene, GRMZM2G050325, encodes a phenazine biosynthesis PhzC/PhzF protein involved in phenylalanine synthesis, and the remaining two genes, GRMZM2G0505384 and GRMZM2G148998, encode proteins with unknown function (Table S4).

TABLE S4

The list of genes with high expression after inoculation in the resistant
line CIMBL47 as compared to the susceptible line SY1035.

| gene | chr | bin | Description |
| --- | --- | --- | --- |
| GRMZM2G148998 | 2 | 2.02 | unknown |
| GRMZM2G050325 | 8 | 8.01 | Phenazine biosynthesis PhzC/PhzF protein |
| GRMZM2G050384 | 8 | 8.01 | unknown |

The last two of the 22 DEGs showed higher expression in susceptible rather than resistant lines after inoculation (FIG. 13). The first gene in bin 2.02 was highly induced in the susceptible line SY1035 during 0.5-1.5 hpi, which encode a peroxisomal (S)-2-hydroxy-acid oxidase GLO1 that may be involved in the defense response signaling pathway. The second gene in bin 8.08 were highly expressed in the susceptible SY1035 compared with the resistant CIMBL47 at 0.5 hpi and thereafter, which is related to carbohydrate-binding activity (Table S5).

TABLE S5

The list of genes with high expression after inoculation in the
susceptible line SY1035 as compared to the resistant line CIMBL47

| gene | chr | bin | Description |
| --- | --- | --- | --- |
| GRMZM2G076239 | 2 | 2.02 | Peroxisomal (S)-2-hydroxy-acid oxidase GLO1 |
| GRMZM2G074462 | 8 | 8.08 | Carbohydrate-binding-like fold |

Taken together, the 22 genes show immediate responses to the pathogen challenge by regulating their gene expression levels. We hypothesized that these genes may form the first layer of defense in resistance to *Fusarium* ear rot, and the allelic difference at these genes may be responsible for differential resistance among different maize lines.

Analysis of Plant Hormone Signal Transduction and Phenylpropanoid Biosynthesis

Analysis of transcriptome reprogramming clearly indicates that plant hormone signal transduction and phenylpropanoid biosynthesis are among the most important pathways in defense to *Fusarium* ear rot. Thus, we investigated the expression levels of those genes involved in the two pathways. Generally, a large proportion of genes involved in the two pathways showed differential expressions upon pathogen challenge (FIGS. 4, 5).

The genes involved in signal transduction pathways of plant growth (auxin, cytokinine, gibberellin, and brassinosteroid) or ripening (ethylene) hormones were mostly downregulated, such as AUX1 genes in auxin, B-ARR in cytokinine, BRI in brassinosteroid, and EIN2/3 genes in ethylene, etc. By contrast, the genes related to stress response hormones, like abscisic acid and jasmonic acid, were up-regulated, such as SnRK2 and PYL genes in abscisic acid. Interestingly, NPR1-encoding genes acting in the signal transduction of salicylic acid, a key defense hormone to biotrophic pathogens, showed a complicated expression pattern with upregulation during 0 to 3 hpi and downregulation thereafter (FIG. 14 and 15). These findings suggest that the plant would alter the growth and defense tradeoff in the early defense to ear rot disease by modulating various hormone signal transduction pathways.

Of the 70 genes detected in the GWAS, some were found to be involved in the hormone signal transduction pathway, such as GRMZM2G039867, GRMZM2G004528, GRMZM2G074267, and GRMZM2G116557. The first two genes, GRMZM2G039867 and GRMZM2G004528, separately encoding a NPR1 regulatory protein and an inositol-3-phosphate synthase were highly induced in the resistant line CIMBL47 in the very early time past pathogen attack. The last two genes, GRMZM2G074267 and GRMZM2G116557, encoding auxin efflux carrier component and auxin response factor involved in the auxin signaling pathway were downregulated to the lowest points in the susceptible line SY1035 at 1.5 hpi (FIG. 3).

Phenylpropanoid was believed to be a core crosstalk substance in lots of development and defense related genes which serves as precursors for numbers of defense compounds in plants, including phytoalexins and lignin (Alessandra et al. 2017). The biosynthesis of phenylpropanoid was obvious to be greatly promoted upon pathogen challenge in the early time. Taking the 1.5 hpi for example, almost all key genes towards biosynthesis of defense metabolites were highly induced in the resistant line CIMBL47 as compared with the susceptible line SY1035 (FIG. 5). Interestingly, some potential resistance genes detected in the GWAS were also involved in phenylpropanoid biosynthesis. For instance, the gene GRMZM2G050325, encoding PhzC/PhzF protein for phenazine biosynthesis, was highly induced in the resistant line CIMBL47 after pathogen inoculation, as compared with the susceptible line SY1035.

Materials and Methods

Plant Materials

The genome-wide association analysis was conducted with a panel of 508 diverse inbred lines (CAM508) in China Agricultural University. All CAM508 lines were evaluated for their resistance to maize ear rot in year 2016 in Beijing, 2016-2017 in Hainan, and 2018 in Beijing. We adopted a completely randomized plot design with three replicates for each of three environmental conditions. Each RIL was planted with 17 kernels in a 4.0-m row, and the distance between two adjacent plants was 0.25 m and the row spacing was 0.50 m. For RNA-seq, we selected the most resistant line CIMBL47 and the most susceptible line SY1035 from the GWAS population.

Artificial Inoculation and Phenotyping in the Field

The sterilized maize kernels were used as substrate for *F. verticillioides*. The maize kernels were boiled until the grain was slightly cracked, then placed into a 1 L jar (⅓-½ filled).

The kernels were autoclaved for 20 minutes at 121° C. After cooling down to room temperature, the kernels were inoculated in an aseptic table with one piece of F *verticillioides* of about 1-cm diameter, followed by incubation in an incubator with constant temperature of 28° C. for about 2 weeks. One day before inoculation, the *F. verticillioides* spores were washed down from the grains using sterile water and the concentration was adjusted to $5 \times 10^6$ spores $ml^{-1}$ with a hemocytometer. Just before inoculation in the field, the *F. verticillioides* spores were added with 2 μL/mL Tween-80 surfactant and mixed well. Each plant was artificially inoculated on its kernels about 15 days after flowering with nail punch method, in which 1-ml spores was injected into the kernel per time with two injections per ear. After injection, the punch point was sealed with waterproof tape in case that spore suspension would not leak through it. At the maturity stage about 45 days after flowering, each plant was evaluated for its disease symptom. The disease severity of each ear was defined into five grades according to the percentage of infected kernels area exhibiting visual symptoms: 0=0-1%, 0.25=2-10%, 0.5=11-25%, 0.75=26-50%, and 1=50-100%, followed by conversion into disease severity index (DSI) (Grau et al. 1982).

$$DSI\ (\%) = \Sigma(grade \times number\ of\ plants\ in\ the\ grade) \times 100/(5 \times total\ number\ of\ plants).$$

Genome-Wide Association Study

The GWAS was performed using a mixed linear model (MLM) which took the impact of population structure and kinship coefficients into account. The high-quality SNPs used in the GWAS were the same as described by Li (Li et al. 2013). Totally, about 560,000 polymorphic SNPs were selected, which were filtered based on the minor allele frequency (MAF)≥05. Analyses were performed with the software TASSEL 5.2.43. False discovery rate (FDR)≤0.05 was used to identify significant associations and the threshold P value was determined by the Q-Q plot of the model, the maizeGDB genome browser was used to retrieve the candidate resistance genes, which are resided in the 100-kb interval, from 50-kb upstream and downstream of the significant SNPs from the GWAS.

RNA-Seq and Detection of Differentially Expressed Genes (DEGs)

Both resistant CIMBL47 and susceptible SY1035 lines were grown in the field, the ears at 15 days after flowering were collected in the field. The kernel was cut in the middle, and soaked one half in the sterile water and the other half in the $5 \times 10^6$ spores $ml^{-1}$ spore suspension for 5 minutes. Thereafter, all half-kernels were transferred to PDA medium and cultured in an incubator at 28° C. Kernel samples were collected in an aseptic table at time points of 0, 0.5, 1.5, 3, and 6 hours after culture (FIG. 16), and immediately frozen in liquid nitrogen and stored at −80° C. until RNA extraction. The protocol of total RNA extraction was performed under the guidance of Invitrogen manufacturer. The procedure of RNA-seq was described by Zhong (Zhong et al. 2018). A fraction of 100 ng Poly(A) RNA from each sample was fragmented for RNA-seq library construction according to the manufacturer's recommendation (Illumina) and sequenced on the Illumina Hiseq3000. Three biological replicates of each sample were implemented in the RNA-seq experiments. Clean reads were used for mapping, calculation, and normalization of gene expression. Reads were aligned to the masked maize genome database EnsembleZea_mays.AGPv3.26 (http://plants.ensembl.org/Zea_mays/Info/Index). Calculation and normalization of gene expression were based on the FPKM (Fragments Per Kilobase of exon model per Million mapped reads) using Cufflinks, version 2.1.1. Differentially expressed genes (DEGs) were defined using the false discovery rate (FDR) $(1 \times 10^{-10})$, as determined using the Benjamini and Hochberg's procedure. The parameters used for screening of DEGs were the fold change (FC) of the expression level (FC≥2 or FC≤0.5 under P-value 50.05, FDR 50.05) compared to the expression level in the control transcriptome. GO enrichment and KEGG enrichment (KEGG enriched pathway map) were performed using the obtained DEGs. According to the GO and KEGG enrichment, we plotted the histogram distribution of differential genes and the KEGG scatter plot and the KEGG-enriched pathway map.

Integration of Data from GWAS and Transcriptome

Based on the RNA-seq data, we calculated the ratios of genome-wide up- and down-regulated DEGs in every time point after inoculation. Meanwhile, we calculated the ratios of up- and down-regulated DEGs within the 100-kb intervals corresponding to significant SNPs in the GWAS. Then, we compared the DEG ratios of genome-wide genes and potential resistance genes detected in the GWAS between resistant CIMBL47 and susceptible SY1035 lines and between pathogen inoculation and water-treated control. For those DEGs from potential resistance genes detected in the GWAS, we divided them into several groups according to their unique expression patterns.

Results

In the GWAS analysis, we found a total of 70 genes to cover or localize adjacent to the SNPs that were significantly associated with the ear rot resistance. As expected, many candidate resistance genes are resided in the regions where disease resistance QTL have been detected in the previous linkage mapping studies. For instance, we found bin 3.04 harbors numbers of candidate genes, which encode cytochrome P450 family (GRMZM2G169152), PR5-like receptor kinase (GRMZM2G467671), leaf rust 10 disease-resistance locus receptor-like kinase (GRMZM2G013790), two heat shock proteins (GRMZM2G437100 and GRMZM2G422240), and etc. The bin 3.04 has been regarded as a hotspot for many disease resistance QTLs in maize, like *Fusarium* ear rot (Ding et al. 2008; Perez et al. 2001), *Fusarium* stalk rot (Pe' et al. 1993), Sugarcane mosaic virus (Xi et al. 2008; Wang et al. 2003), Head smut (Chen 2006; Liu et al 2016), North corn leaf blight (Ma et al 2014; WANG et al. 2010), and among others. Apart from bin 3.04, other chromosomal regions harboring the significant SNPs were also detected to cover resistance QTL identified previously. In bin 5.05, a resistance QTL to *Fusarium* ear rot could explain 13% of the total phenotypic variation (Robertson et al. 2006). In bin 7.03, a QTL was found to confer resistance to both *Fusarium* ear rot and fumonisin B1 (Maschietto et al. 2017). The bin 9.07 also covers the significant SNPs detected in other GWAS studies (Zila et al. 2013; Ju et al. 2017), and harbors resistance QTL in mapping studies (Maschietto et al. 2017, Aida et al 2016). We detected some genes in bin 9.07 encoding enzyme active protein including two U-box superfamily proteins, which might be involved in the PCD progress (FIG. 12).

Given that resistance-related genes may act very early in defense to ear rot disease, we conducted an improved RNA-seq analysis, trying to reveal all potential candidate genes. We selected the extreme resistant (CIMBL47) and susceptible (SY1035) lines from the GWAS population. The 15-day-old kernels that are most vulnerable to *Fusarium* ear rot were sampled for pathogen inoculation. Each kernel was cut into two halves in the middle, one half was treated with sterilized water and the other with the spore suspension for 5 minutes, followed by transferring to PDA medium for culture at 28° C. This method enabled the pathogen to directly contact the embryo/endosperm with maximum exposure, ensuring the resistant-related genes could be evenly and quickly induced to pathogen invasion. Moreover, we sampled the kernels at very early time at 0, 0.5, 1.5, 3, and 6 hpi. Just as expected, numbers of candidate resistance genes in the GWAS showed differential gene expression levels between CIMBL47 and SY1035 and between control and pathogen inoculation even as early as 0hpi (sampled immediately after 5-min pathogen inoculation), and peaked their expressions as early as 0.5 or 1.5 hpi (FIG. 3). This is consistent with the ear-rot resistance gene ZmAuxRP1 that showed its highest expression level at 3 hours after pathogen inoculation (Ye et al. 2018).

Compared with the susceptible line SY1035, the resistant line CIMBL47 showed more up-regulated genes in the early time post inoculation, peaking at 0.5 hpi or 1.5 hpi (Table 2; FIG. 3). Most DEGs are enriched in the plant hormone signal transduction pathway, phenylpropanoid biosynthesis, glutathione metabolism, drug metabolism by cytochrome P450, and glyoxylate and dicarboxylate metabolism. Intriguingly, the plant hormone signal transduction is ranked as the top pathway enriched in DEGs in all sampling points, in which the genes related to growth hormones were mostly down-regulated or with the decreasing tendency in the resistant line CIMBL47 compared to the susceptible line SY1035, like EIN3, AUX related genes; while the genes related to defense hormones, like abscisic acid and jasmonic acid, were up-regulated, including SnRK2 genes. It was reported that plant growth hormone auxin renders plant more vulnerable for pathogen attack by negatively regulating SA signaling pathway and promoting production of expansins and extensins (Catele et al., 2000; Wang et al., 2007).

These findings strongly imply that the balance between growth and defense plays a key role in maize resistance to *Fusarium* ear rot. Coincidentally, the ear rot resistance gene ZmAuxRP1 is also involved in growth-defense tradeoff (Ye et al. 2018). The phenylpropanoid biosynthesis is ranked as the second pathway enriched in DEGs, and almost all genes in the biosynthesis pathway were up-regulated upon pathogen challenge. This suggests that secondary defense metabolites also play an important role in early ear-rot resistance.

We noticed that cytochrome P450 gene family was also enriched in DEGs. P450 gene family participates in plant disease resistance by regulating lipid metabolism and affecting the synthesis and activity of jasmonic acid (JA). Besides, as a multifunctional oxidase, cytochrome P450 plays a key role in the defense response to pathogen invasion by manipulating the biosynthesis of secondary metabolite, including phenylpropanoids, flavonoids, alkaloids, anthraquinones, genus glycosides, plant hormones, etc. (Narusaka et al. 2004; Takemoto et al. 1999; Hemm et al. 2003; Koo et al. 2011). Thus, the current study demonstrates maize resistance to *Fusarium* ear rot may depend on multiple defense pathways.

Integrating GWAS and transcriptome data revealed a number of candidate genes in GWAS that were differentially expressed after pathogen inoculation, such as cytochrome P450 family gene (GRMZM2G169152), PR5-like receptor kinase gene (GRMZM2G467671), leaf rust disease locus receptor-like kinase gene (GRMZM2G013790), heat shock protein genes (GRMZM2G437100 and GRMZM2G422240), genes in the plant hormone signal transduction (GRMZM2G039867, GRMZM5G004528, GRMZM2G074267, and GRMZM2G116557), and etc. In the resistant CIMBL47 line, candidate genes related to cytochrome P450, phenylpropanoid and plant hormone signal transduction pathways, such as GRMZM2G169152, GRMZM2G467671, GRMZM2G039867, and GRMZM2G050325, were highly induced by pathogen invasion. Although we are currently not sure about the exact role these genes play in ear rot resistance, they still are believed useful to identify, select and/or produce plants with increased resistance to ear rot.

In summary, upon challenge with *F. verticillioides*, the changes of plant hormones indicate the plant is to undergo growth-defense tradeoff to optimize its fitness in face to the pathogen attack. A burst of phenylpropanoid biosynthesis is to reinforce its fortification via the promotion of biosynthesis of the defense compounds. The induction of cytochrome P450 gene family could cause a series of changes of defense metabolites, including phenylpropanoids, flavonoids, alkaloids, anthraquinones, genus glycosides, plant hormones, etc. Following these very early changes, other plant immune responses, such as glutathione metabolism and glyoxylate and dicarboxylate metabolism, are sequentially activated to jointly counter-attack *F. verticillioides* invasion.

The invention claimed is:

1. A method of identifying or selecting a maize plant having enhanced ear rot resistance, the method comprising the steps of:

a) isolating a nucleic acid from a maize cell or maize plant part;

b) detecting, in said cell or plant part the presence of a marker associated with increased ear rot resistance, wherein said marker is located within a chromosomal interval of maize chromosome 8 corresponding to physical positions 164,507,475 to 172,699,565 of maize B73 reference genome; wherein the detecting is carried out by PCR amplification and wherein PCR comprises at least one corresponding probe or primer selected from any one of SEQ ID NOs: 773-868, 1241-1248, and 1361-1368; and c) identifying or selecting said plant on the basis of the presence of the marker detected in b).

2. The method of claim 1, wherein said maize chromosome 8 corresponding to physical positions 164,507,475 to 172,699,565 of maize B73 reference genome comprises at least one of an A allele at a position corresponding to physical position 164990912 of maize B73 reference genome and a C allele at a position corresponding to physical position 172218916 of maize B73 reference genome.

3. The method of claim 2, wherein said maize chromosome 8 corresponding to physical positions 164,507,475 to 172,699,565 of maize B73 reference genome comprises an A allele at a position corresponding to physical position 164990912 of maize B73 reference genome and a C allele at a position corresponding to physical position 172218916 of maize B73 reference genome.

4. The method of claim 1, wherein detecting comprises in said maize chromosome 8 corresponding to physical positions 164,507,475 to 172,699,565 of maize B73 reference genome, detecting at least one of an A allele at a position corresponding to physical position 164990912 of maize B73 reference genome and a C allele at a position corresponding to physical position 172218916 of maize B73 reference genome.

5. The method of claim 1, wherein detecting in said chromosomal interval comprises detecting on chromosome 8 within 400K bp upstream or downstream of at least one of an A allele at a position corresponding to physical position 164990912 of maize B73 reference genome and a C allele at a position corresponding to physical position 172218916 of maize B73 reference genome.

6. The method of claim 1, further comprising:

(a) crossing the maize plant that comprises said marker within its genome with itself or another maize plant to yield progeny maize plants comprising the marker within their genome.

7. The method of claim 6, further comprising (b) repeating the crossing step of (a) at least 2 times to generate further progeny maize plants comprising the marker within their genome.

8. A method of producing a maize plant having enhanced ear rot resistance, the method comprising the steps of:

a) isolating a nucleic acid from a maize cell or maize plant part;

b) detecting, in said cell or plant part the presence of at least one marker associated with said increased ear rot resistance, wherein said at least one marker is located within a chromosomal interval of maize chromosome 8 corresponding to physical positions 164,507,475 to 172,699,565 of maize B73 reference genome; and wherein said detecting comprises detecting within said chromosomal interval on chromosome 8 within 400K bp upstream or downstream of at least one of an A allele at a position corresponding to physical position 164990912 of maize B73 reference genome and a C allele at a position corresponding to physical position 172218916 of maize B73 reference genome; and c) crossing a maize plant that comprises said marker within its genome with another maize plant that does not comprise said marker to yield a progeny maize plant comprising the marker within its genome.

9. An elite maize plant having ear rot resistance and comprising at least one marker associated with said ear rot resistance, wherein said at least one marker is located within a chromosomal interval of maize chromosome 8 corresponding to physical positions 164,507,475 to 172,699,565 of maize B73 reference genome; and wherein said at least one marker is selected from the group consisting of:

a) an A allele at a position corresponding to physical position 164990912 of maize B73 reference genome on maize chromosome 8;

b) a C allele at a position corresponding to physical position 172218916 of maize B73 reference genome on maize chromosome 8;

c) an A allele at a position corresponding to physical position 164546096 of maize B73 reference genome on maize chromosome 8;

d) an A allele at a position corresponding to physical position 164679493 of maize B73 reference genome on maize chromosome 8;

e) an A allele at a position corresponding to physical position 164886047 of maize B73 reference genome on maize chromosome 8;

f) an A allele at a position corresponding to physical position 164963082 of maize B73 reference genome on maize chromosome 8;

g) an A allele at a position corresponding to physical position 164993163 of maize B73 reference genome on maize chromosome 8;

h) an A allele at a position corresponding to physical position 165151326 of maize B73 reference genome on maize chromosome 8;

i) an A allele at a position corresponding to physical position 165269767 of maize B73 reference genome on maize chromosome 8;

j) an A allele at a position corresponding to physical position 165290988 of maize B73 reference genome on maize chromosome 8;

k) an A allele at a position corresponding to physical position 165309200 of maize B73 reference genome on maize chromosome 8;

l) an A allele at a position corresponding to physical position 165343030 of maize B73 reference genome on maize chromosome 8;

m) an A allele at a position corresponding to physical position 165482649 of maize B73 reference genome on maize chromosome 8;

n) an A allele at a position corresponding to physical position 171781842 of maize B73 reference genome on maize chromosome 8;

o) an A allele at a position corresponding to physical position 171833160 of maize B73 reference genome on maize chromosome 8;

p) an A allele at a position corresponding to physical position 171863486 of maize B73 reference genome on maize chromosome 8;

q) an A allele at a position corresponding to physical position 172025007 of maize B73 reference genome on maize chromosome 8;

r) an A allele at a position corresponding to physical position 172040252 of maize B73 reference genome on maize chromosome 8;

s) an A allele at a position corresponding to physical position 172131684 of maize B73 reference genome on maize chromosome 8;

t) an A allele at a position corresponding to physical position 172155970 of maize B73 reference genome on maize chromosome 8;

u) an A allele at a position corresponding to physical position 172336136 of maize B73 reference genome on maize chromosome 8;

v) an A allele at a position corresponding to physical position 172367654 of maize B73 reference genome on maize chromosome 8;

w) an A allele at a position corresponding to physical position 172434600 of maize B73 reference genome on maize chromosome 8;

x) an A allele at a position corresponding to physical position 172502859 of maize B73 reference genome on maize chromosome 8;

y); an A allele at a position corresponding to physical position 172532270 of maize B73 reference genome on maize chromosome 8; and z) an A allele at a position corresponding to physical position 172693261 of maize B73 reference genome on maize chromosome 8.

10. The elite maize plant of claim 9, wherein said maize chromosome 8 corresponding to physical positions 164,507, 475 to 172,699,565 of maize B73 reference genome comprises at least one of an A allele at a position corresponding to physical position 164990912 of maize B73 reference genome and a C allele at a position corresponding to physical position 172218916 of maize B73 reference genome.

11. The elite maize plant of claim 9, wherein said maize chromosome 8 corresponding to physical positions 164,507, 475 to 172,699,565 of maize B73 reference genome comprises all of an A allele at a position corresponding to physical position 164990912 of maize B73 reference genome and a C allele at a position corresponding to physical position 172218916 of maize B73 reference genome.

12. The method of claim 8, wherein said at least one marker is selected from the group consisting of:

i) an A allele at a position corresponding to physical position 164990912 of maize B73 reference genome on maize chromosome 8;

ii) a C allele at a position corresponding to physical position 172218916 of maize B73 reference genome on maize chromosome 8;

iii) an A allele at a position corresponding to physical position 164679493 of maize B73 reference genome on maize chromosome 8;

iv) an A allele at a position corresponding to physical position 164886047 of maize B73 reference genome on maize chromosome 8;

v) an A allele at a position corresponding to physical position 164963082 of maize B73 reference genome on maize chromosome 8;

vi) an A allele at a position corresponding to physical position 164993163 of maize B73 reference genome on maize chromosome 8;

vii) an A allele at a position corresponding to physical position 165151326 of maize B73 reference genome on maize chromosome 8;

viii) an A allele at a position corresponding to physical position 165269767 of maize B73 reference genome on maize chromosome 8;

ix) an A allele at a position corresponding to physical position 165290988 of maize B73 reference genome on maize chromosome 8;

x) an A allele at a position corresponding to physical position 165309200 of maize B73 reference genome on maize chromosome 8;

xi) an A allele at a position corresponding to physical position 165343030 of maize B73 reference genome on maize chromosome 8;

xii) an A allele at a position corresponding to physical position 165482649 of maize B73 reference genome on maize chromosome 8;

xiii) an A allele at a position corresponding to physical position 171781842 of maize B73 reference genome on maize chromosome 8;

xiv) an A allele at a position corresponding to physical position 171833160 of maize B73 reference genome on maize chromosome 8;

XV) an A allele at a position corresponding to physical position 171863486 of maize B73 reference genome on maize chromosome 8;

xvi) an A allele at a position corresponding to physical position 172025007 of maize B73 reference genome on maize chromosome 8;

xvii) an A allele at a position corresponding to physical position 172040252 of maize B73 reference genome on maize chromosome 8;

xviii) an A allele at a position corresponding to physical position 172131684 of maize B73 reference genome on maize chromosome 8;

xix) an A allele at a position corresponding to physical position 172155970 of maize B73 reference genome on maize chromosome 8;

xx) an A allele at a position corresponding to physical position 172336136 of maize B73 reference genome on maize chromosome 8;

xxi) an A allele at a position corresponding to physical position 172367654 of maize B73 reference genome on maize chromosome 8;

xxii) an A allele at a position corresponding to physical position 172434600 of maize B73 reference genome on maize chromosome 8;

xxiii) an A allele at a position corresponding to physical position 172502859 of maize B73 reference genome on maize chromosome 8; and xxiv); an A allele at a position corresponding to physical position 172532270 of maize B73 reference genome on maize chromosome 8.

13. The method of claim 8, wherein said at least one marker is at least one of an A allele at a position corresponding to physical position 164990912 of maize B73 reference genome on maize chromosome 8 and a C allele at a position corresponding to physical position 172218916 of maize B73 reference genome on maize chromosome 8.

14. The method of claim 8, wherein said at least one marker comprises all of an A allele at a position corresponding to physical position 164990912 of maize B73 reference genome on maize chromosome 8 and a C allele at a position corresponding to physical position 172218916 of maize B73 reference genome on maize chromosome 8.

\* \* \* \* \*